United States Patent
Kanno et al.

(10) Patent No.: US 10,017,500 B2
(45) Date of Patent: Jul. 10, 2018

(54) 1,3-BENZODIOXOLE DERIVATIVE

(71) Applicant: DAIICHI SANKYO COMPANY, LIMITED, Tokyo (JP)

(72) Inventors: Osamu Kanno, Tokyo (JP); Jun Watanabe, Tokyo (JP); Takao Horiuchi, Tokyo (JP); Akira Nakao, Tokyo (JP); Keisuke Suzuki, Tokyo (JP); Tomonori Yamasaki, Tokyo (JP); Nobuaki Adachi, Tokyo (JP); Daisuke Honma, Tokyo (JP); Yoshito Hamada, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/123,523

(22) PCT Filed: Mar. 16, 2015

(86) PCT No.: PCT/JP2015/057652
§ 371 (c)(1),
(2) Date: Sep. 2, 2016

(87) PCT Pub. No.: WO2015/141616
PCT Pub. Date: Sep. 24, 2015

(65) Prior Publication Data
US 2017/0073335 A1  Mar. 16, 2017

(30) Foreign Application Priority Data

Mar. 17, 2014 (JP) ................. 2014-053235

(51) Int. Cl.
C07D 405/12 (2006.01)
C07D 405/14 (2006.01)
C07D 417/14 (2006.01)

(52) U.S. Cl.
CPC ......... *C07D 405/12* (2013.01); *C07D 405/14* (2013.01); *C07D 417/14* (2013.01)

(58) Field of Classification Search
CPC .................................................. C07D 405/12
USPC ...................................... 546/283.7; 514/338
See application file for complete search history.

(56) References Cited

FOREIGN PATENT DOCUMENTS

| WO | WO 2009/006577 A2 | 1/2009 |
|---|---|---|
| WO | WO 2013/067296 A1 | 5/2013 |
| WO | WO 2013/067302 A1 | 5/2013 |
| WO | WO 2013/075084 A1 | 5/2013 |
| WO | WO 2013/173441 A1 | 11/2013 |
| WO | WO 2014/055634 A1 | 4/2014 |
| WO | WO 2014/077784 A1 | 5/2014 |

OTHER PUBLICATIONS

Bernd Schuettengruber et al., "Genome Regulation by Polycomb and Trithorax Proteins", Cell, 128, pp. 735-745, Feb. 23, 2007.
Alea A. Millls, "Throwing the Cancer Switch: Reciprocal Roles of Polycomb and Trithorax Proteins", Nature Reviews Cancer, vol. 10, pp. 669-682 Oct. 2010.
Yuri B. Schwartz et al., "Polycomb Silencing Mechanisms and the Management of Genomic Programmes", Nature Reviews Genetics, vol. 8, pp. 9-22, Jan. 2007.
Gotz Laible et al., "Mammalian Homologues of the Polycomb-Group Gene Enhancer of Zeste Mediate Gene Silencing in *Drosophila* Heterochromatin and at S. Cerevisiae Telomeres", The EMBO Journal vol. 16, No. 11, pp. 3219-3232, 1997.
Gotz Laible et al., "The Murine Polycomb-Group Genes Ezh1 and Ezh2 Map Close to Hox Gene Clusters on Mouse Chromosomes 11 and 6", Mammalian Genome 10, pp. 311-314, 1999.
Xiaohua Shen et al., "EZH1 Mediates Methylation on Histone H3 Lysine 27 and Complements EZH2 in Maintaining Stem Cell Identity and Executing Pluripotency", Molecular Cell, 32, pp. 491-502, Nov. 21, 2008.
Raphael Margueron et al., "EZH1 and EZH2 Maintain Repressive Chromatin Through Different Mechanisms", Molecular Cell, 32, pp. 503-518, Nov. 21, 2008.
Elena Ezhkova et al., "EZH1 and EZH2 Cogovern Histone H3K27 Trimethylation and are Essential for Hair Follicle Homeostasis and Would Repair", Genes & Development, 25, pp. 485-498 Feb. 11, 2011.
Evan Bardot et al., "Polycomb Subunits EZH1 and EZH2 Regulate the Merkel Cell Differentiation Program in Skin Stem Cells", The EMBO Journal, vol. 32, pp. 1990-2000, No. 14, 2013.
Makiko Mochizuki-Kashio et al., "Dependency on the Polycom Gene EZH2 Distinguishes Fetal From Adult Hematopoietic Stem Cells", Blood, 118, pp. 6553-6561, Oct. 31, 2011.
Isabel Hidalgo et al., "EZH1 Is Required for Hematopoietic Stem Cell Maintenance and Prevents Senescence-Like Cell Cycle Arrest", Cell Stem Cell, 11, pp. 649-662, Nov. 2, 2012.

(Continued)

*Primary Examiner* — Patricia L Morris
(74) *Attorney, Agent, or Firm* — Foley & Lardner LLP

(57) ABSTRACT

The present invention provides a compound having a particular chemical structure or a pharmacologically acceptable salt thereof which has an excellent inhibitory effect on EZH1 and/or EZH2 activity. The present invention provides a compound having a 1,3-benzodioxole structure represented by the general formula (I) or a pharmacologically acceptable salt thereof, or a pharmaceutical composition comprising the compound (wherein $R^1$, $R^2$, $R^3$, $R^4$, $R^5$, $R^6$, and V in the formula (I) are each as defined in the present specification).

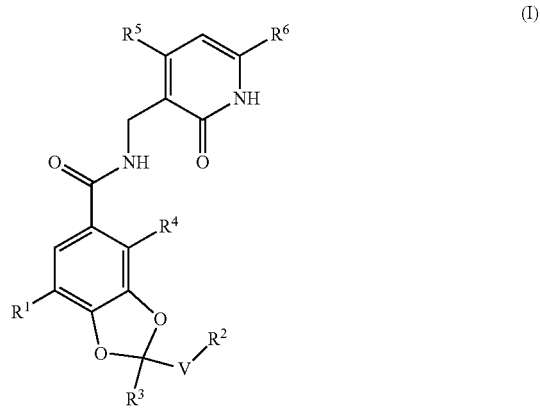

(I)

9 Claims, No Drawings

(56) References Cited

OTHER PUBLICATIONS

Huafeng Xie et al., "Polycomb Repressive Complex 2 Regulates Normal Hematopoietic Stem Cell Function in a Developmental-Stage-Specific Manner", Cell Stem Cell, 14, pp. 68-80, Jan. 2, 2014.
Sooryanarayama Verambally et al., "The Polycomb Group Protein EZH2 Is Involved in Progression of Prostate Cancer", Letters to nature, vol. 419, pp. 624-629, Oct. 10, 2002.
Celina G Kleer et al., "EZH2 Is a Marker of Aggressive Breast Cancer and Promotes Neoplastic Transformation of Breast Epithelial Cells", PNAS, vol. 100, No. 20, pp. 11606-11611, Sep. 30, 2003.
Long-Jun He et al., "Prognostic Significance of Overexpression of EZH2 and H3K27ME3 Proteins in Gastric Cancer", Asian Pacific Journal of Cancer Prevention, vol. 13, pp. 3173-3178, 2012.
Carmen Behrens et al., "EZH2 Protein Expression Associates With the Early Pathogenesis, Tumor Progression, and Prognosis of Non-Small Cell Lung Carcinoma", Clinical Cancer Research, 19, pp. 6556-6565, Oct. 4, 2013.
Chunhua Lu et al., Regulation of Tumor Angiogenesis by EZH2, Cancer Cell, 18, pp. 185-197, Aug. 17, 2010.
Adam D. Toll MD et al., "Implications of Enhancer of Zeste Homologue 2 Expression in Pancreatic Ductal Adenocarcinoma", Human Pathology, 41, pp. 1205-1209, Mar. 5, 2010.
Nina Wagener et al., "Enhancer of Zeste Homolog 2 (EZH2) Expression Is an Independent Prognostic Factor in Renal Cell Carcinoma", BMC Cancer 10, 524, 2010.
Wei Cao MD, PhD et al., "Up-Regulation of Enhancer of Zeste Homolog 2 Is Associated Positively With Cyclin D1 Overexpression and Poor Clinical Overcome in Head and Neck Squamous Cell Carcinoma", Cancer, 118, pp. 2858-2871, Jun. 1, 2012.
Jeffrey A. Simon et al., "Roles of the EZH2 Histone Methyltransferase in Cancer Epigenetics", Mutation Research, 647, pp. 21-29, 2008.
ME Gonzalez et al., "Downregulation of EZH2 Decreases Growth of Estrogen Receptor-Negative Invasive Breast Carcinoma and Requires BRCA1", Oncogene, 28, pp. 843-853, 2009.
Ryan D Morin et al,. Somatic Mutations Altering EZH2 (Tyr641) in Follicular and Diffuse Large B-Cell Lymphomas of Germinal-Center Origin, Nature Genetics, vol. 42, No. 2, pp. 181-185, Feb. 2010.
Tim J. Wigle et al., "The Y641C Mutation of EZH2 Alters Substrate Specificity for Histone H3 Lysine 27 Methylation States", FEBS Letters, 585, pp. 3011-3014, 2011.
Michael T. McCabe et al., Mutation of A677 in Histone Methyltransferase EZH2 in Human B-Cell Lymphoma Promotes Hypertrimethylation of Histone H3 Lysine 27 (H3K27), PNAS, vol. 109, No. 8, pp. 2989-2994, Feb. 21, 2012.
Christina E. Majer et al., "A687V EZH2 Is a Gain-Of-Function Mutation Found in Lymphoma Patients", FEBS Letters, 586, pp. 3448-3451, 2012.
Michael T. McCabe et al., "EZH2 Inhibition As a Therapeutic Strategy for Lymphoma With EZH2-Activating Mutations", Nature, vol. 492, pp. 108-112, Dec. 6, 2012.
Sarah K Knutson et al., "A Selective Inhibitor of EZH2 Blocks H3K27 Methylation and Kills Mutant Lymphoma Cells", Nature Chemical Biology, vol. 8, pp. 890, 896, Sep. 30, 2012.
Tobias Neff et al., "Polycomb Repressive Complex 2 Is Required for MLL-AF9 Leukemia", PNAS, vol. 109, No. 13, pp. 5028-5033, Mar. 27, 2012.
Kyle D. Konze et al., "An Orally Bioavailable Chemical Probe of the Lysine Methyltransferases EZH2 and EZH1", Acs Chemical Biology pp. 1324-1334, Apr. 8, 2013.
Konze et al., "An Orally Bioavailable Chemical Probe of the Lysine Methyltransferases EZH2 and EXH1", ACS Chemical Biology, 2013, 8(6), Jun. 21, 2013, pp. 1324-1334, XP055106961.
Extended European Search Report dated Jun. 29, 2017 in European Patent Application No. 15765525.9.

1,3-BENZODIOXOLE DERIVATIVE

CROSS-REFERENCE TO RELATED APPLICATIONS

The present application is a U.S. national stage application of International Patent Application No. PCT/JP2015/057652, filed Mar. 16, 2015, which claims the benefit of priority to Japanese Patent Application No. 2014-053235, filed Mar. 17, 2014, the entireties of which are hereby incorporated by reference.

TECHNICAL FIELD

The present invention relates to a compound having a particular chemical structure or a pharmacologically acceptable salt thereof which has an excellent inhibitory effect on EZH1 and/or EZH2 activity.

BACKGROUND ART

Chromosomes dynamically control gene replication or transcription by changing their higher-order structures through methylation modification of their constituent DNA and various modifications (acetylation, methylation, phosphorylation, ubiquitination, etc.) of histones (histones H2A, H2B, H3, and H4).

In general, trimethylation of lysine at the fourth position counted from the N-terminus of histone H3 (H3K4me3) functions to activate transcription, whereas trimethylation of lysine at the 27th position (H3K27me3) functions to suppress transcription. The former and latter modifications are performed by a trithorax complex and Polycomb repressive complex 2 (PRC2), respectively (Non Patent Literature 1 and 2).

The Polycomb gene group was identified as a gene controlling the embryogenesis of *Drosophila* and is also conserved in vertebrates (Non Patent Literature 3). In *Drosophila*, the enhancer of zeste protein is a catalytic subunit responsible for the H3K27 methylation modification of PRC2. Both EZH1 (enhancer of zeste homolog 1 (*Drosophila*)) and EZH2 (enhancer of zeste homolog 2 (*Drosophila*)) are mammalian homologs of the *Drosophila* enhancer of zeste (Non Patent Literature 4 and 5). The enzyme activity domains (SET domains) of EZH1 and EZH2 have high homology. In humans or mice, two types of PRC2 exist (PRC2-EZH1 and PRC2-EZH2) which contain EZH1 or EZH2 as a catalytic unit (Non Patent Literature 6 and 7).

In ES cells, EZH1 and EZH2 function cooperatively to participate in maintenance of ES cells (Non Patent Literature 6). EZH1 and EZH2 also act cooperatively on the formation and maintenance of hair follicles and the differentiation of Merkel cells, and both have been reported to also play an important role in maintaining hematopoietic stem cells (Non Patent Literature 8 to 12).

Overexpression of EZH2 has to date been reported in many cancers including prostate cancer, breast cancer, stomach cancer, lung cancer, ovarian cancer, pancreatic cancer, kidney cancer, and head and neck cancer, and the poor prognosis in some of these cancers reportedly correlates with overexpression of EZH2 (Non Patent Literature 13 to 21). There are reports stating that EZH2 knockdown of a cell line derived from such a cancer inhibits cell growth (Non Patent Literature 13 and 22). When EZH2 is overexpressed in an epithelial non-cancer cell line, phenotypes characteristic of cancers appear, such as invasiveness and increased cell growth in a soft agar medium (Non Patent Literature 14).

In follicular lymphoma or follicular center B cell-type diffuse large B-cell lymphoma, somatic mutations have been found in tyrosine 641, alanine 677, and alanine 687 (Y641F, Y641N, Y641S, Y641H, Y641C, A677G, and A687V) of EZH2, and these mutations have been reported to render EZH2 hyperactive to significantly increase intracellular H3K27me3 modification levels (Non Patent Literature 23 to 26). Compounds specifically inhibiting the enzyme activity of EZH2 inhibit, both in vitro and in vivo (xenograft models), the growth of a cancer cell line having such a somatic mutation in EZH2 (Non Patent Literature 27 and 28).

These facts suggest that knockdown of EZH2 or inhibition of its enzyme activity is useful in the treatment of cancers involving overexpression of EZH2 or a somatic mutation in EZH2.

Although much is known about the malignant transformation of cells containing EZH2, much remains to be analyzed on the relation of EZH1 to the malignant transformation of cells. However, it has recently been found that general inhibition of PRC2 suppresses the progression of acute myeloid leukemia caused by MLL-AF9 fusion gene, whereas inhibition of EZH2 alone is not sufficient for this suppression (Non Patent Literature 29). This means that inhibition of PRC2-EZH2 alone is insufficient for suppressing acute myeloid leukemia caused by MLL-AF9 fusion gene, and that simultaneous inhibition of PRC2-EZH1 and PRC2-EZH2 is necessary for this purpose.

CITATION LIST

Non Patent Literature

Non Patent Literature 1: Cell, 128, 735-745 (2007)
Non Patent Literature 2: Nat. Rev. Cancer, 10, 669-682 (2010)
Non Patent Literature 3: Nat. Rev. Genet., 8, 9-22 (2007)
Non Patent Literature 4: EMBO J., 16, 3219-3232 (1997)
Non Patent Literature 5: Mamm. Genome., 10, 311-314 (1999)
Non Patent Literature 6: Mol. Cell, 32, 491-502 (2008)
Non Patent Literature 7: Mol. Cell, 32, 503-518 (2008)
Non Patent Literature 8: Genes Dev., 25, 485-498 (2011)
Non Patent Literature 9: EMBO J., 32, 1990-2000 (2013)
Non Patent Literature 10: Blood, 118, 6553-6561 (2011)
Non Patent Literature 11: Cell Stem Cell, 11, 649-662 (2012)
Non Patent Literature 12: Cell Stem Cell, 14, 68-80 (2014)
Non Patent Literature 13: Nature, 419, 624-629 (2002)
Non Patent Literature 14: Proc. Natl. Acad. Sci. USA, 100, 11606-11611 (2003)
Non Patent Literature 15: Asian Pac. J. Cancer Prev., 13, 3173-3178 (2012)
Non Patent Literature 16: Clin. Cancer Res., 19, 6556-6565 (2013)
Non Patent Literature 17: Cancer Cell, 18, 185-197 (2010)
Non Patent Literature 18: Hum. Pathol., 41, 1205-1209 (2010)
Non Patent Literature 19: BMC Cancer, 10, 524 (2010)
Non Patent Literature 20: Cancer, 118, 2858-2871 (2012)
Non Patent Literature 21: Mutat Res., 647, 21-29 (2008)
Non Patent Literature 22: Oncogene, 28, 843-853 (2009)
Non Patent Literature 23: Nat. Genet., 42, 181-185 (2010)

Non Patent Literature 24: FEBS Lett., 585, 3011-3014 (2011)
Non Patent Literature 25: Proc. Natl. Acad. Sci. USA, 109, 2989-2994 (2012)
Non Patent Literature 26: FEBS Lett., 586, 3448-3451 (2012)
Non Patent Literature 27: Nature, 492, 108-112 (2012)
Non Patent Literature 28: Nat. Chem. Biol., 8, 890-896 (2012)
Non Patent Literature 29: Proc. Natl. Acad. Sci. USA, 109, 5028-5033 (2012)

SUMMARY OF INVENTION

Technical Problem

An object of the present invention is to provide a novel low-molecular weight compound that has excellent EZH1 and/or EZH2 activity and exhibits an antitumor effect.

Solution to Problem

The compound of the present invention has the effect of inhibiting both EZH1 and EZH2 methyltransferase activity. This compound has an anticancer effect on cancers dependent on EZH1 alone, cancers dependent on EZH2 alone, and cancers dependent on both EZH1 and EZH2, and offers treatment of these cancers.

The present invention relates to the following (1) to (16):

(1) A compound represented by the general formula (I) or a pharmacologically acceptable salt thereof:

[Formula 1]

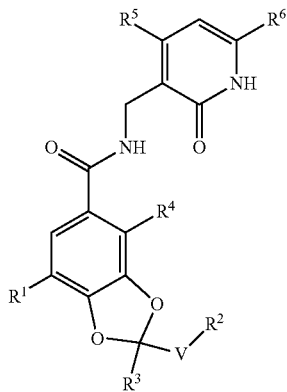

(I)

wherein $R^1$ represents a hydrogen atom, a halogen atom, a $C_1$-$C_6$ alkyl group optionally having 1 to 3 halogen atoms, a $C_1$-$C_6$ alkoxy group optionally having 1 to 3 halogen atoms, a $C_3$-$C_6$ cycloalkyl group, a $C_1$-$C_6$ alkylcarbonyl group, a $C_2$-$C_6$ alkenyl group, a $C_2$-$C_6$ alkynyl group, a $C_3$-$C_6$ cycloalkenyl group, a phenyl group, a 5- or 6-membered aromatic heterocyclic group having, in the ring, 1 to 3 heteroatoms independently selected from the group consisting of a nitrogen atom, an oxygen atom, and a sulfur atom, or a 5- or 6-membered aliphatic heterocyclic group optionally having an unsaturated bond in a portion of the ring and having, in the ring, 1 or 2 heteroatoms independently selected from the group consisting of a nitrogen atom, an oxygen atom, and a sulfur atom, wherein the phenyl group, the 5- or 6-membered aromatic heterocyclic group, and the 5- or 6-membered aliphatic heterocyclic group optionally having an unsaturated bond in a portion of the ring each optionally have 1 to 3 substituents independently selected from group A described below, V represents a single bond, a $C_1$-$C_6$ alkylene group, or an oxy-$C_1$-$C_6$ alkylene group, $R^2$ represents a hydrogen atom, a $C_1$-$C_6$ alkyl group, a $C_3$-$C_6$ cycloalkyl group, a bicyclo-$C_5$-$C_8$ cycloalkyl group, a 5- or 6-membered aliphatic heterocyclic group having, in the ring, 1 or 2 heteroatoms independently selected from the group consisting of a nitrogen atom, an oxygen atom, and a sulfur atom, or a spiro ring group containing two spiro-fused rings independently selected from the group consisting of a 4- to 6-membered aliphatic heterocyclic ring having, in the ring, 1 or 2 heteroatoms independently selected from the group consisting of a nitrogen atom, an oxygen atom, and a sulfur atom and a $C_3$-$C_6$ cycloalkyl ring, wherein the $C_1$-$C_6$ alkyl group, the $C_3$-$C_6$ cycloalkyl group, the bicyclo-$C_5$-$C_8$ cycloalkyl group, the 5- or 6-membered aliphatic heterocyclic group, and the spiro ring group each optionally have 1 to 3 substituents independently selected from group C described below, $R^3$ represents a $C_1$-$C_6$ alkyl group, $R^4$ represents a halogen atom or a $C_1$-$C_6$ alkyl group optionally having 1 to 3 halogen atoms, $R^5$ represents a $C_1$-$C_6$ alkyl group or a $C_1$-$C_6$ alkoxy group, $R^6$ represents a $C_1$-$C_6$ alkyl group, group A consists of a halogen atom, a $C_1$-$C_6$ alkyl group, a $C_1$-$C_6$ alkoxy group, and a 5- or 6-membered aliphatic heterocyclic group having, in the ring, 1 or 2 heteroatoms independently selected from the group consisting of a nitrogen atom, an oxygen atom, and a sulfur atom (wherein the $C_1$-$C_6$ alkyl group, the $C_1$-$C_6$ alkoxy group, and the 5- or 6-membered aliphatic heterocyclic group each optionally have 1 to 3 substituents independently selected from group B described below), group B consists of a halogen atom, a $C_1$-$C_6$ alkyl group, and a 5- or 6-membered aliphatic heterocyclic group having, in the ring, 1 or 2 heteroatoms independently selected from the group consisting of a nitrogen atom, an oxygen atom, and a sulfur atom, and group C consists of a hydroxy group, a formyl group, a $C_1$-$C_6$ alkyl group, a $C_1$-$C_6$ alkylcarbonyl group, a $C_1$-$C_6$ alkoxy group, a $C_1$-$C_6$ alkylsulfonyl group, $-NR^{20}R^{21}$, a $C_1$-$C_6$ alkoxy-$C_1$-$C_6$ alkyl group, a di-$C_1$-$C_6$ alkylamino-$C_1$-$C_6$ alkyl group, and a 4- to 6-membered aliphatic heterocyclic group having, in the ring, 1 or 2 heteroatoms independently selected from the group consisting of a nitrogen atom, an oxygen atom, and a sulfur atom (wherein $R^{20}$ and $R^{21}$ each independently represent a hydrogen atom, a formyl group, or a $C_1$-$C_6$ alkyl group).

(2) The compound according to (1) or a pharmacologically acceptable salt thereof, wherein in the formula (I), $R^1$ represents a hydrogen atom, a halogen atom, a $C_1$-$C_6$ alkyl group, a $C_1$-$C_6$ alkoxy group, a $C_3$-$C_6$ cycloalkyl group, a $C_2$-$C_6$ alkenyl group, a $C_2$-$C_6$ alkynyl group, a phenyl group, a $C_3$-$C_6$ cycloalkenyl group, a 5- or 6-membered aromatic heterocyclic group having, in the ring, 1 to 3 heteroatoms independently selected from the group consisting of a nitrogen atom, an oxygen atom, and a sulfur atom, or a 5- or 6-membered aliphatic heterocyclic group optionally having an unsaturated bond in a portion of the ring and having, in the ring, 1 or 2 heteroatoms independently selected from the group consisting of a nitrogen atom, an oxygen atom, and a sulfur atom.

(3) The compound according to (1) or (2) or a pharmacologically acceptable salt thereof, wherein $R^1$ represents a hydrogen atom, a halogen atom, a methyl group, an ethyl group, a methoxy group, an ethoxy group, a cyclopropyl group, a vinyl group, an acetylene group, a phenyl group, a cyclohexenyl group, a dihydropyranyl group, or a thiazolyl group.

(4) The compound according to any one of (1) to (3) or a pharmacologically acceptable salt thereof, wherein $R^2$ represents a $C_1$-$C_6$ alkyl group, a $C_3$-$C_6$ cycloalkyl group, or a 5- or 6-membered aliphatic heterocyclic group having, in the ring, 1 or 2 heteroatoms independently selected from the group consisting of a nitrogen atom, an oxygen atom, and a sulfur atom, wherein
the $C_1$-$C_6$ alkyl group, the $C_3$-$C_6$ cycloalkyl group, and the 5- or 6-membered aliphatic heterocyclic group each optionally have 1 to 3 substituents independently selected from the group consisting of a $C_1$-$C_6$ alkyl group, a $C_1$-$C_6$ alkylsulfonyl group, a $C_1$-$C_6$ alkylamino group, and a di-$C_1$-$C_6$ alkylamino group.

(5) The compound according to any one of (1) to (4) or a pharmacologically acceptable salt thereof, wherein
V represents a single bond or a methylene group,
$R^2$ represents a methyl group, a cyclohexyl group, a tetrahydropyranyl group, or a piperidyl group, and
$R^3$ represents a methyl group, wherein
the cyclohexyl group, the tetrahydropyranyl group, and the piperidyl group each have one substituent independently selected from the group consisting of a methyl group, an ethyl group, an ethylsulfonyl group, a methylamino group, a dimethylamino group, and an ethylmethylamino group.

(6) A compound represented by the general formula (II) or a pharmacologically acceptable salt thereof:

[Formula 2]

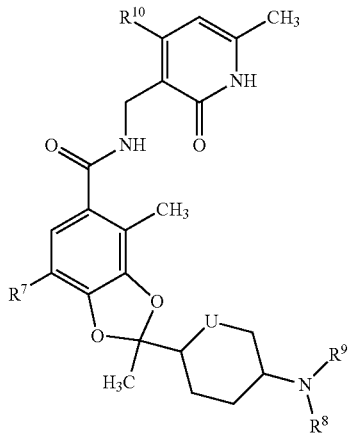

(II)

wherein
$R^7$ represents a hydrogen atom, a halogen atom, a methyl group, an ethyl group, or a cyclopropyl group;
$R^8$ and $R^9$ each independently represent a hydrogen atom, a methyl group, or an ethyl group;
$R^{10}$ represents a methyl group, an ethyl group, or a methoxy group; and
U represents an oxygen atom or $CH_2$.

(7) Any one compound selected from the following group or a pharmacologically acceptable salt thereof:

7-bromo-N-[(4,6-dimethyl-2-oxo-1,2-dihydropyridin-3-yl)methyl]-2-(1-ethyl-4-piperidyl)-2,4-dimethyl-1,3-benzodioxole-5-carboxamide,
7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
(2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
7-bromo-2-[trans-4-(dimethylamino)cyclohexyl]-N-[(4-methoxy-6-methyl-2-oxo-1,2-dihydropyridin-3-yl)methyl]-2,4-dimethyl-1,3-benzodioxole-5-carboxamide,
7-bromo-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide,
7-bromo-2-[trans-4-(dimethylamino)cyclohexyl]-2,4-dimethyl-N-[(6-methyl-2-oxo-4-propyl-1,2-dihydropyridin-3-yl)methyl]-1,3-benzodioxole-5-carboxamide,
7-bromo-N-[(4,6-dimethyl-2-oxo-1,2-dihydropyridin-3-yl)methyl]-2-[trans-4-[N-ethyl(N-methyl)amino]cyclohexyl]-2,4-dimethyl-1,3-benzodioxole-5-carboxamide,
7-bromo-2-[[cis-4-(dimethylamino)cyclohexyl]methyl]-N-[(4,6-dimethyl-2-oxo-1,2-dihydropyridin-3-yl)methyl]-2,4-dimethyl-1,3-benzodioxole-5-carboxamide,
7-chloro-N-[(4,6-dimethyl-2-oxo-1,2-dihydropyridin-3-yl)methyl]-2,4-dimethyl-2-[trans-4-(methylamino)cyclohexyl]-1,3-benzodioxole-5-carboxamide,
7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
(2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
7-chloro-2-[trans-4-(dimethylamino)cyclohexyl]-N-[(4-methoxy-6-methyl-2-oxo-1,2-dihydropyridin-3-yl)methyl]-2,4-dimethyl-1,3-benzodioxole-5-carboxamide,
7-chloro-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide,
2-[trans-4-(dimethylamino)cyclohexyl]-N-[(4,6-dimethyl-2-oxo-1,2-dihydropyridin-3-yl)methyl]-7-fluoro-2,4-dimethyl-1,3-benzodioxole-5-carboxamide,
2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide,
(2S)-2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide,
4,7-dichloro-2-[trans-4-(dimethylamino)cyclohexyl]-N-[(4,6-dimethyl-2-oxo-1,2-dihydropyridin-3-yl)methyl]-2-methyl-1,3-benzodioxole-5-carboxamide,
7-(cyclopenten-1-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
2-[trans-4-(dimethylamino)cyclohexyl]-N-[(4,6-dimethyl-2-oxo-1,2-dihydropyridin-3-yl)methyl]-2,4-dimethyl-7-phenyl-1,3-benzodioxole-5-carboxamide,
7-(cyclohexen-1-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
7-(3,6-dihydro-2H-pyran-4-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
2-[trans-4-(dimethylamino)cyclohexyl]-N-[(4,6-dimethyl-2-oxo-1,2-dihydropyridin-3-yl)methyl]-2,4-dimethyl-7-vinyl-1,3-benzodioxole-5-carboxamide, 2-(trans-4-(dimethylamino)cyclohexyl)-N-[(4,6-dimethyl-2-oxo-1,2-dihydropyridin-3-yl)methyl]-7-ethynyl-2,4-dimethyl-1,3-benzodioxole-5-carboxamide, 7-cyclopropyl-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, 2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and 2-[trans-4-(dimethylamino)cyclohexyl]-N-[(4,6-dimethyl-2-oxo-1,2-dihydropyridin-3-yl)methyl]-7-ethyl-2,4-dimethyl-1,3-benzodioxole-5-carboxamide.

(8) Any one compound selected from the following group or a pharmacologically acceptable salt thereof:

7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, 2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide, (2S)-2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide, 4,7-dichloro-2-[trans-4-(dimethylamino)cyclohexyl]-N-[(4,6-dimethyl-2-oxo-1,2-dihydropyridin-3-yl)methyl]-2-methyl-1,3-benzodioxole-5-carboxamide, 2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and 2-[trans-4-(dimethylamino)cyclohexyl]-N-[(4,6-dimethyl-2-oxo-1,2-dihydropyridin-3-yl)methyl]-7-ethyl-2,4-dimethyl-1,3-benzodioxole-5-carboxamide.

(9) A pharmaceutical composition comprising a compound according to any one of (1) to (8) or a pharmacologically acceptable salt thereof as an active ingredient.

(10) An EZH1 and/or EZH2 enzyme activity inhibitor comprising a compound according to any one of (1) to (8) or a pharmacologically acceptable salt thereof as an active ingredient.

(11) A therapeutic agent for tumors that is capable of treating the tumor by inhibiting EZH1 and/or EZH2 enzyme activity, the therapeutic agent comprising a compound according to any one of (1) to (8) or a pharmacologically acceptable salt thereof as an active ingredient.

(12) An antitumor agent comprising a compound according to any one of (1) to (8) or a pharmacologically acceptable salt thereof as an active ingredient.

(13) The antitumor agent according to (12), wherein the tumor is lymphoma, a rhabdoid tumor, leukemia, lung cancer, stomach cancer, prostate cancer, colorectal cancer, ovarian cancer, or liver cancer.

(14) A therapeutic agent for tumors that exhibit overexpression of EZH1 and/or EZH2, the therapeutic agent comprising a compound according to any one of (1) to (8) or a pharmacologically acceptable salt thereof as an active ingredient.

(15) A therapeutic agent for tumors having a mutation in EZH1 and/or EZH2, the therapeutic agent comprising a compound according to any one of (1) to (8) or a pharmacologically acceptable salt thereof as an active ingredient.

(16) A therapeutic agent for tumors having a SWI/SNF complex mutation, the therapeutic agent comprising a compound according to any one of (1) to (8) or a pharmacologically acceptable salt thereof as an active ingredient.

Advantageous Effects of Invention

The compound of the present invention or the pharmacologically acceptable salt thereof has excellent EZH1 and/or EZH2 inhibitory activity and inhibits cell growth. Thus, the compound of the present invention or the pharmacologically acceptable salt thereof is useful as an antitumor agent, particularly, a therapeutic agent for tumors such as lymphoma, rhabdoid tumors, leukemia, lung cancer, stomach cancer, prostate cancer, colorectal cancer, ovarian cancer, or/and liver cancer. The compound of the present invention or the pharmacologically acceptable salt thereof is effective as a therapeutic drug for tumors that can be treated by inhibiting EZH1 and EZH2 enzyme activity, including the tumors described above.

DESCRIPTION OF EMBODIMENTS

In the present invention, the "halogen atom" is a fluorine atom, a chlorine atom, a bromine atom, or an iodine atom.

In the present invention, the "$C_1$-$C_6$ alkyl group" refers to a linear or branched alkyl group having 1 to 6 carbon atoms. Examples thereof include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, and a 4-methylpentyl group.

In the present invention, the "$C_3$-$C_6$ cycloalkyl group" is a cyclopropyl group, a cyclobutyl group, a cyclopentyl group, or a cyclohexyl group.

In the present invention, the "$C_1$-$C_6$ alkoxy group" refers to a $C_1$-$C_6$ alkoxy group formed from the $C_1$-$C_6$ alkyl group mentioned above. Examples thereof include a methoxy group, an ethoxy group, a n-propoxy group, an isopropoxy group, a butoxy group, an isobutoxy group, a sec-butoxy group, a tert-butoxy group, a pentoxy group, an isopentoxy group, a 2-methylbutoxy group, a hexyloxy, and an isohexyloxy group.

In the present invention, the "$C_1$-$C_6$ alkylcarbonyl group" refers to a group in which a carbonyl group is substituted by one $C_1$-$C_6$ alkyl group mentioned above. Examples thereof include an acetyl group, an ethylcarbonyl group, a propylcarbonyl group, and an isopropylcarbonyl group.

In the present invention, the "$C_1$-$C_6$ alkylene group" refers to a group in which one $C_1$-$C_6$ alkyl group mentioned above forms a divalent substituent. Examples thereof include a methylene group, an ethylene group, a propylene group, and a butylene group.

In the present invention, the "oxy-$C_1$-$C_6$ alkylene group" refers to a group in which one $C_1$-$C_6$ alkylene group mentioned above is substituted by one oxy group. Examples thereof include an oxymethylene group and an oxyethylene group. The oxy group binds to $R^2$.

In the present invention, the "$C_2$-$C_6$ alkenyl group" refers to a linear or branched alkenyl group having 2 to 6 carbon atoms. Examples thereof include a vinyl group, an allyl group, a 1-propenyl group, an isopropenyl group, a 2-methyl-1-propenyl group, a 2-methyl-2-propenyl group, a 1-butenyl group, a 2-butenyl group, a 3-butenyl group, a 1-pentenyl group, a 1-hexenyl group, a 1,3-hexadienyl group, and a 1,5-hexadienyl group.

In the present invention, the "$C_2$-$C_6$ alkynyl group" refers to a linear or branched alkynyl group having 2 to 6 carbon atoms. Examples thereof include an ethynyl group, a 1-propynyl group, a 2-propynyl group, a 1-butynyl group, a 2-butynyl group, a 3-butynyl group, a 1-ethynyl-2-propynyl group, a 1-methyl-2-propynyl group, a 1-pentynyl group, a 1-hexynyl group, a 1,3-hexadiynyl group, and a 1,5-hexadiynyl group.

In the present invention, the "$C_1$-$C_6$ alkoxy-$C_1$-$C_6$ alkyl group" refers to a group in which the $C_1$-$C_6$ alkyl group mentioned above is substituted by one $C_1$-$C_6$ alkoxy group mentioned above. Examples thereof include a methoxymethyl group, an ethoxymethyl group, a propoxymethyl group, an isopropoxymethyl group, a methoxyethyl group, an ethoxyethyl group, a propoxyethyl group, and an isopropoxyethyl group.

In the present invention, the "$C_1$-$C_6$ alkylsulfonyl group" refers to a group in which a sulfonyl group is substituted by one $C_1$-$C_6$ alkyl group mentioned above. Examples thereof include a methylsulfonyl group, an ethylsulfonyl group, a propylsulfonyl group, and an isopropylsulfonyl group.

In the present invention, the "di-$C_1$-$C_6$ alkylamino-$C_1$-$C_6$ alkyl group" refers to a group in which the $C_1$-$C_6$ alkyl group mentioned above is substituted by an amino group substituted by two $C_1$-$C_6$ alkyl groups mentioned above. Examples thereof include a dimethylaminomethyl group, a dimethylaminoethyl group, and a dimethylaminopropyl group.

In the present invention, the "$C_3$-$C_6$ cycloalkenyl group" is a cyclopropenyl group, a cyclobutenyl group, a cyclopentenyl group, or a cyclohexenyl group.

In the present invention, the "aromatic heterocyclic group" refers to a group derived from a 5- or 6-membered monocyclic aromatic compound containing 1 to 3 atoms each independently selected from the group consisting of a nitrogen atom, an oxygen atom, and a sulfur atom in addition to carbon as atoms constituting the ring. Examples thereof include a furyl group, a thienyl group, a pyrrolyl group, an oxazolyl group, an isoxazolyl group, a thiazolyl group, an isothiazolyl group, an imidazolyl group, an oxadiazolyl group, a thiadiazolyl group, a triazinyl group, a pyrazolyl group, a pyridyl group, a pyrazyl group, a pyrimidinyl group, and a pyridazinyl group.

In the present invention, the "aliphatic heterocyclic group" refers to a group derived from a 3- to 6-membered monocyclic aliphatic cyclic compound having a saturated ring and containing 1 or 2 atoms each independently selected from the group consisting of a nitrogen atom, an oxygen atom, and a sulfur atom in addition to carbon as atoms constituting the ring. Examples thereof include an oxiranyl group, an aziridinyl group, a thiiranyl group, an oxetanyl group, an azetidinyl group, a thietanyl group, a tetrahydrofuranyl group, a pyrrolidinyl group, a tetrahydrothiophenyl group, a tetrahydropyranyl group, a piperazinyl group, a tetrahydrothiopyranyl group, a morpholino group, a morpholinyl group, and a piperidinyl group.

In the present invention, the "aliphatic heterocyclic group optionally having an unsaturated bond in a portion of the ring" refers to a group derived from a 3- to 6-membered monocyclic aliphatic cyclic compound optionally containing a double bond in the ring and containing 1 or 2 atoms each independently selected from the group consisting of a nitrogen atom, an oxygen atom, and a sulfur atom in addition to carbon as atoms constituting the ring. Examples thereof include the aliphatic heterocyclic group mentioned above, an azirinyl group, an oxirenyl group, a thiirenyl group, a dihydropyrrolyl group, a dihydrofuranyl group, a dihydrothiophenyl group, a dihydropyranyl group, a tetrahydropyridinyl group, and a dihydrothiopyranyl group.

In the present invention, the "bicyclo-$C_5$-$C_8$ cycloalkyl group" refers to a group derived from an aliphatic hydrocarbon compound in which two cycloalkyl rings share two atoms. Examples thereof include a bicyclo[1.1.1]pentyl group, a bicyclo[2.1.0]pentyl group, a bicyclo[2.1.1]hexyl group, a norbornanyl group, and a bicyclo[2.2.2]octanyl group.

In the present invention, the "spiro ring group" refers to a group derived from a cyclic compound in which the aliphatic heterocyclic group mentioned above and/or the $C_3$-$C_6$ cycloalkyl ring mentioned above are bonded by sharing one atom and have no linkage through any other bridge. Examples thereof include a spiro[3.3]heptanyl group and an azaspiro[3.3]heptanyl group.

In the present invention, the term "tumor" is not limited to malignant tumors and includes every type of tumor, for example, carcinoma, sarcoma, and benign tumors. Particularly, malignant tumors are also referred to as "cancer".

In the present invention, "EZH1 and/or EZH2 enzyme activity" means enzyme activity that is possessed by EZH1 and/or EZH2 and introduces methyl groups to lysine 27 of histone H3.

In the present invention, "overexpression of EZH1 and/or EZH2" means that the expression level of the EZH1 protein and/or the EZH2 protein is increased by enhanced gene transcription activity, promoted translation, suppressed proteolysis, improved protein stabilization, etc.

In the present invention, the phrase "having a mutation in EZH1 and/or EZH2" means that a mutation exists in the nucleotide sequence and/or the amino acid sequence of EZH1 and/or EZH2. For example, somatic mutations in tyrosine 641, alanine 677, and alanine 687 (Y641F, Y641N, Y641S, Y641H, Y641C, A677G, and A687V) of EZH2 are found.

In the present invention, the "SWI/SNF complex" means a chromatin structure conversion factor complex that acts antagonistically on PRC2. The SWI/SNF complex controls activities essential for cell survival, such as DNA transcription, replication, and repair by changing a nucleosome structure in an ATP dependent manner.

In the present invention, the phrase "having a SWI/SNF complex mutation" means that a mutation exists in the nucleotide sequence and/or the amino acid sequence of a subunit constituting the SWI/SNF complex. SWI/SNF complex mutations are known as inactivating mutations in cancers. For example, rhabdoid tumors having a deletion mutation in subunit SNF5 are known.

Next, each preferred substituent in the general formula (I) will be described.

$R^1$ is preferably a hydrogen atom, a halogen atom, a methyl group, an ethyl group, a cyclopropyl group, a vinyl group, an acetylene group, a phenyl group, a cyclohexenyl group, a dihydropyranyl group, or a thiazolyl group, more preferably a bromine atom, a chlorine atom, or a methyl group.

V is preferably a single bond or a methylene group, more preferably a single bond.

$R^2$ is preferably a methyl group, a N-ethyl-piperidinyl group, a N-ethylsulfonyl-piperidinyl group, a dimethylamino-tetrahydropyranyl group, a methylamino-cyclohexyl group, a dimethylamino-cyclohexyl group, or an ethyl (methyl)amino-cyclohexyl group.

$R^3$ is preferably a methyl group.

According to a preferred combination of V, $R^2$, and $R^3$, V is a single bond, $R^2$ is a dimethylamino-cyclohexyl group, and $R^3$ is a methyl group.

$R^4$ is preferably a chlorine atom, a bromine atom, or a methyl group.

$R^5$ is preferably a methyl group, an ethyl group, or a methoxy group.

$R^6$ is preferably a methyl group.

The compound represented by the general formula (I) of the present invention can form a pharmaceutically acceptable salt, if desired. The pharmaceutically acceptable salt refers to a salt that has no significant toxicity and can be used as a drug. The compound represented by the general formula (I) of the present invention can form a salt through reaction with an acid when having a basic group.

Examples of the salt based on a basic group include: hydrohalides such as hydrofluoride, hydrochloride, hydrobromide, and hydroiodide; inorganic acid salts such as nitrate, perchlorate, sulfate, and phosphate; $C_1$-$C_6$ alkylsulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, ascorbate, tartrate, oxalate, adipate, and maleate; and amino acid salts such as glycine salt, lysine salt, arginine salt, ornithine salt, glutamate, and aspartate.

The compound represented by the general formula (I) of the present invention or the salt thereof, when left in air or recrystallized, may incorporate water molecule(s) to form a hydrate. Such a hydrate is also included in the salt of the present invention.

The compound represented by the general formula (I) of the present invention or the salt thereof, when left in a solvent or recrystallized, may absorb a certain kind of solvent to form a solvate. Such a solvate is also included in the salt of the present invention.

The present invention also encompasses a compound that serves as an active ingredient in the pharmaceutical composition of the present invention and that is converted to compound (1) through reaction with an enzyme, gastric acid, or the like under physiological conditions in vivo, i.e., a "pharmaceutically acceptable prodrug compound" that is converted to compound (1) by enzymatic oxidation, reduction, hydrolysis, etc., or is converted to compound (1) by hydrolysis, etc., by gastric acid or the like.

Examples of the prodrug of compound (1) containing an amino group can include compounds in which the amino group is acylated, alkylated, or phosphorylated (e.g., compounds in which the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated). Examples of the prodrug of compound (1) containing a hydroxy group include compounds in which the hydroxy group is acylated, alkylated, phosphorylated, or borated (e.g., compounds in which the hydroxy group is acetylated, palmitoylated, propanoylated, pivaloylated, succinylated, fumarylated, alanylated, or dimethylaminomethylcarbonylated). Examples of the prodrug of compound (1) containing a carboxy group include compounds in which the carboxy group is esterified or amidated (e.g., compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated).

The prodrug of the compound of the present invention can be produced from compound (1) by a method known in the art. The prodrug of the compound of the present invention also includes a compound that is converted to compound (1) under physiological conditions as described in "Iyakuhin No Kaihatsu (Development of Pharmaceuticals in English)", Vol. 7, Bunshi Sekkei (Molecular Design in English), Hirokawa-Shoten Ltd., 1990, pp. 163-198.

The compound represented by the general formula (I) of the present invention or the pharmacologically acceptable salt thereof encompasses all stereoisomers.

For the compound of the present invention, its isomers and mixtures of these isomers are all represented by a single formula, i.e., the general formula (I). Thus, the present invention includes all of these isomers and even mixtures of these isomers at arbitrary ratios.

The compound of the present invention may also contain unnatural proportions of atomic isotopes at one or more of the atoms constituting such a compound. Examples of the atomic isotopes include deuterium ($^2$H), tritium ($^3$H), iodine-125 ($^{125}$I), and carbon-14 ($^{14}$C). The compound may be radiolabeled with a radioisotope such as tritium ($^3$H), iodine-125 ($^{125}$I), or carbon-14 ($^{14}$C). The radiolabeled compound is useful as a therapeutic or prophylactic agent, a research reagent (e.g., an assay reagent), and a diagnostic agent (e.g., an in vivo diagnostic imaging agent). All isotopic variants of the compound of the present invention are included in the scope of the present invention, regardless of being radioactive or not.

The inhibitory effect on EZH1 and/or EZH2 enzyme activity according to the present invention can be measured by, for example, the methods of Test Examples 1 to 3.

The cell growth inhibitory activity of the compound of the present invention can be examined by use of a growth inhibition test method usually employed by those skilled in the art. For example, the cell growth inhibitory activity can be measured by the method of Test Example 4.

In vivo antitumor activity can be examined by use of a growth inhibition test method usually employed by those skilled in the art. For example, the in vivo antitumor activity can be measured by the methods of Test Examples 5 to 8.

The compound of the present invention can be used in the treatment of tumors. The compound of the present invention can be used in the treatment of, for example, lymphoma, rhabdoid tumors, leukemia, lung cancer, stomach cancer, prostate cancer, colorectal cancer, ovarian cancer, or liver cancer.

It has been suggested that EZH1 and/or EZH2 are involved in cancer growth, survival, etc. Therefore, the compound of the present invention is preferably used for tumors that exhibit an increased expression level of EZH1 and/or EZH2, and/or tumors having a mutation in EZH1 and/or EZH2.

Tumors in the prostate, the breast, the stomach, the lung, the ovary, the pancreas, the kidney, or the head and neck are known as tumors that exhibit an increased expression level of EZH1 and/or EZH2.

An increase in the expression level of EZH1 and/or EZH2 can be confirmed by examining the expression level or the like of EZH1 and/or EZH2 in a test tissue (e.g., collected by blood collection or biopsy) of a patient by use of a method known in the art such as Western blotting, ELISA, Northern blotting, quantitative PCR, analysis using DNA chip immunohistochemical staining, etc., or a pathological approach.

The presence of a mutation in EZH1 and/or EZH2 can be confirmed by examining the nucleotide sequence of the genomic DNA.

The SWI/SNF complex acts antagonistically on PRC2. Therefore, PRC2 is presumed to be hyperactive in cancers involving a deletion mutation in its subunit. The compound of the present invention can be used in the treatment of such cancers.

The presence of a mutation in the SWI/SNF complex can be confirmed by examining the nucleotide sequence of the genomic DNA.

Rhabdoid tumors involving a deletion mutation in the subunit SNF5 are known as tumors having a SWI/SNF complex mutation.

The compound of the present invention may be used in combination with an additional antitumor agent. Examples thereof include antitumor antibiotics, antitumor plant components, BRM (biological response modifiers), hormones, vitamins, antitumor antibodies, molecular target drugs, and other antitumor agents.

More specifically, examples of alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and others such as busulfan, improsulfan tosylate, and dacarbazine.

Examples of various antimetabolites include: purine antimetabolites such as 6-mercaptopurine, 6-thioguanine, and thioinosine; pyrimidine antimetabolites such as fluorouracil, tegafur, tegafur uracil, carmofur, doxifluridine, broxuridine, cytarabine, and enocitabine; and antifolates such as methotrexate and trimetrexate.

Examples of the antitumor antibiotics include: anthracycline antibiotic antitumor agents such as mitomycin C, bleomycin, peplomycin, daunorubicin, aclarubicin, doxorubicin, pirarubicin, THP-adriamycin, 4'-epidoxorubicin, and epirubicin; and others such as chromomycin A3 and actinomycin D.

Examples of the antitumor plant components include: *vinca* alkaloids such as vindesine, vincristine, and vinblastine; taxanes such as paclitaxel and docetaxel; and epipodophyllotoxins such as etoposide and teniposide.

Examples of the BRM include tumor necrosis factors and indomethacin.

Examples of the hormones include hydrocortisone, dexamethasone, methylprednisolone, prednisolone, prasterone, betamethasone, triamcinolone, oxymetholone, nandrolone, metenolone, fosfestrol, ethynyl estradiol, chlormadinone, and medroxyprogesterone.

Examples of the vitamins include vitamin C and vitamin A.

Examples of the antitumor antibodies and the molecular target drugs include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

The compound of the present invention or the pharmacologically acceptable salt thereof can be administered in various forms. Examples of the dosage form include tablets, capsules, granules, emulsions, pills, powders, and syrups (solutions) for oral administration and injections (intravenous, intramuscular, subcutaneous, or intraperitoneal administration), drip infusions, and suppositories (rectal administration) for parenteral administration. These various preparations can be formulated according to routine methods using aids that may be usually used in the field of pharmaceutical formulation techniques such as excipients, binders, disintegrants, lubricants, corrigents, solubilizers, suspending agents, and coating agents, in addition to the active ingredient.

For use as a tablet, examples of carriers that can be used include: excipients such as lactose, saccharose, sodium chloride, glucose, urea, starch, calcium carbonate, kaolin, crystalline cellulose, and silicic acid; binders such as water, ethanol, propanol, simple syrup, glucose solutions, starch solutions, gelatin solutions, carboxymethylcellulose, shellac, methylcellulose, potassium phosphate, and polyvinylpyrrolidone; disintegrants such as dry starch, sodium alginate, agar powder, laminaran powder, sodium bicarbonate, calcium carbonate, polyoxyethylene sorbitan fatty acid esters, sodium lauryl sulfate, monoglyceride stearate, starch, and lactose; disintegration inhibitors such as saccharose, stearin, cocoa butter, and hydrogenated oil; absorption promoters such as quaternary ammonium salts and sodium lauryl sulfate; moisturizing agents such as glycerin and starch; adsorbents such as starch, lactose, kaolin, bentonite, and colloidal silicic acid; and lubricants such as purified talc, stearate, boric acid powder, and polyethylene glycol. Alternatively, tablets coated in a usual manner, for example, sugar coated tablets, gelatin coated tablets, enteric coated tablets, film coated tablets, double layer tablets, and multilayered tablets may be prepared, if necessary.

For use as a pill, examples of carriers that can be used include: excipients such as glucose, lactose, cocoa butter, starch, hydrogenated plant oil, kaolin, and talc; binders such as gum arabic powder, powdered tragacanth, gelatin, and ethanol; and disintegrants such as laminaran and agar.

For use as a suppository, conventional carriers known in the art can be widely used. Examples thereof include polyethylene glycol, cocoa butter, higher alcohols, esters of higher alcohols, gelatin, and semisynthetic glyceride.

For use as an injection, solutions, emulsions, or suspensions can be used. These solutions, emulsions, or suspensions are preferably sterilized and adjusted to be isotonic to blood. Any solvent that can be used as a medical diluent can be used without limitations in the production of these solutions, emulsions, or suspensions. Examples thereof include water, ethanol, propylene glycol, ethoxylated isostearyl alcohol, polyoxylated isostearyl alcohol, and polyoxyethylene sorbitan fatty acid esters. In this case, each preparation may contain common salt, glucose, or glycerin in an amount sufficient for preparing an isotonic solution. Also, each preparation may contain a usual solubilizer, buffer, soothing agent, and the like.

These preparations may also contain a colorant, a preservative, a fragrance, a flavor, a sweetener, and the like, if necessary, and may further contain an additional pharmaceutical product.

The amount of the active ingredient compound contained in each of these preparations is not particularly limited and is appropriately selected in a wide range. The composition usually contains 0.5 to 70% by weight, preferably 1 to 30% by weight of the compound with respect to the total weight.

The amount of the compound used differs depending on the symptoms, age, etc. of a patient (warm-blooded animal, particularly a human). The daily dose for oral administration to an adult human is 2000 mg (preferably 100 mg) as the upper limit and 0.1 mg (preferably 1 mg, more preferably 10 mg) as the lower limit and is desirably administered once to 6 times a day according to the symptoms.

[Production Method]

Next, a typical method for producing the compound represented by the general formula (I) will be described. The compound of the present invention can be produced by various production methods. The production method shown below is given for illustrative purposes. It should be understood that the present invention is not limited by this example.

The compound represented by the general formula (I) and intermediates for production thereof can be produced through the use of various reactions known in the art as described below.

The compound of the present invention or the pharmacologically acceptable salt thereof can be produced by use of various production methods known in the art taking into account the chemical properties of the backbone and its substituents. The methods known in the art are methods described in, for example, "Organic Functional Group Preparations", 2nd ed., Academic Press, Inc., 1989 and "Comprehensive Organic Transformations", VCH Publishers Inc., 1989.

Depending on the type of functional group(s) present in the compound, functional group(s) in a starting material or an intermediate may be protected with an appropriate protective group, or may be replaced with a group that can be readily converted to the functional group. Such an approach may be effective for the production technique.

Examples of such a functional group include an amino group, a hydroxy group, and a carboxy group. Examples of their protective groups include protective groups described in T. W. Greene and P. G. Wuts, "Protective Groups in Organic Synthesis (4th ed., 2006)."

The protective group or the group that can be readily converted to the functional group can be appropriately selected for use according to the reaction conditions of each production method for compound production.

According to such a method, reaction can be carried out after introduction of the group, followed by the removal of the protective group or the conversion to the desired group according to the need to obtain the desired compound.

A prodrug of the compound can be produced by, as in the case of the protective group mentioned above, introducing a particular group into a starting material or an intermediate, or by carrying out a reaction using the obtained compound. The reaction for producing the prodrug can be carried out by use of a method generally known to those skilled in the art such as conventional esterification, amidation, dehydration, or hydrogenation.

Hereinafter, methods for producing compounds will be described. However, the production method of the present invention is not limited to the methods described below by any means.

Method A-(a) is a method which involves: halogenating compound (A0) by step A-1; then ketalizing the resulting compound A1 to produce compound (A2) (step A-2); further hydrolyzing the compound (A2) by step A-3; and then amidating the resulting compound (A3) by step A-4 using a condensing agent to produce compound (A4).

Method A-(a)

[Formula 3]

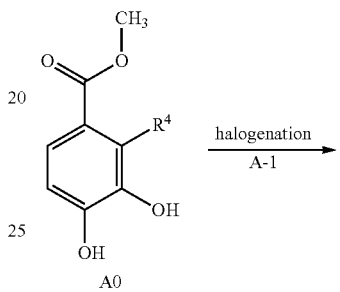

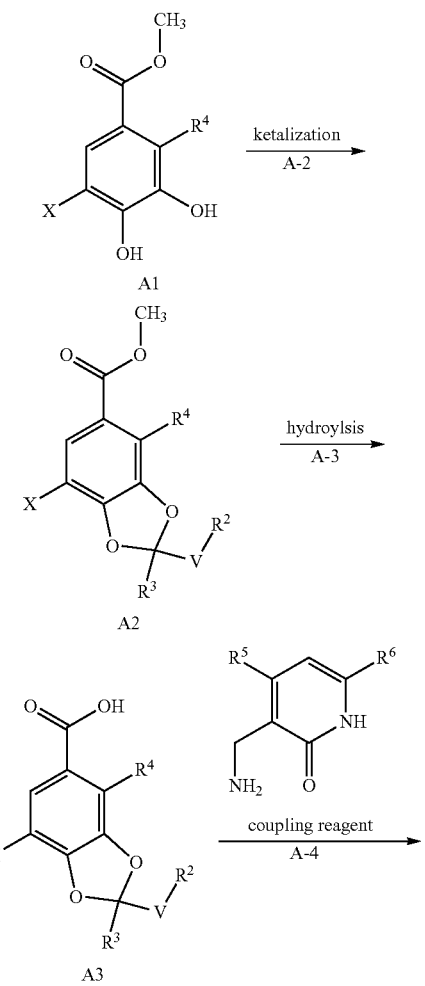

-continued

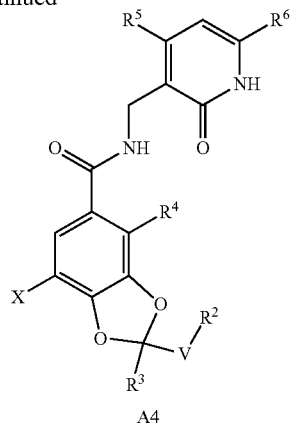

A4 wherein $R^2$, $R^3$, $R^4$, $R^5$, $R^6$, and V are as defined above, and X represents a chlorine atom or a bromine atom.

Step A-1 (Halogenation Reaction):

(1) Chlorination:

This step involves stirring compound (A0) for 0.5 to 24 hours under cooling or under heating in the presence of an equal amount or an excess amount of a chlorinating agent in a solvent inert to the reaction to obtain compound (A1) (X=Cl). This compound is preferably obtained by stirring at 0 to 60° C. for 0.5 to 12 hours. The solvent used in this reaction is not particularly limited as long as the solvent is inert to the reaction. Examples thereof include water, acetonitrile, tetrahydrofuran, ethyl acetate, acetic acid, dichloromethane, and mixtures thereof. Examples of the chlorinating agent include sulfuryl chloride, N-chlorosuccinimide (NCS), and chlorine. 1 to 2 equivalents of an additive such as p-anisole can be used for preventing by-products and improving yields.

(2) Bromination:

This step involves stirring compound (A0) for 0.5 to 24 hours under cooling or under heating in the presence of an equal amount or an excess amount of a brominating agent in a solvent inert to the reaction to obtain compound A1 (X=Br). This compound is preferably obtained by stirring at 0 to 60° C. for 0.5 to 12 hours. The solvent used in this reaction is not particularly limited as long as the solvent is inert to the reaction. Examples thereof include tetrahydrofuran, ethyl acetate, acetic acid, dichloromethane, and mixtures thereof. Examples of the brominating agent include N-bromosuccinimide (NBS) and bromine. An equal amount or an excess amount of an additive such as p-anisole can be used for preventing by-products and improving yields.

Step A-2 (Ketalization Reaction):

(1) In the Case of Using Ketone:

This step involves heating compound (A1) to reflux for 1 to 72 hours under reflux conditions using 0.01 to 0.5 equivalents of an acid catalyst in a solvent inert to the reaction, while dehydrating the compound using a Dean-Stark apparatus or the like to obtain compound (A2). This compound is preferably obtained by heating compound (A1) to reflux at 80 to 120° C. for 3 to 24 hours using 0.1 to 0.3 equivalents of an acid catalyst, while dehydrating the compound using a Dean-Stark apparatus or the like. The solvent used in this reaction is not particularly limited as long as the solvent is inert to the reaction. Examples thereof include benzene, toluene, and xylene. Examples of the acid catalyst include hydrochloric acid, sulfuric acid, phosphoric acid, p-toluenesulfonic acid, and montmorillonite K10.

(2) In the Case of Using Acetylene Derivative:

The reaction can be carried out under conditions shown in the following literature (Ming Li et al., J. Org. Chem., 73, 8658-8660 (2008)). This step involves stirring compound (A1) for 1 to 24 hours under heating conditions using an equal amount or an excess amount of an acetylene derivative and 0.01 to 0.3 equivalents of a Ru catalyst in a solvent inert to the reaction to obtain compound (A2). This compound is preferably obtained by stirring at 60 to 150° C. for 1 to 6 hours using 0.01 to 0.1 equivalents of a Ru catalyst. The solvent used in this reaction is not particularly limited as long as the solvent is inert to the reaction. Examples thereof include benzene, toluene, and xylene. Examples of the Ru catalyst include, but are not limited to, triruthenium(0) dodecacarbonyl. The product can be obtained in good yield even from a low reactive acetylene derivative by use of 0.01 to 0.5 equivalents of a phosphine ligand. Examples of the phosphine ligand used in this reaction include triphenylphosphine, (2-biphenyl)di-tert-butylphosphine (JohnPhos), 2-dicyclohexylphosphino-2',6'-diisopropoxybiphenyl (RuPhos), and 5-(di-tert-butylphosphino)-1',3',5'-triphenyl-1'H-[1,4']bipyrazole (BippyPhos). The Ru catalyst and each ligand can be purchased from Sigma-Aldrich Co., Strem Chemicals Inc., etc.

Step A-3 (Hydrolysis):

This step involves stirring compound (A2) for 3 to 96 hours under cooling or under heating using an equal amount or an excess amount of an aqueous alkali solution in a solvent to obtain compound (A3). This compound is preferably obtained by stirring at room temperature to 60° C. for 3 to 48 hours. The solvent used in this reaction is not particularly limited as long as the solvent does not inhibit the reaction. Examples thereof include methanol, ethanol, tetrahydrofuran, dimethoxyethane, acetonitrile, and mixtures thereof. Examples of the alkali include inorganic bases such as lithium hydroxide, sodium hydroxide, and potassium hydroxide.

Step A-4 (Amidation Reaction):

This step involves stirring compound (A3) for 1 to 24 hours under cooling or under heating using an equal amount or an excess amount of a corresponding amine and a condensing agent in a solvent inert to the reaction to obtain compound (A4). This compound is preferably obtained by stirring at room temperature to 120° C. for 1 to 8 hours. The solvent used in this reaction is not particularly limited as long as the solvent is inert to the reaction. Examples thereof include N,N-dimethylformamide, dimethylacetamide, dichloromethane, 1,2-dichloroethane, chloroform, tetrahydrofuran, 1,2-dimethoxyethane, acetonitrile, and mixtures thereof. Examples of the condensing agent include dicyclocarbodiimide (DCC), 1-ethyl-3-(3-dimethylaminopropyl) carbodiimide (EDCI), and 1,1'-carbonyldiimidazole. Use of an additive may be preferred for the reaction. Examples of the additive include N-hydroxysuccinimide (HOSu), 1-hydroxybenzotriazole (HOBt), and 1-hydroxy-7-azabenzotriazole (HOAt). In addition, an organic base such as triethylamine or diisopropylethylamine, or an inorganic base such as potassium carbonate, sodium carbonate, potassium hydroxide, or sodium hydroxide may be advantageous for the smooth progression of the reaction.

Method A-(b) is a method which involves deprotecting a protective group for the amino group contained in $R^2$ or $R^3$ in compound (A4a) in which the amino group contained in $R^2$ or $R^3$ of the compound (A4) synthesized in method A-(a) has the protective group, and then carrying out alkylation, acylation, sulfonylation, or the like to produce compound (A5) (step A-5). Depending on the properties of the compound, the steps may be carried out in a different order such that compound (A2) is first subjected to step A-5, followed by step A-3 (hydrolysis) and step A-4 (amidation reaction).

Method A-(b)

[Formula 4]

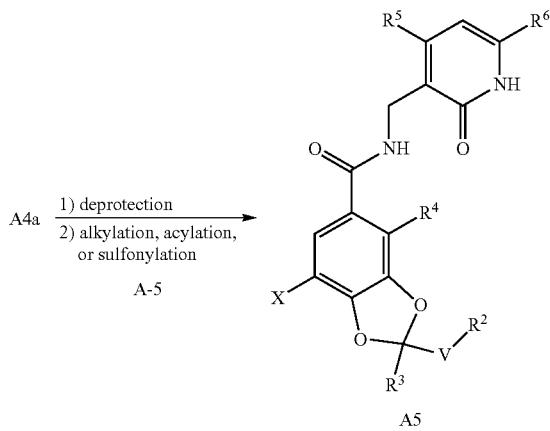

wherein $R^2$, $R^3$, $R^4$, $R^5$, $R^6$, and V are as defined above, and X represents a chlorine atom or a bromine atom.

Step A-5

(1) Deprotection of Amino Group:

(In the Case of Boc Group)

This step involves stirring compound (A4a) containing a Boc group for 0.5 to 24 hours under cooling or under heating in the presence of an acid in a solvent inert to the reaction to obtain an amine. This compound is preferably obtained by stirring at 0° C. to room temperature for 0.5 to 12 hours. The solvent used in this reaction is not particularly limited as long as the solvent is inert to the reaction. Examples thereof include methanol, ethanol, tetrahydrofuran, 1,2-dimethoxyethane, 1,4-dioxane, ethyl acetate, dichloromethane, 1,2-dichloroethane, chloroform, and mixtures thereof. Examples of the acid include hydrochloric acid-methanol, hydrochloric acid-1,4-dioxane, hydrochloric acid-ethyl acetate, and trifluoroacetic acid.

(In the Case of Cbz Group)

This step involves stirring compound (A4a) containing a Cbz group for 0.5 to 12 hours under a hydrogen atmosphere under cooling or under heating in the presence of a reducing catalyst in a solvent inert to the reaction to obtain an amine. This compound is preferably obtained by stirring at room temperature to 40° C. for 0.5 to 6 hours under a hydrogen atmosphere. The solvent used in this reaction is not particularly limited as long as the solvent is inert to the reaction. Examples thereof can include methanol, ethanol, tetrahydrofuran, water, and mixtures thereof. Examples of the reducing catalyst include palladium-carbon, Raney nickel, platinum-carbon, and platinum oxide.

(2) Alkylation, Acylation, or Sulfonylation:

(Alkylation)

This step involves stirring the amine obtained by deprotection for 0.5 to 24 hours under cooling or under heating using an equal amount or an excess amount of a corresponding alkyl halide or dialkylsulfuric acid in the presence of a base in a solvent inert to the reaction to obtain compound (A5). This compound is preferably obtained by stirring at 0° C. to 60° C. for 0.5 to 12 hours. The solvent used in this reaction is not particularly limited as long as the solvent is inert to the reaction. Examples thereof can include tetrahydrofuran, 1,2-dimethoxyethane, acetonitrile, dichloromethane, 1,2-dichloroethane, chloroform, N,N-dimethylformamide, and mixtures thereof. Examples of the base include organic bases such as triethylamine and diisopropylethylamine, and inorganic bases such as potassium carbonate, sodium carbonate, potassium hydroxide, and sodium hydroxide.

Alternatively, an equal amount or an excess amount of a corresponding aldehyde and ketone may be added to the amine obtained by deprotection in a solvent inert to the reaction, and the mixture can be stirred for 0.5 to 24 hours under cooling or under heating in the presence of a reducing agent to obtain compound A5. This compound is preferably obtained by stirring at 0 to 60° C. for 0.5 to 12 hours. The solvent used in this reaction is not particularly limited as long as the solvent is inert to the reaction. Examples thereof can include methanol, ethanol, tetrahydrofuran, 1,2-dimethoxyethane, dichloromethane, 1,2-dichloroethane, chloroform, and mixtures thereof. Examples of the reducing agent include sodium cyanoborohydride, sodium triacetoxyborohydride, and sodium borohydride. Alternatively, a reducing catalyst such as palladium-carbon, Raney nickel, platinum-carbon, or platinum oxide may be used instead of the reducing agent under a hydrogen atmosphere.

(Acylation)

This step involves stirring the amine obtained by deprotection for 0.5 to 24 hours under cooling or under heating using an equal amount or an excess amount of a corresponding acyl chloride or carboxylic anhydride in the presence of a base in a solvent inert to the reaction to obtain compound (A5). This compound is preferably obtained by stirring at 0 to 60° C. for 0.5 to 6 hours. The solvent used in this reaction is not particularly limited as long as the solvent is inert to the reaction. Examples thereof can include tetrahydrofuran, 1,2-dimethoxyethane, acetonitrile, dichloromethane, 1,2-dichloroethane, chloroform, and mixtures thereof. Examples of the base include organic bases such as triethylamine and diisopropylethylamine, and inorganic bases such as potassium carbonate, sodium carbonate, potassium hydroxide, and sodium hydroxide.

(Sulfonylation)

This step involves stirring the amine obtained by deprotection for 0.5 to 24 hours under cooling or under heating using an equal amount or an excess amount of a corresponding sulfonyl chloride or sulfonic anhydride in the presence of a base in a solvent inert to the reaction to obtain compound A5. This compound is preferably obtained by stirring at 0 to 60° C. for 0.5 to 6 hours. The solvent used in this reaction is not particularly limited as long as the solvent is inert to the reaction. Examples thereof can include tetrahydrofuran, 1,2-dimethoxyethane, acetonitrile, dichloromethane, 1,2-dichloroethane, chloroform, and mixtures thereof. Examples of the base include organic bases such as triethylamine and diisopropylethylamine, and inorganic bases such as potassium carbonate, sodium carbonate, potassium hydroxide, and sodium hydroxide.

Method A-(c) is a method which involves deprotecting a protective group (ketal group) for the carbonyl group contained in $R^2$ or $R^3$ in compound (A4b) in which the carbonyl group contained in $R^2$ or $R^3$ of the compound (A4) synthesized in method A-(a) has the protective group (ketal group), and subsequently carrying out reductive amination or the like using an amine to produce compound (A6). Depending on the properties of the compound, the steps may be carried out in a different order such that compound (A2) is first subjected to step A-6, followed by step A-3 (hydrolysis) and step A-4 (amidation reaction).

Method A-(c)

[Formula 5]

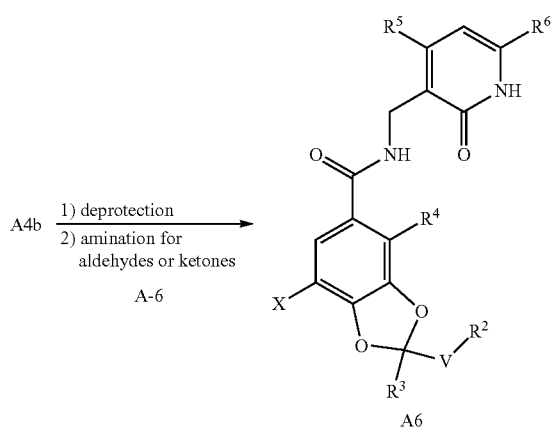

wherein $R^2$, $R^3$, $R^4$, $R^5$, $R^6$, and V are as defined above, and X represents a chlorine atom or a bromine atom.

Step A-6

(1) This step involves stirring compound (A4b) containing a carbonyl group protected with ketal for 0.5 to 48 hours under cooling or under heating in the presence of a catalytic amount to an excess amount of an acid in an aqueous solvent inert to the reaction to obtain a carbonyl compound. This compound is preferably obtained by stirring at 0 to 60° C. for 0.5 to 24 hours. The aqueous solvent used in this reaction is not particularly limited as long as the solvent does not inhibit the reaction. Examples thereof can include aqueous solvents such as methanol, ethanol, tetrahydrofuran, 1,2-dimethoxyethane, 1,4-dioxane, acetonitrile, and mixtures thereof. Examples of the acid include hydrochloric acid, sulfuric acid, hydrochloric acid-methanol, hydrochloric acid-1,4-dioxane, hydrochloric acid-ethyl acetate, acetic acid, p-toluenesulfonic acid, and pyridinium p-toluenesulfonate.

(2) This step involves adding an equal amount or an excess amount of a corresponding primary or secondary amine to the carbonyl compound obtained in the preceding step in a solvent inert to the reaction, and stirring the mixture for 0.5 to 24 hours under cooling or under heating in the presence of a reducing agent to also obtain compound (A6). This compound is preferably obtained by stirring at 0 to 60° C. for 0.5 to 12 hours. The solvent used in this reaction is not particularly limited as long as the solvent is inert to the reaction. Examples thereof can include methanol, ethanol, tetrahydrofuran, 1,2-dimethoxyethane, dichloromethane, 1,2-dichloroethane, chloroform, and mixtures thereof. Examples of the reducing agent include sodium cyanoborohydride, sodium triacetoxyborohydride, and sodium borohydride. Alternatively, a reducing catalyst such as palladium-carbon, Raney nickel, platinum-carbon, or platinum oxide may be used instead of the reducing agent under a hydrogen atmosphere.

Method A-(d) is a method which involves deprotecting a protective group for the hydroxy group in $R^2$ in compound (A2a') in which the hydroxy group in $R^2$ of the compound (A2) synthesized in method A-(a) has the protective group, and trifluoromethanesulfonylating the hydroxy group, followed by the introduction of a substituent through a subsequent substitution reaction. After the introduction of a substituent, step A-8 (ester hydrolysis) and step A-9 (amidation) can be carried out to produce compound (A9). When $R^2$ contains a protected amino group, the deprotection of the amino group and subsequent reaction such as alkylation, acylation, or sulfonylation can be carried out in the same way as in method A-(b).

Method A-(d)

[Formula 6]

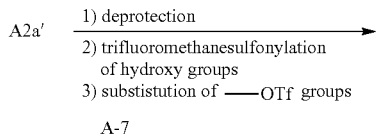

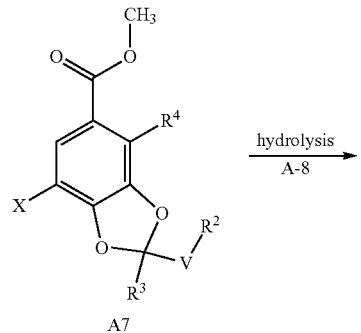

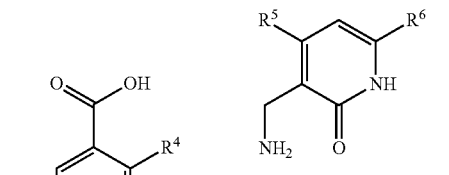

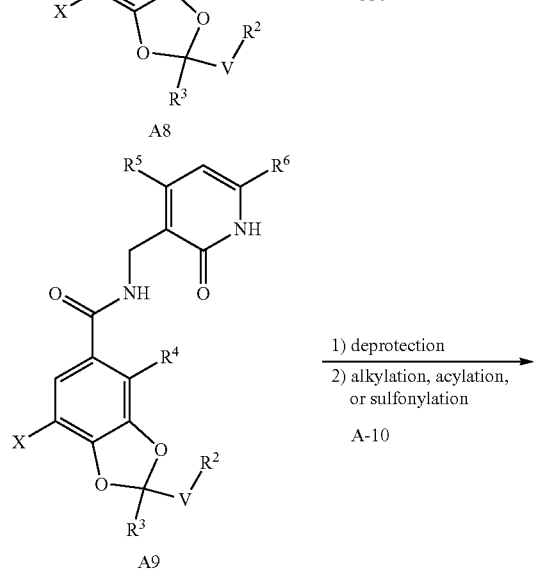

-continued

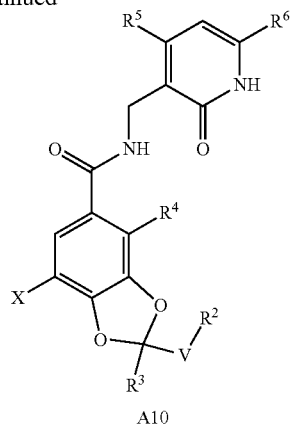

A10 wherein $R^2$, $R^3$, $R^4$, $R^5$, $R^6$, and V are as defined above, and X represents a chlorine atom or a bromine atom.

Step A-7

(1) Deprotection of Hydroxy Group (In the Case of Tetrahydropyranyl (THP) Group, 1-Ethoxyethyl Group, Methoxymethyl Group, Methoxyethoxymethyl Group, or the Like)

This step involves stirring compound (A2a') containing a hydroxy group protected with the protective group mentioned above for 0.5 to 48 hours under cooling or under heating in the presence of a catalytic amount to an excess amount of an acid in a solvent to obtain an alcohol compound. This compound is preferably obtained by stirring at 0 to 60° C. for 0.5 to 24 hours. The solvent used in this reaction is not particularly limited as long as the solvent does not inhibit the reaction. Examples thereof can include methanol, ethanol, tetrahydrofuran, 1,2-dimethoxyethane, 1,4-dioxane, acetonitrile, water, and mixtures thereof. Examples of the acid include hydrochloric acid, sulfuric acid, hydrochloric acid-methanol, hydrochloric acid-1,4-dioxane, hydrochloric acid-ethyl acetate, acetic acid, p-toluenesulfonic acid, and pyridinium p-toluenesulfonate.

(In the Case of Silyl Group)

This step involves stirring compound (A2a') containing a hydroxy group protected with a silyl group for 0.5 to 48 hours under cooling or under heating using an equal amount or an excess amount of a desilylation reagent in a solvent to obtain an alcohol compound. This compound is preferably obtained by stirring at 0 to 60° C. for 0.5 to 24 hours. The solvent used in this reaction is not particularly limited as long as the solvent does not inhibit the reaction. Examples thereof can include methanol, ethanol, tetrahydrofuran, 1,2-dimethoxyethane, 1,4-dioxane, acetonitrile, water, and mixtures thereof. Examples of the desilylation reagent include acids, tetrabutyl ammonium fluoride (TBAF), hydrogen fluoride, and pyridine hydrofluoride. Examples of the acid can include hydrochloric acid, sulfuric acid, hydrochloric acid-methanol, hydrochloric acid-1,4-dioxane, hydrochloric acid-ethyl acetate, acetic acid, p-toluenesulfonic acid, and trifluoroacetic acid. The reaction may be carried out using a catalytic amount of the acid.

(2) This step involves stirring the alcohol compound obtained by the preceding step for 0.5 to 48 hours under cooling or under heating using an equal amount or an excess amount of a trifluoromethanesulfonylation reagent in the presence of a base in a solvent inert to the reaction to obtain a trifluoromethanesulfonyloxy compound. This compound is preferably obtained by stirring at −20° C. to room temperature for 0.5 to 24 hours. The solvent used in this reaction is not particularly limited as long as the solvent is inert to the reaction. Examples thereof can include tetrahydrofuran, 1,2-dimethoxyethane, 1,4-dioxane, acetonitrile, dichloromethane, chloroform, 1,2-dichloroethane, chloroform, and mixtures thereof. Examples of the trifluoromethanesulfonylation reagent include trifluoromethanesulfonic anhydride, trifluoromethanesulfonic acid chloride, and N-phenyl bis(trifluoromethanesulfonimide). Examples of the base include organic bases such as triethylamine and diisopropylethylamine, and inorganic bases such as potassium carbonate, sodium carbonate, potassium hydroxide, and sodium hydroxide.

(3) This step involves stirring the trifluoromethanesulfonyloxy compound obtained by the preceding step for 0.5 to 48 hours under cooling or under heating using an equal amount or an excess amount of a nucleophilic reagent in the presence or absence of a base in a solvent inert to the reaction to obtain compound (A7). This compound is preferably obtained by stirring at −78 to 80° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, acetonitrile, dichloromethane, 1,2-dichloroethane, chloroform, N,N-dimethylformamide, dimethylacetamide, dimethyl sulfoxide, and mixtures thereof. Examples of the nucleophilic reagent include primary and secondary amines, and are complexes such as Gilman reagents. Examples of the base include organic bases such as triethylamine and diisopropylethylamine, inorganic bases such as potassium carbonate, sodium carbonate, potassium hydroxide, and sodium hydroxide.

Step A-8: This step can be carried out in the same way as in step A-3.

Step A-9: This step can be carried out in the same way as in step A-4.

Step A-10: This step can be carried out in the same way as in step A-5.

Method B is a method which employs the compound (A1) (X=Br) synthesized by method A as a starting material and involves converting the bromine atom to F by use of lithiation and subsequent use of an electrophilic fluorinating agent to produce fluorine intermediate (B6), and further carrying out ketalization (B-7), hydrolysis (B-8), amidation (B-9), and conversion of an amino group (B-10) in the same way as in method A to produce compound (B9) or compound (B10). Depending on the properties of the compound, the steps may be carried out in a different order such that compound (B7) is first subjected to step B-10, followed by step B-8 (hydrolysis) and step B-9 (amidation reaction).

Method B

[Formula 7]

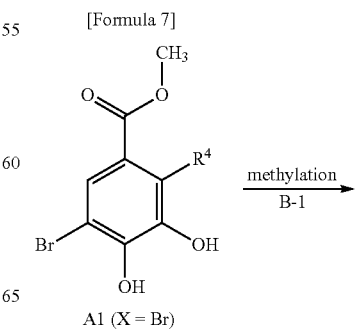

A1 (X = Br)

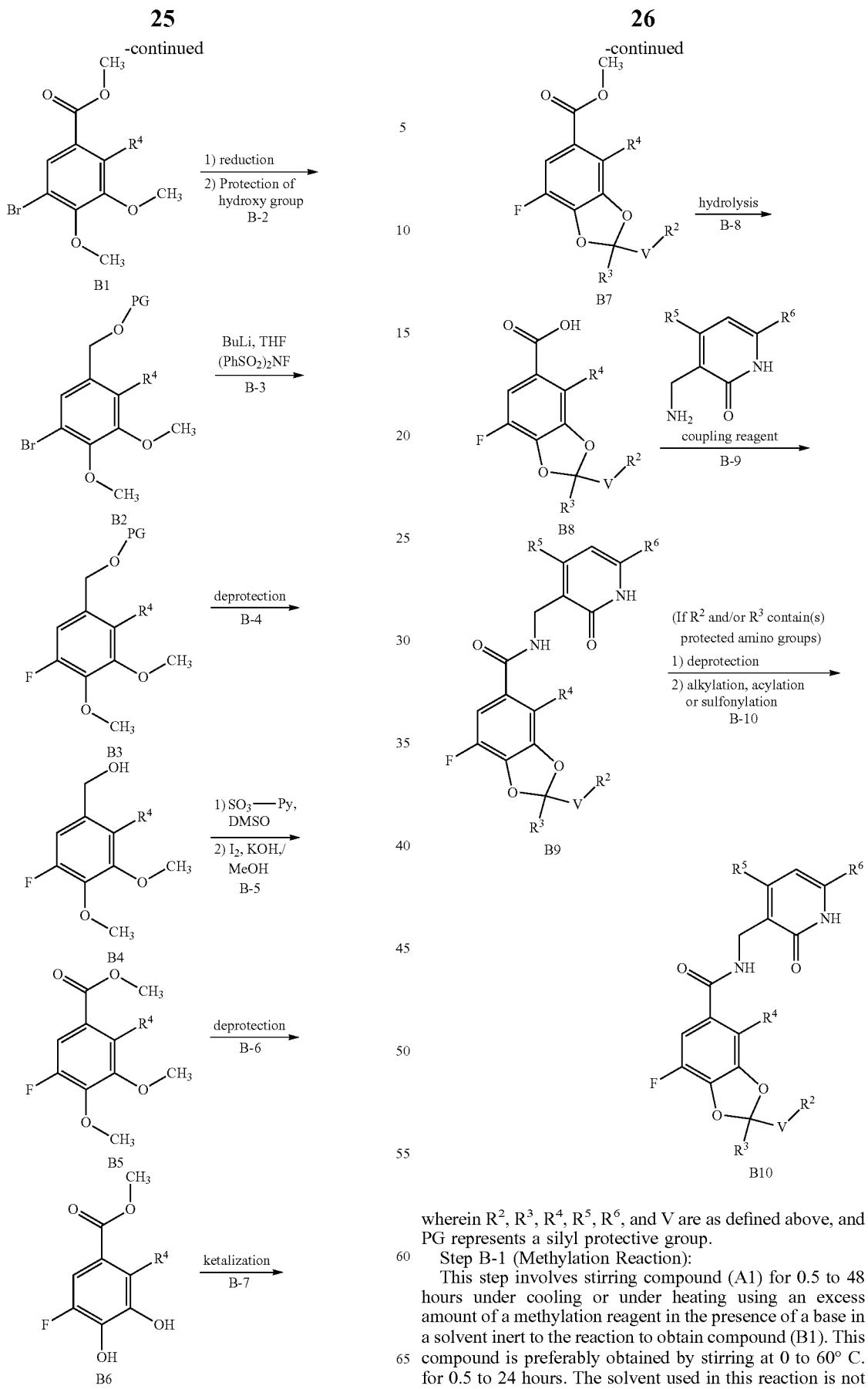

wherein $R^2$, $R^3$, $R^4$, $R^5$, $R^6$, and V are as defined above, and PG represents a silyl protective group.

Step B-1 (Methylation Reaction):

This step involves stirring compound (A1) for 0.5 to 48 hours under cooling or under heating using an excess amount of a methylation reagent in the presence of a base in a solvent inert to the reaction to obtain compound (B1). This compound is preferably obtained by stirring at 0 to 60° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, acetonitrile, dichloromethane, 1,2-dichloroethane, chloroform, N,N-dimethylformamide, dimethyl sulfoxide, and mixtures thereof. Examples of the methylation reagent include methyl iodide and methyl sulfate. Examples of the base include organic bases such as triethylamine and diisopropylethylamine, and inorganic bases such as potassium carbonate, sodium carbonate, potassium hydroxide, and sodium hydroxide.

Step B-2

(1) Reduction of Ester:

This step involves stirring compound (B1) for 0.5 to 48 hours under cooling or under heating using an equal amount or an excess amount of a reducing agent in a solvent inert to the reaction to obtain an alcohol compound. This compound is preferably obtained by stirring at −78° C. to room temperature for 0.5 to 24 hours. The solvent used in this reaction is not particularly limited as long as the solvent is inert to the reaction. Examples thereof can include tetrahydrofuran, 1,2-dimethoxyethane, 1,4-dioxane, and mixtures thereof. Examples of the reducing agent include lithium aluminum hydride, diisobutyl aluminum hydride, and sodium bis(2-methoxyethoxy)aluminum hydride.

(2) Protection of Hydroxy Group with Silyl Group:

This step involves stirring the alcohol obtained by the preceding step for 0.5 to 48 hours under cooling or under heating using an equal amount or an excess amount of a silylating agent in the presence of a base in a solvent inert to the reaction to obtain compound (B3). This compound is preferably obtained by stirring at 0 to 60° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, acetonitrile, dichloromethane, 1,2-dichloroethane, chloroform, N,N-dimethylformamide, dimethyl sulfoxide, and mixtures thereof. Examples of the silylating agent include trimethylchlorosilane, trimethylsilyl trifluoromethanesulfonate, triethylchlorosilane, triethylsilyl trifluoromethanesulfonate, triisopropylchlorosilane, triisopropylsilyl trifluoromethanesulfonate, tert-butyldimethylchlorosilane, tert-butyldimethylsilyl trifluoromethanesulfonate, tert-butyldiphenylchlorosilane, and tert-butyldiphenylsilyl trifluoromethanesulfonate. Examples of the base include organic bases such as triethylamine, diisopropylethylamine, imidazole, and 4-dimethylaminopyridine, and inorganic bases such as potassium carbonate, sodium carbonate, potassium hydroxide, and sodium hydroxide.

Step B-3 (Fluorination):

This step involves lithiating the compound (B2) obtained by the preceding step with an organic lithium reagent or the like under cooling in a solvent inert to the reaction, and stirring the resulting compound for 0.5 to 48 hours under cooling or under heating using an equal amount or an excess amount of a fluorinating agent to obtain compound (B3). This compound is preferably obtained by stirring at −78° C. to room temperature for 0.5 to 24 hours. The solvent used in this reaction is not particularly limited as long as the solvent is inert to the reaction. Examples thereof can include tetrahydrofuran, 1,2-dimethoxyethane, 1,4-dioxane, and mixtures thereof. Examples of the organic lithium reagent include n-butyllithium, sec-butyllithium, and tert-butyllithium. Examples of the fluorinating agent include N-fluorobenzenesulfonimide and N-fluoropyridinium triflate.

Step B-4 (Deprotection):

This step involves stirring compound (B3) for 0.5 to 48 hours under cooling or under heating using an equal amount or an excess amount of a desilylation reagent in a solvent to obtain compound (B4). This compound is preferably obtained by stirring at 0 to 60° C. for 0.5 to 24 hours. The solvent used in this reaction is not particularly limited as long as the solvent does not inhibit the reaction. Examples thereof can include methanol, ethanol, tetrahydrofuran, 1,2-dimethoxyethane, 1,4-dioxane, acetonitrile, water, and mixtures thereof. Examples of the desilylation reagent include acids, tetrabutyl ammonium fluoride (TBAF), hydrogen fluoride, and pyridine hydrofluoride. Examples of the acid can include hydrochloric acid, sulfuric acid, hydrochloric acid-methanol, hydrochloric acid-1,4-dioxane, hydrochloric acid-ethyl acetate, acetic acid, p-toluenesulfonic acid, and trifluoroacetic acid. The reaction may be carried out using a catalytic amount of the acid.

Step B-5 (Oxidation into Aldehyde and Methyl Ester synthesis)

(1) Oxidation into Aldehyde:

This step involves stirring compound (B4) for 0.5 to 48 hours under cooling or under heating using an equal amount or an excess amount of an oxidizing agent in a solvent inert to the reaction to obtain an aldehyde compound. This compound is preferably obtained by stirring at −78 to 60° C. for 0.5 to 24 hours. The solvent used in this reaction is not particularly limited as long as the solvent is inert to the reaction. Examples thereof can include dimethyl sulfoxide, dichloromethane, 1,2-dichloroethane, chloroform, and mixtures thereof. Examples of the oxidizing agent include dimethyl sulfoxide and acetic anhydride (Albright-Goldman oxidation), dimethyl sulfoxide, $SO_3$-pyridine, and triethylamine (Parikh-Doering oxidation), dimethyl sulfoxide, N,N'-dicyclohexylcarbodiimide, and trifluoroacetic acid (Pfitzner-Moffatt oxidation), dimethyl sulfoxide, manganese dioxide, or oxalyl chloride and triethylamine (Swern oxidation).

(2) Methyl Ester Synthesis:

This step involves stirring the aldehyde obtained by the preceding step for 0.5 to 48 hours under cooling or under heating using an equal amount or an excess amount of iodine in the presence of a base in a solvent to obtain compound (B5). This compound is preferably obtained by stirring at 0° C. to room temperature for 0.5 to 24 hours. The solvent used in this reaction is not particularly limited as long as the solvent does not inhibit the reaction. Examples thereof can include methanol. Examples of the base include potassium carbonate, sodium carbonate, potassium hydroxide, and sodium hydroxide.

Step B-6 (Deprotection of Catechol):

This step involves stirring compound (B5) for 0.5 to 48 hours under cooling or under heating using an equal amount or an excess amount of a deprotection reagent in a solvent inert to the reaction to obtain compound (B6). This compound is preferably obtained by stirring at −78 to 60° C. for 0.5 to 24 hours. The solvent used in this reaction is not particularly limited as long as the solvent is inert to the reaction. Examples thereof can include dichloromethane, 1,2-dichloroethane, chloroform, and mixtures thereof. Examples of the deprotection reagent include boron tribromide, boron trichloride, aluminum chloride, aluminum bromide, and magnesium iodide.

Step B-7 can be carried out in the same way as in step A-2.
Step B-8 can be carried out in the same way as in step A-3.
Step B-9 can be carried out in the same way as in step A-4.

Step B-10 can be carried out in the same way as in step A-5.

Method C employs the compound (A1) (X=Cl or Br) synthesized by method A as a starting material. Halogen is replaced with an alkyl group (Rc) to produce an intermediate (C1), and ketalization (C-2), hydrolysis (C-3), amidation (C-4), and conversion of an amino group (C-5) can be further carried out in the same way as in method A to produce compound (C4) or compound (C5). Depending on the properties of the compound, the steps may be carried out in a different order such that compound (C2) is first subjected to step C-5, followed by step C-3 (hydrolysis) and step C-4 (amidation reaction).

Method C

[Formula 8]

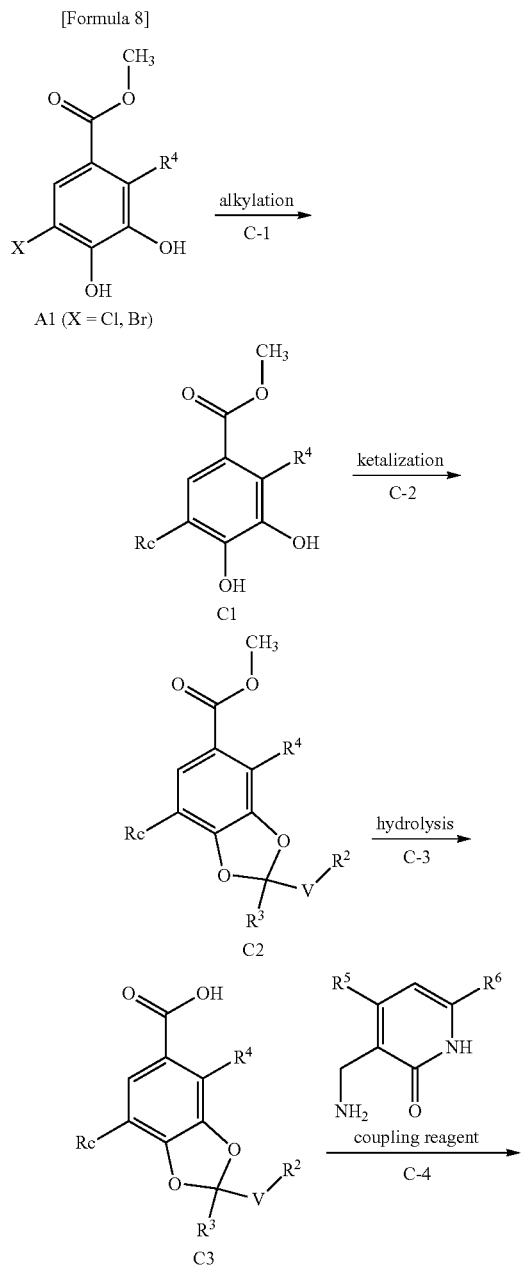

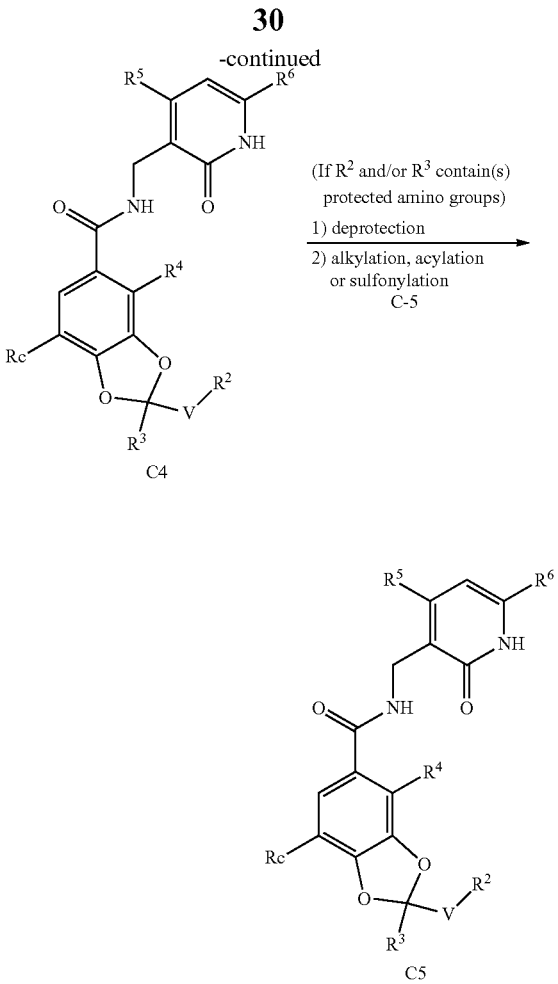

wherein $R^2$, $R^3$, $R^4$, $R^5$, $R^6$, and V are as defined above, Rc represents a $C_1$-$C_6$ alkyl group, and X represents a chlorine atom or a bromine atom.

The reaction of step C-1 (alkylation reaction) can be carried out under the conditions shown in the following literature (Adv. Synth. Catal., 348, 686-690 (2006)). This step involves stirring compound (A1) for 0.5 to 48 hours under cooling or under heating using an equal amount or an excess amount of an alkylation reagent, a palladium catalyst, and a ligand in a solvent inert to the reaction to obtain compound (C1). This compound is preferably obtained by stirring at room temperature to 80° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, benzene, toluene, xylene, hexane, and mixtures thereof. Examples of the alkylation reagent include trialkyl aluminum-tertiary amine adducts such as trimethyl aluminum-1,4-diazabicyclo[2.2.2]octane adducts and triethyl aluminum-1,4-diazabicyclo[2.2.2]octane adducts. Examples of the palladium catalyst can include tris(dibenzylideneacetone)dipalladium and tetrakis(triphenylphosphine)palladium. Examples of the ligand include 2-(dicyclohexylphosphino)-2'-(dimethylamino)biphenyl (DavePhos), 2-dicyclohexylphosphino-2',4',6'-triisopropylbiphenyl (Xphos), and 2-di-tert-butylphosphino-2',4',6'-triisopropylbiphenyl (t-BuXPhos).

Step C-2 can be carried out in the same way as in step A-2.

Step C-3 can be carried out in the same way as in step A-3.

Step C-4 can be carried out in the same way as in step A-4.

Step C-5 can be carried out in the same way as in step A-5.

Method D is a method which employs the compound (A1) (X=Br) synthesized by method A as a starting material and involves converting the bromine atom to a hydroxy group to produce an alkoxy intermediate (D4), and further carrying out ketalization (D-5), hydrolysis (D-6), amidation (D-7), and conversion of an amino group (D-8) in the same way as in method A to produce compound (D7) or compound (D8). Depending on the properties of the compound, the steps may be carried out in a different order such that compound (D5) is first subjected to step D-8, followed by step D-6 (hydrolysis) and step D-7 (amidation reaction).

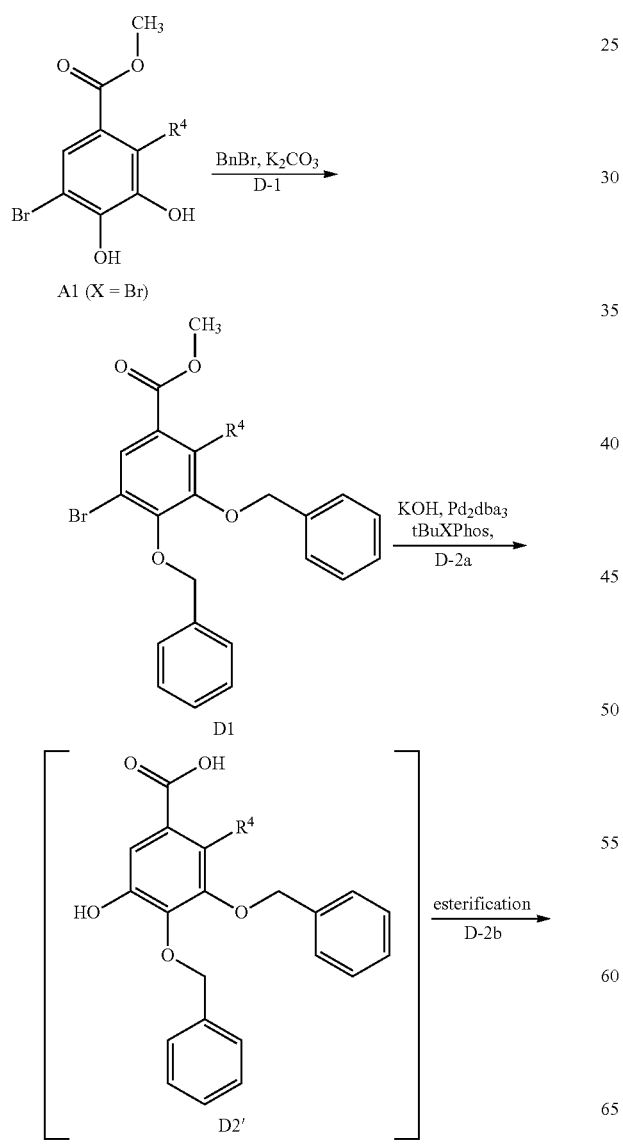

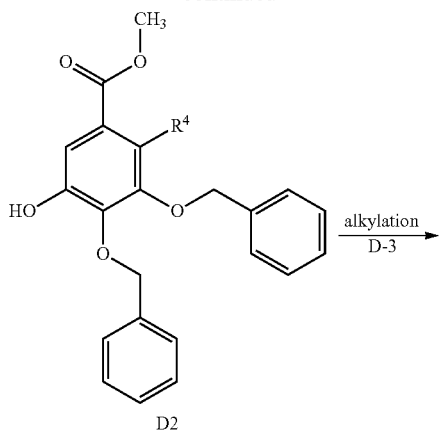

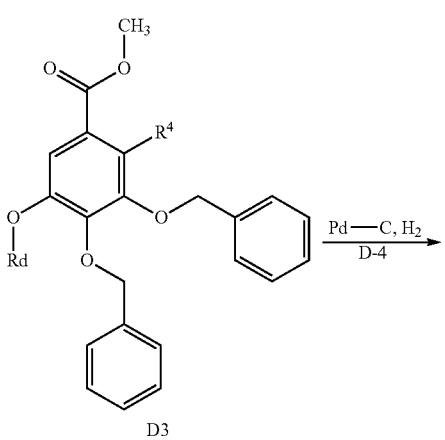

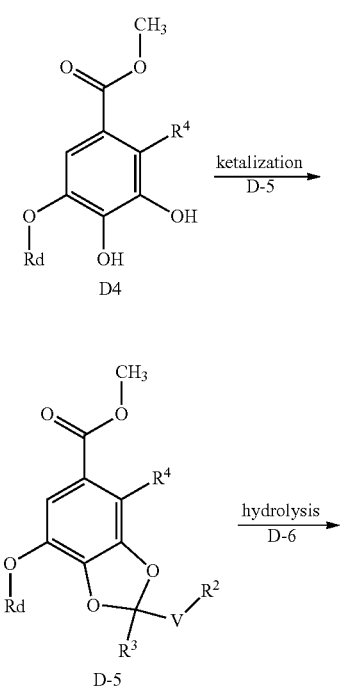

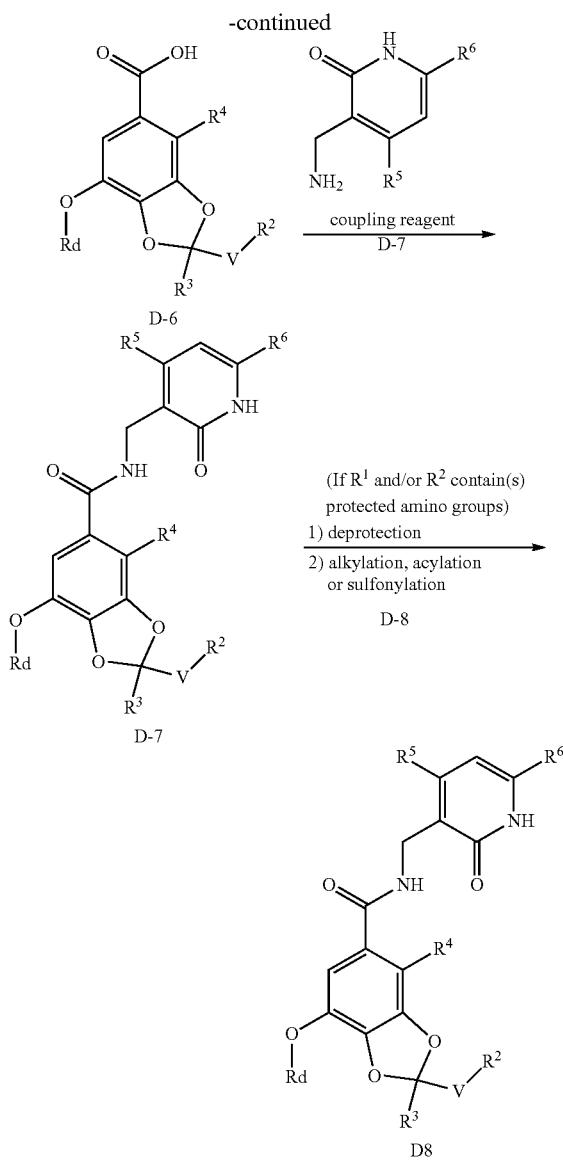

wherein $R^2$, $R^3$, $R^4$, $R^5$, $R^6$, and V are as defined above, and Rd represents a $C_1$-$C_6$ alkyl group.

Step D-1 (Protection with Benzyl Ether):

Compound (D1) can be obtained in the same way as in step B-1 using compound (A1) and an equal amount or an excess amount of a benzyl halide.

Step D-2a (Substitution Reaction):

This step involves stirring compound (D1) for 0.5 to 48 hours under cooling or under heating using an equal amount or an excess amount of an alkali metal hydroxide, a palladium catalyst, and a ligand in a solvent inert to the reaction to obtain compound (D2). This compound is preferably obtained by stirring at room temperature to 80° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, water, and mixtures thereof. Examples of the alkali metal hydroxide include potassium hydroxide, sodium hydroxide, and lithium hydroxide. Examples of the palladium catalyst can include tris(dibenzylideneacetone)dipalladium and tetrakis(triphenylphosphine)palladium. Examples of the ligand include 2-(dicyclohexylphosphino)-2'-(dimethylamino)biphenyl (DavePhos), 2-dicyclohexylphosphino-2',4',6'-triisopropylbiphenyl (Xphos), and 2-di-tert-butylphosphino-2',4',6'-triisopropylbiphenyl (t-BuXPhos).

If compound (D2') is obtained by the hydrolysis of an ester in step D-2a, the methyl ester can be synthesized again in step D-2b.

Step D-2b (Methyl Esterification):

This step involves stirring compound (D2') for 0.5 to 48 hours under cooling or under heating in the presence of an acid in a methanol solvent to obtain compound (D2). This compound is preferably obtained by stirring at room temperature to reflux temperature for 0.5 to 24 hours. Examples of the acid used in this reaction include hydrochloric acid, sulfuric acid, hydrochloric acid-methanol, hydrochloric acid-1,4-dioxane, and p-toluenesulfonic acid.

Step D-3 (Alkylation Reaction):

This step involves obtaining compound (D3) in the same way as in step B-1 using compound (D2) and an equal amount or an excess amount of an alkyl halide or dialkylsulfuric acid, etc.

When Rd represents a methyl group, compound (D3) can be synthesized by the methylation of compound (D2') in one step in the same way as in step B-1.

Step D-4 (Deprotection Reaction):

This step involves stirring compound (D3) for 0.5 to 24 hours under a hydrogen atmosphere under cooling or under heating using a reducing catalyst in a solvent inert to the reaction to obtain compound (D4). This compound is preferably obtained by stirring at room temperature to 40° C. for 0.5 to 6 hours. The solvent used in this reaction is not particularly limited as long as the solvent is inert to the reaction. Examples thereof can include methanol, ethanol, tetrahydrofuran, 1,2-dimethoxyethane, water, and mixtures thereof. Examples of the reducing catalyst include palladium-carbon, Raney nickel, platinum-carbon, and platinum oxide.

Step D-5 can be carried out in the same way as in step A-2.
Step D-6 can be carried out in the same way as in step A-3.
Step D-7 can be carried out in the same way as in step A-4.
Step D-8 can be carried out in the same way as in step A-5.

Method E is a method which involves subjecting compound (E0) to dichlorination (E-1) and esterification (E-2) to produce compound (E2), and further carrying out ketalization (E-3), hydrolysis (E-4), amidation (E-5), and conversion of an amino group (E-6) in the same way as in method A to produce compound (E6). Depending on the properties of the compound, the steps may be carried out in a different order such that compound (E3) is first subjected to step E-6, followed by step E-4 (hydrolysis) and step E-5 (amidation reaction).

Method E

[Formula 10]

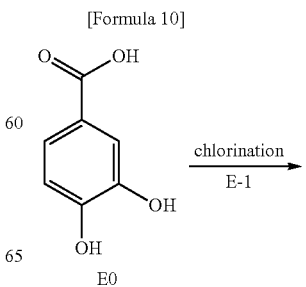

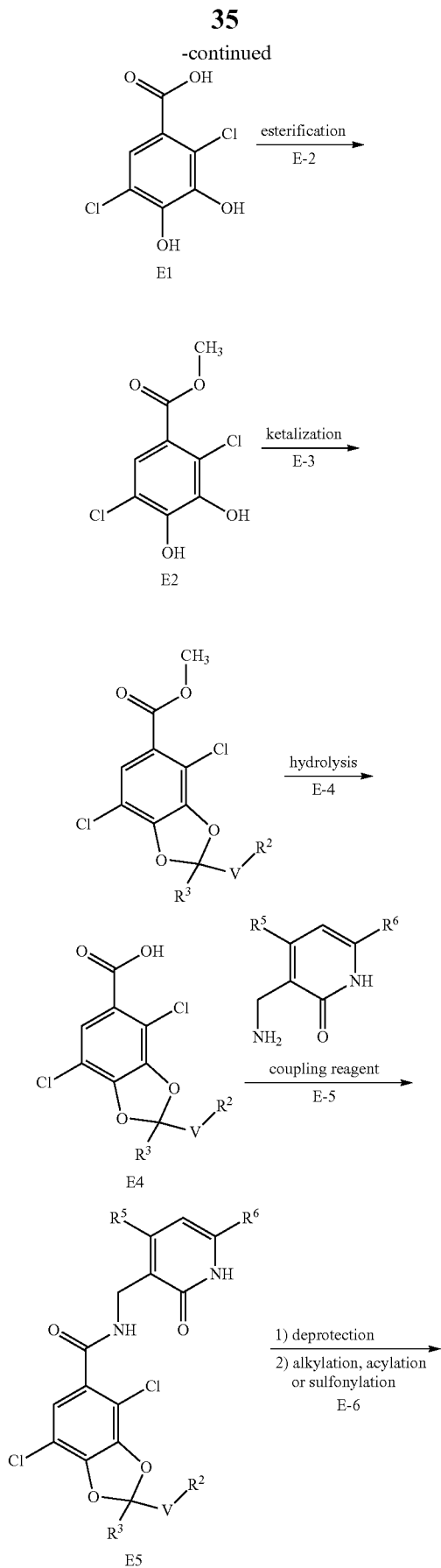

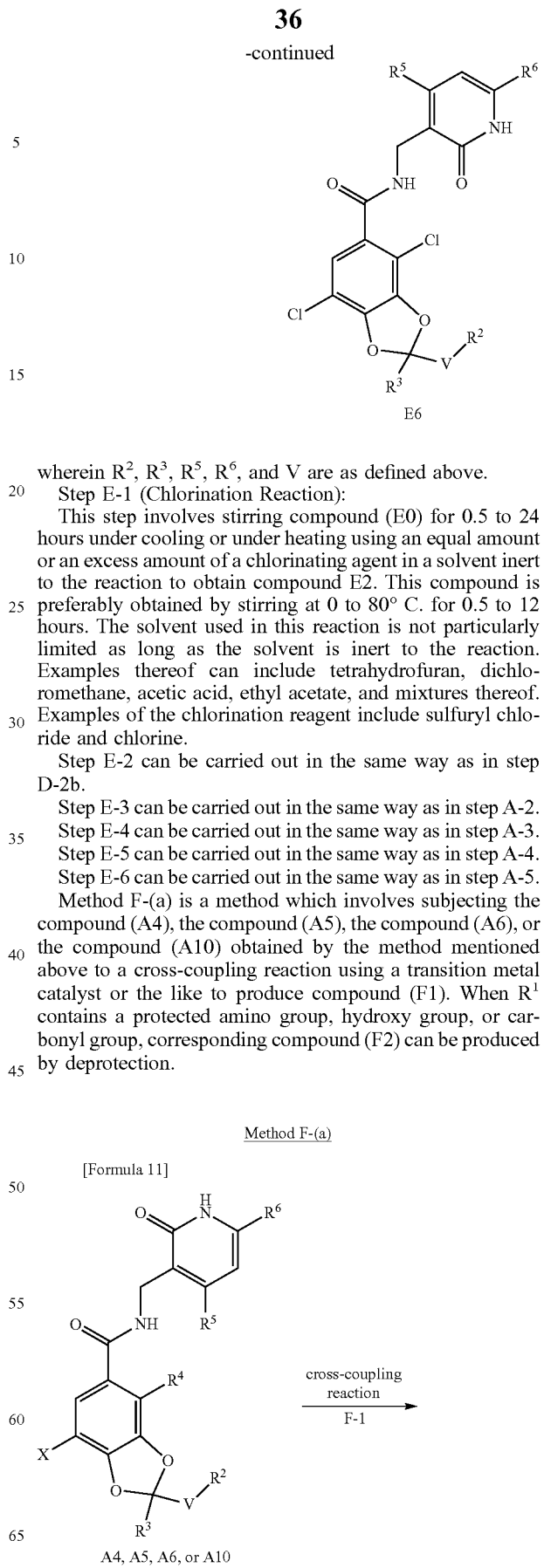

wherein $R^2$, $R^3$, $R^5$, $R^6$, and V are as defined above.

Step E-1 (Chlorination Reaction):

This step involves stirring compound (E0) for 0.5 to 24 hours under cooling or under heating using an equal amount or an excess amount of a chlorinating agent in a solvent inert to the reaction to obtain compound E2. This compound is preferably obtained by stirring at 0 to 80° C. for 0.5 to 12 hours. The solvent used in this reaction is not particularly limited as long as the solvent is inert to the reaction. Examples thereof can include tetrahydrofuran, dichloromethane, acetic acid, ethyl acetate, and mixtures thereof. Examples of the chlorination reagent include sulfuryl chloride and chlorine.

Step E-2 can be carried out in the same way as in step D-2b.

Step E-3 can be carried out in the same way as in step A-2.
Step E-4 can be carried out in the same way as in step A-3.
Step E-5 can be carried out in the same way as in step A-4.
Step E-6 can be carried out in the same way as in step A-5.

Method F-(a) is a method which involves subjecting the compound (A4), the compound (A5), the compound (A6), or the compound (A10) obtained by the method mentioned above to a cross-coupling reaction using a transition metal catalyst or the like to produce compound (F1). When $R^1$ contains a protected amino group, hydroxy group, or carbonyl group, corresponding compound (F2) can be produced by deprotection.

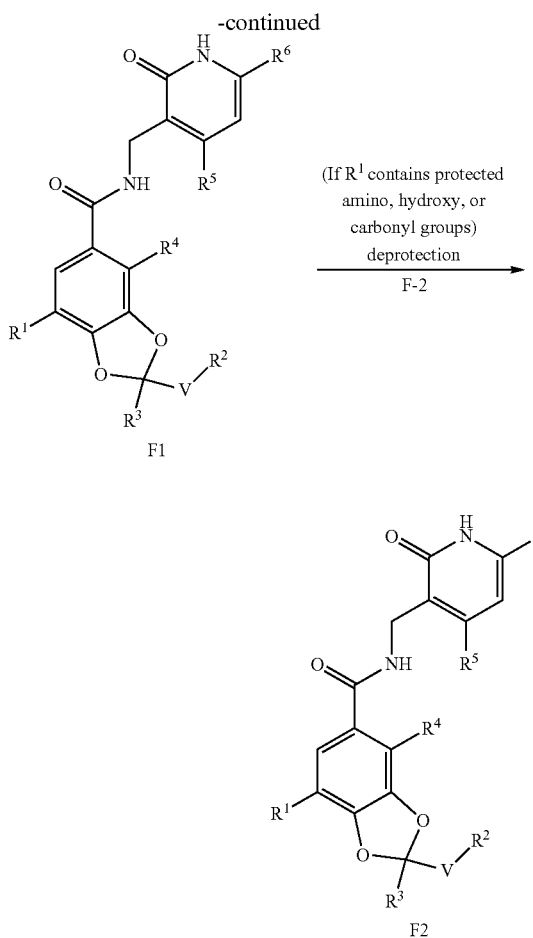

wherein $R^2$, $R^3$, $R^4$, $R^5$, $R^6$, and V are as defined above, and X represents a chlorine atom or a bromine atom.

Step F-1 (Cross-Coupling Reaction):

This step involves stirring compound (A4), compound (A5), compound (A6), or compound (A10) for 0.5 to 24 hours under heating conditions using a palladium catalyst or a nickel catalyst and an equal amount or an excess amount of boronic acid, boronic acid pinacol ester (for Suzuki-Miyaura coupling), an organic tin reagent (for Stille coupling), or an alkene compound (for Heck reaction) in the presence of a base in a solvent inert to the reaction to obtain compound (F1). This compound is preferably obtained by stirring at 60 to 120° C. for 0.5 to 12 hours. The solvent used in this reaction is not particularly limited as long as the solvent is inert to the reaction. Examples thereof can include methanol, ethanol, tetrahydrofuran, 1,2-dimethoxyethane, 1,4-dioxane, water, N,N-dimethylformamide, dimethyl sulfoxide, benzene, toluene, xylene, and mixtures thereof. Examples of the palladium catalyst include tetrakis(triphenylphosphine)palladium, [1,1'-bis(diphenylphosphino)ferrocene]dichloropalladium, tris(dibenzylideneacetone)dipalladium, palladium acetate, palladium acetylacetonate, and bis(triphenylphosphine)palladium dichloride. Examples of the nickel catalyst include [1,1'-bis(diphenylphosphino)ferrocene]nickel dichloride and bis(triphenylphosphine)nickel dichloride. Examples of the base include organic bases such as triethylamine, diisopropylethylamine, 1,8-diazabicyclo[5.4.0]-7-undecene (DBU), and 1,5-diazabicyclo[4.3.0]-5-nonene (DBN), and inorganic bases such as potassium bicarbonate, sodium bicarbonate, potassium carbonate, sodium carbonate, potassium hydroxide, sodium hydroxide, potassium phosphate, and sodium phosphate.

Step F-2 (Deprotection):

(When $R^1$ Contains a Protected Amino Group)

This step can be carried out in the same way as in step A-5(1).

(When $R^1$ Contains a Protected Hydroxy Group)

This step can be carried out in the same way as in step A-7(1).

(When $R^1$ Contains a Protected Carbonyl Group)

This step can be carried out in the same way as in step A-6(1).

Method F-(b) is a method which involves converting the compound (F1) obtained by method F-(a) in which the substituent $R^1$ is a vinyl group, to an aldehyde by oxidative cleavage (F-3), followed by step F-4 of producing an alkene compound through Wittig-type reaction or producing an alkyne compound by use of the Seyferth-Gilbert method (or the Ohira-Bestmann method) or the like. When $R^2$ or $R^3$ in compound (F4) contains a protected amino group, compound F5 can be produced by the removal of the protective group, followed by alkylation, acylation, sulfonylation, or the like (F-5).

Method F-(b)

[Formula 12]

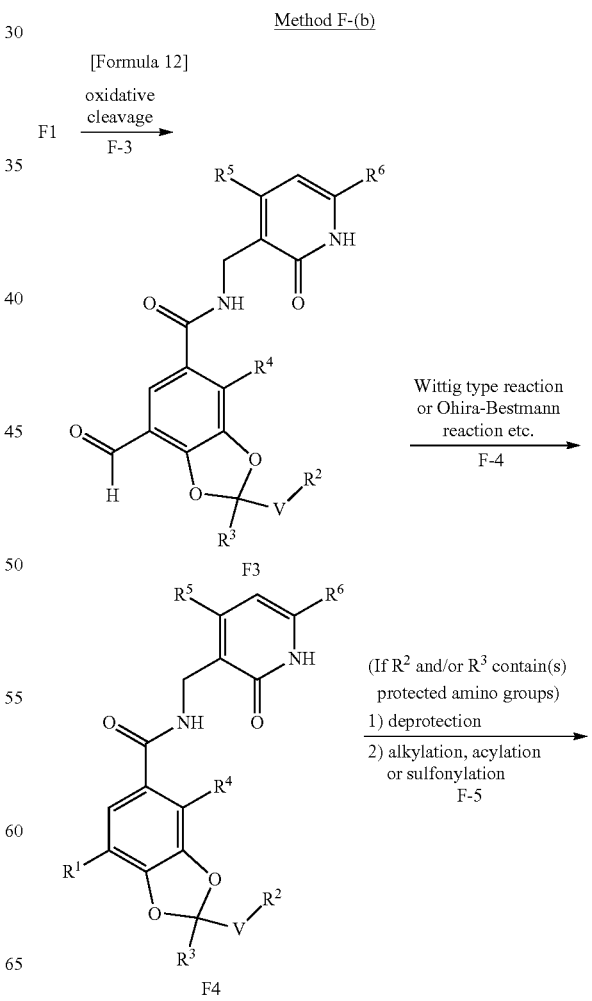

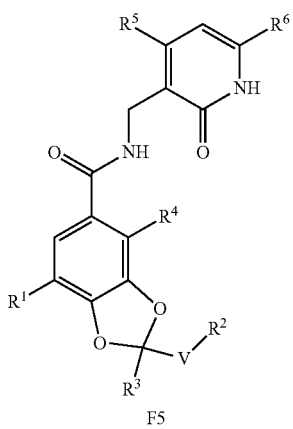

F5 wherein $R^2$, $R^3$, $R^4$, $R^5$, $R^6$, and V are as defined above.

Step F-3 (Oxidative Cleavage Reaction):

This step involves stirring compound (F1) for 0.5 to 48 hours under cooling or under heating conditions using an oxidizing catalyst and an equal amount or an excess amount of an oxidizing agent in a solvent inert to the reaction to obtain compound (F3). This compound is preferably obtained by stirring at 0 to 40° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, water, and mixtures thereof. Examples of the oxidizing catalyst include osmium tetroxide and microencapsulated osmium tetroxide. Examples of the oxidizing agent include sodium periodate and potassium periodate.

Step F-4:

(In the Case of Synthesizing Alkene)

This step involves stirring compound (F3) for 0.5 to 24 hours under cooling or under heating conditions using an equal amount or an excess amount of a corresponding Wittig reagent, Horner-Wadsworth-Emmonds reagent, or the like in the presence of a base in a solvent inert to the reaction to obtain compound (F4). This compound is preferably obtained by stirring at −78° C. to room temperature for 0.5 to 12 hours. The solvent used in this reaction is not particularly limited as long as the solvent is inert to the reaction. Examples thereof can include diethyl ether, tetrahydrofuran, 1,2-dimethoxyethane, 1,4-dioxane, and mixtures thereof. Examples of the base include n-butyllithium, sec-butyllithium, tert-butyllithium, lithium diisopropylamide (LDA), lithium bis(trimethylsilyl)amide (LHMDS), sodium hydride, potassium tert-butoxide, 1,8-diazabicyclo[5.4.0]-7-undecene (DBU), and 1,5-diazabicyclo[4.3.0]-5-nonene (DBN).

(In the Case of Synthesizing Alkyne)

This step involves stirring compound (F3) for 0.5 to 48 hours under cooling or under heating conditions using an equal amount or an excess amount of dimethyl diazomethylphosphonate (Seyferth-Gilbert reagent), dimethyl (1-diazo-2-oxopropyl)phosphonate (Ohira-Bestmann reagent), or the like in the presence of a base in a solvent inert to the reaction to obtain compound (F4). This compound is preferably obtained by stirring at −78° C. to room temperature for 0.5 to 24 hours. The solvent used in this reaction is not particularly limited as long as the solvent is inert to the reaction. Examples thereof can include diethyl ether, tetrahydrofuran, 1,2-dimethoxyethane, 1,4-dioxane, methanol, ethanol, and mixtures thereof. Examples of the base include n-butyllithium, potassium tert-butoxide, sodium carbonate, and potassium carbonate.

Alternatively, compound (F3) may be stirred for 0.5 to 48 hours under cooling or under heating conditions using an equal amount or an excess amount of carbon tetrabromide and triphenylphosphine in a solvent inert to the reaction to obtain a dibromoolefin intermediate, and this intermediate can be treated with an excess amount of a base to obtain compound (F4) (Corey-Fuchs method). This compound is preferably obtained by stirring at 0° C. to room temperature for 0.5 to 24 hours. The solvent used in this reaction is not particularly limited as long as the solvent is inert to the reaction. Examples thereof include dichloromethane, 1,2-dichloroethane, chloroform, diethyl ether, tetrahydrofuran, 1,2-dimethoxyethane, 1,4-dioxane, and mixtures thereof for the synthesis of a dibromoolefin intermediate and include diethyl ether, tetrahydrofuran, 1,2-dimethoxyethane, 1,4-dioxane, and mixtures thereof for the step of treating the dibromoolefin intermediate with a base to obtain compound F4. Examples of the base used in this reaction include n-butyllithium, sec-butyllithium, and tert-butyllithium.

Step F-5 can be Carried Out in the Same Way as in Step A-5.

Method G is a step which involves dehalogenating the compound (A4), the compound (A5), the compound (A6), the compound (A10), or the compound (F1) (when the substituent $R^1$ is a chlorine atom, a bromine atom, or a $C_2$-$C_6$ alkenyl group) obtained by the methods mentioned above through a hydrogenation reaction or reducing the double bond to produce compound (G1).

Method G

[Formula 13]

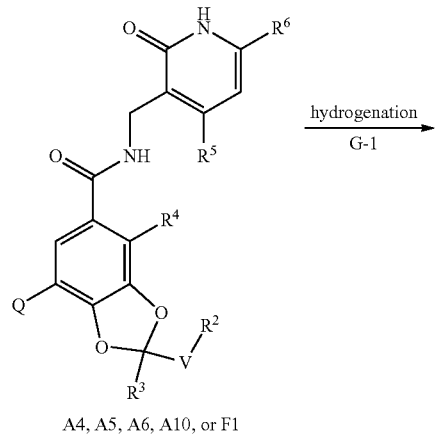

A4, A5, A6, A10, or F1

-continued

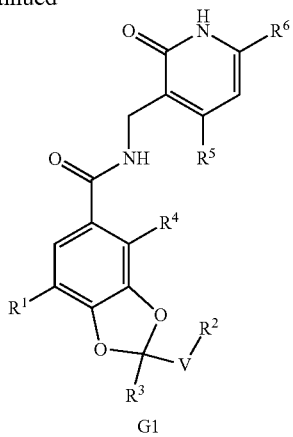

G1 wherein $R^2$, $R^3$, $R^4$, $R^5$, $R^6$, and V are as defined above, and Q represents a chlorine atom, a bromine atom, or a $C_2$-$C_6$ alkenyl group.

Step G:

This step involves stirring compound (A4), compound (A5), compound (A6), compound (A10), or compound (F1) (when the substituent $R^1$ is a $C_2$-$C_6$ alkenyl group) for 0.5 to 48 hours under a hydrogen atmosphere under cooling or under heating conditions using a reducing catalyst in a solvent inert to the reaction to obtain compound (G1). This compound is preferably obtained by stirring at room temperature to 40° C. for 0.5 to 24 hours. The solvent used in this reaction is not particularly limited as long as the solvent is inert to the reaction. Examples thereof can include tetrahydrofuran, 1,2-dimethoxyethane, 1,4-dioxane, water, methanol, ethanol, and mixtures thereof. Examples of the reducing catalyst include palladium-carbon, Raney nickel, platinum-carbon, and platinum oxide.

The compounds produced by these methods can each be isolated and purified by a method known in the art, for example, extraction, precipitation, distillation, chromatography, fractional crystallization, or recrystallization.

When each compound or intermediate for production has asymmetric carbon(s), enantiomers are present. These enantiomers can each be isolated and purified by a routine method such as fractional crystallization (salt resolution) by recrystallization with an appropriate salt, or column chromatography. Examples of references for the method for resolving a racemate to enantiomers include J. Jacques et al. "Enantiomers, Racemates and Resolution, John Wiley And Sons, Inc.".

EXAMPLES

Abbreviations in the Reference Examples and Examples are as follows: Me=methyl, tBu=tert-butyl, and TBDMS=tert-butyldimethylsilyl.

Reference Example 1 (Step A-1)

Methyl 5-bromo-3,4-dihydroxy-2-methylbenzoate (A1a: X=Br, $R^4$=Me)

Methyl 3,4-dihydroxy-2-methylbenzoate (43.1 g, 237 mmol) was dissolved in acetic acid (250 mL) and dichloromethane (250 mL). To the solution, a solution of bromine (37.8 g, 237 mmol) in dichloromethane (20 mL) was added dropwise over 15 minutes under ice cooling, and the mixture was stirred at this temperature for 4 hours. Bromine (3.78 g, 23.7 mmol) was further added thereto, and the mixture was stirred for 1.5 hours under ice cooling. Then, ice water was added to the reaction solution, followed by extraction with ethyl acetate. The organic layer was washed with an aqueous sodium sulfite solution and saturated saline and then concentrated under reduced pressure. The obtained residue was washed with dichloromethane to obtain the title compound (50.4 g, 193 mmol, 82% yield).

$^1$H-NMR (400 MHz, CDCl$_3$) δ: 2.47 (3H, s), 3.87 (3H, s), 5.61 (1H, br s), 5.83 (1H, br s), 7.67 (1H, s).

MS (ESI) m/z: 259, 261 (M−H)$^-$.

Reference Example 2 (Step A-1)

Methyl 5-chloro-3,4-dihydroxy-2-methylbenzoate (A1b: X=Cl, $R^4$=Me)

Methyl 3,4-dihydroxy-2-methylbenzoate (12.1 g, 66.2 mmol) was dissolved in ethyl acetate (265 mL). To the solution, N-chlorosuccinimide (13.3 g, 99.2 mmol) was added, and the mixture was stirred at room temperature for 1 hour. Then, p-anisole (7.15 g, 66.2 mmol) was added thereto, and the mixture was further stirred for 15 minutes. The reaction solution was washed with water and saturated saline, dried over magnesium sulfate, and then concentrated under reduced pressure. The obtained residue was washed with dichloromethane to obtain the title compound (8.03 g, 37.1 mmol, 56% yield).

$^1$H-NMR (400 MHz, DMSO-d$_6$) δ: 2.34 (3H, s), 3.76 (3H, s), 7.36 (1H, s), 9.11 (1H, br s), 9.96 (1H, br s).

MS (ESI) m/z: 215 (M−H)$^-$.

Reference Example 3

Methyl 5-fluoro-3,4-dihydroxy-2-methylbenzoate (A1c: X=F, $R^4$=Me)

[Formula 14]

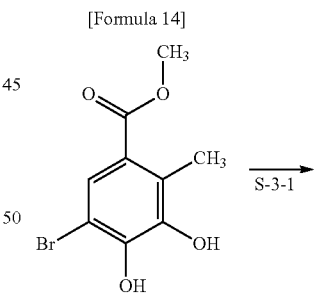

A1a

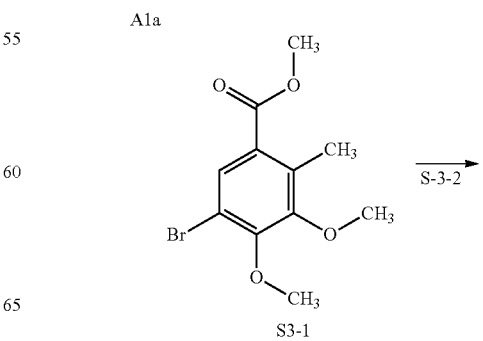

S3-1

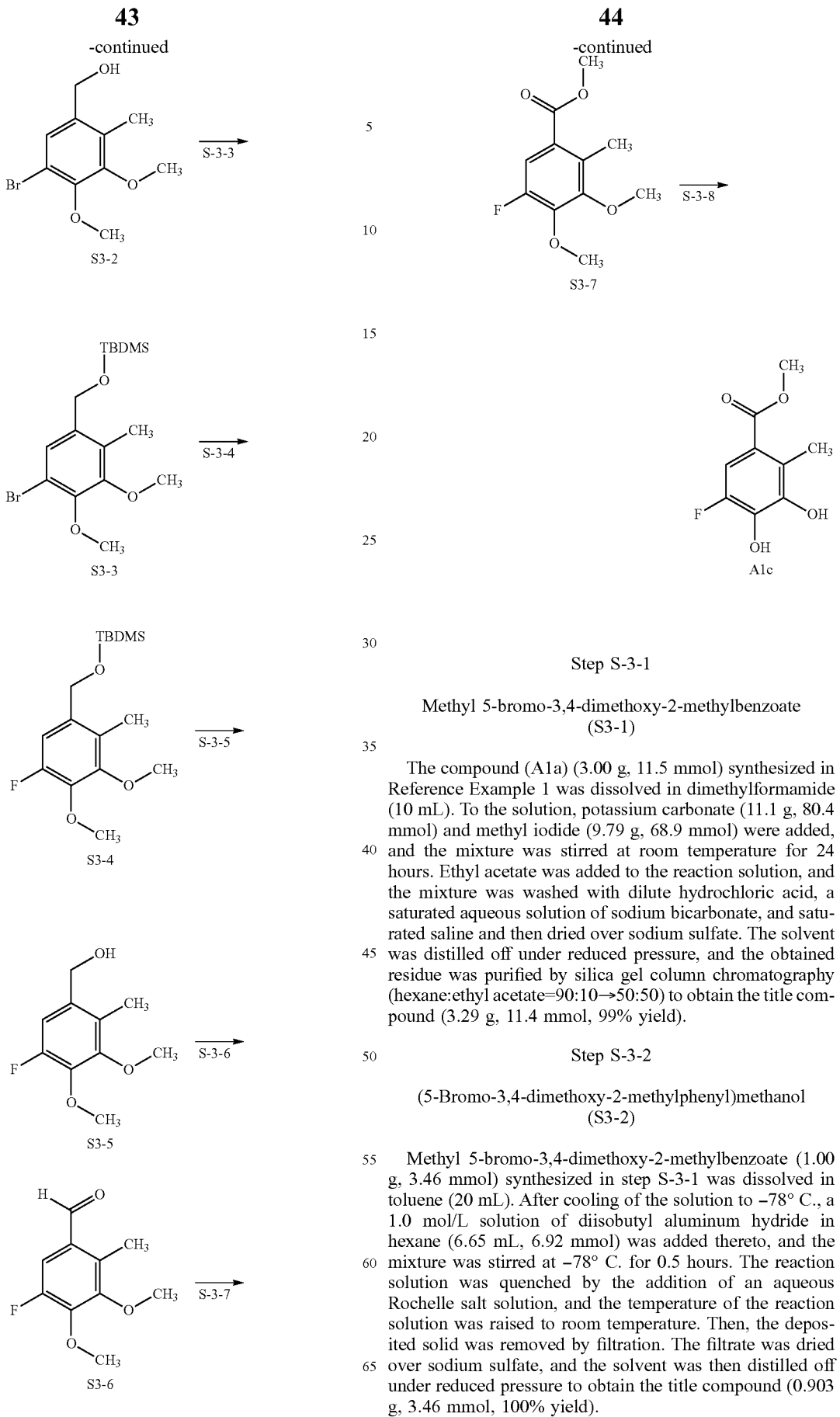

Step S-3-1

Methyl 5-bromo-3,4-dimethoxy-2-methylbenzoate (S3-1)

The compound (A1a) (3.00 g, 11.5 mmol) synthesized in Reference Example 1 was dissolved in dimethylformamide (10 mL). To the solution, potassium carbonate (11.1 g, 80.4 mmol) and methyl iodide (9.79 g, 68.9 mmol) were added, and the mixture was stirred at room temperature for 24 hours. Ethyl acetate was added to the reaction solution, and the mixture was washed with dilute hydrochloric acid, a saturated aqueous solution of sodium bicarbonate, and saturated saline and then dried over sodium sulfate. The solvent was distilled off under reduced pressure, and the obtained residue was purified by silica gel column chromatography (hexane:ethyl acetate=90:10→50:50) to obtain the title compound (3.29 g, 11.4 mmol, 99% yield).

Step S-3-2

(5-Bromo-3,4-dimethoxy-2-methylphenyl)methanol (S3-2)

Methyl 5-bromo-3,4-dimethoxy-2-methylbenzoate (1.00 g, 3.46 mmol) synthesized in step S-3-1 was dissolved in toluene (20 mL). After cooling of the solution to −78° C., a 1.0 mol/L solution of diisobutyl aluminum hydride in hexane (6.65 mL, 6.92 mmol) was added thereto, and the mixture was stirred at −78° C. for 0.5 hours. The reaction solution was quenched by the addition of an aqueous Rochelle salt solution, and the temperature of the reaction solution was raised to room temperature. Then, the deposited solid was removed by filtration. The filtrate was dried over sodium sulfate, and the solvent was then distilled off under reduced pressure to obtain the title compound (0.903 g, 3.46 mmol, 100% yield).

$^1$H-NMR (400 MHz, CDCl$_3$) δ: 1.67 (1H, t, J=5.2 Hz), 2.21 (3H, s), 3.84 (3H, s), 3.87 (3H, s) 4.62 (2H, d, J=5.2 Hz), 7.33 (1H, s).

Step S-3-3

(5-Bromo-3,4-dimethoxy-2-methylphenyl)methoxy-tert-butyldimethylsilane (S3-3)

(5-Bromo-3,4-dimethoxy-2-methylphenyl)methanol (0.903 g, 3.46 mmol) synthesized in step S-3-2 was dissolved in dichloromethane (10 mL). To the solution, t-butyldimethylsilyl chloride (0.626 g, 4.15 mmol), triethylamine (1.82 g, 18.0 mmol), and 4-dimethylaminopyridine (0.423 g, 3.46 mmol) were added at room temperature, and the mixture was stirred for 2 hours. Ethyl acetate was added to the reaction solution, and the organic layer was washed with water, a saturated aqueous solution of sodium bicarbonate, and saturated saline and then dried over sodium sulfate. The solvent was distilled off under reduced pressure, and the obtained residue was purified by silica gel column chromatography (hexane:ethyl acetate=90:10→50:50) to obtain the title compound (1.22 g, 3.25 mmol, 93% yield).

Step S-3-4 tert-Butyl-[(5-fluoro-3,4-dimethoxy-2-methylphenyl)methoxy]dimethylsilane (S3-4)

A solution of (5-bromo-3,4-dimethoxy-2-methylphenyl)methoxy-tert-butyldimethylsilane (1.22 g, 3.25 mmol) synthesized in step S-3-3 in tetrahydrofuran (20 mL) was cooled to −78° C. A 1.6 M solution of n-butyllithium in hexane (1.67 mL, 2.66 mmol) was added dropwise thereto, and the mixture was then stirred at this temperature for 5 minutes. A solution of N-fluorobenzenesulfonimide (1.09 g, 3.46 mmol) in tetrahydrofuran (10 mL) was added dropwise thereto, and the mixture was stirred at −78° C. for 1 hour. The reaction solution was quenched with a saturated aqueous solution of ammonium chloride, and the temperature of the reaction solution was raised to room temperature, followed by extraction by the addition of ethyl acetate. The organic layer was washed with water, a saturated aqueous solution of sodium bicarbonate, and saturated saline and then dried over sodium sulfate. The solvent was distilled off under reduced pressure, and the obtained residue was purified by silica gel column chromatography (hexane:ethyl acetate=90:10→50:50) to obtain the title compound (0.738 g, 2.35 mmol, 88% yield).

Step S-3-5

(5-Fluoro-3,4-dimethoxy-2-methylphenyl)methanol (S3-5)

To tert-butyl-[(5-fluoro-3,4-dimethoxy-2-methylphenyl)methoxy]dimethylsilane (0.738 g, 2.35 mmol) synthesized in step S-3-4, a 1 M solution of tetrabutyl ammonium fluoride in tetrahydrofuran (4 mL) was added, and the mixture was stirred at room temperature for 1 hour. The reaction solution was concentrated, and the obtained residue was purified by silica gel column chromatography (hexane: ethyl acetate=70:30→20:80) to obtain the title compound (0.340 g, 1.70 mmol, 70% yield).

$^1$H-NMR (400 MHz, CDCl$_3$) δ: 1.70 (1H, br s), 2.18 (3H, s), 3.84 (3H, s), 3.94 (3H, s) 4.60-4.67 (2H, m), 6.93 (1H, d, J=11.6 Hz).

Step S-3-6

5-Fluoro-3,4-dimethoxy-2-methylbenzaldehyde (S3-6)

(5-Fluoro-3,4-dimethoxy-2-methylphenyl)methanol (0.340 g, 1.70 mmol) synthesized in step S-3-5 and triethylamine (0.137 g, 1.36 mmol) were dissolved in dichloromethane (2 mL). To the solution, dimethyl sulfoxide (0.4 mL) and SO$_3$-pyridine (0.162 g, 1.02 mmol) were added under ice cooling. The mixture was stirred for 1 hour under ice cooling and then further stirred at room temperature for 16 hours. Water was added to the reaction solution, followed by extraction with ethyl acetate. The organic layer was washed with water, a saturated aqueous solution of sodium bicarbonate, and saturated saline and then dried over sodium sulfate. The solvent was distilled off under reduced pressure, and the obtained residue was purified by silica gel column chromatography (hexane:ethyl acetate=75:25→50:50) to obtain the title compound (0.313 g, 1.57 mmol, 93% yield).

$^1$H-NMR (400 MHz, CDCl$_3$) δ: 2.54 (3H, s), 3.85 (3H, s), 4.07 (3H, s), 7.37 (1H, d, J=11.6 Hz), 10.17 (1H, s).

Step S-3-7

Methyl 5-fluoro-3,4-dimethoxy-2-methylbenzoate (S3-7)

5-Fluoro-3,4-dimethoxy-2-methylbenzaldehyde (0.313 g, 1.57 mmol) synthesized in step S-3-6 was dissolved in anhydrous methanol (6 mL). To the solution, potassium hydroxide (0.266 g, 4.73 mmol) and iodine (0.521 g, 2.05 mmol) were added under ice cooling, and the mixture was stirred for 1.5 hours. A saturated aqueous solution of sodium bisulfite was added thereto until the red brown color disappeared, followed by extraction with ethyl acetate. The organic layer was washed with water, a saturated aqueous solution of sodium bicarbonate, and saturated saline and then dried over sodium sulfate. The solvent was distilled off under reduced pressure, and the obtained residue was purified by silica gel column chromatography (hexane:ethyl acetate=75:25→50:50) to obtain the title compound (0.325 g, 1.42 mmol, 90% yield).

$^1$H-NMR (400 MHz, CDCl$_3$) δ: 2.46 (3H, s), 3.82 (3H, s), 3.87 (3H, s) 4.02 (3H, s), 7.46 (1H, d, J=11.9 Hz).

Step S-3-8

Methyl 5-fluoro-3,4-dihydroxy-2-methylbenzoate (Compound (A1c): X=F, R$^4$=Me)

Methyl 5-fluoro-3,4-dimethoxy-2-methylbenzoate (0.325 g, 1.42 mmol) synthesized in step S-3-7 was dissolved in dichloromethane (6 mL). After cooling of the solution to 78° C., a 1 M solution of boron tribromide in dichloromethane (3.55 mL, 3.55 mmol) was added thereto, and the mixture was stirred at this temperature for 1 hour and then stirred at room temperature for 20 hours. Methanol was added to the reaction solution, and the mixture was stirred for approximately 1 hour. Then, water was added thereto, followed by extraction with dichloromethane. The organic layer was washed with water and saturated saline and then dried over sodium sulfate. The solvent was distilled off under reduced pressure to obtain the title compound (0.265 g, 1.32 mmol, 93% yield).

$^1$H-NMR (400 MHz, CDCl$_3$) δ: 2.48 (3H, s), 3.86 (3H, s), 7.32 (1H, d, J=11.2 Hz).

Reference Example 4 (Step C-1)

Methyl 3,4-dihydroxy-2,5-dimethylbenzoate (A1d: X=Me, R$^4$=Me)

The compound (A1a) (3.44 g, 13.2 mmol) synthesized in Reference Example 1 was dissolved in tetrahydrofuran (80 mL). To the solution, bis(trimethyl aluminum)-1,4-diazabicyclo[2.2.2]octane (5.40 g, 21.1 mmol), tris(dibenzylideneacetone)dipalladium(0) (0.181, 0.198 mmol), and 2-dicyclohexylphosphino-2',4',6'-triisopropylbiphenyl (0.188 g, 0.395 mmol) were added, and the mixture was heated to reflux at 75° C. for 3 hours under the current of nitrogen. The reaction solution was brought back to room temperature and quenched by the addition of 1 N hydrochloric acid. After extraction with ethyl acetate, the organic phase was washed with water and saturated saline and dried over sodium sulfate. After concentration under reduced pressure, the obtained residue was purified by silica gel column chromatography (hexane:ethyl acetate=80:20→60:40) to obtain the title compound (2.23 g, 11.4 mmol, 86% yield).

$^1$H-NMR (400 MHz, CDCl$_3$) δ: 2.24 (3H, s), 2.48 (3H, s), 3.85 (3H, s), 5.23 (1H, br s), 5.58 (1H, br s), 7.39 (1H, s).

MS (ESI) m/z: 195 (M–H)$^-$.

Reference Example 5

Methyl 3,4-dihydroxy-5-methoxy-2-methylbenzoate (A1e: X=OMe, R$^4$=Me)

[Formula 15]

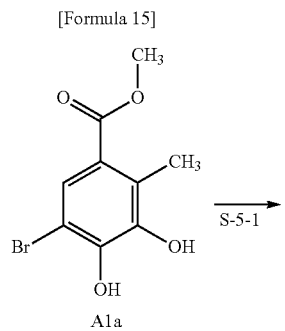

A1a

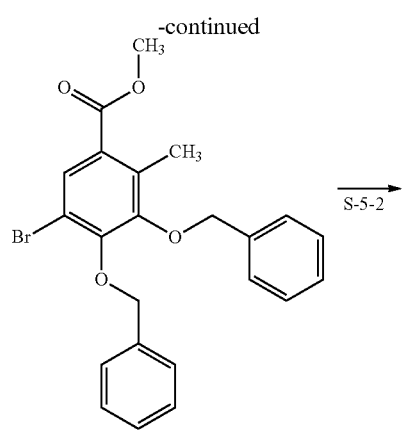

S5-1

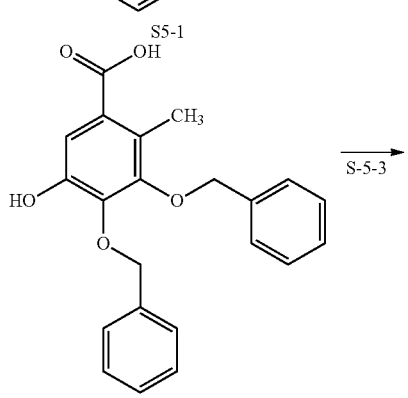

S5-2

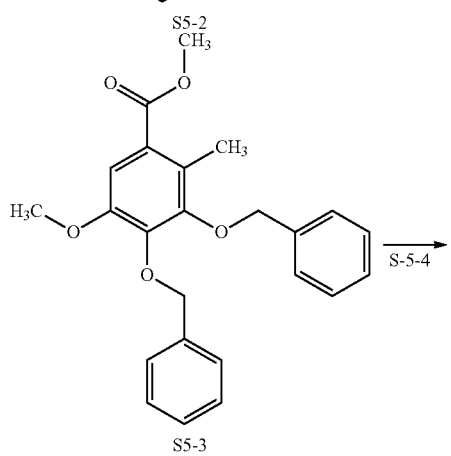

S5-3

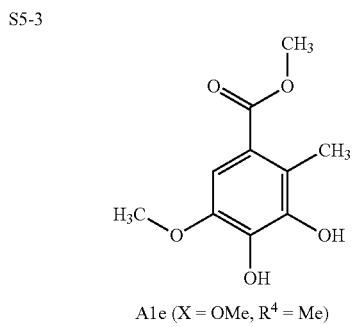

A1e (X = OMe, R$^4$ = Me)

Step S-5-1

Methyl 3,4-dibenzyloxy-5-bromo-2-methylbenzoate (S5-1)

The title compound (0.550 g, 1.24 mmol, 64% yield) was obtained through the same reaction as in step S-3-1 using the compound (A1a) (0.500 g, 1.92 mmol) synthesized in Reference Example 1 and benzyl bromide (1.31 g, 7.66 mmol).

$^1$H-NMR (400 MHz, CDCl$_3$) δ: 2.46 (3H, s), 3.88 (3H, s), 4.97 (2H, s), 5.10 (2H, s), 7.30-7.53 (10H, m), 7.50 (1H, s)

Step S-5-2

3,4-Dibenzyloxy-5-hydroxy-2-methylbenzoic Acid (S5-2)

Methyl 3,4-dibenzyloxy-5-bromo-2-methylbenzoate (0.150 g, 0.340 mmol) synthesized in step S-5-1 was dissolved in a 1,4-dioxane:water (4:1) mixed solvent. To the solution, potassium hydroxide (0.095 g, 1.70 mmol), tris (dibenzylideneacetone)dipalladium(0) (0.031 g, 0.034 mmol), and 2-di-tert-butylphosphino-2',4',6'-triisopropylbiphenyl (0.028 g, 0.068 mmol) were added, and the mixture was stirred at 90° C. for 3 hours. The reaction solution was neutralized, followed by extraction with ethyl acetate. The organic layer was washed with water, a saturated aqueous solution of sodium bicarbonate, and saturated saline and then dried over sodium sulfate. The solvent was distilled off under reduced pressure to obtain the title compound (0.123 g, 0.340 mmol, 100% yield).

Step S-5-3

Methyl 3,4-dibenzyloxy-5-methoxy-2-methylbenzoate (S5-3)

The title compound (0.133 g, 0.340 mmol, 100% yield) was obtained through the same reaction as in step S-3-1 using 3,4-dibenzyloxy-5-hydroxy-2-methylbenzoic acid (0.123 g, 0.340 mmol) synthesized in step S-5-2.

Step S-5-4

Methyl 3,4-dihydroxy-5-methoxy-2-methylbenzoate (Compound (A1e): X=OMe, R$^4$=Me)

Ethyl 3,4-dibenzyloxy-5-methoxy-2-methylbenzoate (0.133 g, 0.340 mmol) synthesized in step S-5-3 was dissolved in methanol (2 mL). To the solution, 7.5% palladium-carbon was added, and the mixture was stirred for 1 hour under a hydrogen atmosphere. The catalyst was filtered, and the filtrate was then concentrated to obtain the title compound (0.077 g, 0.340 mmol, 100% yield).

Reference Example 6

Methyl 2,5-dichloro-3,4-dihydroxybenzoate (Compound (E2))

Step S-6-1

2,5-Dichloro-3,4-dihydroxybenzoic Acid

To a solution of 3,4-dihydroxybenzoic acid hydrate (12.2 g, 70.8 mmol) in acetic acid (45 mL), sulfuryl chloride (14.0 mL, 173 mmol) was added dropwise at 50° C. over 30 minutes, and the mixture was further stirred for 17 hours. The reaction mixture was cooled to 0° C., and insoluble matter was then collected by filtration, washed with hexane, and then dried under reduced pressure at room temperature to obtain the title compound (2.68 g, 12.0 mmol, 17% yield).

$^1$H-NMR (400 MHz, DMSO-d$_6$) δ: 7.37 (1H, s), 9.95 (1H, br s), 10.42 (1H, br s).

MS (APCI) m/z: 221 (M–H)$^-$.

Step S-6-2

Methyl 2,5-dichloro-3,4-dihydroxybenzoate (Compound (E2))

To a solution of 2,5-dichloro-3,4-dihydroxybenzoic acid (2.68 g, 12.0 mmol) synthesized in step S-6-1 in methanol (30 mL), sulfuric acid (1.40 mL, 26.3 mmol) was added, and the mixture was refluxed for 15 hours. The reaction solution was concentrated under reduced pressure. To the obtained residue, ethyl acetate was then added, and the organic layer was washed with water and saturated saline and dried over anhydrous sodium sulfate. The solvent was concentrated under reduced pressure to obtain the title compound (2.89 g, 11.4 mmol, 95% yield).

$^1$H-NMR (400 MHz, DMSO-d$_6$) δ: 3.76 (3H, s), 7.37 (1H, s).

MS (APCI) m/z: 235 (M–H)$^-$.

Reference Example 7 tert-Butyl N-(1-ethynyl-3-bicyclo[1.1.1]pentanyl) carbamate (S7)

[Formula 16]

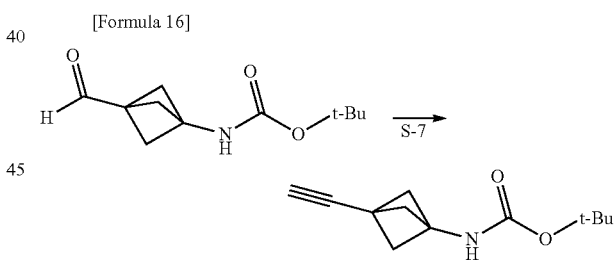

To a solution of tert-butyl (3-formylbicyclo[1.1.1]pent-1-yl)carbamate (0.697 g, 3.30 mmol) in methanol (20 mL), potassium carbonate (0.957 g, 6.92 mmol) and 1-diazo-1-dimethoxyphosphoryl-propan-2-one (0.520 mL, 3.46 mmol) were added, and the mixture was stirred at room temperature for 1 hour. Water was added to the reaction solution, followed by extraction with ethyl acetate. The organic layer was washed with saturated saline and then dried over anhydrous sodium sulfate. The solvent was distilled off under reduced pressure, and the obtained residue was purified by silica gel column chromatography (hexane:ethyl acetate=100:0→82:18) to obtain the title compound (0.564 g, 2.72 mmol, 82% yield).

$^1$H-NMR (400 MHz, CDCl$_3$) δ: 1.44 (9H, s), 2.16 (1H, s), 2.29 (6H, s), 4.95 (1H, br s).

Reference Example 8 tert-Butyl N-(6-ethynylspiro[3.3]heptan-2-yl)carbamate (S8-2)

[Formula 17]

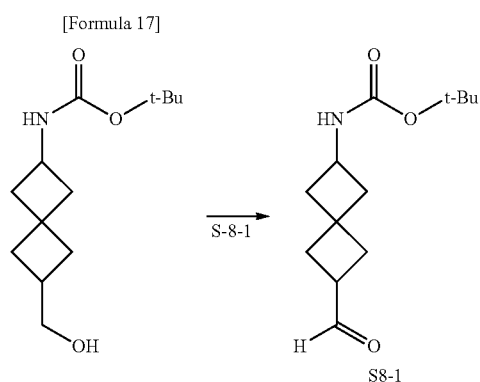

Step S-8-1 tert-Butyl N-(6-formylspiro[3.3]heptan-2-yl)carbamate (S8-1)

To a solution of tert-butyl N-[6-(hydroxymethyl)spiro[3.3]heptan-2-yl]carbamate (3.10 g, 12.8 mmol) in dichloromethane (62 mL), a Dess-Martin reagent (8.17 g, 19.3 mmol) was added, and the mixture was stirred at room temperature for 1 hour. A saturated aqueous solution of sodium thiosulfate was added to the reaction solution, followed by extraction with ethyl acetate. The organic layer was washed with a saturated aqueous solution of sodium bicarbonate and saturated saline and then dried over anhydrous sodium sulfate. The solvent was distilled off under reduced pressure, and the obtained residue was purified by silica gel chromatography (hexane:ethyl acetate=80:20) to obtain the title compound (2.87 g, 12.0 mmol, 93% yield).

$^1$H-NMR (400 MHz, CDCl$_3$) δ: 1.43 (9H, s), 1.73-1.90 (2H, m), 2.01-2.15 (1H, m), 2.20-2.36 (4H, m), 2.45-2.55 (1H, m), 3.03-3.13 (1H, m), 3.92-4.08 (1H, m), 4.59 (1H, br s), 9.69 (1H, d, J=1.8 Hz).

Step S-8-2 tert-Butyl N-(6-ethynylspiro[3.3]heptan-2-yl)carbamate (S8-2)

The title compound (1.95 g, 8.29 mmol, 71% yield) was obtained through the same reaction as in Reference Example 7 using tert-butyl N-(6-formylspiro[3.3]heptan-2-yl)carbamate (2.80 g, 11.7 mmol) synthesized in step S-8-1.

$^1$H-NMR (400 MHz, CDCl$_3$) δ: 1.43 (9H, s), 1.77-1.84 (2H, m), 2.08-2.26 (4H, m), 2.34-2.50 (3H, m), 2.84-2.94 (1H, m), 3.93-4.08 (1H, m), 4.58 (1H, br s).

Reference Example 9 tert-Butyl 6-ethynyl-2-azaspiro[3.3]heptane-2-carboxylate (S9-2)

[Formula 18]

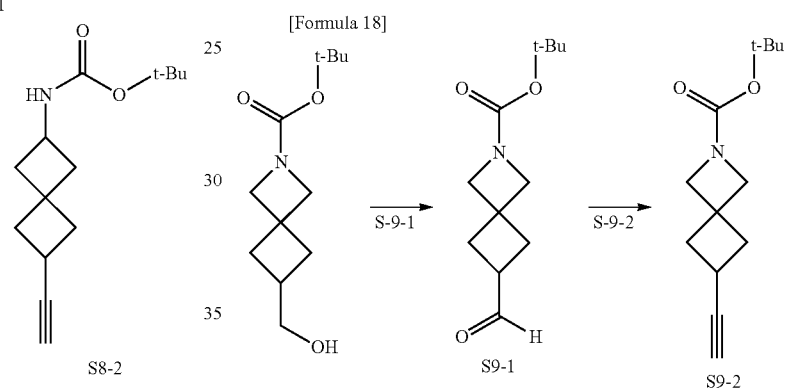

Step S-9-1 tert-Butyl 6-formyl-2-azaspiro[3.3]heptane-2-carboxylate (S9-1)

The title compound (1.60 g, 7.10 mmol, 90% yield) was obtained through the same reaction as in step S-8-1 using tert-butyl 6-(hydroxymethyl)-2-azaspiro[3.3]heptane-2-carboxylate (1.80 g, 7.92 mmol). The obtained crude product was subjected to the next step without being purified.

Step S-9-2 tert-Butyl 6-ethynyl-2-azaspiro[3.3]heptane-2-carboxylate (S9-2)

The title compound (0.95 g, 4.29 mmol, 60% yield) was obtained through the same reaction as in step S-7 using tert-butyl 6-formyl-2-azaspiro[3.3]heptane-2-carboxylate (1.60 g, 7.11 mmol) synthesized in step S-9-1.

$^1$H-NMR (400 MHz, CDCl3) δ: 1.43 (9H, s), 2.15 (1H, d, J=2.4 Hz), 2.23-2.33 (2H, m), 2.45-2.55 (2H, m), 2.82-2.93 (1H, m), 3.85-3.95 (4H, m).

Reference Example 10 tert-Butyl 4-prop-2-ynylpiperidine-1-carboxylate (S10)

[Formula 19]

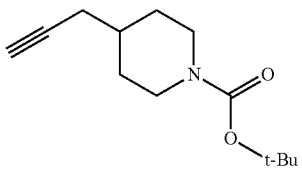

S10

The title compound (3.24 g, 14.5 mmol, 77% yield) was obtained through the same reaction as in Reference Example 7 using tert-butyl 4-(2-oxoethyl)piperidine-1-carboxylate (4.30 g, 18.9 mmol).

$^1$H-NMR (400 MHz, CDCl$_3$) δ: 1.12-1.31 (2H, m), 1.46 (9H, s), 1.56-1.70 (1H, m), 1.72-1.81 (2H, m), 1.99 (1H, t, J=2.6 Hz), 2.15 (2H, dd, J=6.7, 2.6 Hz), 2.61-2.78 (2H, m), 3.98-4.27 (2H, m).

Reference Example 11 tert-Butyl N-(cis-4-prop-2-ynylcyclohexyl)carbamate (S11)

[Formula 20]

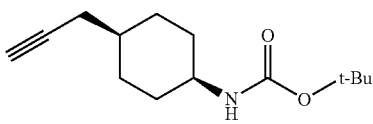

S11

The title compound (1.20 g, 5.05 mmol, 55% yield) was obtained through the same reaction as in Reference Example 7 using tert-butyl N-[cis-4-(2-oxoethyl)cyclohexyl]carbamate (2.20 g, 9.12 mmol).

$^1$H-NMR (400 MHz, CDCl3) δ: 1.23-1.35 (2H, m), 1.45 (9H, s), 1.53-1.73 (7H, m), 1.98 (1H, t, J=2.6 Hz), 2.14 (2H, dd, J=6.7, 2.6 Hz), 3.67-3.82 (1H, m), 4.64 (1H, br s).

Reference Example 12 tert-Butyl N-(trans-4-prop-2-ynylcyclohexyl)carbamate (S12)

[Formula 21]

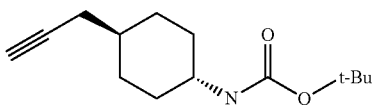

S12

The title compound (1.14 g, 4.78 mmol, 66% yield) was obtained through the same reaction as in Reference Example 7 using tert-butyl N-[trans-4-(2-oxoethyl)cyclohexyl]carbamate (1.74 g, 7.22 mmol).

$^1$H-NMR (400 MHz, CDCl3) δ: 1.03-1.20 (4H, m), 1.44 (9H, s), 1.84-1.92 (2H, m), 1.97 (1H, t, J=2.6 Hz), 1.99-2.05 (2H, m), 2.10 (2H, dd, J=6.7, 2.6 Hz), 3.30-3.46 (1H, m), 4.37 (1 h, br s).

Reference Example 13 tert-Butyl N-(trans-4-ethynylcyclohexyl)carbamate (S13)

[Formula 22]

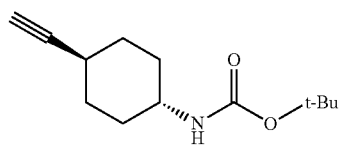

S13

The title compound (0.639 g, 2.86 mmol, 77% yield) was obtained through the same reaction as in Reference Example 7 using tert-butyl N-(trans-4-formylcyclohexyl)carbamate (0.839 g, 3.69 mmol).

1H-NMR (400 MHz, CDCl3) δ: 1.04-1.17 (2H, m), 1.42-1.55 (2H, m), 1.44 (9H, s), 1.94-2.05 (4H, m), 2.04 (1H, d, J=2.5 Hz), 2.16-2.25 (1H, m), 3.34-3.50 (1H, m), 4.29-4.43 (1H, br s).

Reference Example 14 tert-Butyl N-(trans-4-ethynylcyclohexyl)-N-methyl-carbamate (S14)

[Formula 23]

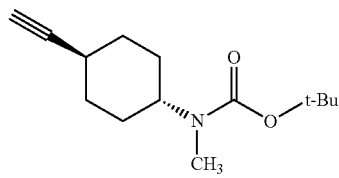

S14

The title compound (2.50 g, 10.5 mmol, 69% yield) was obtained through the same reaction as in Reference Example 7 using tert-butyl N-(trans-4-formylcyclohexyl)-N-methyl-carbamate (3.70 g, 15.3 mmol) synthesized according to the method described in WO 2003053933.

$^1$H-NMR (400 MHz, CDCl$_3$) δ: 1.33-1.60 (4H, m), 1.46 (9H, s), 1.65-1.75 (2H, m), 2.01-2.20 (3H, m), 2.05 (1H, d, J=2.5 Hz), 2.70 (3H, br s), 3.67-4.13 (1H, br m).

Reference Example 15

8-Ethynyl-1,4-dioxaspiro[4.5]decane (S15)

[Formula 24]

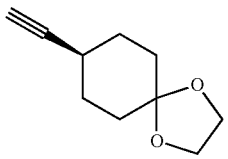

S15

The title compound (1.69 g, 10.1 mmol, 82% yield) was obtained through the same reaction as in Reference Example 7 using 1,4-dioxaspiro[4.5]decane-8-carbaldehyde (2.11 g, 12.4 mmol) synthesized according to the method described in WO 2010132247.

$^1$H-NMR (400 MHz, CDCl$_3$) δ: 1.51-1.61 (2H, m), 1.68-1.79 (2H, m), 1.80-1.92 (4H, m), 2.04 (1H, d, J=2.4 Hz), 2.43-2.53 (1H, m), 3.90-3.99 (4H, m).

Reference Example 16 tert-Butyl N-[(4-ethynylcyclohexyl)methyl]carbamate (S16)

[Formula 25]

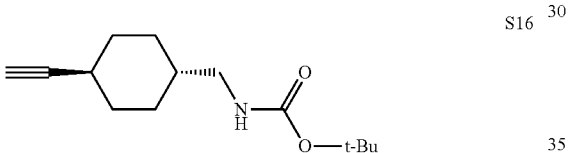

S16

The title compound (1.97 g, 8.30 mmol, 86% yield) was obtained through the same reaction as in Reference Example 7 using tert-butyl N-[(4-formylcyclohexyl)methyl]carbamate (2.34 g, 9.70 mmol) synthesized according to the method described in WO 2007103295.

$^1$H-NMR (400 MHz, CDCl$_3$) δ: 0.86-0.99 (2H, m), 1.30-1.48 (3H, m), 1.44 (9H, s), 1.72-1.81 (2H, m), 1.97-2.06 (2H, m), 2.05 (1H, d, J=2.4 Hz), 2.13-2.23 (1H, m), 2.93-2.99 (2H, m), 4.52-4.61 (1H, br m).

Example 1

7-Bromo-N-[(4,6-dimethyl-2-oxo-1,2-dihydropyridin-3-yl)methyl]-2,4-dimethyl-2-(tetrahydrofuran-3-yl)-1,3-benzodioxole-5-carboxamide (1)

[Formula 26]

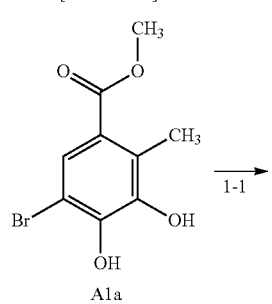

A1a

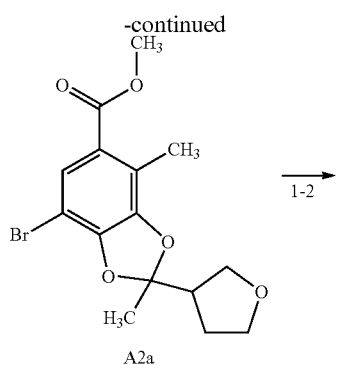

A2a

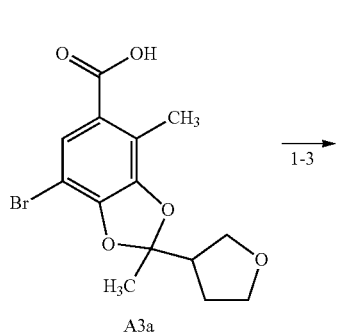

A3a

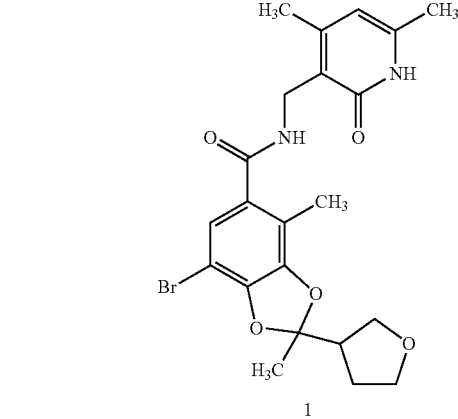

1

Step 1-1

Methyl 7-bromo-2,4-dimethyl-2-(tetrahydrofuran-3-yl)-1,3-benzodioxole-5-carboxylate (A2a)

To a solution of the compound (A1a) (1.00 g, 3.83 mmol) synthesized in Reference Example 1 in toluene (15 mL), triruthenium(0) dodecacarbonyl (0.122 g, 0.192 mmol) and triphenylphosphine (0.101 g, 0.383 mmol) were added, and the mixture was stirred for a while at 120° C. under a nitrogen atmosphere. Then, a solution of 3-ethynyltetrahydrofuran (1.11 g, 11.5 mmol) in toluene (5 mL) was added dropwise thereto, and the mixture was further stirred at 120°

C. for 2 hours. After the completion of the reaction, the solvent was distilled off under reduced pressure, and the obtained residue was purified by silica gel column chromatography (hexane:ethyl acetate=95:5→70:30) to obtain the title compound (1.13 g, 3.16 mmol, 83% yield).

$^1$H-NMR (400 MHz, CDCl$_3$) δ: 1.70 (3H, s), 1.89-2.00 (1H, m), 2.02-2.13 (1H, m), 2.38 (3H, s), 2.85-2.94 (1H, m), 3.73-3.83 (2H, m), 3.85 (3H, s), 3.87-3.96 (2H, m), 7.69 (1H, s).

MS (ESI) m/z: 357, 359 (M+H)$^+$.

Step 1-2

7-Bromo-2,4-dimethyl-2-(tetrahydrofuran-3-yl)-1,3-benzodioxole-5-carboxylic acid (A3a)

To the compound (A2a) (1.13 g, 3.16 mmol) synthesized in step 1-1, tetrahydrofuran (6 mL) and methanol (3 mL) were added, further a 2 M aqueous sodium hydroxide solution (3.16 mL, 6.32 mmol) was added, and the mixture was stirred at room temperature for 16 hours. After the completion of the reaction, the reaction solution was neutralized by the addition of 2 M hydrochloric acid (3.16 mL, 6.32 mmol), followed by extraction by the addition of dichloromethane. The obtained organic layer was concentrated under reduced pressure to obtain the title compound (1.05 g, 3.07 mmol, 97% yield).

$^1$H-NMR (400 MHz, CDCl$_3$) δ: 1.70 (3H, s), 1.88-2.01 (1H, m), 2.04-2.14 (1H, m), 2.44 (3H, s), 2.86-2.96 (1H, m), 3.75-3.84 (2H, m), 3.87-3.98 (2H, m), 7.84 (1H, s).

MS (ESI) m/z: 341, 343 (M−H)$^−$.

Step 1-3

7-Bromo-N-[(4,6-dimethyl-2-oxo-1,2-dihydropyridin-3-yl)methyl]-2,4-dimethyl-2-(tetrahydrofuran-3-yl)-1,3-benzodioxole-5-carboxamide (1)

To a solution of the compound (A3a) (1.05 g, 3.07 mmol) synthesized in step 1-2 in dimethylformamide (10 mL), 3-(aminomethyl)-4,6-dimethyl-1H-pyridin-2-one hydrochloride (0.868 g, 4.60 mmol), 1-ethyl-3-(3-dimethylaminopropyl)carbodiimide hydrochloride (0.882 g, 4.60 mmol), and 1-hydroxy-7-azabenzotriazole (0.627 g, 4.60 mmol) were added, and the mixture was stirred at 100° C. for 1.5 hours under a nitrogen atmosphere. After the completion of the reaction, water was added to the reaction solution, and the deposited solid was collected by filtration and dissolved again in dichloromethane. Then, the solution was purified by silica gel column chromatography (hexane:ethyl acetate=2: 98→0:100, and dichloromethane:methanol=100:0→90:10) to obtain the title compound (0.863 g, 1.81 mmol, 59% yield).

$^1$H-NMR (400 MHz, DMSO-d$_6$) δ: 1.63 (3H, s), 1.72-1.83 (1H, m), 1.93-2.04 (1H, m), 2.10 (6H, s), 2.17 (3H, s), 2.88-2.97 (1H, m), 3.55-3.68 (2H, m), 3.71-3.83 (2H, m), 4.21 (2H, d, J=4.9 Hz), 5.86 (1H, s), 6.97 (1H, s), 8.16 (1H, t, J=4.9 Hz), 11.49 (1H, s).

MS (ESI) m/z: 477, 479 (M+H)$^+$.

Example 2

7-Bromo-N-[(4,6-dimethyl-2-oxo-1,2-dihydropyridin-3-yl)methyl]-2,4-dimethyl-2-(tetrahydropyran-4-yl)-1,3-benzodioxole-5-carboxamide (2)

[Formula 27]

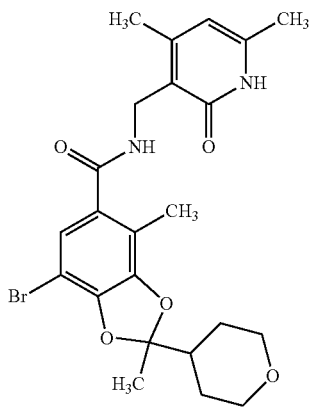

Step 2-1

Methyl 7-bromo-2,4-dimethyl-2-(tetrahydropyran-4-yl)-1,3-benzodioxole-5-carboxylate (A2b)

The title compound (0.861 g, 2.32 mmol, 61% yield) was obtained through the same reaction as in step 1-1 using the compound (A1a) (1.00 g, 3.83 mmol) synthesized in Reference Example 1 and 4-ethynyltetrahydro-2H-pyran (1.27 g, 11.5 mmol).

$^1$H-NMR (400 MHz, CDCl$_3$) δ: 1.53-1.68 (2H, m), 1.67 (3H, s), 1.68-1.77 (2H, m), 2.07-2.17 (1H, m), 2.39 (3H, s), 3.33-3.43 (2H, m), 3.85 (3H, s), 4.01-4.08 (2H, m), 7.68 (1H, s).

Step 2-2

7-Bromo-2,4-dimethyl-2-(tetrahydropyran-4-yl)-1,3-benzodioxole-5-carboxylic Acid (A3b)

The title compound (0.796 g, 2.23 mmol, 96% yield) was obtained through the same reaction as in step 1-2 using the compound (A2b) (0.861 g, 2.32 mmol) synthesized in step 2-1.

MS (ESI) m/z: 355, 357 (M−H)$^−$.

Step 2-3

7-Bromo-N-[(4,6-dimethyl-2-oxo-1,2-dihydropyridin-3-yl)methyl]-2,4-dimethyl-2-(tetrahydropyran-4-yl)-1,3-benzodioxole-5-carboxamide (2)

The title compound (0.556 g, 1.13 mmol, 51% yield) was obtained through the same reaction as in step 1-3 using the compound (A3b) (0.796 g, 2.23 mmol) synthesized in step 2-2.

$^1$H-NMR (400 MHz, DMSO-$d_6$) δ: 1.34-1.44 (2H, m), 1.57-1.66 (2H, m), 1.62 (3H, s), 2.11 (6H, s), 2.14-2.19 (4H, m), 3.24-3.32 (2H, m), 3.88 (2H, m), 4.21 (2H, d, J=5.0 Hz), 5.85 (1H, s), 6.95 (1H, s), 8.14 (1H, t, J=5.0 Hz), 11.49 (1H, s).

MS (ESI) m/z: 491, 493 (M+H)$^+$.

Example 3

7-Bromo-2-[3-(dimethylamino)-1-bicyclo[1.1.1]pentanyl]-N-[(4,6-dimethyl-2-oxo-1,2-dihydropyridin-3-yl)methyl]-2,4-dimethyl-1,3-benzodioxole-5-carboxamide (3)

[Formula 28]

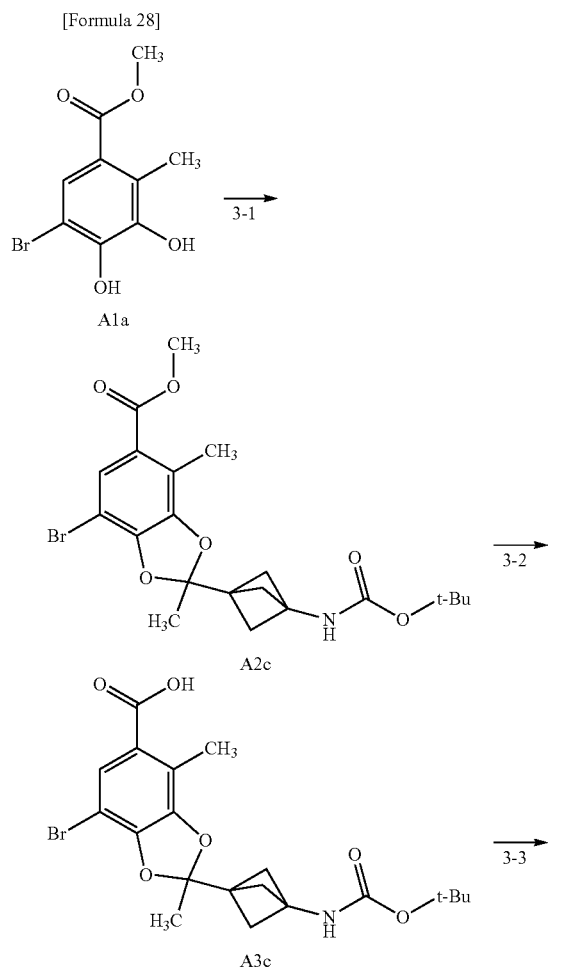

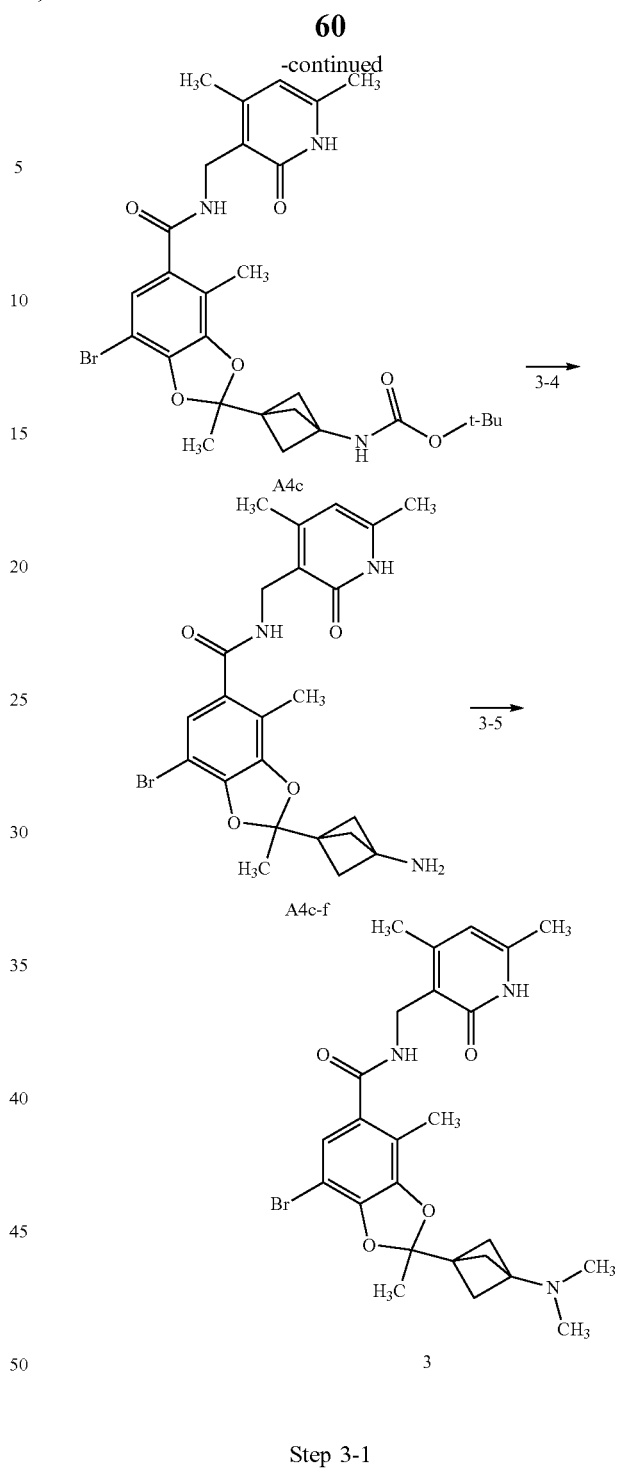

Step 3-1

Methyl 7-bromo-2-[3-(tert-butoxycarbonylamino)-1-bicyclo[1.1.1]pentanyl]-2,4-dimethyl-1,3-benzodioxole-5-carboxylate (A2c)

The title compound (0.495 g, 1.06 mmol, 61% yield) was obtained through the same reaction as in step 1-1 using the compound (A1a) (0.450 g, 1.72 mmol) synthesized in Reference Example 1 and the compound (S7) (0.536 g, 2.59 mmol) synthesized in Reference Example 7.

$^1$H-NMR (400 MHz, CDCl$_3$) δ: 1.43 (9H, s), 1.72 (3H, s), 1.95-2.15 (6H, m), 2.37 (3H, s), 3.85 (3H, s), 4.96 (1H, br s), 7.67 (1H, s).

Step 3-2

7-Bromo-2-[3-(tert-butoxycarbonylamino)-1-bicyclo[1.1.1]pentanyl]-2,4-dimethyl-1,3-benzodioxole-5-carboxylic Acid (A3c)

The title compound (0.467 g, 1.03 mmol, 98% yield) was obtained through the same reaction as in step 1-2 using the compound (A2c) (0.495 g, 1.06 mmol) synthesized in step 3-1.

Step 3-3 tert-Butyl N-[1-[7-bromo-5-[(4,6-dimethyl-2-oxo-1H-pyridin-3-yl)methylcarbamoyl]-2,4-dimethyl-1,3-benzodioxol-2-yl]-3-bicyclo[1.1.1]pentanyl]carbamate (A4c)

The title compound (0.572 g, 0.973 mmol, 94% yield) was obtained through the same reaction as in step 1-3 using the compound (A3c) (0.469 g, 1.03 mmol) synthesized in step 3-2.

$^1$H-NMR (400 MHz, CDCl$_3$) δ: 1.43 (9H, s), 1.68 (3H, s), 1.98-2.10 (6H, m), 2.21 (3H, s), 2.26 (3H, s), 2.37 (3H, s), 4.49 (2H, d, J=6.1 Hz), 4.99 (1H, s), 5.96 (1H, s), 7.00 (1H, s), 7.20-7.25 (1H, m).

MS (APCI) m/z: 588, 590 (M+H)$^+$.

Step 3-4

2-(3-Amino-1-bicyclo[1.1.1]pentanyl)-7-bromo-N-[(4,6-dimethyl-2-oxo-1,2-dihydropyridin-3-yl)methyl]-2,4-dimethyl-1,3-benzodioxole-5-carboxamide (A4c-f)

The compound (A4c) (0.572 g, 0.973 mmol) synthesized in step 3-3 was dissolved in methanol (2 mL). To the solution, a 4 M solution of hydrochloric acid in 1,4-dioxane (2.07 mL, 8.23 mmol) was added, and the mixture was stirred at room temperature for 1.5 hours. After the completion of the reaction, the reaction solution was neutralized by the addition of a saturated aqueous solution of sodium bicarbonate, followed by extraction using 20% methanol in chloroform. The organic layer was washed with saturated saline, dried over sodium sulfate, and then concentrated under reduced pressure to obtain the title compound (0.404 g, 0.827 mmol, 85% yield).

Step 3-5

7-Bromo-2-[3-(dimethylamino)-1-bicyclo[1.1.1]pentanyl]-N-[(4,6-dimethyl-2-oxo-1,2-dihydropyridin-3-yl)methyl]-2,4-dimethyl-1,3-benzodioxole-5-carboxamide (3)

The compound (A4c-f) (0.404 g, 0.827 mmol) synthesized in step 3-4 was dissolved in methanol (7.5 mL). To the solution, a 37% aqueous formaldehyde solution (0.141 g, 1.74 mmol) was added, and the mixture was stirred at room temperature for 10 minutes. Then, sodium triacetoxyborohydride (0.923 g, 4.14 mmol) was added thereto, and the mixture was stirred at room temperature for 18 hours. After the completion of the reaction, the reaction solution was neutralized with a 1 M aqueous sodium hydroxide solution, followed by extraction using 20% methanol in chloroform. The organic layer was washed with saturated saline, dried over sodium sulfate, and then concentrated under reduced pressure, and the obtained residue was purified by basic silica gel column chromatography (ethyl acetate:methanol=100:0→4 96:4) to obtain the title compound (0.309 g, 0.597 mmol, 72% yield).

$^1$H-NMR (400 MHz, DMSO-d$_6$) δ: 1.65 (6H, s), 1.67 (3H, s), 2.07 (6H, s), 2.10 (3H, s), 2.11 (3H, s), 2.17 (3H, s), 4.21 (2H, d, J=4.9 Hz), 5.86 (1H, s), 6.94 (1H, s), 8.15 (1H, t, J=4.9 Hz), 11.49 (1H, s).

MS (APCI) m/z: 516, 518 (M+H)$^+$.

Example 4

7-Bromo-2-[2-(dimethylamino)spiro[3.3]heptan-6-yl]-N-[(4,6-dimethyl-2-oxo-1,2-dihydropyridin-3-yl)methyl]-2,4-dimethyl-1,3-benzodioxole-5-carboxamide (4)

Step 4-1

Methyl 7-bromo-2-[2-(tert-butoxycarbonylamino)spiro[3.3]heptan-6-yl]-2,4-dimethyl-1,3-benzodioxole-5-carboxylate (A2d)

The title compound (0.657 g, 1.32 mmol, 86% yield) was obtained through the same reaction as in step 1-1 using the compound (A1a) (0.400 g, 1.53 mmol) synthesized in Reference Example 1 and the compound (S8-2) (0.541 g, 2.59 mmol) synthesized in Reference Example 8.

$^1$H-NMR (400 MHz, CDCl$_3$) δ: 1.42 (9H, s), 1.56 (3H, s), 1.71-1.84 (2H, m), 1.95-2.09 (3H, m), 2.10-2.15 (1H, m), 2.30-2.39 (1H, m), 2.38 (3H, s), 2.42-2.51 (1H, m), 2.69-2.78 (1H, m), 3.85 (3H, s), 3.91-4.02 (1H, m), 4.52-4.65 (1H, m), 7.66 (1H, br s).

Step 4-2

7-Bromo-2-[2-(tert-butoxycarbonylamino)spiro[3.3]heptan-6-yl]-2,4-dimethyl-1,3-benzodioxole-5-carboxylic Acid (A3d)

The title compound (0.603 g, 1.25 mmol, 95% yield) was obtained through the same reaction as in step 1-2 using the compound (A2d) (0.657 g, 1.32 mmol) synthesized in step 4-1.

Step 4-3 tert-Butyl N-[6-[7-bromo-5-[(4,6-dimethyl-2-oxo-1,2-dihydropyridin-3-yl)methylcarbamoyl]-2,4-dimethyl-1,3-benzodioxol-2-yl]spiro[3.3]heptan-2-yl]carbamate (A4d)

The title compound (0.519 g, 0.842 mmol, 67% yield) was obtained through the same reaction as in step 1-3 using the compound (A3d) (0.603 g, 1.25 mmol) synthesized in step 4-2.

$^1$H-NMR (400 MHz, CDCl$_3$) δ: 1.42 (9H, s), 1.53 (3H, s), 1.70-1.84 (2H, m), 1.92-2.14 (4H, m), 2.22 (3H, s), 2.26 (3H, s), 2.30-2.36 (1H, m), 2.37 (3H, s), 2.40-2.49 (1H, m), 2.66-2.76 (1H, m), 3.89-4.05 (1H, m), 4.50 (2H, d, J=5.5 Hz), 4.54-4.64 (1H, m), 5.96 (1H, s), 7.00 (1H, s), 7.22 (1H, br s).

MS (APCI) m/z: 616, 618 (M+H)$^+$.

Step 4-4

2-(2-Aminospiro[3.3]heptan-6-yl)-7-bromo-N-[4,6-dimethyl-2-oxo-1,2-dihydropyridin-3-yl)methyl]-2,4-dimethyl-1,3-benzodioxole-5-carboxamide (A4d-f)

The title compound (0.435 g, 0.842 mmol, 100% yield) was obtained through the same reaction as in step 3-4 using the compound (A4d) (0.519 g, 0.842 mmol) synthesized in step 4-3.

MS (APCI) m/z: 516, 518 (M+H)$^+$.

Step 4-5

7-Bromo-2-[2-(dimethylamino)spiro[3.3]heptan-6-yl]-N-[(4,6-dimethyl-2-oxo-1,2-dihydropyridin-3-yl)methyl]-2,4-dimethyl-1,3-benzodioxole-5-carboxamide (4)

The title compound (0.353 g, 0.648 mmol, 77% yield) was obtained through the same reaction as in step 3-5 using the compound (A4d-f) (0.435 g, 0.842 mmol) synthesized in step 4-4.

$^1$H-NMR (400 MHz, DMSO-d$_6$) δ: 1.53 (3H, s), 1.58-1.78 (2H, m), 1.79-2.01 (9H, m), 2.01-2.08 (1H, m), 2.10 (3H, s), 2.10 (3H, s), 2.16 (3H, s), 2.30-2.44 (1H, m), 2.71-2.83 (1H, m), 4.21 (2H, d, J=4.3 Hz), 5.85 (1H, s), 6.93 (1H, s), 8.15 (1H, t, J=4.3 Hz), 11.48 (1H, s).

MS (APCI) m/z: 544, 546 (M+H)$^+$.

Example 5

7-Bromo-N-[(4,6-dimethyl-2-oxo-1,2-dihydropyridin-3-yl)methyl]-2-(2-ethyl-2-azaspiro[3.3]heptan-6-yl)-2,4-dimethyl-1,3-benzodioxole-5-carboxamide (5)

Step 5-1 tert-Butyl 6-(7-bromo-5-methoxycarbonyl-2,4-dimethyl-1,3-benzodioxol-2-yl)-2-azaspiro[3.3]heptane-2-carboxylate (A2e)

The title compound (0.727 g, 1.51 mmol, 98% yield) was obtained through the same reaction as in step 1-1 using the compound (A1a) (0.400 g, 1.53 mmol) synthesized in Reference Example 1 and the compound (S9-2) (0.407 g, 1.84 mmol) synthesized in Reference Example 9.

$^1$H-NMR (400 MHz, CDCl$_3$) δ: 1.42 (9H, s), 1.58 (3H, s), 2.12-2.20 (2H, m), 2.26-2.34 (2H, m), 2.39 (3H, s), 2.67-2.76 (1H, m), 3.86 (3H, s), 3.86-3.88 (2H, m), 3.88-3.91 (2H, m), 7.68 (1H, s).

Step 5-2

7-Bromo-2-(2-tert-butoxycarbonyl-2-azaspiro[3.3]heptan-6-yl)-2,4-dimethyl-1,3-benzodioxole-5-carboxylic Acid (A3e)

The title compound (0.706 g, 1.51 mmol, 100% yield) was obtained through the same reaction as in step 1-2 using the compound (A2e) (0.727 g, 1.51 mmol) synthesized in step 5-1.

Step 5-3 tert-Butyl 6-[7-bromo-5-[(4,6-dimethyl-2-oxo-1,2-dihydropyridin-3-yl)methylcarbamoyl]-2,4-dimethyl-1,3-benzodioxol-2-yl]-2-azaspiro[3.3]heptane-2-carboxylate (A4e)

The title compound (0.723 g, 1.20 mmol, 80% yield) was obtained through the same reaction as in step 1-3 using the compound (A3e) (0.706 g, 1.51 mmol) synthesized in step 5-2.

$^1$H-NMR (400 MHz, CDCl$_3$) δ: 1.42 (9H, s), 1.55 (3H, s), 2.11-2.20 (2H, m), 2.23 (3H, s), 2.25-2.31 (2H, m), 2.27 (3H, s), 2.37 (3H, s), 2.64-2.73 (1H, m), 3.82-3.86 (2H, m), 3.86-3.90 (2H, m), 4.44-4.56 (2H, m), 5.97 (1H, s), 7.01 (1H, s).

MS (APCI) m/z: 602, 604 (M+H)$^+$.

Step 5-4

2-(2-Azaspiro[3.3]heptan-6-yl)-7-bromo-N-[(4,6-dimethyl-2-oxo-1,2-dihydropyridin-3-yl)methyl]-2,4-dimethyl-1,3-benzodioxole-5-carboxamide (A4e-f)

The title compound (0.603 g, 1.20 mmol, 100% yield) was obtained through the same reaction as in step 3-4 using the compound (A4e) (0.723 g, 1.20 mmol) synthesized in step 5-3.

MS (APCI) m/z: 502, 504 (M+H)$^+$.

Step 5-5

7-Bromo-N-[(4,6-dimethyl-2-oxo-1,2-dihydropyridin-3-yl)methyl]-2-(2-ethyl-2-azaspiro[3.3]heptan-6-yl)-2,4-dimethyl-1,3-benzodioxole-5-carboxamide (5)

The title compound (0.202 g, 0.380 mmol, 32% yield) was obtained through the same reaction as in step 3-5 using the compound (A4e-f) (0.603 g, 1.20 mmol) synthesized in step 5-4 and acetaldehyde (0.793 g, 18.0 mmol).

$^1$H-NMR (400 MHz, DMSO-d$_6$) δ: 1.11-1.21 (4H, m), 1.59 (3H, s), 1.75-1.90 (5H, m), 2.02-2.09 (1H, m), 2.10 (3H, s), 2.11 (3H, s), 2.13 (6H, s), 2.16 (3H, s), 4.21 (2H, d, J=4.9 Hz), 5.85 (1H, s), 6.94 (1H, s), 8.14 (1H, t, J=4.9 Hz), 11.48 (1H, s).

MS (APCI) m/z: 530, 532 (M+H)$^+$.

Example 6

7-Bromo-N-[(4,6-dimethyl-2-oxo-1,2-dihydropyridin-3-yl)methyl]-2,4-dimethyl-2-(1-methylpyrrolidin-3-yl)-1,3-benzodioxole-5-carboxamide (6)

[Formula 29]

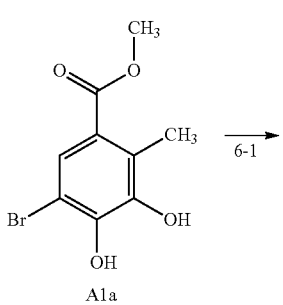

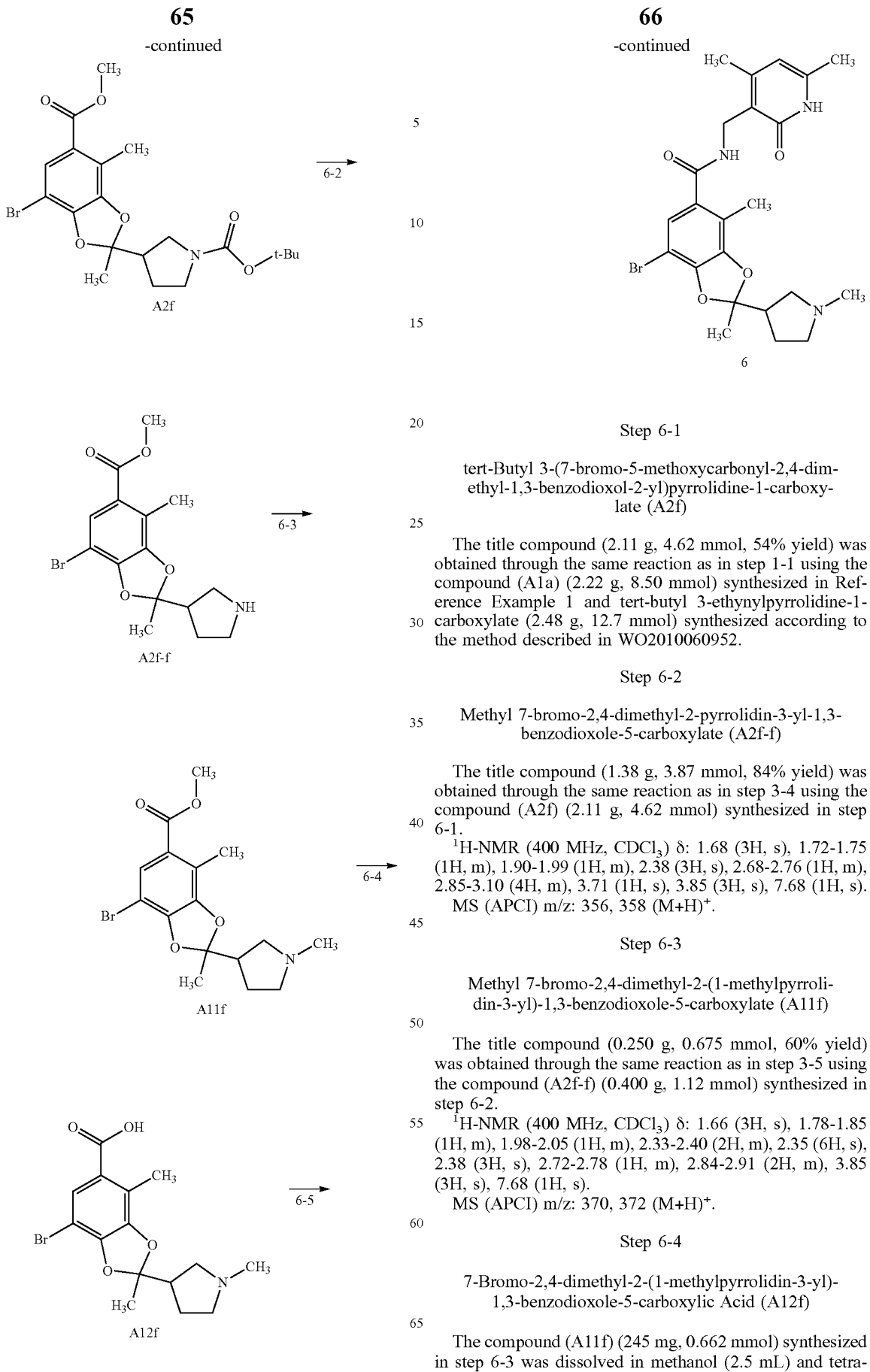

Step 6-1 tert-Butyl 3-(7-bromo-5-methoxycarbonyl-2,4-dimethyl-1,3-benzodioxol-2-yl)pyrrolidine-1-carboxylate (A2f)

The title compound (2.11 g, 4.62 mmol, 54% yield) was obtained through the same reaction as in step 1-1 using the compound (A1a) (2.22 g, 8.50 mmol) synthesized in Reference Example 1 and tert-butyl 3-ethynylpyrrolidine-1-carboxylate (2.48 g, 12.7 mmol) synthesized according to the method described in WO2010060952.

Step 6-2

Methyl 7-bromo-2,4-dimethyl-2-pyrrolidin-3-yl-1,3-benzodioxole-5-carboxylate (A2f-f)

The title compound (1.38 g, 3.87 mmol, 84% yield) was obtained through the same reaction as in step 3-4 using the compound (A2f) (2.11 g, 4.62 mmol) synthesized in step 6-1.
$^1$H-NMR (400 MHz, CDCl$_3$) δ: 1.68 (3H, s), 1.72-1.75 (1H, m), 1.90-1.99 (1H, m), 2.38 (3H, s), 2.68-2.76 (1H, m), 2.85-3.10 (4H, m), 3.71 (1H, s), 3.85 (3H, s), 7.68 (1H, s).
MS (APCI) m/z: 356, 358 (M+H)$^+$.

Step 6-3

Methyl 7-bromo-2,4-dimethyl-2-(1-methylpyrrolidin-3-yl)-1,3-benzodioxole-5-carboxylate (A11f)

The title compound (0.250 g, 0.675 mmol, 60% yield) was obtained through the same reaction as in step 3-5 using the compound (A2f-f) (0.400 g, 1.12 mmol) synthesized in step 6-2.
$^1$H-NMR (400 MHz, CDCl$_3$) δ: 1.66 (3H, s), 1.78-1.85 (1H, m), 1.98-2.05 (1H, m), 2.33-2.40 (2H, m), 2.35 (6H, s), 2.38 (3H, s), 2.72-2.78 (1H, m), 2.84-2.91 (2H, m), 3.85 (3H, s), 7.68 (1H, s).
MS (APCI) m/z: 370, 372 (M+H)$^+$.

Step 6-4

7-Bromo-2,4-dimethyl-2-(1-methylpyrrolidin-3-yl)-1,3-benzodioxole-5-carboxylic Acid (A12f)

The compound (A11f) (245 mg, 0.662 mmol) synthesized in step 6-3 was dissolved in methanol (2.5 mL) and tetrahydrofuran (5 mL). To the solution, a 1 M aqueous sodium hydroxide solution (1.70 mL 1.70 mmol) was added under ice cooling, and the mixture was stirred at room temperature for 7 hours. After the completion of the reaction, the reaction solution was neutralized with 1 M hydrochloric acid, and the solvent was concentrated under reduced pressure to obtain 7-bromo-2,4-dimethyl-2-(1-methylpyrrolidin-3-yl)-1,3-benzodioxole-5-carboxylic acid (0.197 g, 0.552 mmol, 83% yield).

$^1$H-NMR (400 MHz, CD$_3$OD) δ: 1.68 (3H, s), 2.04-2.13 (1H, m), 2.21-2.32 (1H, m), 2.28 (3H, s), 2.81 (3H, s), 3.35-3.12 (4H, m), 3.41-3.48 (1H, m), 7.30 (1H, s).

MS (ESI) m/z: 356, 358 (M+H)$^+$.

Step 6-5

7-Bromo-N-[(4,6-dimethyl-2-oxo-1,2-dihydropyridin-3-yl)methyl]-2,4-dimethyl-2-(1-methylpyrrolidin-3-yl)-1,3-benzodioxole-5-carboxamide (6)

The title compound (0.078 g, 0.159 mmol, 29% yield) was obtained through the same reaction as in step 1-3 using the compound (A12f) (0.196 g, 0.550 mmol) synthesized in step 6-4.

$^1$H-NMR (400 MHz, CD$_3$OD) δ: 1.64 (3H, s), 1.82-1.89 (1H, m), 2.00-2.08 (1H, m), 2.16 (3H, d, J=3.0 Hz), 2.24 (3H, s), 2.35 (3H, s), 2.36 (3H, s), 2.40-2.51 (2H, m), 2.78-2.85 (1H, m), 2.88-2.97 (2H, m), 4.42 (2H, s), 4.62 (1H, s), 6.10 (1H, s), 7.01 (1H, s).

MS (ESI) m/z: 490, 492 (M+H)$^+$.

Example 7

(2R)-7-Bromo-N-[(4,6-dimethyl-2-oxo-1,2-dihydropyridin-3-yl)methyl]-2-(1-ethyl-4-piperidyl)-2,4-dimethyl-1,3-benzodioxole-5-carboxamide (7)

[Formula 30]

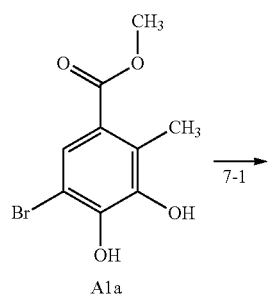

A1a

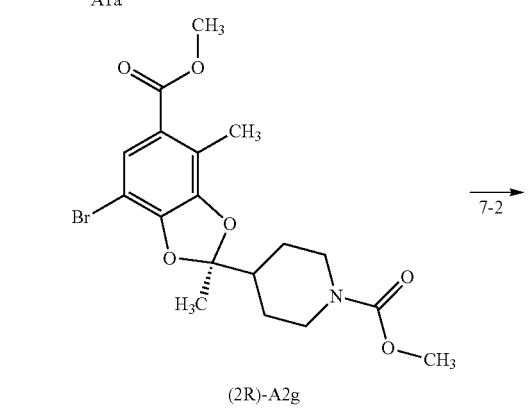

(2R)-A2g

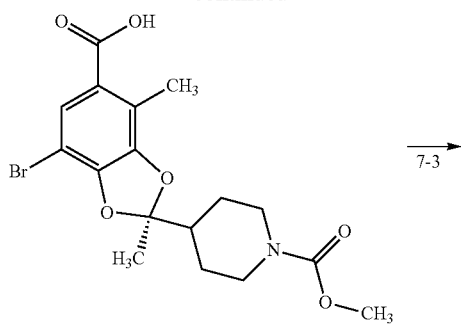

(2R)-A3g

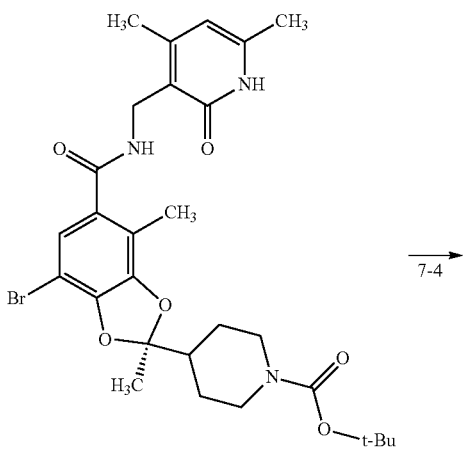

(2R)-A4g-p

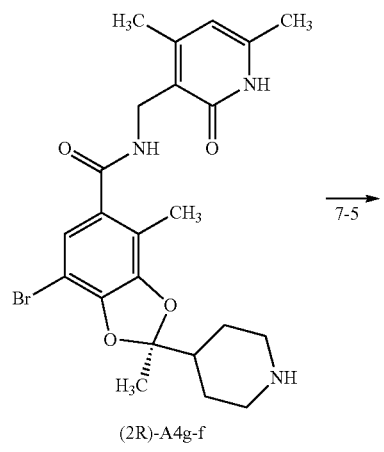

(2R)-A4g-f

-continued

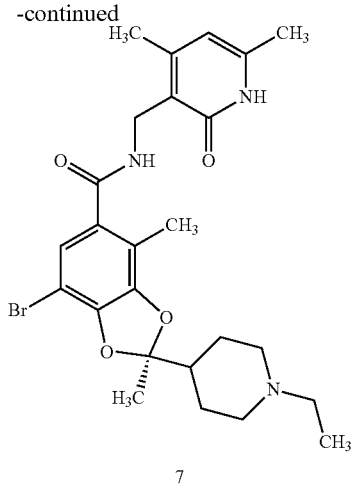

Step 7-1 tert-Butyl 4-[(2R)-7-bromo-5-methoxycarbonyl-2,4-dimethyl-1,3-benzodioxol-2-yl]piperidine-1-carboxylate ((2R)-A2g)

A racemate of the title compound (4.76 g, 10.1 mmol, 35% yield) was obtained through the same reaction as in step 1-1 using the compound (A1a) (7.50 g, 28.7 mmol) synthesized in Reference Example 1 and tert-butyl 4-ethynylpiperidine-1-carboxylate (9.02 g, 43.1 mmol) synthesized according to the method described in WO 2008156739.

$^1$H-NMR (400 MHz, CDCl$_3$) δ: 1.34-1.49 (2H, m), 1.45 (9H, s), 1.64 (3H, s), 1.77-1.86 (2H, m), 1.96-2.05 (1H, m), 2.38 (3H, s), 2.61-2.71 (2H, m), 3.85 (3H, s), 4.05-4.35 (2H, m), 7.67 (1H, s).

This compound was resolved into each enantiomer under the following conditions:
Column: Daicel CHIRALCEL OZ-H 4.6 mm ID×250 mm L
Elution solvent: 100% acetonitrile
Flow rate: 1.00 mL/min
Temperature: 25° C.
First peak: 5.7 min (specific rotation [α]$_D^{20}$=−4.0 (C=1.0, chloroform))
Second peak: 6.9 min (specific rotation [α]$_D^{20}$=+3.6 (C=1.0, chloroform))

The following steps were carried out using the compound ((2R)-A2g) of the second peak that was separated using a preparative chiral column and identified as the R form.

Step 7-2

(2R)-7-Bromo-2-(1-tert-butoxycarbonyl-4-piperidyl)-2,4-dimethyl-1,3-benzodioxole-5-carboxylic Acid ((2R)-A3g)

The title compound (9.41 g, 20.6 mmol, 100% yield) was obtained through the same reaction as in step 1-2 using the compound ((2R)-A2g) (9.70 g, 20.6 mmol) synthesized in step 7-1.

Step 7-3 tert-Butyl 4-[(2R)-7-bromo-5-[(4,6-dimethyl-2-oxo-1,2-dihydropyridin-3-yl)methylcarbamoyl]-2,4-dimethyl-1,3-benzodioxol-2-yl]piperidine-1-carboxylate ((2R)-A4g-p)

The title compound (10.8 g, 18.3 mmol, 89% yield) was obtained through the same reaction as in step 1-3 using the compound ((2R)-A3g) (9.41 g, 20.6 mmol) synthesized in step 7-2.

$^1$H-NMR (400 MHz, CDCl$_3$) δ: 1.30-1.45 (2H, m), 1.45 (9H, s), 1.62 (3H, s), 1.76-1.86 (2H, m), 1.94-2.02 (1H, m), 2.22 (3H, s), 2.27 (3H, s), 2.37 (3H, s), 2.60-2.71 (2H, m), 4.19 (2H, m), 4.50 (2H, d, J=6.1 Hz), 5.97 (1H, s), 7.01 (1H, s), 7.23-7.27 (1H, m), 12.24 (1H, br s).
MS (APCI) m/z: 590, 592 (M+H)$^+$.

Step 7-4

(2R)-7-Bromo-N-[(4,6-dimethyl-2-oxo-1,2-dihydropyridin-3-yl)methyl]-2,4-dimethyl-2-(4-piperidyl)-1,3-benzodioxole-5-carboxamide ((2R)-A4g-f)

The title compound (8.96 g, 18.3 mmol, 100% yield) was obtained through the same reaction as in step 3-4 using the compound ((2R)-A4g-p) (10.8 g, 18.3 mmol) synthesized in step 7-3.
MS (APCI) m/z: 490, 492 (M+H)$^+$.

Step 7-5

(2R)-7-Bromo-N-[(4,6-dimethyl-2-oxo-1,2-dihydropyridin-3-yl)methyl]-2-(1-ethyl-4-piperidyl)-2,4-dimethyl-1,3-benzodioxole-5-carboxamide (7)

The title compound (5.40 g, 10.4 mmol, 57% yield) was obtained through the same reaction as in step 3-5 using the compound ((2R)-A4g-f) (8.96 g, 18.3 mmol) synthesized in step 7-4 and acetaldehyde (12.1 g, 274 mmol).

$^1$H-NMR (400 MHz, DMSO-d$_6$) δ: 0.96 (3H, t, J=7.3 Hz), 1.30-1.40 (2H, m), 1.61 (3H, s), 1.65-1.73 (2H, m), 1.73-1.88 (3H, m), 2.10 (3H, s), 2.11 (3H, s), 2.16 (3H, s), 2.27 (2H, q, J=6.7 Hz), 2.87-2.93 (2H, m), 4.21 (2H, d, J=4.9 Hz), 5.85 (1H, s), 6.94 (1H, s), 8.14 (1H, t, J=4.9 Hz), 11.48 (1H, s).
MS (APCI) m/z: 518, 520 (M+H)$^+$.

Example 8

(2R)-7-Bromo-N-[(4,6-dimethyl-2-oxo-1,2-dihydropyridin-3-yl)methyl]-2,4-dimethyl-2-(1-methyl-4-piperidyl)-1,3-benzodioxole-5-carboxamide (8)

The title compound (0.271 g, 0.537 mmol, 88% yield) was obtained through the same methylation reaction as in step 3-5 using the compound ((2R)-A4g-f) (0.300 g, 0.612 mmol) synthesized in step 7-4.

$^1$H-NMR (400 MHz, DMSO-d$_6$) δ: 1.30-1.43 (2H, m), 1.61 (3H, s), 1.64-1.71 (2H, m), 1.74-1.85 (3H, m), 2.10 (3H, s), 2.11 (3H, s), 2.12 (3H, s), 2.16 (3H, s), 2.76-2.83

(2H, m), 4.21 (2H, d, J=4.9 Hz), 5.85 (1H, s), 6.94 (1H, s), 8.14 (1H, t, J=4.9 Hz), 11.48 (1H, s).

MS (APCI) m/z: 504, 506 (M+H)$^+$.

Example 9

(2R)-7-Bromo-N-[(4,6-dimethyl-2-oxo-1,2-dihydropyridin-3-yl)methyl]-2,4-dimethyl-2-(1-propyl-4-piperidyl)-1,3-benzodioxole-5-carboxamide (9)

The title compound (0.136 g, 0.255 mmol, 42% yield) was obtained through the same propylation reaction as in step 3-5 using the compound ((2R)-A4g-f) (0.301 g, 0.614 mmol) synthesized in step 7-4 and propionaldehyde (0.535 g, 9.20 mmol).

$^1$H-NMR (400 MHz, DMSO-d$_6$) δ: 0.82 (3H, t, J=7.6 Hz), 1.29-1.44 (4H, m), 1.61 (3H, s), 1.65-1.73 (2H, m), 1.75-1.87 (3H, m), 2.10 (3H, s), 2.11 (3H, s), 2.16-2.21 (2H, m), 2.17 (3H, s), 2.86-2.93 (2H, m), 4.21 (2H, d, J=4.9 Hz), 5.85 (1H, s), 6.94 (1H, s), 8.14 (1H, t, J=4.9 Hz), 11.48 (1H, s).

MS (APCI) m/z: 532, 534 (M+H)$^+$.

Example 10

(2R)-7-Bromo-N-[(4,6-dimethyl-2-oxo-1H-pyridin-3-yl)methyl]-2-[1-(2-methoxyethyl)-4-piperidyl]-2,4-dimethyl-1,3-benzodioxole-5-carboxamide (10)

To a solution of the compound ((2R)-A4g-f) (0.300 g, 0.612 mmol) synthesized in step 7-4 in dimethylformamide (10 mL), N,N-diisopropylethylamine (0.131 g, 1.01 mmol) and 2-bromoethyl methyl ether (0.141 g, 1.01 mmol) were added, and the mixture was stirred at 45° C. for 8 hours. After the completion of the reaction, the reaction solution was concentrated, and the residue was purified by basic silica gel column chromatography (ethyl acetate:methanol=100:0→93:7) to obtain the title compound (0.200 g, 0.364 mmol, 60% yield).

$^1$H-NMR (400 MHz, DMSO-d$_6$) δ: 1.28-1.41 (2H, m), 1.61 (3H, s), 1.62-1.71 (2H, m), 1.78-1.93 (3H, m), 2.10 (3H, s), 2.11 (3H, s), 2.16 (3H, s), 2.41 (2H, t, J=6.0 Hz), 2.86-2.94 (2H, m), 3.21 (3H, s), 3.39 (2H, t, J=6.0 Hz), 4.21 (2H, d, J=4.9 Hz), 5.85 (1H, s), 6.94 (1H, s), 8.14 (1H, t, J=4.9 Hz), 11.48 (1H, s).

MS (APCI) m/z: 548, 550 (M+H)$^+$.

Example 11

(2R)-7-Bromo-N-[(4,6-dimethyl-2-oxo-1,2-dihydropyridin-3-yl)methyl]-2-(1-ethylsulfonyl-4-piperidyl)-2,4-dimethyl-1,3-benzodioxole-5-carboxamide (11)

The compound ((2R)-A4g-f) (0.390 g, 0.795 mmol) synthesized in step 7-4 was dissolved in dichloromethane (5 mL). To the solution, triethylamine (0.131 g, 1.29 mmol) was added, then ethanesulfonyl chloride (0.123 g, 0.954 mmol) was added under ice cooling, and the mixture was stirred at room temperature for 4 hours. After the completion of the reaction, water was added to the reaction solution, followed by extraction with chloroform. The extract was concentrated. The organic layer was washed with saturated saline, dried over sodium sulfate, and then concentrated under reduced pressure, and the obtained residue was purified by silica gel column chromatography (chloroform:methanol=100:0→96:4) to obtain the title compound (0.367 g, 0.631 mmol, 79% yield).

$^1$H-NMR (400 MHz, DMSO-d$_6$) δ: 1.19 (3H, t, J=7.3 Hz), 1.28-1.40 (2H, m), 1.63 (3H, s), 1.80-1.88 (2H, m), 2.02-2.10 (1H, m), 2.11 (6H, s), 2.17 (3H, s), 2.73-2.82 (2H, m), 3.02 (2H, q, J=7.3 Hz), 3.65-3.70 (2H, m), 4.21 (2H, d, J=4.9 Hz), 5.86 (1H, s), 6.96 (1H, s), 8.15 (1H, t, J=4.9 Hz), 11.49 (1H, s).

MS (APCI) m/z: 582, 584 (M+H)$^+$.

Example 12

(2R)-7-Bromo-2-(1-ethyl-4-piperidyl)-2,4-dimethyl-N-[(6-methyl-2-oxo-4-propyl-1,2-dihydropyridin-3-yl)methyl]-1,3-benzodioxole-5-carboxamide (12)

Step 12-1 tert-Butyl 4-[(2R)-7-bromo-2,4-dimethyl-5-[(6-methyl-2-oxo-4-propyl-1,2-dihydropyridin-3-yl)methylcarbamoyl]-1,3-benzodioxol-2-yl]piperidine-1-carboxylate ((2R)-A4h)

The title compound (1.83 g, 2.95 mmol, 67% yield) was obtained through the same reaction as in step 1-3 using the compound ((2R)-A3g) (2.00 g, 4.38 mmol) synthesized in step 7-2 and 3-(aminomethyl)-6-methyl-4-propyl-1H-pyridin-2-one (0.869 g, 4.82 mmol) synthesized according to the method described in WO2011140324.

$^1$H-NMR (400 MHz, CDCl$_3$) δ: 0.99 (3H, t, J=7.6 Hz), 1.33-1.43 (2H, m), 1.45 (9H, s), 1.58-1.69 (5H, m), 1.76-1.84 (2H, m), 1.93-2.02 (1H, m), 2.21 (3H, s), 2.27 (3H, s), 2.66 (4H, m), 4.21 (2H, br s), 4.51 (2H, d, J=5.5 Hz), 5.96 (1H, s), 7.00 (1H, s).

MS (APCI) m/z: 618, 620 (M+H)$^+$.

Step 12-2

(2R)-7-Bromo-2,4-dimethyl-N-[(6-methyl-2-oxo-4-propyl-1,2-dihydropyridin-3-yl)methyl]-2-(4-piperidyl)-1,3-benzodioxole-5-carboxamide ((2R)-A4h-f)

The title compound (1.53 g, 2.95 mmol, 100% yield) was obtained through the same reaction as in step 3-4 using the compound ((2R)-A4h) (1.83 g, 2.95 mmol) synthesized in step 12-1.

MS (APCI) m/z: 518, 520 (M+H)$^+$.

Step 12-3

(2R)-7-Bromo-2-(1-ethyl-4-piperidyl)-2,4-dimethyl-N-[(6-methyl-2-oxo-4-propyl-1,2-dihydropyridin-3-yl)methyl]-1,3-benzodioxole-5-carboxamide (12)

The title compound (0.387 g, 0.707 mmol, 37% yield) was obtained through the same reaction as in step 3-5 using the compound ((2R)-A4h-f) (1.00 g, 1.93 mmol) synthesized in step 12-2 and acetaldehyde (1.28 g, 28.9 mmol).

$^1$H-NMR (400 MHz, DMSO-d$_6$) δ: 0.91 (3H, t, J=7.6 Hz), 0.96 (3H, t, J=7.2 Hz), 1.29-1.40 (2H, m), 1.46-1.56 (2H, m), 1.61 (3H, s), 1.65-1.73 (2H, m), 1.74-1.88 (3H, m), 2.10 (3H, s), 2.12 (3H, s), 2.27 (2H, q, J=7.2 Hz), 2.44-2.49 (2H, m), 2.82-2.94 (2H, m), 4.22 (2H, d, J=4.9 Hz), 5.88 (1H, s), 6.93 (1H, s), 8.12 (1H, t, J=4.9 Hz), 11.49 (1H, s).

MS (APCI) m/z: 546, 548 (M+H)$^+$.

Examples 13 and 14

[Formula 31]

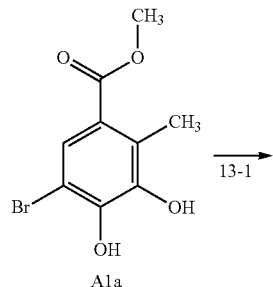
A1a

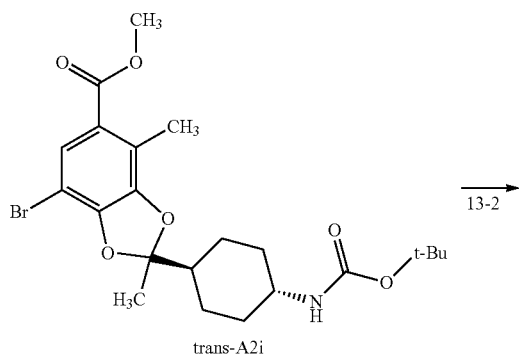
trans-A2i

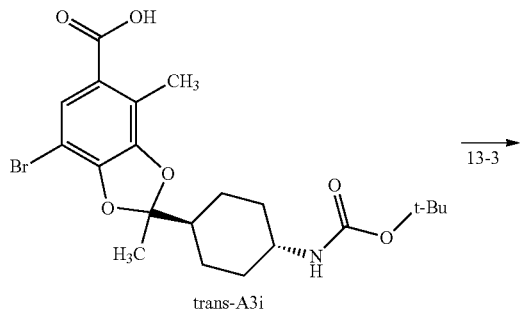
trans-A3i

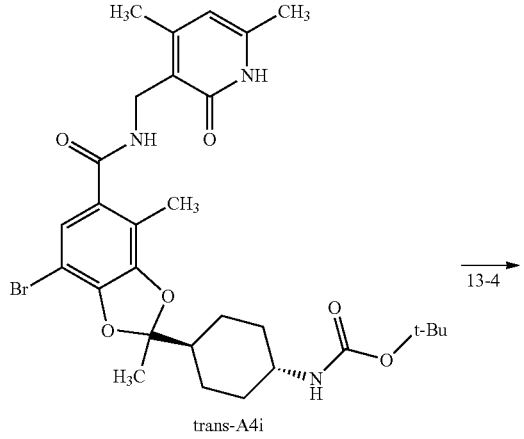
trans-A4i

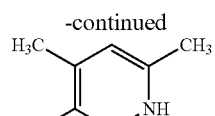
-continued

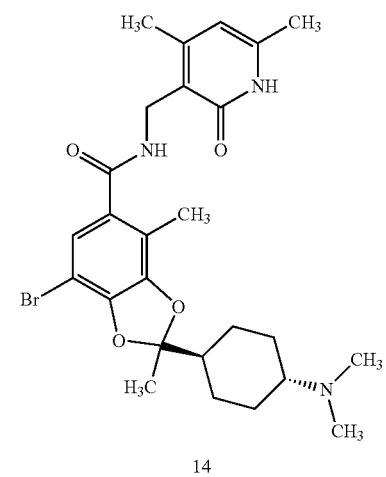 [SMILES: CCc1cc(C)[nH]c(=O)c1CNC(=O)c1cc(Br)c2c(c1C)OC(C)([C@H]1CC[C@H](N(C)C)CC1)O2]
13

14

Example 13

2-(trans-4-Aminocyclohexyl)-7-bromo-N-[(4,6-dimethyl-2-oxo-1,2-dihydropyridin-3-yl)methyl]-2,4-dimethyl-1,3-benzodioxole-5-carboxamide (13)

Step 13-1

Methyl 7-bromo-2-[trans-4-(tert-butoxycarbonylamino)cyclohexyl]-2,4-dimethyl-1,3-benzodioxole-5-carboxylate (trans-A2i)

The title compound (38.9 g, 80.3 mmol, 89% yield) was obtained through the same reaction as in step 1-1 using the compound (A1a) (23.5 g, 90.0 mmol) synthesized in Reference Example 1, the compound (S13) (9.02 g, 43.1 mmol) synthesized in Reference Example 13, triruthenium(0) dodecacarbonyl (1.44 g, 2.25 mmol), and 5-(di-tert-butylphosphino)-1',3',5'-triphenyl-1'H-[1,4']bipyrazole (3.42 g, 6.75 mmol).

$^1$H-NMR (400 MHz, CDCl$_3$) δ: 1.04-1.15 (2H, m), 1.25-1.38 (2H, m), 1.44 (9H, s), 1.63 (3H, s), 1.79-1.87 (1H, m), 1.91-1.99 (2H, m), 2.04-2.12 (2H, m), 2.38 (3H, s), 3.31-3.46 (1H, m), 3.84 (3H, s), 4.37 (1H, br s), 7.67 (1H, s).

Step 13-2

7-Bromo-2-[trans-4-(tert-butoxycarbonylamino)cyclohexyl]-2,4-dimethyl-1,3-benzodioxole-5-carboxylic Acid (trans-A3i)

The title compound (22.8 g, 48.5 mmol, 100% yield) was obtained through the same reaction as in step 1-2 using the compound (trans-A2i) (23.5 g, 48.5 mmol) synthesized in step 13-1.

$^1$H-NMR (400 MHz, CDCl$_3$) δ: 1.04-1.16 (2H, m), 1.25-1.38 (2H, m), 1.44 (9H, s), 1.64 (3H, s), 1.80-1.90 (1H, m), 1.92-2.00 (2H, m), 2.06-2.16 (2H, m), 2.41 (3H, s), 3.35-3.48 (1H, m), 4.40 (1H, br s), 7.80 (1H, s).

MS (ESI) m/z: 468, 470 (M−H)$^-$.

Step 13-3 tert-Butyl N-[trans-4-[7-bromo-5-[(4,6-dimethyl-2-oxo-1,2-dihydropyridin-3-yl)methylcarbamoyl]-2,4-dimethyl-1,3-benzodioxol-2-yl]cyclohexyl]carbamate (trans-A4i)

The title compound (26.8 g, 44.3 mmol, 91% yield) was obtained through the same reaction as in step 1-3 using the compound (trans-A3i) (22.8 g, 48.5 mmol) synthesized in step 13-2.

$^1$H-NMR (400 MHz, CDCl$_3$) δ: 1.02-1.15 (2H, m), 1.23-1.40 (2H, m), 1.43 (9H, s), 1.59 (3H, s), 1.75-1.84 (1H, m), 1.89-1.97 (2H, m), 2.02-2.10 (2H, m), 2.21 (3H, s), 2.26 (3H, s), 2.37 (3H, s), 3.34-3.45 (1H, m), 4.39 (1H, d, J=8.4 Hz), 4.49 (2H, d, J=5.5 Hz), 5.96 (1H, s), 7.00 (1H, s), 7.21 (1H, t, J=5.5 Hz).

MS (ESI) m/z: 604, 606 (M+H)$^+$.

Step 13-4

2-(trans-4-Aminocyclohexyl)-7-bromo-N-[(4,6-dimethyl-2-oxo-1,2-dihydropyridin-3-yl)methyl]-2,4-dimethyl-1,3-benzodioxole-5-carboxamide (13)

The title compound (4.20 g, 8.33 mmol, 83% yield) was obtained through the same reaction as in step 3-4 using the compound (trans-A4i) (6.04 g, 9.99 mmol) synthesized in step 13-3, followed by purification by basic silica gel chromatography (ethyl acetate:methanol=100:0→30:70).

$^1$H-NMR (400 MHz, DMSO-d$_6$) δ: 0.93-1.05 (2H, m), 1.08-1.23 (2H, m), 1.59 (3H, s), 1.73-1.85 (5H, m), 2.10 (3H, s), 2.11 (3H, s), 2.16 (3H, s), 2.39-2.49 (1H, m), 4.21 (2H, d, J=4.9 Hz), 5.85 (1H, s), 6.94 (1H, s), 8.14 (1H, t, J=4.9 Hz).

MS (ESI) m/z: 504, 506 (M+H)$^+$.

Example 14

7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (14)

Step 14

The title compound (20.0 g, 37.6 mmol, 90% yield) was obtained through the same reaction as in step 3-5 using the compound (13) (21.0 g, 41.6 mmol) synthesized in step 13-4.

$^1$H-NMR (400 MHz, DMSO-d$_6$) δ: 1.08-1.23 (4H, m), 1.59 (3H, s), 1.75-1.90 (5H, m), 2.02-2.09 (1H, m), 2.10 (3H, s), 2.11 (3H, s), 2.13 (6H, s), 2.16 (3H, s), 4.21 (2H, d, J=4.9 Hz), 5.85 (1H, s), 6.94 (1H, s), 8.14 (1H, t, J=4.9 Hz), 11.48 (1H, s).

MS (APCI) m/z: 532, 534 (M+H)$^+$.

This compound was resolved into each enantiomer under the following conditions:
Column: Daicel CHIRALCEL OZ-3 4.6 mm ID×150 mm L
Elution solvent: n-hexane:ethanol:diethylamine=60:40:0.04 (V/V)
Flow rate: 1.00 mL/min
Temperature: 35° C.
First peak: 4.4 min (specific rotation $[α]_D^{20}$=−7.2 (C=1.0, chloroform))
Second peak: 6.6 min (specific rotation $[α]_D^{20}$=+9.0 (C=1.0, chloroform))

Example 15

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (15)

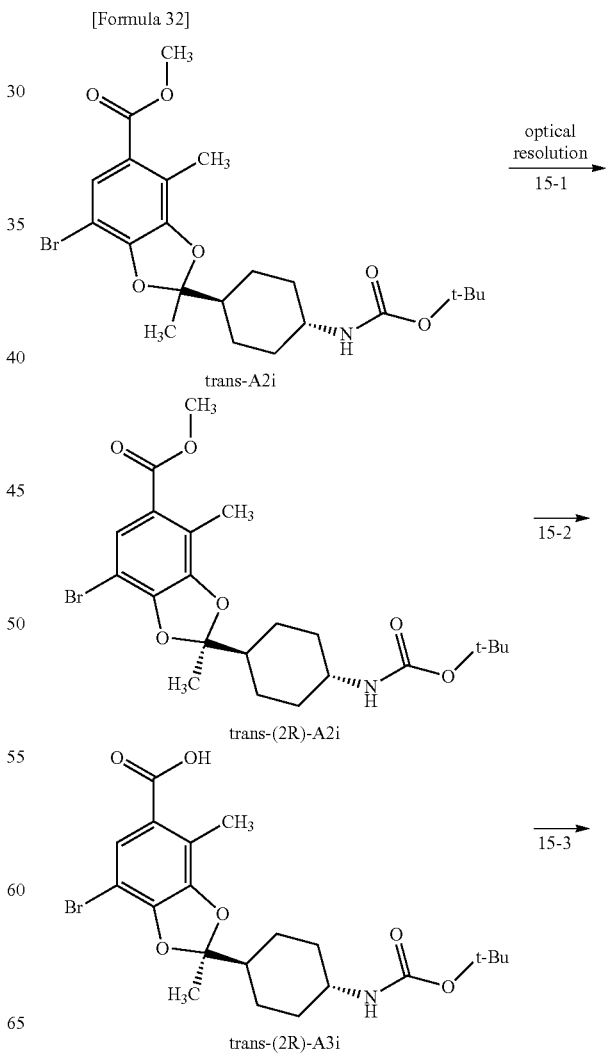

[Formula 32]

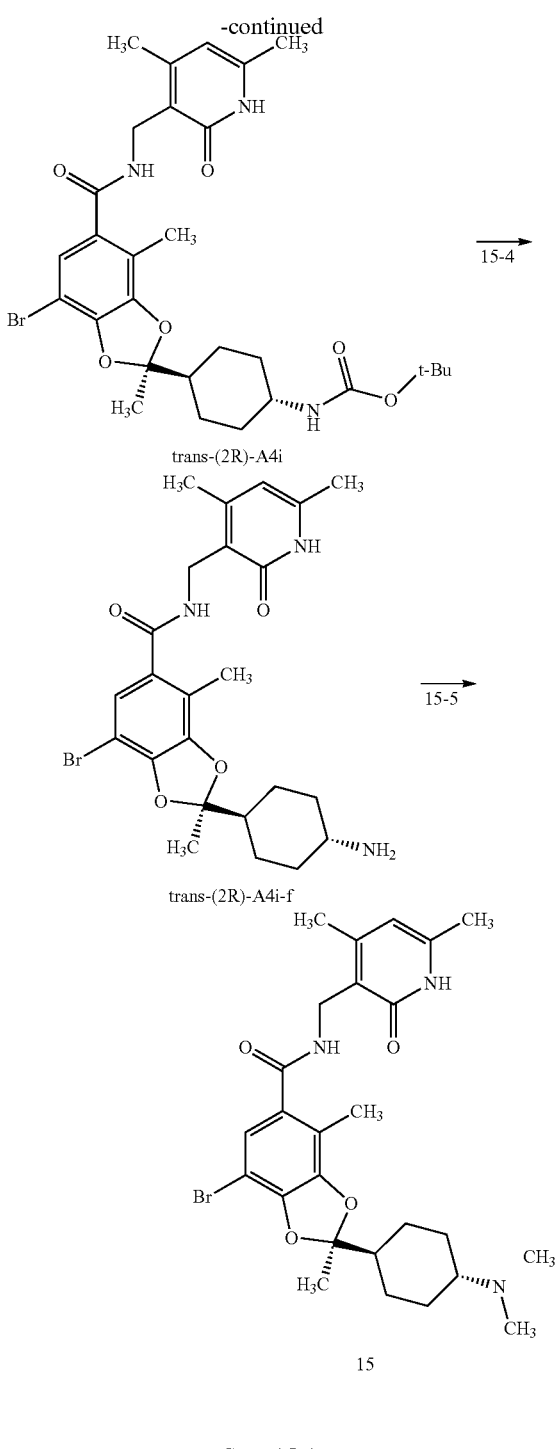

trans-(2R)-A4i trans-(2R)-A4i-f

15

Step 15-1

(2R)-Methyl 7-bromo-2-[trans-4-(tert-butoxycarbonylamino)cyclohexyl]-2,4-dimethyl-1,3-benzodioxole-5-carboxylate (trans-(2R)-A2i)

The compound (trans-A2i) synthesized in step 13-1 was resolved into each enantiomer under the following conditions:
Column: Daicel CHIRALCEL OZ-H 4.6 mm ID×250 mm L
Elution solvent: n-hexane:ethanol=98:2 (V/V)
Flow rate: 1.00 mL/min
Temperature: 25° C.

First peak: 11.2 min (specific rotation $[\alpha]_D^{20}$=−6.5 (C=1.0, chloroform))
Second peak: 12.3 min (specific rotation $[\alpha]_D^{20}$=+6.3 (C=1.0, chloroform))

The following steps were carried out using the compound (trans-(2R)-A2i) of the second peak that was separated using a preparative chiral column and identified as the R form.

Step 15-2

(2R)-7-Bromo-2-[trans-4-(tert-butoxycarbonylamino)cyclohexyl]-2,4-dimethyl-1,3-benzodioxole-5-carboxylic Acid (trans-(2R)-A3i)

The title compound (0.903 g, 1.92 mmol, 97% yield) was obtained through the same reaction as in step 1-2 using the compound (trans-(2R)-A2i) (second peak, 0.956 g, 1.97 mmol) separated in step 15-1.

Step 15-3 tert-Butyl N-[trans-4-[(2R)-7-bromo-5-[(4,6-dimethyl-2-oxo-1,2-dihydropyridin-3-yl)methylcarbamoyl]-2,4-dimethyl-1,3-benzodioxol-2-yl]cyclohexyl]carbamate (trans-(2R)-A4i)

The title compound (0.801 g, 1.32 mmol, 69% yield) was obtained through the same reaction as in step 1-3 using the compound (trans-(2R)-A3i) (0.903 g, 1.92 mmol) synthesized in step 15-2.
$^1$H-NMR (400 MHz, CDCl$_3$) δ: 1.03-1.15 (2H, m), 1.21-1.38 (2H, m), 1.44 (9H, s), 1.59 (3H, s), 1.75-1.84 (1H, m), 1.89-1.97 (2H, m), 2.02-2.10 (2H, m), 2.21 (3H, s), 2.26 (3H, s), 2.37 (3H, s), 3.34-3.45 (1H, m), 4.41-4.45 (1H, m), 4.49 (2H, d, J=6.0 Hz), 5.95 (1H, s), 7.00 (1H, s), 7.18 (1H, t, J=6.0 Hz).
MS (APCI) m/z: 604, 606 (M+H)$^+$.

Step 15-4

(2R)-2-(trans-4-Aminocyclohexyl)-7-bromo-N-[(4,6-dimethyl-2-oxo-1,2-dihydropyridin-3-yl)methyl]-2,4-dimethyl-1,3-benzodioxole-5-carboxamide (trans-(2R)-A4i-f)

The title compound (0.668 g, 1.32 mmol, 100% yield) was obtained through the same reaction as in step 3-4 using the compound (trans-(2R)-A4i) (0.801 g, 1.32 mmol) synthesized in step 15-3.
$^1$H-NMR (400 MHz, DMSO-d$_6$) δ: 0.93-1.05 (2H, m), 1.08-1.23 (2H, m), 1.59 (3H, s), 1.73-1.85 (5H, m), 2.10 (3H, s), 2.11 (3H, s), 2.16 (3H, s), 2.39-2.49 (1H, m), 4.21 (2H, d, J=4.9 Hz), 5.85 (1H, s), 6.94 (1H, s), 8.14 (1H, t, J=4.9 Hz).
MS (ESI) m/z: 504, 506 (M+H)$^+$.

Step 15-5

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (15)

The title compound (0.616 g, 1.16 mmol, 87% yield) was obtained through the same reaction as in step 3-5 using the compound (trans-(2R)-A4i-f) (0.668 g, 1.32 mmol) synthesized in step 15-4.

$^1$H-NMR (400 MHz, DMSO-d$_6$) δ: 1.08-1.20 (4H, m), 1.59 (3H, s), 1.75-1.90 (5H, m), 2.02-2.12 (1H, m), 2.09 (3H, s), 2.11 (3H, s), 2.13 (6H, s), 2.16 (3H, s), 4.21 (2H, d, J=4.9 Hz), 5.85 (1H, s), 6.93 (1H, s), 8.12 (1H, t, J=4.9 Hz), 11.47 (1H, s).

MS (APCI) m/z: 532, 534 (M+H)$^+$.

Specific rotation [α]$_D^{20}$=−7.2 (C=1.0, chloroform)

This compound agreed with the compound of the first peak obtained under the resolution conditions using a chiral column described in Example 14.

Example 16

7-Bromo-2-[trans-4-(dimethylamino)cyclohexyl]-N-[(4-methoxy-6-methyl-2-oxo-1,2-dihydropyridin-3-yl)methyl]-2,4-dimethyl-1,3-benzodioxole-5-carboxamide (16)

Step 16-1 tert-Butyl N-[trans-4-[7-bromo-5-[(4-methoxy-6-methyl-2-oxo-1H-pyridin-3-yl)methylcarbamoyl]-2,4-dimethyl-1,3-benzodioxol-2-yl]cyclohexyl]carbamate The title compound (0.237 g, 0.382 mmol, 74% yield) was obtained through the same reaction as in step 1-3 using 7-bromo-2-[trans-4-(tert-butoxycarbonylamino)cyclohexyl]-2,4-dimethyl-1,3-benzodioxole-5-carboxylic acid (0.243 g, 0.517 mmol) synthesized in step 13-2 and 3-(aminomethyl)-4-methoxy-6-methyl-1H-pyridin-2-one hydrochloride (0.116 g, 0.568 mmol) synthesized according to the method described in WO20131201042.

$^1$H-NMR (400 MHz, DMSO-d$_6$) δ: 1.06-1.21 (4H, m), 1.35 (9H, s), 1.59 (3H, s), 1.73-1.85 (5H, m), 2.10 (3H, s), 2.18 (3H, s), 3.07-3.20 (1H, m), 3.78 (3H, s), 4.14 (2H, d, J=4.4 Hz), 6.09 (1H, s), 6.74 (1H, d, J=8.0 Hz), 6.93 (1H, s), 7.95 (1H, t, J=4.4 Hz), 11.45 (1H, s).

MS (APCI) m/z: 620, 622 (M+H)$^+$.

Step 16-2

2-(trans-4-Aminocyclohexyl)-7-bromo-N-[(4-methoxy-6-methyl-2-oxo-1H-pyridin-3-yl)methyl]-2,4-dimethyl-1,3-benzodioxole-5-carboxamide The title compound (0.187 g, 0.359 mmol, 94% yield) was obtained through the same reaction as in step 3-4 using tert-butyl N-[trans-4-[7-bromo-5-[(4-methoxy-6-methyl-2-oxo-1H-pyridin-3-yl)methylcarbamoyl]-2,4-dimethyl-1,3-benzodioxol-2-yl]cyclohexyl]carbamate (0.237 g, 0.382 mmol) synthesized in step 16-1.

$^1$H-NMR (400 MHz, DMSO-d$_6$) δ: 0.89-1.04 (2H, m), 1.06-1.23 (2H, m), 1.57 (3H, s), 1.71-1.83 (5H, m), 2.09 (3H, s), 2.17 (3H, s), 2.37-2.50 (1H, m), 3.55 (3H, s), 3.78 (3H, s), 4.15 (2H, d, J=4.8 Hz), 6.09 (1H, s), 6.92 (1H, s), 7.93 (1H, t, J=4.8 Hz).

MS (APCI) m/z: 520, 522 (M+H)$^+$.

Step 16-3

7-Bromo-2-[trans-4-(dimethylamino)cyclohexyl]-N-[(4-methoxy-6-methyl-2-oxo-1H-pyridin-3-yl)methyl]-2,4-dimethyl-1,3-benzodioxole-5-carboxamide The title compound (0.126 g, 0.229 mmol, 64% yield) was obtained through the same reaction as in step 3-5 using 2-(trans-4-aminocyclohexyl)-7-bromo-N-[(4-methoxy-6-methyl-2-oxo-1H-pyridin-3-yl)methyl]-2,4-dimethyl-1,3-benzodioxole-5-carboxamide (0.187 g, 0.359 mmol) synthesized in step 16-2.

$^1$H-NMR (400 MHz, DMSO-d$_6$) δ: 1.06-1.22 (4H, m), 1.58 (3H, s), 1.72-1.90 (5H, m), 2.00-2.21 (1H, m), 2.09 (3H, s), 2.12 (6H, s), 2.16 (3H, s), 3.78 (3H, s), 4.15 (2H, d, J=4.4 Hz), 6.08 (1H, s), 6.91 (1H, s), 7.93 (1H, t, J=4.4 Hz), 11.4 (1H, br s).

MS (APCI) m/z: 548, 550 (M+H)$^+$.

Example 17

7-Bromo-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide (17)

[Formula 33]

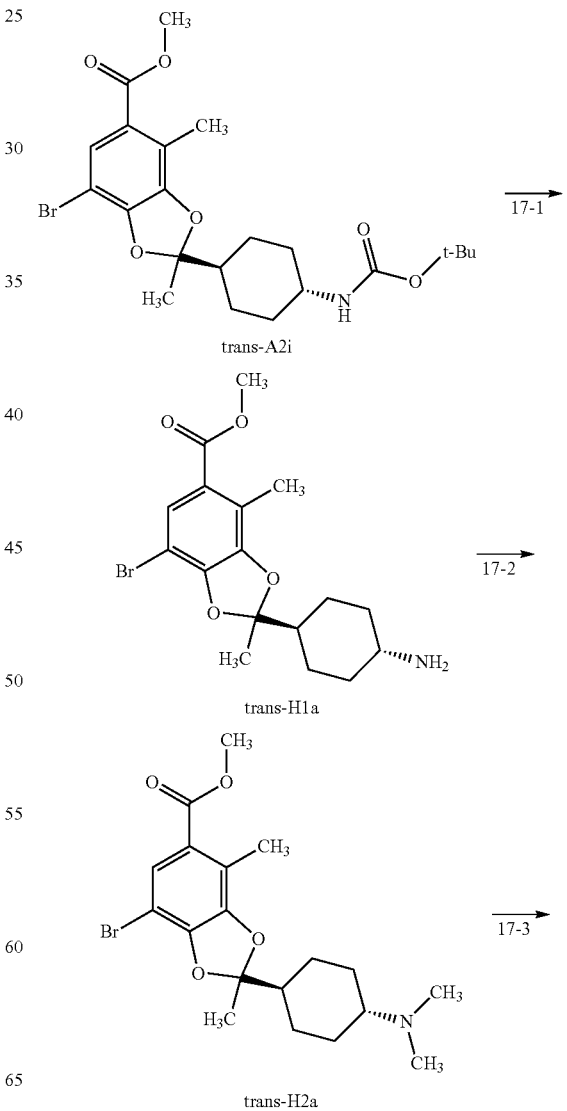

-continued

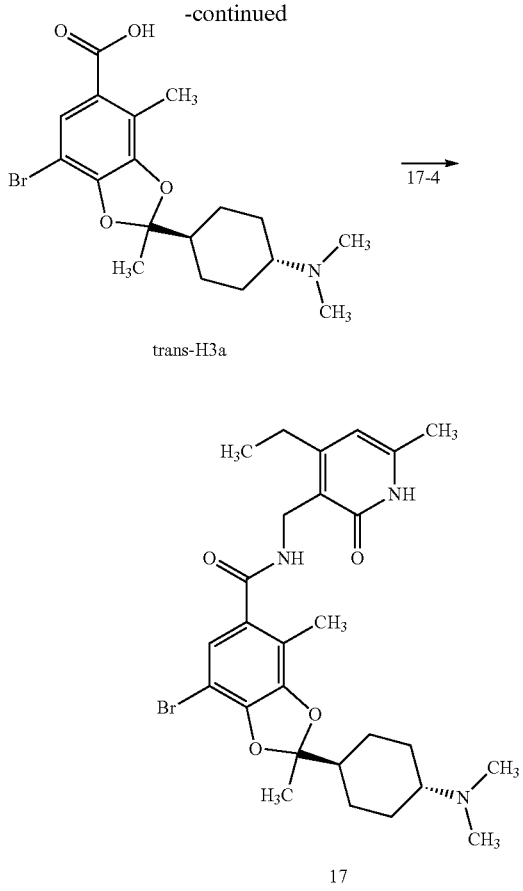

trans-H3a

17

Step 17-1

Methyl 2-(trans-4-aminocyclohexyl)-7-bromo-2,4-dimethyl-1,3-benzodioxole-5-carboxylate (trans-H1a)

The title compound (0.160 g, 0.417 mmol, 100% yield) was obtained through the same reaction as in step 3-4 using the compound (trans-A2i) (0.200 g, 0.413 mmol) synthesized in step 13-1.

$^1$H-NMR (400 MHz, CDCl$_3$) δ: 1.05-1.15 (2H, m), 1.24-1.33 (2H, m), 1.63 (3H, s), 1.80-1.88 (1H, m), 1.89-1.97 (4H, m), 2.38 (3H, s), 2.60-2.68 (1H, m), 3.85 (3H, d, J=1.2 Hz), 7.67 (1H, s).

MS (ESI) m/z: 384, 386 (M+H)$^+$.

Step 17-2

Methyl 7-bromo-2-[trans-4-(dimethylamino)cyclohexyl]-2,4-dimethyl-1,3-benzodioxole-5-carboxylate (trans-H2a)

The title compound (0.124 g, 0.417 mmol, 93% yield) was obtained through the same reaction as in step 3-5 using the compound (trans-H1a) (0.124 g, 0.413 mmol) synthesized in step 17-1.

$^1$H-NMR (400 MHz, CDCl$_3$) δ: 1.16-1.31 (4H, m), 1.63 (3H, s), 1.78-1.86 (1H, m), 1.90-2.05 (4H, m), 2.10-2.20 (1H, m), 2.27 (6H, s), 2.38 (3H, s), 3.84 (3H, s), 7.66 (1H, s).

MS (ESI) m/z: 412, 414 (M+H)$^+$.

Step 17-3

7-Bromo-2-[trans-4-(dimethylamino)cyclohexyl]-2,4-dimethyl-1,3-benzodioxole-5-carboxylic Acid (trans-H3a)

The title compound (0.597 g, 0.505 mmol, 47% yield) was obtained through the same reaction as in step 6-4 using the compound (trans-H2a) (0.523 g, 1.27 mmol) synthesized in step 17-2.

MS (ESI) m/z: 398, 400 (M+H)$^+$.

Step 17-4

7-Bromo-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide (17)

The title compound (0.245 g, 0.448 mmol, 75% yield) was obtained through the same reaction as in step 1-3 using the compound (trans-H3a) (0.238 g, 0.597 mmol) synthesized in step 17-3 and 3-(aminomethyl)-4-ethyl-6-methyl-1H-pyridin-2-one (0.119 g, 0.717 mmol) synthesized according to the method described in WO2011140324.

$^1$H-NMR (400 MHz, CDCl$_3$) δ: 1.20 (3H, t, J=7.7 Hz), 1.21-1.30 (4H, m), 1.60 (3H, s), 1.75-1.90 (1H, m), 1.92-2.02 (2H, m), 2.22 (3H, s), 2.27 (6H, s), 2.28 (3H, s), 2.71 (2H, q, J=7.7 Hz), 4.52 (2H, d, J=5.5 Hz), 5.99 (1H, s), 6.99 (1H, s), 7.26 (1H, t, J=5.5 Hz).

MS (ESI) m/z: 546, 548 (M+H)$^+$.

Example 18

7-Bromo-2-[trans-4-(dimethylamino)cyclohexyl]-2,4-dimethyl-N-[(6-methyl-2-oxo-4-propyl-1,2-dihydropyridin-3-yl)methyl]-1,3-benzodioxole-5-carboxamide (18)

The title compound (0.314 g, 0.560 mmol, 75% yield) was obtained through the same reaction as in step 1-3 using the compound (trans-H3a) (0.297 g, 0.745 mmol) synthesized in step 17-3 and 3-(aminomethyl)-6-methyl-4-propyl-1H-pyridin-2-one (0.161 g, 0.894 mmol) synthesized according to the method described in WO2011140324.

$^1$H-NMR (400 MHz, CDCl$_3$) δ: 0.99 (3H, t, J=7.3 Hz), 1.19-1.28 (4H, m), 1.60 (3H, s), 1.76-1.84 (1H, m), 1.92-1.98 (4H, m), 2.09-2.17 (1H, m), 2.21 (3H, s), 2.27 (9H, s), 2.62-2.68 (2H, m), 4.51 (2H, d, J=5.0 Hz), 5.96 (1H, s), 6.99 (1H, s), 7.25 (1H, t, J=5.0 Hz).

MS (ESI) m/z: 560, 562 (M+H)$^+$.

Example 19

7-Bromo-N-[(4,6-dimethyl-2-oxo-1,2-dihydropyridin-3-yl)methyl]-2-[trans-4-(ethylamino)cyclohexyl]-2,4-dimethyl-1,3-benzodioxole-5-carboxamide (19)

The title compound (0.360 g, 0.676 mmol, 68% yield) was obtained through the same reaction as in step 3-5 using the compound (13) (0.500 g, 0.992 mmol) synthesized in step 13-4 and acetaldehyde (0.440 g, 9.99 mmol).

$^1$H-NMR (400 MHz, DMSO-d$_6$) δ: 0.90-1.02 (2H, m), 0.97 (3H, t, J=7.2 Hz), 1.08-1.22 (2H, m), 1.59 (3H, s), 1.75-1.85 (3H, m), 1.85-1.94 (2H, m), 2.10 (3H, s), 2.11 (3H, s), 2.16 (3H, s), 2.23-2.33 (1H, m), 2.52 (2H, q, J=7.2 Hz), 4.21 (2H, d, J=4.9 Hz), 5.85 (1H, s), 6.93 (1H, s), 8.12 (1H, t, J=4.9 Hz).

MS (ESI) m/z: 532, 534 (M+H)$^+$.

Example 20

7-Bromo-N-[(4,6-dimethyl-2-oxo-1,2-dihydropyridin-3-yl)methyl]-2-[trans-4-[N-ethyl(N-methyl)amino]cyclohexyl]-2,4-dimethyl-1,3-benzodioxole-5-carboxamide (20)

The title compound (0.065 g, 0.119 mmol, 63% yield) was obtained through the same reaction as in step 3-5 using the compound (19) (0.100 g, 0.188 mmol) synthesized in Example 19.

$^1$H-NMR (400 MHz, DMSO-d$_6$) δ: 0.94 (3H, t, J=7.2 Hz), 1.08-1.27 (2H, m), 1.59 (3H, s), 1.72-1.90 (5H, m), 2.10 (3H, s), 2.11 (6H, s), 2.16 (3H, s), 2.24-2.343 (1H, m), 2.41 (2H, q, J=7.2 Hz), 4.21 (2H, d, J=4.9 Hz), 5.86 (1H, s), 6.94 (1H, s), 8.13 (1H, t, J=4.9 Hz), 11.48 (1H, br s).

MS (ESI) m/z: 546, 548 (M+H)$^+$.

Example 21

7-Bromo-2-[trans-4-(diethylamino)cyclohexyl]-N-[(4,6-dimethyl-2-oxo-1,2-dihydropyridin-3-yl)methyl]-2,4-dimethyl-1,3-benzodioxole-5-carboxamide (21)

The title compound (0.065 g, 0.116 mmol, 39% yield) was obtained through the same reaction as in step 3-5 using the compound (19) (0.160 g, 0.300 mmol) synthesized in Example 19 and acetaldehyde (0.132 g, 3.00 mmol).

$^1$H-NMR (400 MHz, DMSO-d$_6$) δ: 0.93 (6H, t, J=7.2 Hz), 1.08-1.27 (4H, m), 1.59 (3H, s), 1.72-1.90 (5H, m), 2.10 (3H, s), 2.11 (3H, s), 2.17 (3H, s), 2.44 (4H, q, J=7.2 Hz), 4.21 (2H, d, J=4.9 Hz), 5.86 (1H, s), 6.94 (1H, s), 8.14 (1H, t, J=4.9 Hz), 11.49 (1H, br s).

MS (ESI) m/z: 560, 562 (M+H)$^+$.

Example 22

7-Bromo-2-[(2S,5R)-5-(dimethylamino)tetrahydropyran-2-yl]-N-[(4,6-dimethyl-2-oxo-1,2-dihydropyridin-3-yl)methyl]-2,4-dimethyl-1,3-benzodioxole-5-carboxamide (22)

Step 22-1

Methyl 7-bromo-2-[(2S,5R)-5-(tert-butoxycarbonylamino)tetrahydropyran-2-yl]-2,4-dimethyl-1,3-benzodioxole-5-carboxylate The title compound (0.443 g, 0.911 mmol, 59% yield) was obtained through the same reaction as in step 13-1 using the compound (A1a) (0.400 g, 1.53 mmol) synthesized in Reference Example 1 and tert-butyl N-[(3R,6S)-6-ethynyltetrahydropyran-3-yl]carbamate (0.414 g, 1.84 mmol) synthesized according to the method described in WO 2007105154.

$^1$H-NMR (400 MHz, CDCl$_3$) δ: 1.22-1.34 (1H, m), 1.45 (9H, s), 1.52-1.63 (1H, m), 1.67-1.76 (3H, m), 1.80-1.90 (1H, m), 2.10-2.19 (1H, m), 2.39 (3H, s), 2.99-3.07 (1H, m), 3.45-3.51 (1H, m), 3.55-3.70 (1H, m), 3.85 (3H, s), 4.10-4.19 (1H, m), 4.21-4.41 (1H, m), 7.68 (1H, s).

Step 22-2

7-Bromo-2-[(2S,5R)-5-(tert-butoxycarbonylamino)tetrahydropyran-2-yl]-2,4-dimethyl-1,3-benzodioxole-5-carboxylic Acid The title compound (0.423 g, 0.895 mmol, 98% yield) was obtained through the same reaction as in step 1-2 using methyl 7-bromo-2-[(2S,5R)-5-(tert-butoxycarbonylamino)tetrahydropyran-2-yl]-2,4-dimethyl-1,3-benzodioxole-5-carboxylate (0.443 g, 0.911 mmol) synthesized in step 22-1.

Step 22-3 tert-Butyl N-[(3R,6S)-6-[7-bromo-5-[(4,6-dimethyl-2-oxo-1,2-dihydropyridin-3-yl)methylcarbamoyl]-2,4-dimethyl-1,3-benzodioxol-2-yl]tetrahydropyran-3-yl]carbamate The title compound (0.212 g, 0.349 mmol, 39% yield) was obtained through the same reaction as in step 1-3 using 7-bromo-2-[(2S,5R)-5-(tert-butoxycarbonylamino)tetrahydropyran-2-yl]-2,4-dimethyl-1,3-benzodioxole-5-carboxylic acid (0.423 g, 0.895 mmol) synthesized in step 22-2.

$^1$H-NMR (400 MHz, CDCl$_3$) δ: 1.21-1.34 (1H, m), 1.43 (9H, s), 1.50-1.62 (1H, m), 1.67 (3H, s), 1.75-1.87 (1H, m), 2.05-2.17 (1H, m), 2.23 (3H, s), 2.26 (3H, s), 2.36 (3H, s), 2.97-3.06 (1H, m), 3.41-3.48 (1H, m), 3.52-3.74 (1H, m), 4.09-4.19 (1H, m), 4.21-4.32 (1H, m), 4.49 (2H, d, J=5.5 Hz), 5.97 (1H, s), 7.01 (1H, s), 12.35 (1H, br s).

MS (APCI) m/z: 606, 608 (M+H)$^+$.

Step 22-4

2-[(2S,5R)-5-Aminotetrahydropyran-2-yl]-7-bromo-N-[(4,6-dimethyl-2-oxo-1,2-dihydropyridin-3-yl)methyl]-2,4-dimethyl-1,3-benzodioxole-5-carboxamide The title compound (0.177 g, 0.350 mmol, 100% yield) was obtained through the same reaction as in step 3-4 using tert-butyl N-[(3R,6S)-6-[7-bromo-5-[(4,6-dimethyl-2-oxo-1,2-dihydropyridin-3-yl)methylcarbamoyl]-2,4-dimethyl-1,3-benzodioxol-2-yl]tetrahydropyran-3-yl]carbamate (0.212 g, 0.349 mmol) synthesized in step 22-3.

MS (APCI) m/z: 506, 508 (M+H)$^+$.

Step 22-5

7-Bromo-2-[(2S,5R)-5-(dimethylamino)tetrahydropyran-2-yl]-N-[(4,6-dimethyl-2-oxo-1,2-dihydropyridin-3-yl)methyl]-2,4-dimethyl-1,3-benzodioxole-5-carboxamide (22)

The title compound (0.169 g, 0.316 mmol, 90% yield) was obtained through the same reaction as in step 3-5 using 2-[(2S,5R)-5-aminotetrahydropyran-2-yl]-7-bromo-N-[(4,6-dimethyl-2-oxo-1,2-dihydropyridin-3-yl)methyl]-2,4-dimethyl-1,3-benzodioxole-5-carboxamide (0.177 g, 0.350 mmol) synthesized in step 22-4.

$^1$H-NMR (400 MHz, DMSO-d$_6$) δ: 1.29-1.47 (2H, m), 1.61 (3H, s), 1.73-1.80 (1H, m), 1.93-2.05 (1H, m), 2.09 (3H, s), 2.11 (3H, s), 2.15 (6H, s), 2.16 (3H, s), 2.16-2.23 (1H, m), 3.12-3.20 (1H, m), 3.49-3.56 (1H, m), 3.99-4.05

(1H, m), 4.21 (2H, d, J=5.5 Hz), 5.86 (1H, s), 6.94 (1H, s), 8.15 (1H, t, J=5.5 Hz), 11.49 (1H, s).

MS (APCI) m/z: 534, 536 (M+H)$^+$.

Example 23

2-[trans-4-(Dimethylamino)cyclohexyl]-N-[(4,6-dimethyl-2-oxo-1,2-dihydropyridin-3-yl)methyl]-2,4-dimethyl-1,3-benzodioxole-5-carboxamide (23)

The compound (14) (200 mg, 0.376 mmol) synthesized in Example 14 was dissolved in methanol (5 mL). To the solution, 4 M hydrochloric acid in 1,4-dioxane (0.094 mL, 0.376 mmol) and a 10% palladium-carbon catalyst (0.200 g) were added, and the mixture was stirred at room temperature for 6 hours under a hydrogen atmosphere. After purging with nitrogen, the catalyst was filtered off through celite, and the solvent was distilled off under reduced pressure. The obtained residue was neutralized by the addition of a 1 M aqueous sodium hydroxide solution, followed by extraction with 20% methanol in dichloromethane. The organic layer was washed with saturated saline and then dried over anhydrous sodium sulfate to obtain the title compound (0.098 g, 0.215 mmol, 57% yield) in a debrominated form.

$^1$H-NMR (400 MHz, DMSO-$d_6$) δ: 1.19-1.32 (4H, m), 1.54 (3H, s), 1.75-1.85 (1H, m), 1.93-2.05 (4H, m), 2.19 (3H, s), 2.19-2.29 (1H, m), 2.24 (3H, s), 2.29 (6H, s), 2.35 (3H, s), 4.42 (2H, s), 6.10 (1H, s), 6.54 (1H, d, J=7.9 Hz), 6.84 (1H, d, J=7.9 Hz).

MS (ESI) m/z: 454 (M+H)$^+$.

Example 24

7-Bromo-2-[trans-4-[(dimethylamino)methyl]cyclohexyl]-N-[(4,6-dimethyl-2-oxo-1,2-dihydropyridin-3-yl)methyl]-2,4-dimethyl-1,3-benzodioxole-5-carboxamide (24)

Step 24-1

Methyl 7-bromo-2-[trans-4-[(tert-butoxycarbonylamino)methyl]cyclohexyl]-2,4-dimethyl-1,3-benzodioxole-5-carboxylate The title compound (1.28 g, 2.57 mmol, 84% yield) was obtained through the same reaction as in step 13-1 using the compound (A1a) (0.800 g, 3.06 mmol) synthesized in Reference Example 1 and the compound (S16) (1.09 g, 4.60 mmol) synthesized in Reference Example 16.

$^1$H-NMR (400 MHz, CDCl$_3$) δ: 0.88-1.00 (2H, m), 1.16-1.27 (2H, m), 1.44 (9H, s), 1.63 (3H, s), 1.78-1.88 (3H, m), 1.90-1.98 (2H, m), 2.38 (3H, s), 2.97 (2H, t, J=6.4 Hz), 3.85 (3H, s), 4.59 (1H, br s), 7.66 (1H, s).

Step 24-2

7-Bromo-2-[trans-4-[(tert-butoxycarbonylamino)methyl]cyclohexyl]-2,4-dimethyl-1,3-benzodioxole-5-carboxylic Acid The title compound (1.24 g, 2.57 mmol, 100% yield) was obtained through the same reaction as in step 1-2 using methyl 7-bromo-2-[trans-4-[(tert-butoxycarbonylamino)methyl]cyclohexyl]-2,4-dimethyl-1,3-benzodioxole-5-carboxylate (1.28 g, 2.57 mmol) synthesized in step 24-1.

Step 24-3 tert-Butyl N-[[trans-4-[7-bromo-5-[(4,6-dimethyl-2-oxo-1,2-dihydropyridin-3-yl)methylcarbamoyl]-2,4-dimethyl-1,3-benzodioxol-2-yl]cyclohexyl]methyl]carbamate The title compound (1.26 g, 2.04 mmol, 80% yield) was obtained through the same reaction as in step 1-3 using 7-bromo-2-[trans-4-[(tert-butoxycarbonylamino)methyl]cyclohexyl]-2,4-dimethyl-1,3-benzodioxole-5-carboxylic acid (1.24 g, 2.57 mmol) synthesized in step 24-2.

$^1$H-NMR (400 MHz, CDCl$_3$) δ: 0.88-1.00 (2H, m), 1.15-1.27 (2H, m), 1.43 (9H, s), 1.60 (3H, s), 1.77-1.86 (3H, m), 1.90-1.94 (2H, m), 2.21 (3H, s), 2.26 (3H, s), 2.37 (3H, s), 2.96 (2H, t, J=6.4 Hz), 4.49 (2H, d, J=5.5 Hz), 4.59 (1H, br s), 5.95 (1H, s), 6.99 (1H, s), 7.20 (1H, t, J=5.5 Hz), 11.55 (1H, br s).

MS (ESI) m/z: 618, 620 (M+)

Step 24-4

2-[trans-4-(Aminomethyl)cyclohexyl]-7-bromo-N-[(4,6-dimethyl-2-oxo-1,2-dihydropyridin-3-yl)methyl]-2,4-dimethyl-1,3-benzodioxole-5-carboxamide The title compound (0.923 g, 1.78 mmol, 87% yield) was obtained in an amino form through the same reaction as in step 3-4 using tert-butyl N-[[trans-4-[7-bromo-5-[(4,6-dimethyl-2-oxo-1,2-dihydropyridin-3-yl)methylcarbamoyl]-2,4-dimethyl-1,3-benzodioxol-2-yl]cyclohexyl]methyl]carbamate (1.26 g, 2.04 mmol) synthesized in step 24-3.

MS (ESI) m/z: 518, 520 (M+H)$^+$.

Step 24-5

7-Bromo-2-[trans-4-[(dimethylamino)methyl]cyclohexyl]-N-[(4,6-dimethyl-2-oxo-1,2-dihydropyridin-3-yl)methyl]-2,4-dimethyl-1,3-benzodioxole-5-carboxamide (24)

The title compound (0.116 g, 0.213 mmol, 55% yield) was obtained through the same reaction as in step 3-5 using 2-[trans-4-(aminomethyl)cyclohexyl]-7-bromo-N-[(4,6-dimethyl-2-oxo-1,2-dihydropyridin-3-yl)methyl]-2,4-dimethyl-1,3-benzodioxole-5-carboxamide (0.200 g, 0.386 mmol) synthesized in step 24-4.

$^1$H-NMR (400 MHz, CD$_3$OD) δ: 0.89-1.00 (2H, m), 1.19-1.30 (2H, m), 1.43-1.53 (1H, m), 1.60 (3H, s), 1.81-1.96 (5H, m), 2.14-2.18 (2H, m), 2.17 (3H, s), 2.21 (6H, s), 2.24 (3H, s), 2.35 (3H, s), 4.41 (2H, s), 6.10 (1H, s), 6.98 (1H, s).

MS (ESI) m/z: 546, 548 (M+H)$^+$.

Example 25

7-Bromo-N-[(4,6-dimethyl-2-oxo-1,2-dihydropyridin-3-yl)methyl]-2,4-dimethyl-2-[(1-methyl-4-piperidyl)methyl]-1,3-benzodioxole-5-carboxamide (25)

Step 25-1 tert-Butyl 4-[(7-bromo-5-methoxycarbonyl-2,4-dimethyl-1,3-benzodioxol-2-yl)methyl]piperidine-1-carboxylate The title compound (0.280 g, 0.578 mmol, 76% yield) was obtained through the same reaction as in step 1-1 using the compound (A1a) (0.200 g, 0.766 mmol) synthesized in Reference Example 1 and the compound (S10) (0.257 g, 1.15 mmol) synthesized in Reference Example 10.

¹H-NMR (400 MHz, CDCl₃) δ: 1.13-1.29 (2H, m), 1.45 (9H, s), 1.70 (3H, s), 1.71-1.80 (3H, m), 1.94 (2H, d, J=6.1 Hz), 2.38 (3H, s), 2.64-2.73 (2H, m), 3.85 (3H, s), 3.95-4.15 (2H, m), 7.69 (1H, s).

Step 25-2

7-Bromo-2-[(1-tert-butoxycarbonyl-4-piperidyl)methyl]-2,4-dimethyl-1,3-benzodioxole-5-carboxylic Acid The title compound (0.258 g, 0.548 mmol, 95% yield) was obtained through the same reaction as in step 1-2 using tert-butyl 4-[(7-bromo-5-methoxycarbonyl-2,4-dimethyl-1,3-benzodioxol-2-yl)methyl]piperidine-1-carboxylate (0.280 g, 0.578 mmol) synthesized in step 25-1.

Step 25-3 tert-Butyl 4-[[7-bromo-5-[(4,6-dimethyl-2-oxo-1,2-dihydropyridin-3-yl)methylcarbamoyl]-2,4-dimethyl-1,3-benzodioxol-2-yl]methyl]piperidine-1-carboxylate The title compound (0.327 g, 0.564 mmol, 100% yield) was obtained through the same reaction as in step 1-3 using 7-bromo-2-[(1-tert-butoxycarbonyl-4-piperidyl)methyl]-2,4-dimethyl-1,3-benzodioxole-5-carboxylic acid (0.258 g, 0.548 mmol) synthesized in step 25-2.

¹H-NMR (400 MHz, CDCl₃) δ: 1.10-1.27 (2H, m), 1.44 (9H, s), 1.55-1.65 (1H, m), 1.66 (3H, s), 1.69-1.79 (3H, m), 1.91 (2H, d, J=5.5 Hz), 2.22 (3H, s), 2.27 (3H, s), 2.37 (3H, s), 2.63-2.74 (2H, m), 3.90-4.15 (2H, m), 4.50 (2H, d, J=5.6 Hz), 5.96 (1H, s), 7.02 (1H, s), 7.25 (1H, br s).

MS (APCI) m/z: 604, 606 (M+H)⁺.

Step 25-4

7-Bromo-N-[(4,6-dimethyl-2-oxo-1,2-dihydropyridin-3-yl)methyl]-2,4-dimethyl-2-(4-piperidylmethyl)-1,3-benzodioxole-5-carboxamide The title compound (0.235 g, 0.466 mmol, 83% yield) was obtained through the same reaction as in step 3-4 using tert-butyl 4-[[7-bromo-5-[(4,6-dimethyl-2-oxo-1,2-dihydropyridin-3-yl)methylcarbamoyl]-2,4-dimethyl-1,3-benzodioxol-2-yl]methyl]piperidine-1-carboxylate (0.327 g, 0.564 mmol) synthesized in (Step 25-3.

MS (APCI) m/z: 504, 506 (M+H)⁺.

Step 25-5

7-Bromo-N-[(4,6-dimethyl-2-oxo-1H-pyridin-3-yl)methyl]-2,4-dimethyl-2-[(1-methyl-4-piperidyl)methyl]-1,3-benzodioxole-5-carboxamide (25)

The title compound (0.198 g, 0.382 mmol, 82% yield) was obtained through the same reaction as in step 3-5 using 7-bromo-N-[(4,6-dimethyl-2-oxo-1,2-dihydropyridin-3-yl)methyl]-2,4-dimethyl-2-(4-piperidylmethyl)-1,3-benzodioxole-5-carboxamide (0.235 g, 0.466 mmol) synthesized in step 25-4.

¹H-NMR (400 MHz, DMSO-d₆) δ: 1.12-1.29 (2H, m), 1.40-1.51 (1H, m), 1.64-1.71 (2H, m), 1.65 (3H, s), 1.72-1.82 (2H, m), 1.89 (2H, d, J=6.7 Hz), 2.08 (3H, s), 2.09 (3H, s), 2.11 (3H, s), 2.17 (3H, s), 2.62-2.68 (2H, m), 4.21 (2H, d, J=4.9 Hz), 5.85 (1H, s), 6.95 (1H, s), 8.16 (1H, t, J=4.9 Hz), 11.48 (1H, s).

MS (APCI) m/z: 518, 520 (M+H)⁺.

Example 26

7-Bromo-N-[(4,6-dimethyl-2-oxo-1,2-dihydropyridin-3-yl)methyl]-2-[(1-ethyl-4-piperidyl)methyl]-2,4-dimethyl-1,3-benzodioxole-5-carboxamide (26)

The title compound (0.632 g, 1.19 mmol, 60% yield) was obtained through the same reaction as in step 3-5 using 7-bromo-N-[(4,6-dimethyl-2-oxo-1,2-dihydropyridin-3-yl)methyl]-2,4-dimethyl-2-(4-piperidylmethyl)-1,3-benzodioxole-5-carboxamide (1.00 g, 1.98 mmol) synthesized in step 25-4 and acetaldehyde (0.873 g, 19.8 mmol).

¹H-NMR (400 MHz, DMSO-d₆) δ: 0.94 (3H, t, J=7.0 Hz), 1.12-1.26 (2H, m), 1.38-1.55 (1H, m), 1.65 (3H, s), 1.65-1.72 (2H, m), 1.72-1.82 (2H, m), 1.89 (2H, d, J=6.1 Hz), 2.09 (3H, s), 2.11 (3H, s), 2.17 (3H, s), 2.23 (2H, q, J=7.0 Hz), 2.73-2.80 (2H, m), 4.21 (2H, d, J=4.9 Hz), 5.86 (1H, s), 6.96 (1H, s), 8.17 (1H, t, J=4.9 Hz), 11.50 (1H, s).

MS (APCI) m/z: 532, 534 (M+H)⁺.

Example 27

7-Bromo-2-[[cis-4-(dimethylamino)cyclohexyl]methyl]-N-[(4,6-dimethyl-2-oxo-1,2-dihydropyridin-3-yl)methyl]-2,4-dimethyl-1,3-benzodioxole-5-carboxamide (27)

Step 27-1

Methyl 7-bromo-2-[[cis-4-(tert-butoxycarbonylamino)cyclohexyl]methyl]-2,4-dimethyl-1,3-benzodioxole-5-carboxylate The title compound (1.47 g, 2.96 mmol, 96.4% yield) was obtained through the same reaction as in step 13-1 using the compound (A1a) (0.800 g, 0.3.06 mmol) synthesized in Reference Example 1 and the compound (S11) (1.09 g, 4.60 mmol) synthesized in Reference Example 11.

¹H-NMR (400 MHz, CDCl₃) δ: 1.28-1.37 (2H, m), 1.44 (9H, s), 1.56-1.75 (5H, m), 1.69 (3H, s), 1.94 (2H, d, J=6.7 Hz), 2.37 (3H, s), 3.49 (2H, d, J=4.9 Hz), 3.66-3.74 (1H, m), 3.85 (3H, s), 4.58 (1H, br s), 7.68 (1H, s).

Step 27-2

7-Bromo-2-[[cis-4-(tert-butoxycarbonylamino)cyclohexyl]methyl]-2,4-dimethyl-1,3-benzodioxole-5-carboxylic Acid The title compound (1.43 g, 2.96 mmol, 100% yield) was obtained through the same reaction as in step 1-2 using methyl 7-bromo-2-[[cis-4-(tert-butoxycarbonylamino)cyclohexyl]methyl]-2,4-dimethyl-1,3-benzodioxole-5-carboxylate (1.47 g, 2.96 mmol) synthesized in step 27-1.

MS (ESI) m/z: 506, 508 (M+Na)⁺.

Step 27-3 tert-Butyl N-[cis-4-[[7-bromo-5-[(4,6-dimethyl-2-oxo-1,2-dihydropyridin-3-yl)methylcarbamoyl]-2,4-dimethyl-1,3-benzodioxol-2-yl]methyl]cyclohexyl]carbamate The title compound (1.68 g, 2.71 mmol, 92% yield) was obtained through the same reaction as in step 1-3 using 7-bromo-2-[[cis-4-(tert-butoxycarbonylamino)cyclohexyl]methyl]-2,4-dimethyl-1,3-benzodioxole-5-carboxylic acid (1.43 g, 2.99 mmol) synthesized in step 27-2.
$^1$H-NMR (400 MHz, DMSO-$d_6$) δ: 1.36 (9H, s), 1.40-1.49 (8H, m), 1.66 (3H, s), 1.66-1.75 (1H, m), 1.90 (2H, d, J=6.1 Hz), 2.09 (3H, s), 2.11 (3H, s), 2.17 (3H, s), 3.28-3.37 (1H, m), 4.21 (2H, d, J=5.1 Hz), 5.85 (1H, s), 6.67 (1H, d, J=7.3 Hz), 6.96 (1H, s), 8.14 (1H, t, J=5.1 Hz), 11.48 (1H, br s).
MS (ESI) m/z: 618, 620 (M+H)$^+$.

Step 27-4

2-[(cis-4-Aminocyclohexyl)methyl]-7-bromo-N-[(4,6-dimethyl-2-oxo-1,2-dihydropyridin-3-yl)methyl]-2,4-dimethyl-1,3-benzodioxole-5-carboxamide The title compound (0.961 g, 1.85 mmol, 68% yield) was obtained through the same reaction as in step 3-4 using tert-butyl N-[cis-4-[[7-bromo-5-[(4,6-dimethyl-2-oxo-1,2-dihydropyridin-3-yl)methylcarbamoyl]-2,4-dimethyl-1,3-benzodioxol-2-yl]methyl]cyclohexyl]carbamate (1.68 g, 2.71 mmol) synthesized in step 27-3.
MS (ESI) m/z: 518, 520 (M+H)$^+$.

Step 27-5

7-Bromo-2-[[cis-4-(dimethylamino)cyclohexyl]methyl]-N-[(4,6-dimethyl-2-oxo-1,2-dihydropyridin-3-yl)methyl]-2,4-dimethyl-1,3-benzodioxole-5-carboxamide (27)

The title compound (0.112 g, 0.205 mmol, 53% yield) was obtained through the same reaction as in step 3-5 using 2-[(cis-4-aminocyclohexyl)methyl]-7-bromo-N-[(4,6-dimethyl-2-oxo-1,2-dihydropyridin-3-yl)methyl]-2,4-dimethyl-1,3-benzodioxole-5-carboxamide (0.200 g, 0.386 mmol) synthesized in step 27-4.
$^1$H-NMR (400 MHz, CD$_3$OD) δ: 1.43-1.56 (4H, m), 1.60-1.73 (4H, m), 1.67 (3H, s), 1.92-1.98 (1H, m), 2.02 (2H, d, J=6.1 Hz), 2.13-2.20 (1H, m), 2.15 (3H, s), 2.24 (3H, s), 2.26 (6H, s), 2.35 (3H, s), 4.41 (2H, s), 6.10 (1H, s), 6.99 (1H, s).
MS (ESI) m/z: 546, 548 (M+H)$^+$.

Example 28

7-Bromo-2-[[trans-4-(dimethylamino)cyclohexyl]methyl]-N-[(4,6-dimethyl-2-oxo-1,2-dihydropyridin-3-yl)methyl]-2,4-dimethyl-1,3-benzodioxole-5-carboxamide (28)

Step 28-1

Methyl 7-bromo-2-[[trans-4-(tert-butoxycarbonylamino)cyclohexyl]methyl]-2,4-dimethyl-1,3-benzodioxole-5-carboxylate The title compound (1.17 g, 2.96 mmol, 96% yield) was obtained through the same reaction as in step 13-1 using the compound (A1a) (0.800 g, 0.3.06 mmol) synthesized in Reference Example 1 and the compound (S12) (1.09 g, 4.60 mmol) synthesized in Reference Example 12.
$^1$H-NMR (400 MHz, CDCl$_3$) δ: 1.01-1.17 (4H, m), 1.43 (9H, s), 1.43-1.60 (1H, m), 1.68 (3H, s), 1.82-1.92 (4H, m), 1.98 (2H, d, J=9.7 Hz), 2.37 (3H, s), 3.26-3.40 (1H, m), 3.85 (3H, s), 4.34 (1H, br s), 7.68 (1H, s).

Step 28-2

7-Bromo-2-[[trans-4-(tert-butoxycarbonylamino)cyclohexyl]methyl]-2,4-dimethyl-1,3-benzodioxole-5-carboxylic Acid The title compound (1.14 g, 2.36 mmol, 100% yield) was obtained through the same reaction as in step 1-2 using methyl 7-bromo-2-[[trans-4-(tert-butoxycarbonylamino)cyclohexyl]methyl]-2,4-dimethyl-1,3-benzodioxole-5-carboxylate (1.17 g, 2.36 mmol) synthesized in step 28-1.
MS (ESI) m/z: 482, 484 (M–H)$^-$.

Step 28-3 tert-Butyl N-[trans-4-[[7-bromo-5-[(4,6-dimethyl-2-oxo-1H-pyridin-3-yl)methylcarbamoyl]-2,4-dimethyl-1,3-benzodioxol-2-yl]methyl]cyclohexyl]carbamate The title compound (1.39 g, 2.24 mmol, 95% yield) was obtained through the same reaction as in step 1-3 using 7-bromo-2-[[trans-4-(tert-butoxycarbonylamino)cyclohexyl]methyl]-2,4-dimethyl-1,3-benzodioxole-5-carboxylic acid (1.14 g, 2.36 mmol) synthesized in step 28-2.
$^1$H-NMR (400 MHz, DMSO-$d_6$) δ: 0.96-1.13 (4H, m), 1.30-1.46 (1H, m), 1.36 (9H, s), 1.64 (3H, s), 1.68-1.81 (4H, m), 1.85 (2H, d, J=6.1 Hz), 2.09 (3H, s), 2.11 (3H, s), 2.17 (3H, s), 3.06-3.15 (1H, m), 4.21 (2H, d, J=4.9 Hz), 5.86 (1H, s), 6.64 (1H, d, J=7.9 Hz), 6.95 (1H, s), 8.15 (1H, t, J=4.9 Hz), 11.48 (1H, br s).
MS (ESI) m/z: 618, 620 (M+H)$^+$.

Step 28-4

2-[(trans-4-Aminocyclohexyl)methyl]-7-bromo-N-[(4,6-dimethyl-2-oxo-1,2-dihydropyridin-3-yl)methyl]-2,4-dimethyl-1,3-benzodioxole-5-carboxamide The title compound (0.830 g, 1.60 mmol, 71% yield) was obtained through the same reaction as in step 3-4 using tert-butyl N-[trans-4-[[7-bromo-5-[(4,6-dimethyl-2-oxo-1,2-dihydropyridin-3-yl)methylcarbamoyl]-2,4-dimethyl-1,3-benzodioxol-2-yl]methyl]cyclohexyl]carbamate (1.39 g, 2.24 mmol) synthesized in step 28-3.
MS (ESI) m/z: 518, 520 (M+H)$^+$.

Step 28-5

7-Bromo-2-[[trans-4-(dimethylamino)cyclohexyl]methyl]-N-[(4,6-dimethyl-2-oxo-1,2-dihydropyridin-3-yl)methyl]-2,4-dimethyl-1,3-benzodioxole-5-carboxamide (28)

The title compound (0.137 g, 0.251 mmol, 65% yield) was obtained through the same reaction as in step 3-5 using 2-[(trans-4-aminocyclohexyl)methyl]-7-bromo-N-[(4,6-dimethyl-2-oxo-1,2-dihydropyridin-3-yl)methyl]-2,4-dimethyl-1,3-benzodioxole-5-carboxamide (0.200 g, 0.386 mmol) synthesized in step 28-4.

$^1$H-NMR (400 MHz, CD$_3$OD) δ: 1.00-1.26 (4H, m), 1.46-1.58 (1H, m), 1.65 (3H, s), 1.85-1.99 (4H, m), 1.88 (2H, d, J=6.1 Hz), 2.14 (3H, d, J=2.4 Hz), 2.16-2.22 (1H, m), 2.24 (3H, s), 2.26 (6H, s), 2.35 (3H, s), 4.41 (2H, s), 6.10 (1H, s), 6.99 (1H, s).

MS (ESI) m/z: 546, 548 (M+H)$^+$.

Example 29

(2R)-7-Bromo-N-[(4,6-dimethyl-2-oxo-1,2-dihydropyridin-3-yl)methyl]-2,4-dimethyl-2-[[(3S)-1-methylpyrrolidin-3-yl]oxymethyl]-1,3-benzodioxole-5-carboxamide (29)

Step 29-1 tert-Butyl (3S)-3-[[(2R)-7-bromo-5-methoxycarbonyl-2,4-dimethyl-1,3-benzodioxol-2-yl]methoxy]pyrrolidine-1-carboxylate A racemate of the title compound (1.98 g, 4.07 mmol, 50% yield) was obtained through the same reaction as in step 1-1 using the compound (A1a) (2.15 g, 8.24 mmol) synthesized in Reference Example 1 and tert-butyl (3S)-3-prop-2-ynoxypyrrolidine-1-carboxylate (2.78 g, 12.4 mmol) synthesized according to the method described in J. Am. Chem. Soc., 2010, 132 (8), pp 2570-2572.

$^1$H-NMR (400 MHz, CDCl$_3$) δ: 1.45 (9H, s), 1.74 (3H, s), 1.84-1.93 (2H, m), 2.39 (3H, s), 3.25-3.47 (4H, m), 3.63-3.71 (2H, m), 3.85 (3H, s), 4.13-4.18 (1H, m), 7.69 (1H, s).

This compound was resolved into each diastereomer under the following conditions:
Column: Daicel CHIRALCEL AY-H 4.6 mm ID×250 mm L
Elution solvent: n-hexane:2-propanol=90:10 (V/V)
Flow rate: 1.00 mL/min
Temperature: 40° C.
First peak: 8.4 min
Second peak: 10.3 min The following steps were carried out using the second peak separated using a preparative chiral column.

Step 29-2

(2R)-7-Bromo-2-[[(3S)-1-tert-butoxycarbonylpyrrolidin-3-yl]oxymethyl]-2,4-dimethyl-1,3-benzodioxole-5-carboxylic Acid The title compound (1.17 g, 2.47 mmol, 100% yield) was obtained through the same reaction as in step 1-2 using tert-butyl (3S)-3-[[(2R)-7-bromo-5-methoxycarbonyl-2,4-dimethyl-1,3-benzodioxol-2-yl]methoxy]pyrrolidine-1-carboxylate (second peak, 1.20 g, 2.47 mmol) synthesized in step 29-1.

MS (APCI) m/z: 470, 472 (M−H)$^-$.

Step 29-3 tert-Butyl (3S)-3-[[(2R)-7-bromo-5-[(4,6-dimethyl-2-oxo-1,2-dihydropyridin-3-yl)methylcarbamoyl]-2,4-dimethyl-1,3-benzodioxol-2-yl]methoxy]pyrrolidine-1-carboxylate The title compound (1.32 g, 2.18 mmol, 89% yield) was obtained through the same reaction as in step 1-3 using (2R)-7-bromo-2-[[(3S)-1-tert-butoxycarbonylpyrrolidin-3-yl]oxymethyl]-2,4-dimethyl-1,3-benzodioxole-5-carboxylic acid (1.17 g, 2.47 mmol) synthesized in step 29-2.

$^1$H-NMR (400 MHz, CDCl$_3$) δ: 1.44 (9H, s), 1.71 (3H, br s), 1.82-1.98 (2H, m), 2.23 (3H, s), 2.27 (3H, s), 2.37 (3H, s), 3.29-3.47 (4H, m), 3.64 (2H, s), 4.12-4.17 (1H, m), 4.50 (2H, d, J=6.1 Hz), 5.97 (1H, s), 7.03 (1H, s), 7.29 (1H, br s).

MS (APCI) m/z: 606, 608 (M+H)$^+$.

Step 29-4

(2R)-7-Bromo-N-[(4,6-dimethyl-2-oxo-1,2-dihydropyridin-3-yl)methyl]-2,4-dimethyl-2-[[(3S)-pyrrolidin-3-yl]oxymethyl]-1,3-benzodioxole-5-carboxamide The title compound (1.01 g, 1.99 mmol, 93% yield) was obtained through the same reaction as in step 3-4 using tert-butyl (3S)-3-[[(2R)-7-bromo-5-[(4,6-dimethyl-2-oxo-1,2-dihydropyridin-3-yl)methylcarbamoyl]-2,4-dimethyl-1,3-benzodioxol-2-yl]methoxy]pyrrolidine-1-carboxylate (1.30 g, 2.14 mmol) synthesized in step 29-3.

MS (APCI) m/z: 506, 508 (M+H)$^+$.

Step 29-5

(2R)-7-Bromo-N-[(4,6-dimethyl-2-oxo-1,2-dihydropyridin-3-yl)methyl]-2,4-dimethyl-2-[[(3S)-1-methylpyrrolidin-3-yl]oxymethyl]-1,3-benzodioxole-5-carboxamide (29)

The title compound (0.442 g, 0.849 mmol, 86% yield) was obtained through the same reaction as in step 3-5 using (2R)-7-bromo-N-[(4,6-dimethyl-2-oxo-1,2-dihydropyridin-3-yl)methyl]-2,4-dimethyl-2-[[(3S)-pyrrolidin-3-yl]oxymethyl]-1,3-benzodioxole-5-carboxamide (0.500 g, 0.987 mmol) synthesized in step 29-4.

$^1$H-NMR (400 MHz, DMSO-d$_6$) δ: 1.52-1.61 (1H, m), 1.64 (3H, s), 1.90-2.01 (1H, m), 2.10 (3H, s), 2.11 (3H, s), 2.17 (6H, s), 2.18-2.27 (2H, m), 2.32-2.37 (1H, m), 2.37-2.48 (1H, m), 3.63 (2H, d, J=12.0 Hz), 3.66 (1H, d, J=12.0 Hz), 4.06-4.12 (1H, m), 4.21 (2H, d, J=4.9 Hz), 5.86 (1H, s), 6.96 (1H, s), 8.17 (1H, t, J=4.9 Hz), 11.50 (1H, s).

MS (APCI) m/z: 520, 522 (M+H)$^+$.

Example 30

7-Chloro-2-[2-(dimethylamino)spiro[3.3]heptan-6-yl]-N-[(4,6-dimethyl-2-oxo-1,2-dihydropyridin-3-yl)methyl]-2,4-dimethyl-1,3-benzodioxole-5-carboxamide (30)

Step 30-1

Methyl 2-[2-(tert-butoxycarbonylamino)spiro[3.3]heptan-6-yl]-7-chloro-2,4-dimethyl-1,3-benzodioxole-5-carboxylate The title compound (0.555 g, 1.23 mmol, 89% yield) was obtained through the same reaction as in step 13-1 using the compound (A1b) (0.300 g, 1.38 mmol) synthesized in Reference Example 2 and the compound (S8-2) (0.489 g, 2.08 mmol) synthesized in Reference Example 8.

$^1$H-NMR (400 MHz, CDCl$_3$) δ: 1.41 (9H, s), 1.55 (3H, s), 1.70-1.85 (2H, m), 1.92-2.16 (4H, m), 2.27-2.40 (1H, m), 2.39 (3H, s), 2.40-2.52 (1H, m), 2.67-2.77 (1H, m), 3.84 (3H, s), 3.89-4.02 (1H, m), 4.54-4.68 (1H, m), 7.52 (1H, s).

Step 30-2

2-[2-(tert-Butoxycarbonylamino)spiro[3.3]heptan-6-yl]-7-chloro-2,4-dimethyl-1,3-benzodioxole-5-carboxylic Acid The title compound (0.538 g, 1.23 mmol, 100% yield) was obtained through the same reaction as in step 1-2 using methyl 2-[2-(tert-butoxycarbonylamino)spiro[3.3]heptan-6-yl]-7-chloro-2,4-dimethyl-1,3-benzodioxole-5-carboxylate (0.555 g, 1.23 mmol) synthesized in step 30-1.

MS (APCI) m/z: 436 (M–H)⁻.

Step 30-3 tert-Butyl N-[6-[7-chloro-5-[(4,6-dimethyl-2-oxo-1,2-dihydropyridin-3-yl)methylcarbamoyl]-2,4-dimethyl-1,3-benzodioxol-2-yl]spiro[3.3]heptan-2-yl]carbamate The title compound (0.683 g, 1.20 mmol, 97% yield) was obtained through the same reaction as in step 1-3 using 2-[2-(tert-butoxycarbonylamino)spiro[3.3]heptan-6-yl]-7-chloro-2,4-dimethyl-1,3-benzodioxole-5-carboxylic acid (0.538 g, 1.23 mmol) synthesized in step 30-2.

$^1$H-NMR (400 MHz, CDCl$_3$) δ: 1.41 (9H, s), 1.53 (3H, s), 1.68-1.84 (2H, m), 1.88-1.98 (2H, m), 2.00-2.15 (2H, m), 2.24 (3H, s), 2.25 (3H, s), 2.28-2.40 (1H, m), 2.36 (3H, s), 2.40-2.50 (1H, m), 2.64-2.76 (1H, m), 3.90-4.02 (1H, m), 4.49 (2H, d, J=6.0 Hz), 4.54-4.64 (1H, m), 5.95 (1H, s), 6.87 (1H, s), 7.24 (1H, t, J=6.0 Hz), 11.7 (1H, br s).

MS (APCI) m/z: 572 (M+H)⁺.

Step 30-4

2-(2-Aminospiro[3.3]heptan-6-yl)-7-chloro-N-[(4,6-dimethyl-2-oxo-1,2-dihydropyridin-3-yl)methyl]-2,4-dimethyl-1,3-benzodioxole-5-carboxamide The title compound (0.564 g, 1.20 mmol, 100% yield) was obtained through the same reaction as in step 3-4 using tert-butyl N-[6-[7-chloro-5-[(4,6-dimethyl-2-oxo-1,2-dihydropyridin-3-yl)methylcarbamoyl]-2,4-dimethyl-1,3-benzodioxol-2-yl]spiro[3.3]heptan-2-yl]carbamate (0.683 g, 1.20 mmol) synthesized in step 30-3.

MS (APCI) m/z: 472 (M+H)⁺.

Step 30-5

7-Chloro-2-[2-(dimethylamino)spiro[3.3]heptan-6-yl]-N-[(4,6-dimethyl-2-oxo-1,2-dihydropyridin-3-yl)methyl]-2,4-dimethyl-1,3-benzodioxole-5-carboxamide (30)

The title compound (0.057 g, 0.115 mmol, 21% yield) was obtained through the same reaction as in step 3-5 using 2-(2-aminospiro[3.3]heptan-6-yl)-7-chloro-N-[(4,6-dimethyl-2-oxo-1,2-dihydropyridin-3-yl)methyl]-2,4-dimethyl-1,3-benzodioxole-5-carboxamide (0.257 g, 0.543 mmol) synthesized in step 30-4.

$^1$H-NMR (400 MHz, DMSO-d$_6$) δ: 1.52 (3H, s), 1.59-1.66 (1H, m), 1.67-1.74 (1H, m), 1.78-1.98 (4H, m), 1.94 (6H, s), 2.00-2.13 (2H, m), 2.11 (3H, s), 2.12 (3H, s), 2.17 (3H, s), 2.30-2.42 (1H, m), 2.70-2.82 (1H, m), 4.21 (2H, d, J=4.8 Hz), 5.85 (1H, s), 6.84 (1H, s), 8.14 (1H, t, J=4.8 Hz), 11.47 (1H, br s).

MS (APCI) m/z: 500 (M+H)⁺.

Example 31

(2R)-7-Chloro-N-[(4,6-dimethyl-2-oxo-1,2-dihydropyridin-3-yl)methyl]-2-(1-ethyl-4-piperidyl)-2,4-dimethyl-1,3-benzodioxole-5-carboxamide (31)

Step 31-1 tert-Butyl 4-[(2R)-7-chloro-5-methoxycarbonyl-2,4-dimethyl-1,3-benzodioxol-2-yl]piperidine-1-carboxylate A racemate of the title compound (8.47 g, 19.9 mmol, 50.7% yield) was obtained through the same reaction as in step 1-1 using the compound (A1b) (8.50 g, 39.2 mmol) synthesized in Reference Example 2 and tert-butyl 4-ethynylpiperidine-1-carboxylate (12.3 g, 58.9 mmol) synthesized according to the method described in WO 2008156739.

$^1$H-NMR (400 MHz, CDCl$_3$) δ: 1.30-1.45 (2H, m), 1.46 (9H, s), 1.67 (3H, s), 1.78-1.87 (2H, m), 1.96-2.05 (1H, m), 2.39 (3H, s), 2.58-2.73 (2H, m), 3.85 (3H, s), 4.10 (2H, m), 7.55 (1H, s).

This compound was resolved into each diastereomer under the following conditions:
Column: Daicel CHIRALCEL OZ-H 4.6 mm ID×250 mm L
Elution solvent: n-hexane:2-propanol:methanol=97:1:2 (V/V)
Flow rate: 1.00 mL/min
Temperature: 40° C.
First peak: 7.1 min (specific rotation [α]$_D^{20}$=−18.4 (C=1.0, chloroform))
Second peak: 7.9 min (specific rotation [α]$_D^{20}$=+17.7 (C=1.0, chloroform))

The following steps were carried out using the second peak separated using a preparative chiral column.

Step 31-2

(2R)-2-(1-tert-Butoxycarbonyl-4-piperidyl)-7-chloro-2,4-dimethyl-1,3-benzodioxole-5-carboxylic Acid The title compound (0.827 g, 2.01 mmol, 85% yield) was obtained through the same reaction as in step 1-2 using tert-butyl 4-[(2R)-7-chloro-5-methoxycarbonyl-2,4-dimethyl-1,3-benzodioxol-2-yl]piperidine-1-carboxylate (second peak, 1.01 g, 2.37 mmol) synthesized in step 31-1.

Step 31-3 tert-Butyl 4-[(2R)-7-chloro-5-[(4,6-dimethyl-2-oxo-1,2-dihydropyridin-3-yl)methylcarbamoyl]-2,4-dimethyl-1,3-benzodioxol-2-yl]piperidine-1-carboxylate The title compound (0.986 g, 1.81 mmol, 90% yield) was obtained through the same reaction as in step 1-3 using (2R)-2-(1-tert-butoxycarbonyl-4-piperidyl)-7-chloro-2,4-dimethyl-1,3-benzodioxole-5-carboxylic acid (0.827 g, 2.01 mmol) synthesized in step 31-2.

$^1$H-NMR (400 MHz, CDCl$_3$) δ: 1.31-1.43 (2H, m), 1.45 (9H, s), 1.61 (3H, s), 1.75-1.86 (2H, m), 1.93-2.01 (1H, m), 2.23 (3H, s), 2.26 (3H, s), 2.37 (3H, s), 2.60-2.72 (2H, m), 4.13-4.28 (2H, m), 4.49 (2H, d, J=5.5 Hz), 5.95 (1H, s), 6.88 (1H, s), 7.21 (1H, br s).

MS (APCI) m/z: 546 (M+H)$^+$.

Step 31-4

(2R)-7-Chloro-N-[(4,6-dimethyl-2-oxo-1,2-dihydropyridin-3-yl)methyl]-2,4-dimethyl-2-(4-piperidyl)-1,3-benzodioxole-5-carboxamide The title compound (0.805 g, 1.81 mmol, 100% yield) was obtained through the same reaction as in step 3-4 using tert-butyl 4-[(2R)-7-chloro-5-[(4,6-dimethyl-2-oxo-1,2-dihydropyridin-3-yl)methylcarbamoyl]-2,4-dimethyl-1,3-benzodioxol-2-yl]piperidine-1-carboxylate (0.986 g, 1.81 mmol) synthesized in step 31-3.

MS (APCI) m/z: 446 (M+H)$^+$.

Step 31-5

(2R)-7-Chloro-N-[(4,6-dimethyl-2-oxo-1,2-dihydropyridin-3-yl)methyl]-2-(1-ethyl-4-piperidyl)-2,4-dimethyl-1,3-benzodioxole-5-carboxamide (31)

The title compound (0.508 g, 1.07 mmol, 59% yield) was obtained through the same reaction as in step 3-5 using (2R)-7-chloro-N-[(4,6-dimethyl-2-oxo-1,2-dihydropyridin-3-yl)methyl]-2,4-dimethyl-2-(4-piperidyl)-1,3-benzodioxole-5-carboxamide (0.805 g, 1.81 mmol) synthesized in step 31-4 and acetaldehyde (1.19 g, 27.1 mmol).

$^1$H-NMR (400 MHz, DMSO-d$_6$) δ: 0.96 (3H, t, J=7.3 Hz), 1.29-1.42 (2H, m), 1.61 (3H, s), 1.66-1.89 (5H, m), 2.10 (3H, s), 2.11 (3H, s), 2.17 (3H, s), 2.27 (2H, q, J=7.3 Hz), 2.87-2.88 (2H, m), 4.21 (2H, d, J=4.9 Hz), 5.85 (1H, s), 6.84 (1H, s), 8.14 (1H, t, J=4.9 Hz), 11.48 (1H, s).

MS (APCI) m/z: 474 (M+H)$^+$.

Example 32

7-Chloro-N-[(4,6-dimethyl-2-oxo-1,2-dihydropyridin-3-yl)methyl]-2,4-dimethyl-2-[trans-4-(methylamino)cyclohexyl]-1,3-benzodioxole-5-carboxamide (32)

Step 32-1

Methyl 2-[tarns-4-[tert-butoxycarbonyl(methyl)amino]cyclohexyl]-7-chloro-2,4-dimethyl-1,3-benzodioxole-5-carboxylate The title compound (0.475 g, 1.05 mmol, 76% yield) was obtained through the same reaction as in step 13-1 using the compound (A1b) (0.300 g, 1.38 mmol) synthesized in Reference Example 2 and the compound (S14) (0.493 g, 2.08 mmol) synthesized in Reference Example 14.

$^1$H-NMR (400 MHz, CDCl$_3$) δ: 1.24-1.52 (4H, m), 1.46 (9H, s), 1.63 (3H, s), 1.72-1.86 (3H, m), 1.94-2.05 (2H, m), 2.38 (3H, s), 2.71 (3H, br s), 3.60-4.06 (1H, m), 3.85 (3H, s), 7.53 (1H, s).

Step 32-2

2-[trans-4-[tert-Butoxycarbonyl(methyl)amino]cyclohexyl]-7-chloro-2,4-dimethyl-1,3-benzodioxole-5-carboxylic Acid The title compound (0.460 g, 1.05 mmol, 100% yield) was obtained through the same reaction as in step 1-2 using methyl 2-[trans-4-[tert-butoxycarbonyl(methyl)amino]cyclohexyl]-7-chloro-2,4-dimethyl-1,3-benzodioxole-5-carboxylate (0.475 g, 1.05 mmol) synthesized in step 32-1.

$^1$H-NMR (CDCl$_3$) δ: 1.30-1.52 (4H, m), 1.47 (9H, s), 1.65 (3H, s), 1.72-1.86 (3H, m), 1.94-2.05 (2H, m), 2.38 (3H, s), 2.71 (3H, br s), 7.77 (1H, s).

MS (APCI) m/z: 438 (M−H)$^-$.

Step 32-3 tert-Butyl N-[trans-4-[7-chloro-5-[(4,6-dimethyl-2-oxo-1,2-dihydropyridin-3-yl)methylcarbamoyl]-2,4-dimethyl-1,3-benzodioxol-2-yl]cyclohexyl]-N-methyl-carbamate The title compound (0.559 g, 0.973 mmol, 93% yield) was obtained through the same reaction as in step 1-3 using 2-[trans-4-[tert-butoxycarbonyl(methyl)amino]cyclohexyl]-7-chloro-2,4-dimethyl-1,3-benzodioxole-5-carboxylic acid (0.460 g, 1.05 mmol) synthesized in step 32-2.

$^1$H-NMR (400 MHz, CDCl$_3$) δ: 1.24-1.50 (4H, m), 1.45 (9H, s), 1.59 (3H, s), 1.71-1.81 (3H, m), 1.92-2.02 (2H, m), 2.22 (3H, s), 2.26 (3H, s), 2.36 (3H, s), 2.70 (3H, br s), 3.58-4.06 (1H, br m), 4.49 (2H, d, J=5.2 Hz), 5.96 (1H, s), 6.87 (1H, s), 7.27 (1H, t, J=5.2 Hz), 12.2 (1H, br s).

MS (APCI) m/z: 574 (M+H)$^+$.

Step 32-4

7-Chloro-N-[(4,6-dimethyl-2-oxo-1,2-dihydropyridin-3-yl)methyl]-2,4-dimethyl-2-[trans-4-(methylamino)cyclohexyl]-1,3-benzodioxole-5-carboxamide (32)

The title compound (0.297 g, 0.626 mmol, 64% yield) was obtained through the same reaction as in step 3-4 using tert-butyl N-[trans-4-[7-chloro-5-[(4,6-dimethyl-2-oxo-1,2-dihydropyridin-3-yl)methylcarbamoyl]-2,4-dimethyl-1,3-benzodioxol-2-yl]cyclohexyl]-N-methyl-carbamate (0.559 g, 0.973 mmol) synthesized in step 32-3.

$^1$H-NMR (400 MHz, DMSO-d$_6$) δ: 0.87-0.99 (2H, m), 1.08-1.21 (2H, m), 1.58 (3H, s), 1.74-1.87 (3H, m), 1.87-1.95 (2H, m), 2.05-2.18 (1H, m), 2.10 (6H, s), 2.15 (3H, s), 2.22 (3H, s), 4.20 (2H, d, J=4.8 Hz), 5.84 (1H, s), 6.82 (1H, s), 8.12 (1H, t, J=4.8 Hz).

MS (APCI) m/z: 474 (M+H)$^+$.

Example 33

7-Chloro-N-[(4,6-dimethyl-2-oxo-1,2-dihydropyridin-3-yl)methyl]-2-[trans-4-[formyl(methyl)amino]cyclohexyl]-2,4-dimethyl-1,3-benzodioxole-5-carboxamide (33)

The compound (32) (0.100 g, 0.211 mmol) synthesized in step 32-4 was dissolved in toluene (4 mL) and formic acid (2 mL). To the solution, acetic anhydride (0.001 g, 0.011 mmol) was added, and the mixture was refluxed for 8 hours. The reaction solution was concentrated under reduced pressure, followed by extraction by the addition of ethyl acetate and water. The organic layer was washed with water and saturated saline and dried over sodium sulfate. After concentration under reduced pressure, the obtained residue was purified by silica gel column chromatography (ethyl acetate: methanol=100:0→4 60:40) to obtain the title compound (0.034 g, 0.069 mmol, 33% yield) in a formyl form.

$^1$H-NMR (400 MHz, CD$_3$OD) δ: 1.37-1.47 (2H, m), 1.63 (3H, s), 1.63-1.81 (4H, m), 1.88-1.96 (1H, m), 2.00-2.06 (2H, m), 2.17 (3H, s), 2.24 (3H, s), 2.35 (3H, s), 2.78 (3H, s), 3.45-3.50 (1H, m), 4.41 (2H, s), 6.10 (1H, s), 6.87 (1H, s), 8.12 (1H, s).

MS (ESI) m/z: 502 (M+H)$^+$.

Example 34

7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (34)

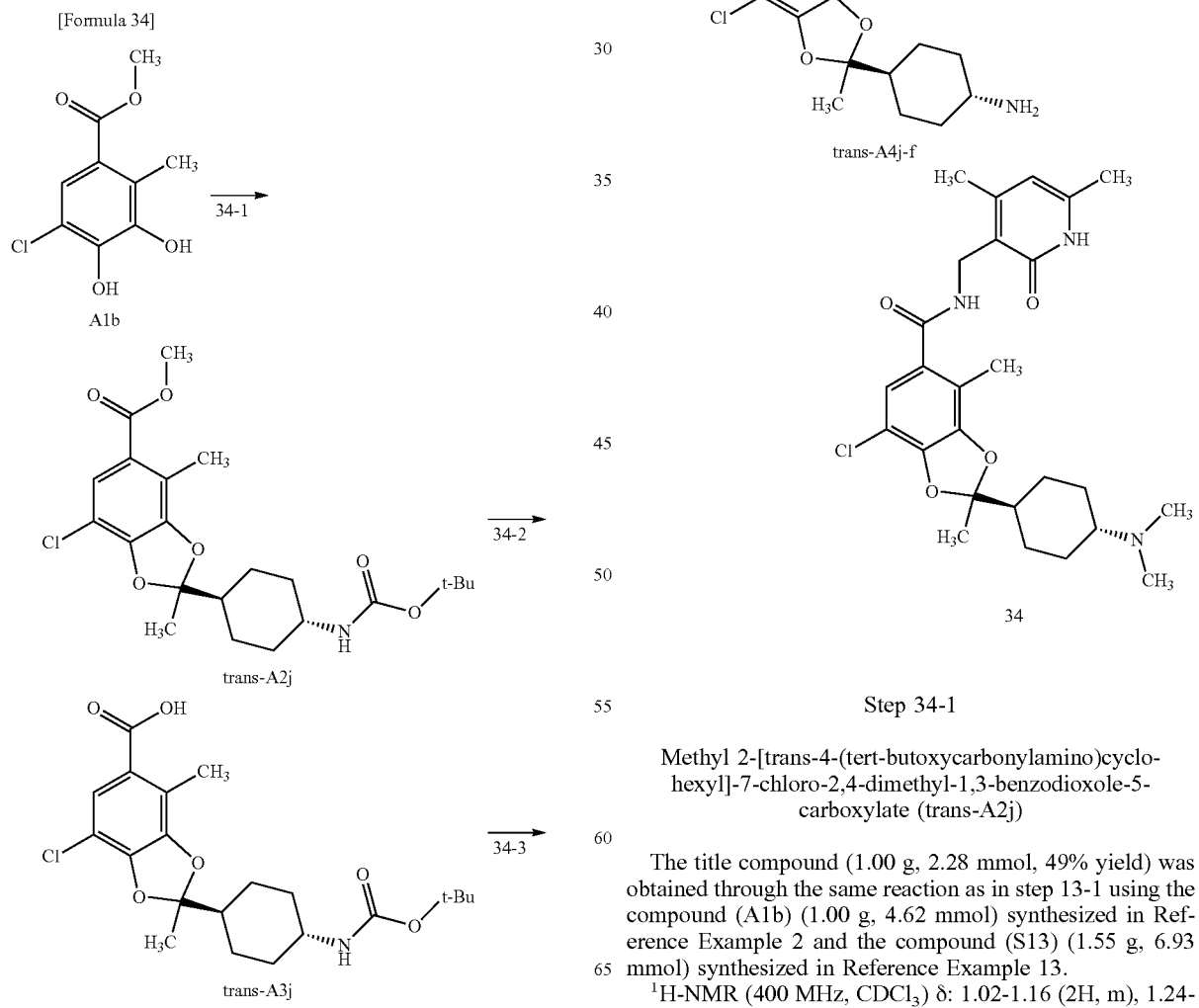

Step 34-1

Methyl 2-[trans-4-(tert-butoxycarbonylamino)cyclohexyl]-7-chloro-2,4-dimethyl-1,3-benzodioxole-5-carboxylate (trans-A2j)

The title compound (1.00 g, 2.28 mmol, 49% yield) was obtained through the same reaction as in step 13-1 using the compound (A1b) (1.00 g, 4.62 mmol) synthesized in Reference Example 2 and the compound (S13) (1.55 g, 6.93 mmol) synthesized in Reference Example 13.

$^1$H-NMR (400 MHz, CDCl$_3$) δ: 1.02-1.16 (2H, m), 1.24-1.40 (2H, m), 1.44 (9H, s), 1.62 (3H, s), 1.78-1.88 (1H, m), 1.91-2.00 (2H, m), 2.04-2.12 (2H, m), 2.38 (3H, s), 3.33-3.46 (1H, m), 3.85 (3H, s), 4.37 (1H, br s), 7.53 (1H, s).

Step 34-2

2-[trans-4-(tert-Butoxycarbonylamino)cyclohexyl]-7-chloro-2,4-dimethyl-1,3-benzodioxole-5-carboxylic Acid (trans-A3j)

The title compound (0.972 g, 2.28 mmol, 100% yield) was obtained through the same reaction as in step 1-2 using the compound (trans-A2j) (1.00 g, 2.28 mmol) synthesized in step 34-1.

$^1$H-NMR (400 MHz, CDCl$_3$) δ: 1.04-1.16 (2H, m), 1.24-1.40 (2H, m), 1.44 (9H, s), 1.64 (3H, s), 1.80-1.88 (1H, m), 1.92-2.02 (2H, m), 2.04-2.14 (2H, m), 2.42 (3H, s), 3.35-3.45 (1H, m), 4.39 (1H, br s), 7.68 (1H, s).

MS (APCI) m/z: 424 (M–H)$^-$.

Step 34-3 tert-Butyl N-[trans-4-[7-chloro-5-[(4,6-dimethyl-2-oxo-1,2-dihydropyridin-3-yl)methylcarbamoyl]-2,4-dimethyl-1,3-benzodioxol-2-yl]cyclohexyl]carbamate (trans-A4j)

The title compound (0.676 g, 1.21 mmol, 52.9% yield) was obtained through the same reaction as in step 1-3 using the compound (trans-A3j) (0.972 g, 2.28 mmol) synthesized in step 34-2.

$^1$H-NMR (400 MHz, CDCl$_3$) δ: 1.02-1.16 (2H, m), 1.23-1.38 (2H, m), 1.44 (9H, s), 1.60 (3H, s), 1.76-1.84 (1H, m), 1.90-1.98 (2H, m), 2.03-2.10 (2H, m), 2.23 (3H, s), 2.26 (3H, s), 2.37 (3H, s), 3.30-3.46 (1H, m), 4.40 (1H, d, J=8.5 Hz), 4.50 (2H, d, J=6.1 Hz), 5.97 (1H, s), 6.88 (1H, s), 7.28 (1H, t, J=6.1 Hz).

MS (APCI) m/z: 560 (M+H)$^+$.

Step 34-4

2-(trans-4-Aminocyclohexyl)-7-chloro-N-[(4,6-dimethyl-2-oxo-1,2-dihydropyridin-3-yl)methyl]-2,4-dimethyl-1,3-benzodioxole-5-carboxamide (trans-A4j-f)

The title compound (0.555 g, 1.21 mmol, 100% yield) was obtained through the same reaction as in step 3-4 using the compound (trans-A4j) (0.676 g, 1.21 mmol) synthesized in step 34-3.

MS (APCI) m/z: 460 (M+H)$^+$.

Step 34-5

7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (34)

The title compound (0.425 g, 0.872 mmol, 72% yield) was obtained through the same reaction as in step 3-5 using the compound (trans-A4j-f) (0.555 g, 1.21 mmol) synthesized in step 34-4.

$^1$H-NMR (400 MHz, DMSO-d$_6$) δ: 1.04-1.21 (4H, m), 1.60 (3H, s), 1.73-1.90 (5H, m), 2.03-2.10 (1H, m), 2.11 (6H, s), 2.14 (6H, s), 2.16 (3H, s), 4.21 (2H, d, J=4.9 Hz), 5.85 (1H, s), 6.84 (1H, s), 8.12 (1H, t, J=4.9 Hz), 11.47 (1H, s).

MS (APCI) m/z: 488 (M+H)$^+$.

This compound was resolved into each enantiomer under the following conditions:

Column: Daicel CHIRALCEL OZ-H 4.6 mm ID×250 mm L
Elution solvent: n-hexane:ethanol:diethylamine=60:40:0.04 (V/V)
Flow rate: 1.00 mL/min
Temperature: 35° C.
First peak: 6.5 min (specific rotation [α]$_D^{20}$=+1.0 (C=1.0, chloroform))
Second peak: 9.6 min (specific rotation [α]$_D^{20}$=–0.9 (C=1.0, chloroform))

Example 35

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (35)

[Formula 35]

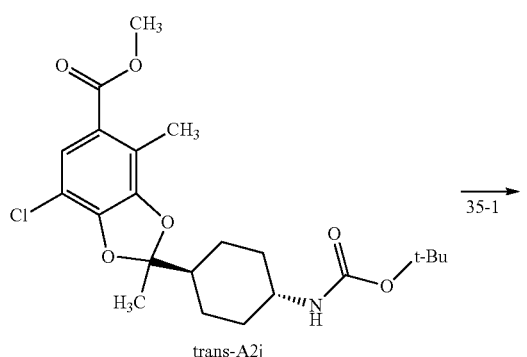

trans-A2j

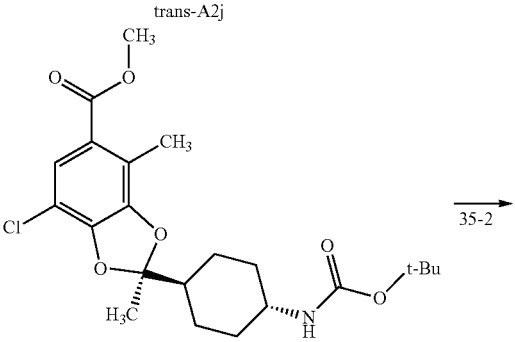

trans-(2R)-A2j

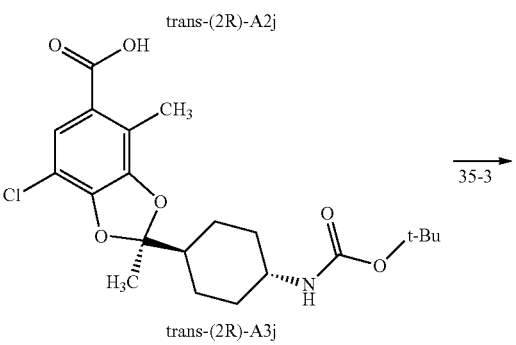

trans-(2R)-A3j

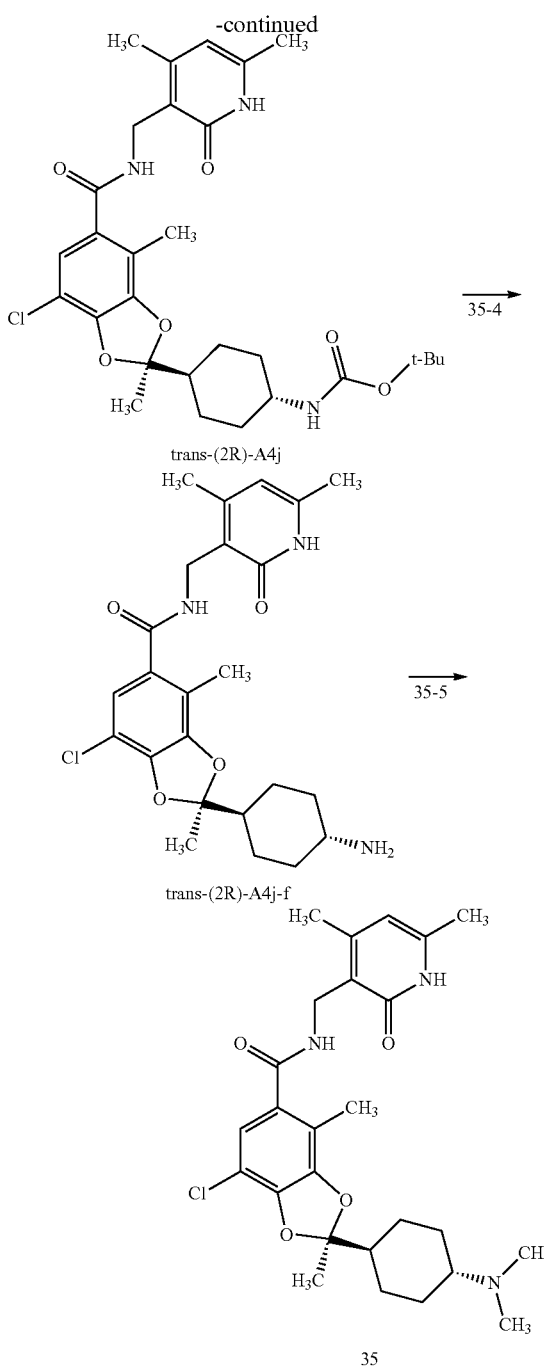

trans-(2R)-A4j trans-(2R)-A4j-f

35

First peak: 10.7 min ($[\alpha]_D^{20}$=−18.3 (C=0.92, chloroform))
Second peak: 11.7 min ($[\alpha]_D^{20}$=+18.3 (C=0.96, chloroform))

The following steps were carried out using the second peak separated using a preparative chiral column.

(Step (35)-2)

(2R)-2-[trans-4-(tert-Butoxycarbonylamino)cyclohexyl]-7-chloro-2,4-dimethyl-1,3-benzodioxole-5-carboxylic Acid (trans-(2R)-A3j)

The title compound (0.227 g, 0.532 mmol, 100% yield) was obtained through the same reaction as in step 1-2 using the compound (trans-(2R)-A2j) (second peak, 0.234 g, 0.532 mmol) separated in step 35-1.

(Step (35)-3)

tert-Butyl N-[trans-4-[(2R)-7-chloro-5-[(4,6-dimethyl-2-oxo-1,2-dihydropyridin-3-yl)methylcarbamoyl]-2,4-dimethyl-1,3-benzodioxol-2-yl]cyclohexyl] carbamate (trans-(2R)-A4j)

The title compound (0.298 g, 0.532 mmol, 100% yield) was obtained through the same reaction as in step 1-3 using the compound (trans-(2R)-A3j) (0.227 g, 0.532 mmol) synthesized in step 35-2.

$^1$H-NMR (400 MHz, CDCl$_3$) δ: 1.01-1.16 (2H, m), 1.23-1.38 (2H, m), 1.44 (9H, s), 1.59 (3H, s), 1.76-1.84 (1H, m), 1.88-1.95 (2H, m), 2.02-2.11 (2H, m), 2.22 (3H, s), 2.25 (3H, s), 2.37 (3H, s), 3.30-3.46 (1H, m), 4.35-4.41 (1H, m), 4.49 (2H, d, J=6.1 Hz), 5.96 (1H, s), 6.87 (1H, s), 7.23 (1H, t, J=6.1 Hz).

MS (APCI) m/z: 560 (M+H)$^+$.

(Step (35)-4)

(2R)-2-(trans-4-Aminocyclohexyl)-7-chloro-N-[(4,6-dimethyl-2-oxo-1,2-dihydropyridin-3-yl)methyl]-2,4-dimethyl-1,3-benzodioxole-5-carboxamide (trans-(2R)-A4j-f)

The title compound (0.241 g, 0.524 mmol, 98% yield) was obtained through the same reaction as in step 3-4 using the compound (trans-(2R)-A4j) (0.298 g, 0.532 mmol) synthesized in step 35-3.

MS (APCI) m/z: 460 (M+H)$^+$.

(Step (35)-5)

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (35)

The title compound (0.187 g, 0.383 mmol, 73% yield) was obtained through the same reaction as in step 3-5 using the compound (trans-(2R)-A4j-f) (0.241 g, 0.524 mmol) synthesized in step 35-4.

$^1$H-NMR (400 MHz, DMSO-d$_6$) δ: 1.08-1.21 (4H, m), 1.59 (3H, s), 1.77-1.90 (5H, m), 2.03-2.09 (1H, m), 2.11 (6H, s), 2.13 (6H, s), 2.16 (3H, s), 4.21 (2H, d, J=4.9 Hz), (Step (35)-1)

Methyl (2R)-2-[trans-4-(tert-butoxycarbonylamino)cyclohexyl]-7-chloro-2,4-dimethyl-1,3-benzodioxole-5-carboxylate (trans-(2R)-A2j)

The compound (trans-A2j) synthesized in step 34-1 was resolved into each enantiomer under the following conditions:
Column: Daicel CHIRALCEL OZ-H 4.6 mm ID×250 mm L
Elution solvent: n-hexane:ethanol=98:2 (V/V)
Flow rate: 1.00 mL/min
Temperature: 25° C.

5.85 (1H, s), 6.84 (1H, s), 8.13 (1H, t, J=4.9 Hz), 11.48 (1H, s).
MS (APCI) m/z: 488 (M+H)⁺.
Specific rotation [α]$_D^{20}$=+1.0 (C=1.0, chloroform)
This compound agreed with the compound of the first peak obtained under the resolution conditions using a chiral column described in Example 34.

Example 36

7-Chloro-2-[trans-4-(dimethylamino)cyclohexyl]-N-[(4-methoxy-6-methyl-2-oxo-1,2-dihydropyridin-3-yl)methyl]-2,4-dimethyl-1,3-benzodioxole-5-carboxamide (36)

The compound of Example 36 was obtained in the same way as in steps 13-3, 13-4, and 13-5.

Step 36-1 tert-Butyl N-[trans-4-[7-chloro-5-[(4-methoxy-6-methyl-2-oxo-1,2-dihydropyridin-3-yl)methylcarbamoyl]-2,4-dimethyl-1,3-benzodioxol-2-yl]cyclohexyl]carbamate The title compound (0.263 g, 0.456 mmol, 80% yield) was obtained through the same reaction as in step 1-3 using the compound (trans-A3j) (0.242 g, 0.568 mmol) synthesized in step 34-2 and 3-(aminomethyl)-4-methoxy-6-methyl-1H-pyridin-2-one hydrochloride (0.128 g, 0.625 mmol) synthesized according to the method described in WO20131201042.
¹H-NMR (400 MHz, DMSO-d₆) δ: 1.05-1.22 (4H, m), 1.35 (9H, s), 1.58 (3H, s), 1.73-1.87 (5H, m), 2.11 (3H, s), 2.17 (3H, s), 3.05-3.22 (1H, m), 3.79 (3H, s), 4.15 (2H, d, J=4.8 Hz), 6.08 (1H, s), 6.73 (1H, d, J=8.0 Hz), 6.81 (1H, s), 7.93 (1H, t, J=4.8 Hz), 11.4 (1H, br s).
MS (APCI) m/z: 576 (M+H)⁺.

Step 36-2

2-(trans-4-Aminocyclohexyl)-7-chloro-N-[(4-methoxy-6-methyl-2-oxo-1,2-dihydropyridin-3-yl)methyl]-2,4-dimethyl-1,3-benzodioxole-5-carboxamide The title compound (0.206 g, 0.434 mmol, 95% yield) was obtained through the same reaction as in step 3-4 using tert-butyl N-[trans-4-[7-chloro-5-[(4-methoxy-6-methyl-2-oxo-1,2-dihydropyridin-3-yl)methylcarbamoyl]-2,4-dimethyl-1,3-benzodioxol-2-yl]cyclohexyl]carbamate (0.263 g, 0.456 mmol) synthesized in step 36-1.
¹H-NMR (400 MHz, DMSO-d₆) δ: 0.91-1.04 (2H, m), 1.08-1.22 (2H, m), 1.58 (3H, s), 1.71-1.82 (5H, m), 2.10 (3H, s), 2.17 (3H, s), 2.38-2.47 (1H, m), 3.56 (2H, s), 3.78 (3H, s), 4.15 (2H, d, J=4.3 Hz), 6.08 (1H, s), 6.81 (1H, s), 7.93 (1H, t, J=4.3 Hz).
MS (APCI) m/z: 476 (M+H)⁺.

Step 36-3

7-Chloro-2-[trans-4-(dimethylamino)cyclohexyl]-N-[(4-methoxy-6-methyl-2-oxo-1,2-dihydropyridin-3-yl)methyl]-2,4-dimethyl-1,3-benzodioxole-5-carboxamide (36)

The title compound (0.157 g, 0.311 mmol, 72% yield) was obtained through the same reaction as in step 3-5 using tert-butyl N-[trans-4-[7-chloro-5-[(4-methoxy-6-methyl-2-oxo-1,2-dihydropyridin-3-yl)methylcarbamoyl]-2,4-dimethyl-1,3-benzodioxol-2-yl]cyclohexyl]carbamate (0.206 g, 0.434 mmol) synthesized in step 36-2.
¹H-NMR (400 MHz, DMSO-d₆) δ: 1.06-1.22 (4H, m), 1.58 (3H, s), 1.72-1.90 (5H, m), 2.00-2.19 (1H, m), 2.10 (3H, s), 2.12 (6H, s), 2.17 (3H, s), 3.78 (3H, s), 4.15 (2H, d, J=4.4 Hz), 6.08 (1H, s), 6.81 (1H, s), 7.93 (1H, t, J=4.4 Hz), 11.4 (1H, brs).
MS (APCI) m/z: 504 (M+H)⁺.

Example 37

7-Chloro-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide (37)

Step 37-1 tert-Butyl N-[trans-4-[7-chloro-5-[(4-ethyl-6-methyl-2-oxo-1,2-dihydropyridin-3-yl)methylcarbamoyl]-2,4-dimethyl-1,3-benzodioxol-2-yl]cyclohexyl]carbamate The title compound (0.528 g, 0.920 mmol, 65% yield) was obtained through the same reaction as in step 1-3 using the compound (trans-A3j) (0.602 g, 1.41 mmol) synthesized in step 34-2 and 3-(aminomethyl)-4-ethyl-6-methyl-1H-pyridin-2-one (0.259 g, 1.56 mmol) synthesized according to the method described in WO2011140324.
¹H-NMR (400 MHz, CDCl₃) δ: 1.02-1.15 (2H, m), 1.20 (3H, t, J=7.5 Hz), 1.25-1.37 (2H, m), 1.43 (9H, s), 1.59 (3H, s), 1.72-1.85 (1H, m), 1.89-1.97 (2H, m), 2.03-2.11 (2H, m), 2.22 (3H, s), 2.27 (3H, s), 2.71 (2H, q, J=7.5 Hz), 3.32-3.45 (1H, m), 4.39 (1H, br s), 4.51 (2H, d, J=5.5 Hz), 5.98 (1H, s), 6.87 (1H, s), 7.22-7.31 (1H, m).
MS (APCI) m/z: 574 (M+H)⁺.

Step 37-2

2-(trans-4-Aminocyclohexyl)-7-chloro-N-[(4-ethyl-6-methyl-2-oxo-1,2-dihydropyridin-3-yl)methyl]-2,4-dimethyl-1,3-benzodioxole-5-carboxamide The title compound (0.436 g, 0.920 mmol, 100% yield) was obtained through the same reaction as in step 3-4 using tert-butyl N-[trans-4-[7-chloro-5-[(4-ethyl-6-methyl-2-oxo-1,2-dihydropyridin-3-yl)methylcarbamoyl]-2,4-dimethyl-1,3-benzodioxol-2-yl]cyclohexyl]carbamate (0.528 g, 0.920 mmol) synthesized in step 37-1.
MS (APCI) m/z: 474 (M+H)⁺.

Step 37-3

7-Chloro-2-[trans-4-(dimethylamino)cyclohexyl]-N-[(4-ethyl-6-methyl-2-oxo-1,2-dihydropyridin-3-yl)methyl]-2,4-dimethyl-1,3-benzodioxole-5-carboxamide (37)

The title compound (0.399 g, 0.794 mmol, 86% yield) was obtained through the same reaction as in step 3-5 using 2-(trans-4-aminocyclohexyl)-7-chloro-N-[(4-ethyl-6-methyl-2-oxo-1,2-dihydropyridin-3-yl)methyl]-2,4-dimethyl-1,3-benzodioxole-5-carboxamide (0.436 g, 0.920 mmol) synthesized in step 37-2.

¹H-NMR (400 MHz, DMSO-d₆) δ: 1.10 (3H, t, J=7.6 Hz), 1.12-1.19 (4H, m), 1.60 (3H, s), 1.77-1.89 (5H, m), 2.03-2.10 (1H, m), 2.11 (3H, s), 2.12 (3H, s), 2.13 (6H, s), 2.51 (2H, q, J=7.6 Hz), 4.23 (2H, d, J=4.9 Hz), 5.90 (1H, s), 6.84 (1H, s), 8.14 (1H, t, J=4.9 Hz), 11.50 (1H, s).
MS (APCI) m/z: 502 (M+H)⁺.

Example 38

7-Chloro-2-[(2S,5R)-5-(dimethylamino)tetrahydropyran-2-yl]-N-[(4,6-dimethyl-2-oxo-1,2-dihydropyridin-3-yl)methyl]-2,4-dimethyl-1,3-benzodioxole-5-carboxamide (38)

Step 38-1

Methyl 2-[(2S,5R)-5-(tert-butoxycarbonylamino)tetrahydropyran-2-yl]-7-chloro-2,4-dimethyl-1,3-benzodioxole-5-carboxylate The title compound (0.379 g, 0.857 mmol, 74% yield) was obtained through the same reaction as in step 13-1 using the compound (A1b) (0.250 g, 1.15 mmol) synthesized in Reference Example 2 and tert-butyl N-[(3R,6S)-6-ethynyltetrahydropyran-3-yl]carbamate (0.390 g, 1.73 mmol) synthesized according to the method described in WO2007105154.
¹H-NMR (400 MHz, CDCl₃) δ: 1.21-1.35 (1H, m), 1.43 (9H, s), 1.52-1.63 (1H, m), 1.70, 1.71 (3H, s×2), 1.81-1.90 (1H, m), 2.10-2.20 (1H, m), 2.40 (3H, s), 2.99-3.07 (1H, m), 3.45-3.51 (1H, m), 3.55-3.70 (1H, m), 3.85 (3H, s), 4.12-4.30 (2H, m), 7.55 (1H, s).

Step 38-2

2-[(2S,5R)-5-(tert-Butoxycarbonylamino)tetrahydropyran-2-yl]-7-chloro-2,4-dimethyl-1,3-benzodioxole-5-carboxylic Acid The title compound (0.346 g, 0.833 mmol, 97% yield) was obtained through the same reaction as in step 1-2 using methyl 2-[(2S,5R)-5-(tert-butoxycarbonylamino)tetrahydropyran-2-yl]-7-chloro-2,4-dimethyl-1,3-benzodioxole-5-carboxylate (0.379 g, 0.858 mmol) synthesized in step 38-1.
MS (APCI) m/z: 426 (M−H)⁻.

Step 38-3 tert-Butyl N-[(3R,6S)-6-[7-chloro-5-[(4,6-dimethyl-2-oxo-1,2-dihydropyridin-3-yl)methylcarbamoyl]-2,4-dimethyl-1,3-benzodioxol-2-yl]tetrahydropyran-3-yl]carbamate The title compound (0.457 g, 0.813 mmol, 100% yield) was obtained through the same reaction as in step 1-3 using 2-[(2S,5R)-5-(tert-butoxycarbonylamino)tetrahydropyran-2-yl]-7-chloro-2,4-dimethyl-1,3-benzodioxole-5-carboxylic acid (0.348 g, 0.814 mmol) synthesized in step 38-2.
¹H-NMR (400 MHz, CDCl₃) δ: 1.21-1.33 (1H, m), 1.43 (9H, s), 1.50-1.72 (1H, m), 1.67, 1.68 (3H, s×2), 1.77-1.88 (1H, m), 2.08-2.17 (1H, m), 2.23 (3H, s), 2.25 (3H, s), 2.36 (3H, s), 2.98-3.06 (1H, m), 3.42-3.48 (1H, m), 3.52-3.74 (1H, m), 4.10-4.20 (1H, m), 4.21-4.32 (1H, m), 4.49 (2H, d, J=5.6 Hz), 5.96 (1H, s), 6.89 (1H, s), 7.24 (1H, t, J=5.6 Hz), 11.73 (1H, br s).
MS (APCI) m/z: 562 (M+H)⁺.

Step 38-4

2-[(2S,5R)-5-Aminotetrahydropyran-2-yl]-7-chloro-N-[(4,6-dimethyl-2-oxo-1,2-dihydropyridin-3-yl)methyl]-2,4-dimethyl-1,3-benzodioxole-5-carboxamide The title compound (0.343 g, 0.742 mmol, 91% yield) was obtained through the same reaction as in step 3-4 using tert-butyl N-[(3R,6S)-6-[7-chloro-5-[(4,6-dimethyl-2-oxo-1,2-dihydropyridin-3-yl)methylcarbamoyl]-2,4-dimethyl-1,3-benzodioxol-2-yl]tetrahydropyran-3-yl]carbamate (0.457 g, 0.813 mmol) synthesized in step 38-3.
¹H-NMR (400 MHz, DMSO-d₆) δ: 1.09-1.22 (1H, m), 1.29-1.44 (1H, m), 1.58 (3H, s), 1.62-1.71 (1H, m), 1.84-1.93 (1H, m), 2.07 (3H, s), 2.09 (3H, s), 2.15 (3H, s), 2.42-2.58 (1H, m), 2.85-2.93 (1H, m), 3.42-3.48 (1H, m), 4.19 (2H, d, J=5.6 Hz), 5.88 (1H, s), 6.81 (1H, s), 8.14 (1H, t, J=5.6 Hz).
MS (APCI) m/z: 462 (M+H)⁺.

Step 38-5

7-Chloro-2-[(2S,5R)-5-(dimethylamino)tetrahydropyran-2-yl]-N-[(4,6-dimethyl-2-oxo-1,2-dihydropyridin-3-yl)methyl]-2,4-dimethyl-1,3-benzodioxole-5-carboxamide (38)

The title compound (0.132 g, 0.269 mmol, 37% yield) was obtained through the same reaction as in step 3-5 using 2-[(2S,5R)-5-aminotetrahydropyran-2-yl]-7-chloro-N-[(4,6-dimethyl-2-oxo-1,2-dihydropyridin-3-yl)methyl]-2,4-dimethyl-1,3-benzodioxole-5-carboxamide (0.337 g, 0.730 mmol) synthesized in step 38-4.
¹H-NMR (400 MHz, DMSO-d₆) δ: 1.30-1.46 (2H, m), 1.60 (3H, s), 1.72-1.80 (1H, m), 1.92-2.01 (1H, m), 2.07-2.19 (1H, m), 2.11 (6H, s), 2.14 (6H, s), 2.16 (3H, s), 3.12-3.20 (1H, m), 3.48-3.54 (1H, m), 3.96-4.05 (1H, m), 4.20 (2H, d, J=4.8 Hz), 5.84 (1H, s), 6.83 (1H, s), 8.14 (1H, t, J=4.8 Hz), 11.47 (1H, br s).
MS (APCI) m/z: 490 (M+H)⁺.

Example 39

7-Chloro-2-[(2S,5R)-5-(dimethylamino)tetrahydropyran-2-yl]-N-[(4-methoxy-6-methyl-2-oxo-1,2-dihydropyridin-3-yl)methyl]-2,4-dimethyl-1,3-benzodioxole-5-carboxamide (39)

Step 39-1 tert-Butyl N-[(3R,6S)-6-[7-chloro-5-[(4-methoxy-6-methyl-2-oxo-1,2-dihydropyridin-3-yl)methylcarbamoyl]-2,4-dimethyl-1,3-benzodioxol-2-yl]tetrahydropyran-3-yl]carbamate The title compound (0.191 g, 0.331 mmol, 86% yield) was obtained through the same reaction as in step 1-3 using 2-[(2S,5R)-5-(tert-butoxycarbonylamino)tetrahydropyran-2-yl]-7-chloro-2,4-dimethyl-1,3-benzodioxole-5-carboxylic acid (0.165 g, 0.386 mmol) synthesized in step 38-2 and 3-(aminomethyl)-4-methoxy-6-methyl-1,2-dihydropyridin- 2-one hydrochloride (0.087 g, 0.424 mmol) synthesized according to the method described in WO 20131201042.

$^1$H-NMR (400 MHz, DMSO-$d_6$) δ: 1.28-1.51 (2H, m), 1.35 (9H, s), 1.61 (3H, s), 1.69-1.78 (1H, m), 1.83-1.92 (1H, m), 2.11 (3H, s), 2.17 (3H, s), 2.94-3.04 (1H, m), 3.25-3.36 (1H, m), 3.46-3.53 (1H, m), 3.76-3.86 (1H, m), 3.78 (3H, s), 4.15 (2H, d, J=4.8 Hz), 6.08 (1H, s), 6.78-6.85 (2H, m), 7.95 (1H, t, J=4.8 Hz), 11.44 (1H, br s). MS APCI m/z: 578 (M+H)$^+$.

Step 39-2

2-[(2S,5R)-5-Aminotetrahydropyran-2-yl]-7-chloro-N-[(4-methoxy-6-methyl-2-oxo-1,2-dihydropyridin-3-yl)methyl]-2,4-dimethyl-1,3-benzodioxole-5-carboxamide The title compound (0.152 g, 0.318 mmol, 97% yield) was obtained through the same reaction as in step 3-4 using tert-butyl N-[(3R,6S)-6-[7-chloro-5-[(4-methoxy-6-methyl-2-oxo-1,2-dihydropyridin-3-yl)methylcarbamoyl]-2,4-dimethyl-1,3-benzodioxol-2-yl]tetrahydropyran-3-yl]carbamate (0.189 g, 0.327 mmol) synthesized in step 39-1.

$^1$H-NMR (400 MHz, DMSO-$d_6$) δ: 1.08-1.23 (1H, m), 1.30-1.47 (1H, m), 1.57-1.73 (1H, m), 1.60 (3H, s), 1.84-1.93 (1H, m), 2.10 (3H, s), 2.16 (3H, s), 2.45-2.59 (1H, m), 2.84-2.92 (1H, m), 3.27-3.37 (1H, m), 3.43-3.49 (1H, m), 3.55 (2H, s), 3.75-3.83 (1H, m), 3.78 (3H, s), 4.15 (1H, d, J=4.4 Hz), 6.08 (1H, s), 6.82 (1H, s), 7.94 (1H, t, J=4.4 Hz). MS (APCI) m/z: 478 (M+H)$^+$.

Step 39-3

7-Chloro-2-[(2S,5R)-5-(dimethylamino)tetrahydropyran-2-yl]-N-[(4-methoxy-6-methyl-2-oxo-1,2-dihydropyridin-3-yl)methyl]-2,4-dimethyl-1,3-benzodioxole-5-carboxamide (39)

The title compound (0.119 g, 0.234 mmol, 97% yield) was obtained through the same reaction as in step 3-5 using 2-[(2S,5R)-5-aminotetrahydropyran-2-yl]-7-chloro-N-[(4-methoxy-6-methyl-2-oxo-1,2-dihydropyridin-3-yl)methyl]-2,4-dimethyl-1,3-benzodioxole-5-carboxamide (0.150 g, 0.314 mmol) synthesized in step 39-2.

$^1$H-NMR (400 MHz, DMSO-$d_6$) δ: 1.28-1.48 (2H, m), 1.61 (3H, s), 1.72-1.80 (1H, m), 1.90-2.02 (1H, m), 2.09-2.20 (1H, m), 2.10 (3H, s), 2.13 (6H, s), 2.17 (3H, s), 3.12-3.20 (1H, m), 3.48-3.54 (1H, m), 3.78 (3H, s), 3.96-4.06 (1H, m), 4.16 (2H, d, J=4.9 Hz), 6.08 (1H, s), 6.83 (1H, s), 7.95 (1H, t, J=4.9H), 11.4 (1H, s). MS (APCI) m/z: 506 (M+H)$^+$.

Example 40

7-Chloro-N-[(4,6-dimethyl-2-oxo-1,2-dihydropyridin-3-yl)methyl]-2,4-dimethyl-2-[(1-methyl-4-piperidyl)methyl]-1,3-benzodioxole-5-carboxamide (40)

Step 40-1 tert-butyl 4-[(7-Chloro-5-methoxycarbonyl-2,4-dimethyl-1,3-benzodioxol-2-yl)methyl]piperidine-1-carboxylate The title compound (1.45 g, 3.30 mmol, 65% yield) was obtained through the same reaction as in step 1-1 using the compound (A1b) (1.10 g, 5.08 mmol) synthesized in Reference Example 2 and the compound (S10) (1.70 g, 7.62 mmol) synthesized in Reference Example 10.

$^1$H-NMR (400 MHz, CDCl$_3$) δ: 1.14-1.30 (2H, m), 1.45 (9H, s), 1.70 (3H, s), 1.72-1.80 (3H, m), 1.94 (2H, d, J=5.5 Hz), 2.39 (3H, s), 2.60-2.80 (2H, m), 3.86 (3H, s), 3.92-4.15 (2H, m), 7.56 (1H, s).

Step 40-2

2-[(1-tert-Butoxycarbonyl-4-piperidyl)methyl]-7-chloro-2,4-dimethyl-1,3-benzodioxole-5-carboxylic Acid The title compound (1.27 g, 2.99 mmol, 91% yield) was obtained through the same reaction as in step 1-2 using tert-butyl 4-[(7-chloro-5-methoxycarbonyl-2,4-dimethyl-1,3-benzodioxol-2-yl)methyl]piperidine-1-carboxylate (1.45 g, 3.30 mmol) synthesized in step 40-1.

Step 40-3 tert-Butyl 4-[[7-chloro-5-[(4,6-dimethyl-2-oxo-1,2-dihydropyridin-3-yl)methylcarbamoyl]-2,4-dimethyl-1,3-benzodioxol-2-yl]methyl]piperidine-1-carboxylate The title compound (1.67 g, 2.98 mmol, 100% yield) was obtained through the same reaction as in step 1-3 using 2-[(1-tert-butoxycarbonyl-4-piperidyl)methyl]-7-chloro-2,4-dimethyl-1,3-benzodioxole-5-carboxylic acid (1.27 g, 2.99 mmol) synthesized in step 40-2.

$^1$H-NMR (400 MHz, CDCl$_3$) δ: 1.11-1.25 (2H, m), 1.44 (9H, s), 1.66 (3H, s), 1.69-1.79 (3H, m), 1.92 (2H, d, J=5.5 Hz), 2.23 (3H, s), 2.26 (3H, s), 2.37 (3H, s), 2.62-2.75 (2H, m), 3.92-4.12 (2H, m), 4.50 (2H, d, J=6.1 Hz), 5.97 (1H, s), 6.90 (1H, s), 7.26 (1H, t, J=6.1 Hz), 12.15 (1H, s). MS (APCI) m/z: 560 (M+H)$^+$.

Step 40-4

7-Chloro-N-[(4,6-dimethyl-2-oxo-1,2-dihydropyridin-3-yl)methyl]-2,4-dimethyl-2-(4-piperidylmethyl)-1,3-benzodioxole-5-carboxamide The title compound (0.619 g, 1.34 mmol, 45% yield) was obtained through the same reaction as in step 3-4 using tert-butyl 4-[[7-chloro-5-[(4,6-dimethyl-2-oxo-1,2-dihydropyridin-3-yl)methylcarbamoyl]-2,4-dimethyl-1,3-benzodioxol-2-yl]methyl]piperidine-1-carboxylate (1.67 g, 2.98 mmol) synthesized in step 40-3.

MS (APCI) m/z: 460 (M+H)$^+$.

Step 40-5

7-Chloro-N-[(4,6-dimethyl-2-oxo-1,2-dihydropyridin-3-yl)methyl]-2,4-dimethyl-2-[(1-methyl-4-piperidyl)methyl]-1,3-benzodioxole-5-carboxamide (40)

The title compound (0.612 g, 1.29 mmol, 96% yield) was obtained through the same reaction as in step 3-5 using 7-chloro-N-[(4,6-dimethyl-2-oxo-1,2-dihydropyridin-3-yl)methyl]-2,4-dimethyl-2-(4-piperidylmethyl)-1,3-benzodioxole-5-carboxamide (0.619 g, 2.98 mmol) synthesized in step 40-4.

$^1$H-NMR (400 MHz, DMSO-$d_6$) δ: 1.15-1.30 (2H, m), 1.41-1.51 (1H, m), 1.65 (3H, s), 1.66-1.71 (2H, m), 1.72-1.82 (2H, m), 1.90 (2H, d, J=6.1 Hz), 2.08 (3H, s), 2.11 (6H, s), 2.17 (3H, s), 2.63-2.69 (2H, m), 4.22 (2H, d, J=4.9 Hz), 5.86 (1H, s), 6.86 (1H, s), 8.16 (1H, t, J=4.9 Hz), 11.49 (1H, s).
MS (APCI) m/z: 474 (M+H)+.

Example 41

7-Bromo-2-[cis-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (41)

Step 41-1

Methyl 7-bromo-2-(1,4-dioxaspiro[4.5]decan-8-yl)-2,4-dimethyl-1,3-benzodioxole-5-carboxylate The title compound (0.923 g, 2.16 mmol, 32% yield) was obtained through the same reaction as in step 1-1 using the compound (A1a) (1.75 g, 6.70 mmol) synthesized in Reference Example 1 and the compound (S15) (1.67 g, 10.1 mmol) synthesized in Reference Example 15.
$^1$H-NMR (400 MHz, CDCl$_3$) δ: 1.51-1.60 (4H, m), 1.64 (3H, s), 1.76-1.99 (5H, m), 2.39 (3H, s), 3.85 (3H, s), 3.95 (4H, s), 7.67 (1H, s).
MS (APCI) m/z: 427, 429 (M+H)+.

Step 41-2

7-Bromo-2-(1,4-dioxaspiro[4.5]decan-8-yl)-2,4-dimethyl-1,3-benzodioxole-5-carboxylic Acid The title compound (0.817 g, 1.98 mmol, 95% yield) was obtained through the same reaction as in step 1-2 using methyl 7-bromo-2-(1,4-dioxaspiro[4.5]decan-8-yl)-2,4-dimethyl-1,3-benzodioxole-5-carboxylate (0.893 g, 2.09 mmol) synthesized in step 41-1.

Step 41-3

7-Bromo-N-[(4,6-dimethyl-2-oxo-1,2-dihydropyridin-3-yl)methyl]-2-(1,4-dioxaspiro[4.5]decan-8-yl)-2,4-dimethyl-1,3-benzodioxole-5-carboxamide The title compound (1.02 g, 1.87 mmol, 95% yield) was obtained through the same reaction as in step 1-3 using 7-bromo-2-(1,4-dioxaspiro[4.5]decan-8-yl)-2,4-dimethyl-1,3-benzodioxole-5-carboxylic acid (0.817 g, 1.98 mmol) synthesized in step 41-2.
$^1$H-NMR (400 MHz, DMSO-d$_6$) δ: 1.30-1.53 (4H, m), 1.60 (3H, s), 1.66-1.73 (2H, m), 1.73-1.81 (2H, m), 1.84-1.99 (1H, m), 2.10 (3H, s), 2.11 (3H, s), 2.16 (3H, s), 3.84 (4H, s), 4.21 (2H, d, J=4.9 Hz), 5.85 (1H, s), 6.94 (1H, s), 8.14 (1H, t, J=4.9 Hz), 11.48 (1H, s).
MS (APCI) m/z: 547, 549 (M+H)+.

Step 41-4

7-Bromo-N-[(4,6-dimethyl-2-oxo-1,2-dihydropyridin-3-yl)methyl]-2,4-dimethyl-2-(4-oxocyclohexyl)-1,3-benzodioxole-5-carboxamide 7-Bromo-N-[(4,6-dimethyl-2-oxo-1,2-dihydropyridin-3-yl)methyl]-2-(1,4-dioxaspiro[4.5]decan-8-yl)-2,4-dimethyl-1,3-benzodioxole-5-carboxamide (0.817 g, 1.98 mmol) synthesized in step 41-3 was dissolved in aqueous tetrahydrofuran (2.4 mL). To the solution, 4 M hydrochloric acid in 1,4-dioxane (0.819 mL, 3.28 mmol) was added, and the mixture was stirred at room temperature for 16 hours. The reaction solution was neutralized by the addition of a saturated aqueous solution of sodium bicarbonate, followed by extraction with chloroform. The organic layer was dried over sodium sulfate. After concentration under reduced pressure, the obtained residue was purified by silica gel column chromatography (methanol:chloroform=100:0→95:5) to obtain the title compound (0.292 g, 0.580 mmol, 35% yield).
MS (APCI) m/z: 503, 505 (M+H)+.

Step 41-5

7-Bromo-2-[cis-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (41)

The title compound (0.089 g, 0.167 mmol, 29% yield) was obtained through the same reaction as in step 3-5 using 7-bromo-N-[(4,6-dimethyl-2-oxo-1,2-dihydropyridin-3-yl)methyl]-2,4-dimethyl-2-(4-oxocyclohexyl)-1,3-benzodioxole-5-carboxamide (0.292 g, 0.580 mmol) synthesized in step 41-4 and a 2.0 M solution of dimethylamine in tetrahydrofuran (2.90 mL, 5.79 mmol).
$^1$H-NMR (400 MHz, DMSO-d$_6$) δ: 1.25-1.39 (2H, m), 1.45-1.54 (4H, m), 1.58 (3H, s), 1.88-1.98 (4H, m), 2.10 (3H, s), 2.11 (3H, s), 2.12 (6H, s), 2.16 (3H, s), 4.21 (2H, d, J=4.9 Hz), 5.85 (1H, s), 6.93 (1H, s), 8.13 (1H, t, J=4.9 Hz), 11.47 (1H, s).
MS (APCI) m/z: 532, 534 (M+H)+.

Example 42

7-Bromo-N-[(4,6-dimethyl-2-oxo-1,2-dihydropyridin-3-yl)methyl]-2,4-dimethyl-2-(piperazin-1-ylmethyl)-1,3-benzodioxole-5-carboxamide (42)

[Formula 36]

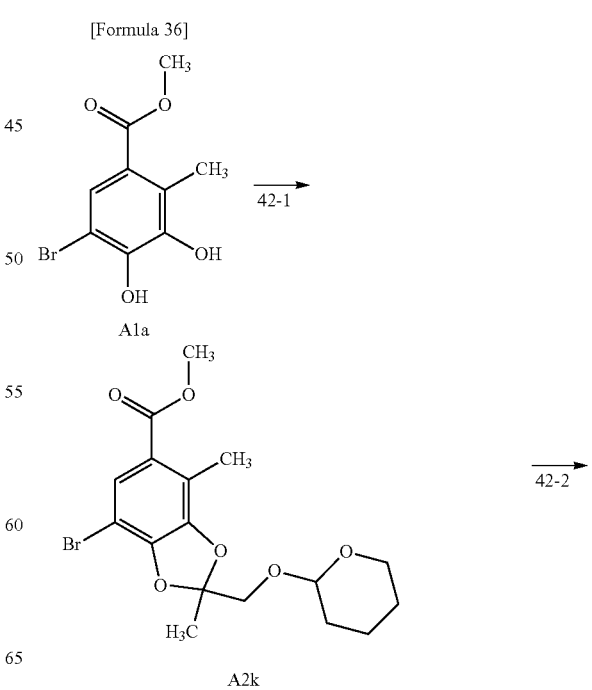

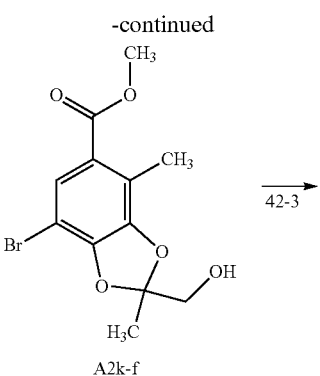

A2k-f

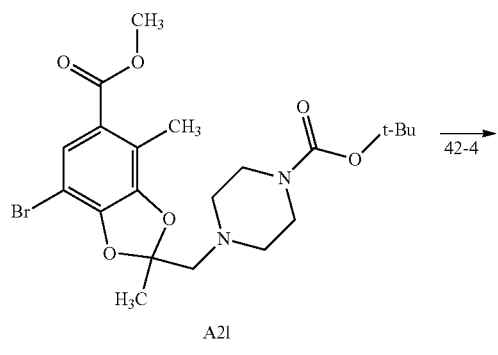

A2l

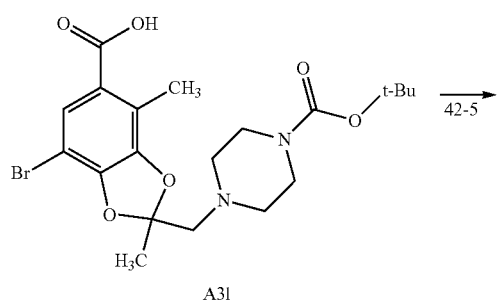

A3l

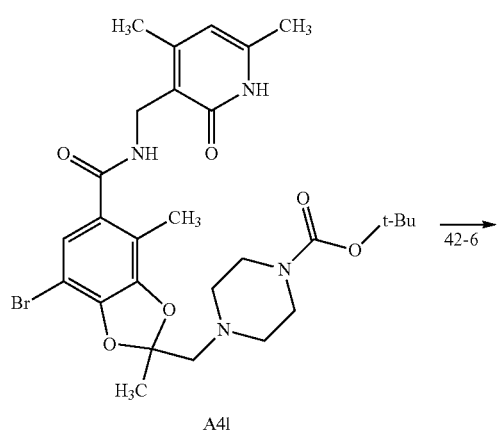

A4l

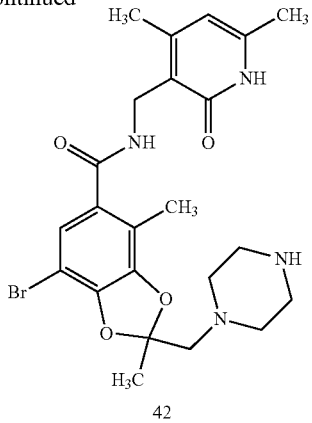

42

Step 42-1

Methyl 7-bromo-2,4-dimethyl-2-(tetrahydropyran-2-yloxymethyl)-1,3-benzodioxole-5-carboxylate (A2k)

The title compound (23.5 g, 58.5 mmol, 80% yield) was obtained through the same reaction as in step 1-1 using the compound (A1a) (19.0 g, 72.8 mmol) synthesized in Reference Example 1 and 2-(2-propynyloxy)tetrahydropyran (20.4 g, 146 mmol).

$^1$H-NMR (400 MHz, CDCl$_3$) δ: 1.40-1.66 (6H, m), 1.77 (3H, s), 2.39 (3H, s), 3.48-3.55 (1H, m), 3.66-3.73 (1H, m), 3.80-3.90 (1H, m), 3.85 (3H, s), 3.88-3.94 (1H, m), 4.70-4.75 (1H, m), 7.68 (1H, s).

Step 42-2

Methyl 7-bromo-2-(hydroxymethyl)-2,4-dimethyl-1,3-benzodioxole-5-carboxylate (A2k-f)

To a solution of the compound (A2k) (21.0 g, 52.3 mmol) synthesized in step 42-1 in methanol (156 mL), p-toluenesulfonic acid hydrate (0.498 g, 2.62 mmol) was added, and the mixture was stirred at room temperature for 5 hours. The solvent in the reaction solution was distilled off, and the obtained residue was diluted with ethyl acetate, washed with a saturated aqueous solution of sodium bicarbonate and saturated saline, and then dried over sodium sulfate. The organic layer was filtered through celite, and the solvent was distilled off under reduced pressure. The obtained residue was purified by silica gel column chromatography (hexane:ethyl acetate=100:0→80:20) to obtain the title compound (11.7 g, 37.0 mmol, 71% yield).

$^1$H-NMR (400 MHz, CDCl$_3$) δ: 1.76 (3H, s), 2.02 (1H, br s), 2.43 (3H, s), 3.87 (2H, d, J=7.2 Hz), 3.88 (3H, s), 3.85 (3H, s), 3.88-3.94 (1H, m), 4.70-4.75 (1H, m), 7.73 (1H, s).
MS (APCI) m/z: 317, 319 (M+H)$^+$.

Step 42-3 tert-Butyl 4-[(7-bromo-5-methoxycarbonyl-2,4-dimethyl-1,3-benzodioxol-2-yl)methyl]piperazine-1-carboxylate (A2l)

The compound (A2k-f) (0.250 g, 0.788 mmol) synthesized in step 42-2 was suspended in acetonitrile (8 mL). To the suspension, triethylamine (0.239 g, 2.36 mmol) and trifluoromethanesulfonic anhydride (0.278 g, 0.985 mmol)

113 were added under ice cooling, and the mixture was then stirred for 1 hour. 1-(tert-Butoxycarbonyl)piperazine (0.220 g, 1.18 mmol) was added to the reaction solution at 0° C., and the mixture was stirred at 60° C. for 15 hours. The reaction solution was diluted with ethyl acetate, washed with a saturated aqueous solution of sodium bicarbonate and saturated saline, and dried over sodium sulfate. After filtration through celite, the solvent was distilled off under reduced pressure, and the obtained residue was purified by silica gel column chromatography (hexane:ethyl acetate=100:0→86:14) to obtain the title compound (0.269 g, 0.554 mmol, 70% yield).

$^1$H-NMR (400 MHz, CDCl$_3$) δ: 1.43 (9H, s), 1.75 (3H, s), 2.37 (3H, s), 2.48-2.60 (4H, m), 2.75 (2H, s), 3.17-3.27 (4H, m), 3.86 (3H, s), 7.68 (1H, s).

MS (APCI) m/z: 485, 487 (M+H)$^+$.

Step 42-4

7-Bromo-2-[(4-tert-butoxycarbonylpiperazin-1-yl)methyl]-2,4-dimethyl-1,3-benzodioxole-5-carboxylic Acid (A3I)

The title compound (0.261 g, 0.554 mmol, 100% yield) was obtained through the same reaction as in step 1-2 using the compound (A2I) (0.269 g, 0.554 mmol) synthesized in step 42-3.

MS (APCI) m/z: 469, 471 (M+H)$^+$.

Step 42-5 tert-Butyl 4-[[7-bromo-5-[(4,6-dimethyl-2-oxo-1,2-dihydropyridin-3-yl)methylcarbamoyl]-2,4-dimethyl-1,3-benzodioxol-2-yl]methyl]piperazine-1-carboxylate (A4I)

The title compound (0.233 g, 0.385 mmol, 70% yield) was obtained through the same reaction as in step 1-3 using the compound (A3I) (0.261 g, 0.554 mmol) synthesized in step 42-4.

$^1$H-NMR (400 MHz, CDCl$_3$) δ: 1.44 (9H, s), 1.72 (3H, s), 2.21 (3H, s), 2.25 (3H, s), 2.37 (3H, s), 2.40-2.70 (4H, m), 2.72 (2H, s), 3.23-3.33 (4H, m), 4.45-4.50 (2H, m), 5.93 (1H, s), 7.00 (1H, s), 7.13-7.18 (1H, m).

MS (APCI) m/z: 605, 607 (M+H)$^+$.

Step 42-6

7-Bromo-N-[(4,6-dimethyl-2-oxo-1,2-dihydropyridin-3-yl)methyl]-2,4-dimethyl-2-(piperazin-1-ylmethyl)-1,3-benzodioxole-5-carboxamide The title compound (0.170 g, 0.336 mmol, 87% yield) was obtained through the same reaction as in step 3-4 using the compound (A4I) (0.233 g, 0.385 mmol) synthesized in step 42-5.

$^1$H-NMR (400 MHz, CDCl$_3$) δ: 1.72 (3H, s), 2.21 (3H, s), 2.26 (3H, s), 2.37 (3H, s), 2.50-2.65 (4H, m), 2.69 (2H, s), 2.71-2.77 (4H, m), 4.48 (2H, d, J=6.1 Hz), 5.94 (1H, s), 7.00 (1H, s), 7.19 (1H, t, J=6.1 Hz).

MS (APCI) m/z: 505, 507 (M+H)$^+$.

Example 43

7-Bromo-N-[(4,6-dimethyl-2-oxo-1,2-dihydropyridin-3-yl)methyl]-2,4-dimethyl-2-[(4-methylpiperazin-1-yl)methyl]-1,3-benzodioxole-5-carboxamide (43)

[Formula 37]

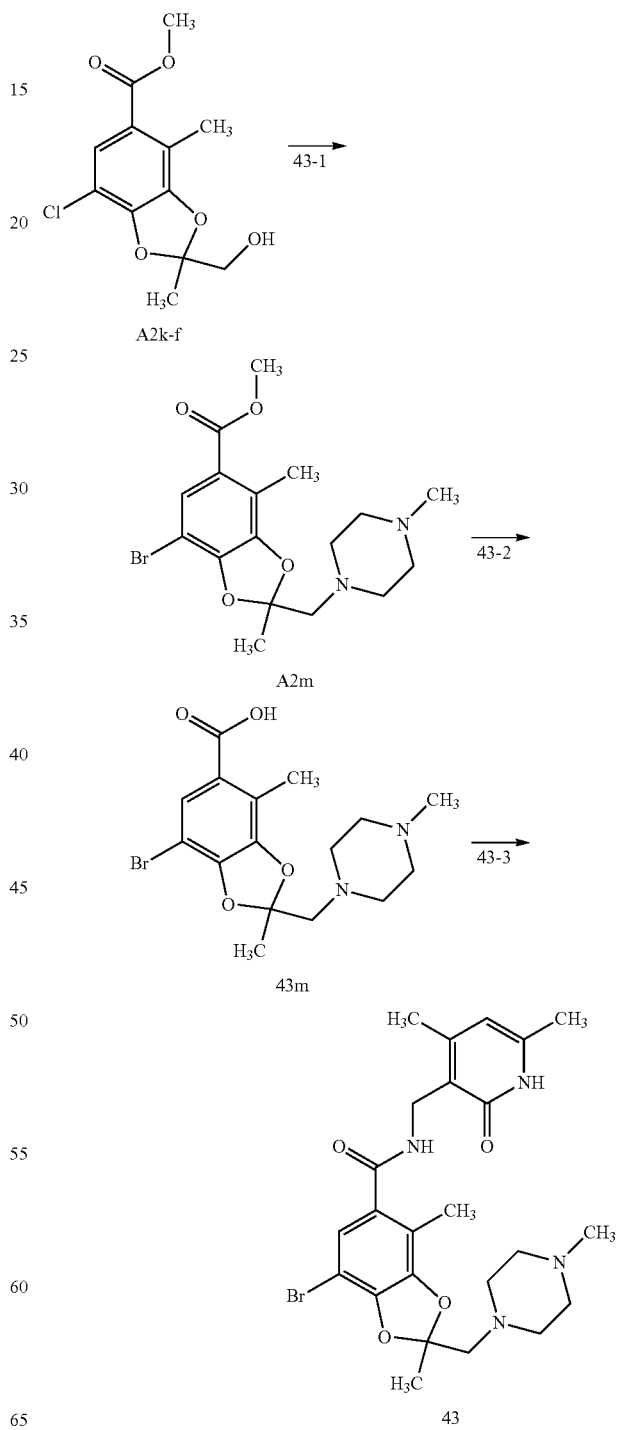

Step 43-1

Methyl 7-bromo-2,4-dimethyl-2-[(4-methylpiperazin-1-yl)methyl]-1,3-benzodioxole-5-carboxylate (A2m)

The title compound (0.138 g, 0.346 mmol, 44% yield) was obtained through the same reaction as in step 42-3 using the compound (A2k-f) (0.250 g, 0.788 mmol) synthesized in step 42-2 and 1-methylpiperazine (0.158 g, 1.58 mmol).

$^1$H-NMR (400 MHz, CDCl$_3$) δ: 1.74 (3H, s), 2.11-2.45 (4H, m), 2.22 (3H, s), 2.37 (3H, s), 2.55-2.80 (4H, m), 2.75 (2H, s), 3.85 (3H, s), 7.68 (1H, s).
MS (APCI) m/z: 399, 401 (M+H)$^+$.

Step 43-2

7-Bromo-2,4-dimethyl-2-[(4-methylpiperazin-1-yl)methyl]-1,3-benzodioxole-5-carboxylic Acid (A3m)

The title compound (0.133 g, 0.346 mmol, 100% yield) was obtained through the same reaction as in step 1-2 using the compound (A2m) (0.138 g, 0.346 mmol) synthesized in step 43-1.
MS (APCI) m/z: 385, 387 (M+H)$^+$.

Step 43-3

7-Bromo-N-[(4,6-dimethyl-2-oxo-1,2-dihydropyridin-3-yl)methyl]-2,4-dimethyl-2-[(4-methylpiperazin-1-yl)methyl]-1,3-benzodioxole-5-carboxamide (43)

The title compound (0.096 g, 0.184 mmol, 53% yield) was obtained through the same reaction as in step 1-3 using the compound (A3m) (0.133 g, 0.346 mmol) synthesized in step 43-2.

$^1$H-NMR (400 MHz, CDCl$_3$) δ: 1.72 (3H, s), 2.15-2.45 (4H, m), 2.22 (6H, s), 2.27 (3H, s), 2.37 (3H, s), 2.55-2.75 (4H, m), 2.72 (2H, s), 4.50 (2H, d, J=5.5 Hz), 5.96 (1H, s), 7.01 (2H, s), 7.20-7.28 (1H, m), 11.85 (1H, br s).
MS (APCI) m/z: 519, 521 (M+H)$^+$.

Example 44

7-Bromo-2-[[4-(dimethylamino)-1-piperidyl]methyl]-N-[(4,6-dimethyl-2-oxo-1,2-dihydropyridin-3-yl)methyl]-2,4-dimethyl-1,3-benzodioxole-5-carboxamide (44)

[Formula 38]

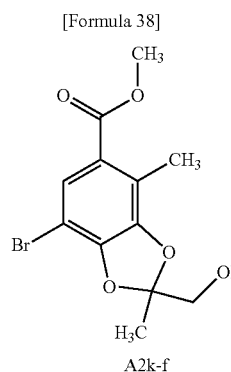

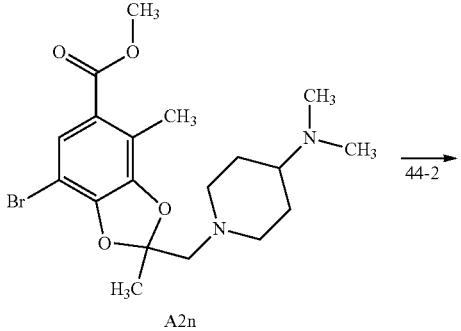

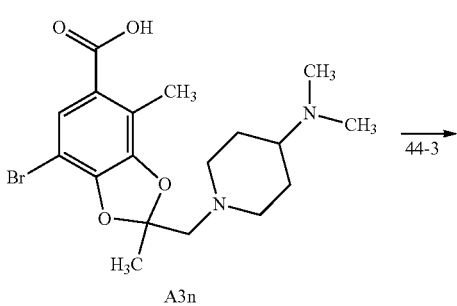

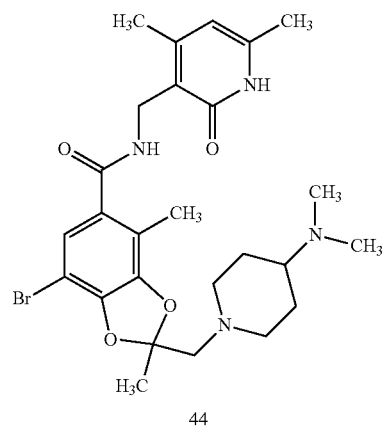

Step 44-1

Methyl-7-bromo-2-[[4-(dimethylamino)-1-piperidyl]methyl]-2,4-dimethyl-1,3-benzodioxole-5-carboxylate (A2n)

The title compound (0.808 g, 1.89 mmol, 100% yield) was obtained through the same reaction as in step 42-3 using the compound (A2k-f) (0.250 g, 0.788 mmol) synthesized in step 42-2 and 4-dimethylaminopiperidine (0.600 g, 1.89 mmol).

$^1$H-NMR (400 MHz, CDCl$_3$) δ: 1.22-1.38 (2H, m), 1.68-1.74 (2H, m), 1.73 (3H, s), 2.00-2.28 (3H, m), 2.30 (6H, s), 2.38 (3H, s), 2.73 (2H, s), 2.95-3.05 (2H, m), 3.84 (3H, s), 7.66 (1H, s).

Step 44-2

7-Bromo-2-[[4-(dimethylamino)-1-piperidyl]methyl]-2,4-dimethyl-1,3-benzodioxole-5-carboxylic Acid (A3n)

The title compound (0.135 g, 0.328 mmol, 100% yield) was obtained through the same reaction as in step 1-2 using the compound (A2n) (0.140 g, 0.328 mmol) synthesized in step 44-1.

Step 44-3

7-Bromo-2-[[4-(dimethylamino)-1-piperidyl]methyl]-N-[(4,6-dimethyl-2-oxo-1,2-dihydropyridin-3-yl)methyl]-2,4-dimethyl-1,3-benzodioxole-5-carboxamide (44)

The title compound (0.048 g, 0.088 mmol, 27% yield) was obtained through the same reaction as in step 1-3 using the compound (A3n) (0.135 g, 0.328 mmol) synthesized in step 44-2.

$^1$H-NMR (400 MHz, DMSO-$d_6$) δ: 1.10-1.23 (2H, m), 1.51-1.63 (2H, m), 1.67 (3H, s), 1.88-1.94 (1H, m), 2.07 (6H, s), 2.10 (3H, s), 2.11 (3H, s), 2.16 (3H, s), 2.12-2.20 (2H, m), 2.70 (2H, s), 2.85-2.92 (2H, m), 4.21 (2H, d, J=4.9 Hz), 5.86 (1H, s), 6.95 (1H, s), 8.11 (1H, d, J=4.9 Hz), 11.50 (1H, br s).

MS (APCI) m/z: 547, 549 (M+H)$^+$.

Example 45

(2R)-7-Bromo-N-[(4,6-dimethyl-2-oxo-1,2-dihydropyridin-3-yl)methyl]-2,4-dimethyl-2-(morpholinomethyl)-1,3-benzodioxole-5-carboxamide (45)

[Formula 39]

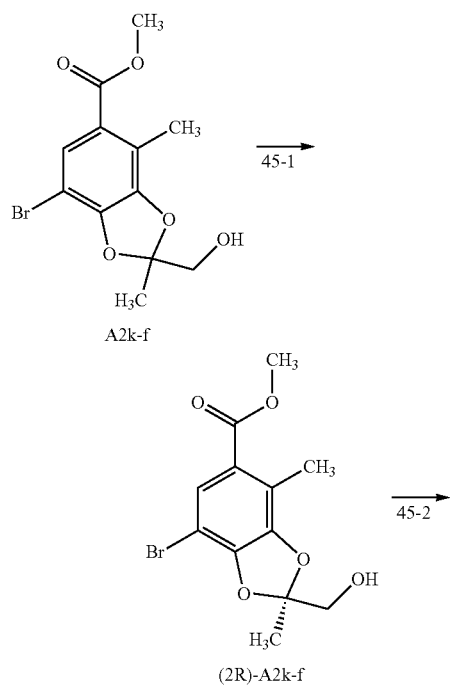

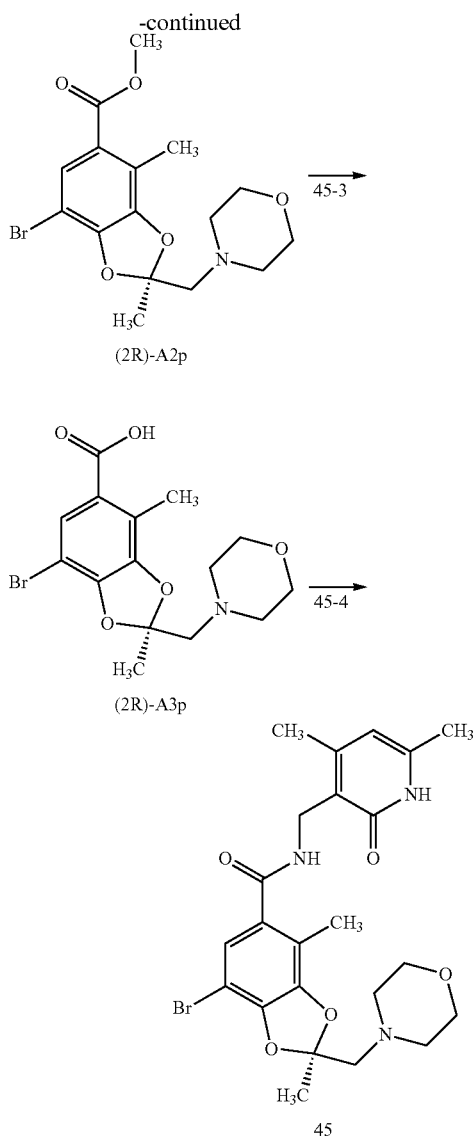

Step 45-1

Methyl (2R)-7-bromo-2,4-dimethyl-2-(hydroxymethyl)-1,3-benzodioxole-5-carboxylate ((2R)-A2k-f)

The compound (A2k-f) synthesized in step 42-2 was resolved into each enantiomer under the following conditions:

Column: Daicel CHIRALCEL OZ-H 4.6 mm ID×250 mm L

Elution solvent: n-hexane:2-propanol=90:10 (V/V)

Flow rate: 1.00 mL/min

Temperature: 25° C.

First peak: 6.6 min (specific rotation [α]$_D^{20}$=+7.1 (C=1.0, chloroform))

Second peak: 7.8 min (specific rotation [α]$_D^{20}$=−6.7 (C=1.0, chloroform))

The following steps were carried out using the first peak separated using a preparative chiral column.

Step 45-2

Methyl (2R)-7-bromo-2,4-dimethyl-2-(morpholinomethyl)-1,3-benzodioxole-5-carboxylate ((2R)-A2p)

The title compound (12.2 g, 31.6 mmol, 100% yield) was obtained through the same reaction as in step 42-3 using the compound ((2R)-A2k-f) (first peak, 10.0 g, 31.5 mmol) synthesized in step 45-1.

$^1$H-NMR (400 MHz, CDCl$_3$) δ: 1.76 (3H, s), 2.37 (3H, s), 2.57-2.62 (4H, m), 2.73 (2H, s), 3.51-3.56 (4H, m), 3.86 (3H, s), 7.68 (1H, s).
MS (ESI) m/z: 386, 388 (M+H)$^+$.

Step 45-3

(2R)-7-Bromo-2,4-dimethyl-2-(morpholinomethyl)-1,3-benzodioxole-5-carboxylic Acid ((2R)-A3p)

The title compound (11.7 g, 31.5 mmol, 100% yield) was obtained through the same reaction as in step 1-2 using the compound ((2R)-A2p) (12.2 g, 31.5 mmol) synthesized in step 45-2.

$^1$H-NMR (400 MHz, CDCl$_3$) δ: 1.77 (3H, s), 2.40 (3H, s), 2.55-2.68 (4H, m), 2.75 (2H, s), 3.50-3.61 (4H, m), 7.82 (1H, s).
MS (ESI) m/z: 370, 372 (M−H)$^-$.

Step 45-4

(2R)-7-Bromo-N-[(4,6-dimethyl-2-oxo-1,2-dihydropyridin-3-yl)methyl]-2,4-dimethyl-2-(morpholinomethyl)-1,3-benzodioxole-5-carboxamide (45)

The title compound (14.1 g, 27.9 mmol, 88% yield) was obtained through the same reaction as in step 1-3 using the compound ((2R)-A3p) (11.7 g, 31.5 mmol) synthesized in step 45-3.

$^1$H-NMR (400 MHz, CDCl$_3$) δ: 1.73 (3H, s), 2.21 (3H, s), 2.27 (3H, s), 2.37 (3H, s), 2.54-2.64 (4H, m), 2.71 (2H, s), 3.55-3.61 (4H, m), 4.50 (2H, d, J=5.5 Hz), 5.96 (1H, s), 7.01 (1H, s), 7.23 (1H, t, J=5.5 Hz), 11.77 (1H, br s).
MS (ESI) m/z: 506, 508 (M+H)$^+$.

Example 46

2-[trans-4-(Dimethylamino)cyclohexyl]-N-[(4,6-dimethyl-2-oxo-1,2-dihydropyridin-3-yl)methyl]-7-fluoro-2,4-dimethyl-1,3-benzodioxole-5-carboxamide (46)

Step 46-1

Methyl 2-[trans-4-(tert-butoxycarbonylamino)cyclohexyl]-7-fluoro-2,4-dimethyl-1,3-benzodioxole-5-carboxylate The title compound (0.563 g, 1.49 mmol, 100% yield) was obtained through the same reaction as in step 13-1 using the compound (A1c) (0.265 g, 1.32 mmol) synthesized in Reference Example 3 and the compound (S13) (0.444 g, 1.99 mmol) synthesized in Reference Example 13.

$^1$H-NMR (400 MHz, CDCl$_3$) δ: 1.05-1.15 (2H, m), 1.30-1.39 (2H, m), 1.44 (9H, s), 1.61 (3H, s), 1.77-1.90 (1H, m), 1.95-2.01 (2H, m), 2.06-2.13 (2H, m), 2.38 (3H, s), 3.30-3.46 (1H, m), 3.85 (3H, s), 4.38 (1H, br s), 7.36 (1H, d, J=11.0 Hz).

Step 46-2

2-[trans-4-(tert-Butoxycarbonylamino)cyclohexyl]-7-fluoro-2,4-dimethyl-1,3-benzodioxole-5-carboxylic Acid The title compound (0.188 g, 0.459 mmol, 93% yield) was obtained through the same reaction as in step 1-2 using methyl 2-[trans-4-(tert-butoxycarbonylamino)cyclohexyl]-7-fluoro-2,4-dimethyl-1,3-benzodioxole-5-carboxylate (0.210 g, 0.495 mmol) synthesized in step 46-1.

Step 46-3 tert-Butyl N-[trans-4-[5-[(4,6-dimethyl-2-oxo-1,2-dihydropyridin-3-yl)methylcarbamoyl]-7-fluoro-2,4-dimethyl-1,3-benzodioxol-2-yl]cyclohexyl]carbamate The title compound (0.208 g, 0.383 mmol, 83% yield) was obtained through the same reaction as in step 1-3 using 2-[trans-4-(tert-butoxycarbonylamino)cyclohexyl]-7-fluoro-2,4-dimethyl-1,3-benzodioxole-5-carboxylic acid (0.188 g, 0.459 mmol) synthesized in step 46-2.

$^1$H-NMR (400 MHz, CDCl$_3$) δ: 1.04-1.13 (2H, m), 1.22-1.36 (2H, m), 1.44 (9H, s), 1.58 (3H, s), 1.73-1.86 (1H, m), 1.89-1.98 (2H, m), 2.03-2.11 (2H, m), 2.22 (3H, s), 2.25 (3H, s), 2.37 (3H, s), 3.32-3.45 (1H, m), 4.36 (1H, br s), 4.49 (2H, d, J=5.6 Hz), 5.95 (1H, s), 6.73 (1H, d, J=10.0 Hz), 7.23 (1H, t, J=5.8 Hz), 11.30 (1H, br s).
MS (APCI) m/z: 544 (M+H)$^+$.

Step 46-4

2-(trans-4-Aminocyclohexyl)-N-[(4,6-dimethyl-2-oxo-1,2-dihydropyridin-3-yl)methyl]-7-fluoro-2,4-dimethyl-1,3-benzodioxole-5-carboxamide The title compound (0.064 g, 0.144 mmol, 98% yield) was obtained through the same reaction as in step 3-4 using tert-butyl N-[trans-4-[5-[(4,6-dimethyl-2-oxo-1,2-dihydropyridin-3-yl)methylcarbamoyl]-7-fluoro-2,4-dimethyl-1,3-benzodioxol-2-yl]cyclohexyl]carbamate (0.080 g, 0.147 mmol) synthesized in step 46-3.

Step 46-5

2-[trans-4-(Dimethylamino)cyclohexyl]-N-[(4,6-dimethyl-2-oxo-1,2-dihydropyridin-3-yl)methyl]-7-fluoro-2,4-dimethyl-1,3-benzodioxole-5-carboxamide (46)

The title compound (0.038 g, 0.081 mmol, 56% yield) was obtained through the same reaction as in step 3-5 using 2-(trans-4-aminocyclohexyl)-N-[(4,6-dimethyl-2-oxo-1,2-dihydropyridin-3-yl)methyl]-7-fluoro-2,4-dimethyl-1,3-benzodioxole-5-carboxamide (0.064 g, 0.144 mmol) synthesized in step 46-4.

$^1$H-NMR (400 MHz, CDCl$_3$) δ: 1.19-1.31 (4H, m), 1.59 (3H, s), 1.77-1.85 (1H, m), 1.96-2.01 (4H, m), 2.21-2.24 (1H, m), 2.23 (3H, s), 2.25 (3H, s), 2.27 (6H, s), 2.37 (3H, s), 4.49 (2H, d, J=5.6 Hz), 5.95 (1H, s), 6.73 (1H, d, J=10.4 Hz), 7.24 (1H, t, J=5.6 Hz), 11.61 (1H, br s).
MS (APCI) m/z: 472 (M+H)$^+$.

Example 47

2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide (47)

Step 47-1

Methyl 2-[trans-4-(tert-butoxycarbonylamino)cyclohexyl]-2,4,7-trimethyl-1,3-benzodioxole-5-carboxylate The title compound (7.99 g, 19.0 mmol, 95% yield) was obtained through the same reaction as in step 13-1 using the compound (A1d) (3.92 g, 20.0 mmol) synthesized in Reference Example 4 and the compound (S13) (6.70 g, 30.0 mmol synthesized in Reference Example 13.

$^1$H-NMR (400 MHz, CDCl$_3$) δ: 1.02-1.15 (2H, m), 1.26-1.37 (2H, m), 1.44 (9H, s), 1.57 (3H, s), 1.75-1.82 (1H, m), 1.90-1.98 (2H, m), 2.03-2.11 (2H, m), 2.16 (3H, s), 2.38 (3H, s), 3.30-3.47 (1H, m), 3.84 (3H, s), 4.37 (1H, br s), 7.36 (1H, s).

MS (ESI) m/z: 442 (M+Na)$^+$.

Step 47-2

2-[trans-4-(tert-Butoxycarbonylamino)cyclohexyl]-2,4,7-trimethyl-1,3-benzodioxole-5-carboxylic Acid The title compound (5.79 g, 14.3 mmol, 75% yield) was obtained through the same reaction as in step 1-2 using methyl 2-[trans-4-(tert-butoxycarbonylamino)cyclohexyl]-2,4,7-trimethyl-1,3-benzodioxole-5-carboxylate (7.99 g, 19.0 mmol) synthesized in step 47-1.

$^1$H-NMR (400 MHz, CDCl$_3$) δ: 1.04-1.16 (2H, m), 1.27-1.37 (2H, m), 1.44 (9H, s), 1.58 (3H, s), 1.76-1.84 (1H, m), 1.92-1.98 (2H, m), 2.03-2.12 (2H, m), 2.18 (3H, s), 2.42 (3H, s), 3.35-3.47 (1H, m), 4.40 (1H, br s), 7.51 (1H, s).

MS (ESI) m/z: 428 (M+Na)$^+$.

Step 47-3 tert-Butyl N-[trans-4-[5-[(4,6-dimethyl-2-oxo-1,2-dihydropyridin-3-yl)methylcarbamoyl]-2,4,7-trimethyl-1,3-benzodioxol-2-yl]cyclohexyl]carbamate The title compound (6.09 g, 11.3 mmol, 79% yield) was obtained through the same reaction as in step 1-3 using 2-[trans-4-(tert-butoxycarbonylamino)cyclohexyl]-2,4,7-trimethyl-1,3-benzodioxole-5-carboxylic acid (5.79 g, 14.3 mmol) synthesized in step 47-2.

$^1$H-NMR (400 MHz, DMSO-d$_6$) δ: 1.05-1.23 (4H, m), 1.36 (9H, s), 1.53 (3H, s), 1.68-1.74 (1H, m), 1.74-1.88 (4H, m), 2.07 (3H, s), 2.09 (3H, s), 2.10 (3H, s), 2.17 (3H, s), 3.08-3.20 (1H, m), 4.22 (2H, d, J=4.9 Hz), 5.85 (1H, s), 6.66 (1H, s), 6.73 (1H, d, J=7.9 Hz), 7.88 (1H, t, J=4.9 Hz), 11.47 (1H, s).

MS (ESI) m/z: 540 (M+H)$^+$.

Step 47-4

2-(trans-4-Aminocyclohexyl)-N-[(4,6-dimethyl-2-oxo-1,2-dihydropyridin-3-yl)methyl]-2,4,7-trimethyl-1,3-benzodioxole-5-carboxamide The title compound (6.25 g, 14.2 mmol, 100% yield) was obtained through the same reaction as in step 3-4 using tert-butyl N-[trans-4-[5-[(4,6-dimethyl-2-oxo-1,2-dihydropyridin-3-yl)methylcarbamoyl]-2,4,7-trimethyl-1,3-benzodioxol-2-yl]cyclohexyl]carbamate (7.68 g, 14.2 mmol) synthesized in step 47-3.

$^1$H-NMR (400 MHz, DMSO-d$_6$) δ: 0.90-1.05 (2H, m), 1.18-1.22 (2H, m), 1.52 (3H, s), 1.67-1.82 (5H, m), 2.07 (3H, s), 2.09 (3H, s), 2.10 (3H, s), 2.17 (3H, s), 2.38-2.48 (1H, m), 4.22 (2H, d, J=4.9 Hz), 5.85 (1H, s), 6.65 (1H, s), 7.87 (1H, t, J=4.9 Hz), 8.23 (1H, s).

MS (ESI) m/z: 440 (M+H)$^+$.

Step 47-5

2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide (47)

The title compound (5.16 g, 11.0 mmol, 78% yield) was obtained through the same reaction as in step 3-5 using 2-(trans-4-aminocyclohexyl)-N-[(4,6-dimethyl-2-oxo-1,2-dihydropyridin-3-yl)methyl]-2,4,7-trimethyl-1,3-benzodioxole-5-carboxamide (6.25 g, 14.2 mmol) synthesized in step 47-4.

$^1$H-NMR (400 MHz, CD$_3$OD) δ: 1.32-1.46 (2H, m), 1.48-1.61 (2H, m), 1.57 (3H, s), 1.88-1.97 (1H, m), 2.07-2.20 (4H, m), 2.11 (4H, s), 2.15 (3H, s), 2.24 (3H, s), 2.36 (3H, s), 2.82 (6H, s), 3.10-3.23 (1H, m), 4.42 (2H, s), 6.11 (1H, s), 6.71 (1H, s).

MS (ESI) m/z: 468 (M+H)$^+$.

This compound was resolved into each enantiomer under the following conditions:
Column: Daicel CHIRALCEL OZ-3 4.6 mm ID×150 mm L
Elution solvent: n-hexane:ethanol:diethylamine=60:40:0.04 (V/V)
Flow rate: 1.00 mL/min
Temperature: 35° C.
First peak: 4.5 min (specific rotation [α]$_D^{20}$=+15.6 (C=1.0, chloroform))
Second peak: 6.2 min (specific rotation [α]$_D^{20}$=−15.6 (C=1.0, chloroform))

Example 48

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide (48)

[Formula 40]

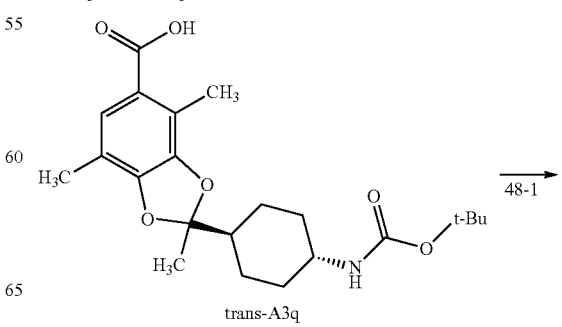

trans-A3q

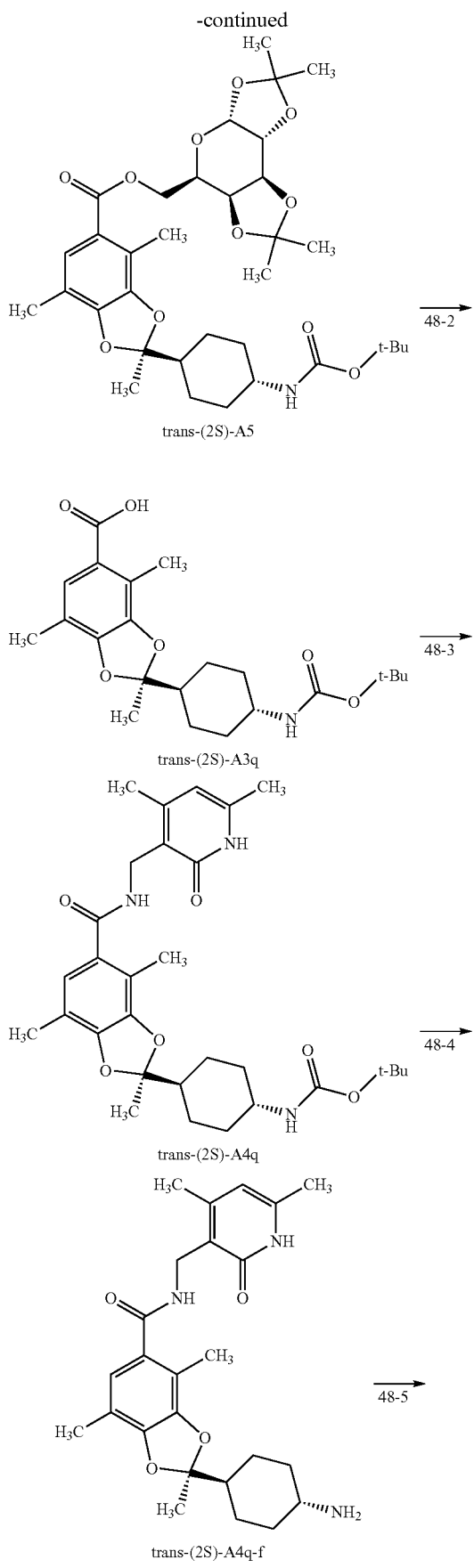

Step 48-1

[(3aR,5R,5aS,8aS,8bR)-2,2,7,7-Tetramethyl-5,5a,8a,8b-tetrahydro-3aH-di[1,3]dioxolo[4,5-a:5',4'-d]pyran-5-yl]methyl (2S)-2-[trans-4-(tert-butoxycarbonylamino)cyclohexyl]-2,4,7-trimethyl-1,3-benzodioxole-5-carboxylate (trans-(2S)-A5)

The title compound (61.5 g, 94.9 mmol, 80% yield) was obtained by esterification under the same conditions as in step 1-3 using the compound (trans-A3q) (48.0 g, 118 mmol) synthesized in step 47-2 and 1,2:3,4-di-O-isopropylidene-α-D-galactopyranose (46.2 g, 178 mmol).

$^1$H-NMR (400 MHz, CDCl$_3$) δ: 1.02-1.15 (2H, m), 1.25-1.37 (2H, m), 1.33 (3H, s), 1.35 (3H, s), 1.44 (9H, s), 1.48 (3H, s), 1.52 (3H, s), 1.56 (3H, s), 1.73-1.83 (1H, m), 1.90-1.98 (2H, m), 2.03-2.10 (2H, m), 2.16 (3H, s), 2.38 (3H, s), 3.32-3.47 (1H, m), 4.14-4.19 (1H, m), 4.29-4.41 (4H, m), 4.42-4.48 (1H, m), 4.62-4.67 (1H, m), 5.56 (1H, J=5.1 Hz), 7.39 (1H, s).

This compound was resolved into each diastereomer under the following conditions:
Column: Daicel CHIRALPAK ID 4.6 mm ID×250 mm L
Elution solvent: n-hexane:2-propanol=70:30 (V/V)
Flow rate: 1.00 mL/min
Temperature: 40° C.
First peak: 7.1 min (specific rotation [α]$_D^{20}$=−63.1 (C=1.0, chloroform))
Second peak: 9.0 min (specific rotation [α]$_D^{20}$=−10.6 (C=1.0, chloroform))

The following steps were carried out using the second peak separated using a preparative chiral column.

Step 48-2

(2S)-2-[trans-4-(tert-Butoxycarbonylamino)cyclohexyl]-2,4,7-trimethyl-1,3-benzodioxole-5-carboxylic Acid (trans-(2S)-A3q)

The title compound (3.86 g, 9.51 mmol, 100% yield) was obtained through the same reaction as in step 1-2 using the compound (trans-(2S)-A5) (second peak, 6.16 g, 9.51 mmol) synthesized in step 48-1.

Step 48-3 tert-Butyl N-[trans-4-[(2S)-5-[(4,6-dimethyl-2-oxo-1,2-dihydropyridin-3-yl)methylcarbamoyl]-2,4,7-trimethyl-1,3-benzodioxol-2-yl]cyclohexyl]carbamate (trans-(2S)-A4q)

The title compound (4.73 g, 8.76 mmol, 92% yield) was obtained through the same reaction as in step 1-3 using the compound (trans-(2S)-A3q) (3.86 g, 9.51 mmol) synthesized in step 48-2.

$^1$H-NMR (400 MHz, CDCl$_3$) δ: 1.01-1.13 (2H, m), 1.20-1.35 (2H, m), 1.44 (9H, s), 1.54 (3H, s), 1.70-1.80 (1H, m), 1.86-1.95 (2H, m), 2.02-2.10 (2H, m), 2.10 (3H, s), 2.23 (6H, s), 2.37 (3H, s), 3.30-3.45 (1H, m), 4.37 (1H, d, J=7.9), 4.50 (2H, d, J=6.1 Hz), 5.94 (1H, s), 6.71 (1H, s), 7.08 (1H, t, J=6.1 Hz), 11.86 (1H, br s).

MS (ESI) m/z: 540 (M+H)$^+$.

Step 48-4

(2S)-2-(trans-4-Aminocyclohexyl)-N-[(4,6-dimethyl-2-oxo-1,2-dihydropyridin-3-yl)methyl]-2,4,7-trimethyl-1,3-benzodioxole-5-carboxamide (trans-(2S)-A4q-f)

The title compound (4.09 g, 8.76 mmol, 100% yield) was obtained through the same reaction as in step 3-4 using the compound (trans-(2S)-A4q) (4.73 g, 8.76 mmol) synthesized in step 48-3.

$^1$H-NMR (400 MHz, CDCl$_3$) δ: 1.01-1.15 (2H, m), 1.18-1.31 (2H, m), 1.54 (3H, s), 1.71-1.81 (1H, m), 1.85-1.94 (4H, m), 2.10 (3H, s), 2.24 (6H, s), 2.37 (3H, s), 2.57-2.66 (1H, m), 3.71 (2H, s), 4.51 (2H, d, J=6.1 Hz), 5.94 (1H, s), 6.71 (1H, s), 7.08-7.14 (1H, m).

MS (ESI) m/z: 440 (M+H)$^+$.

Step 48-5

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide (48)

The title compound (3.03 g, 6.48 mmol, 74% yield) was obtained through the same reaction as in step 3-5 using the compound (trans-(2S)-A4q-f) (4.11 g, 8.82 mmol) synthesized in step 48-4.

$^1$H-NMR (400 MHz, DMSO-d$_6$) δ: 1.05-1.22 (4H, m), 1.53 (3H, s), 1.70-1.90 (5H, m), 2.02-2.10 (1H, m), 2.07 (3H, s), 2.10 (3H, s), 2.11 (3H, s), 2.13 (6H, s), 2.17 (3H, s), 4.22 (2H, d, J=5.5 Hz), 5.85 (1H, s), 6.66 (1H, s), 7.88 (1H, t, J=5.5 Hz), 11.48 (1H, br s).

MS (ESI) m/z: 468 (M+H)$^+$.

Specific rotation $[α]_D^{20}$=+15.6 (C=1.0, chloroform)

This compound agreed with the compound of the first peak obtained under the resolution conditions using a chiral column described in Example 47.

Example 49

2-[(2S,5R)-5-(Dimethylamino)tetrahydropyran-2-yl]-N-[(4,6-dimethyl-2-oxo-1,2-dihydropyridin-3-yl)methyl]-2,4,7-trimethyl-1,3-benzodioxole-5-carboxamide (49)

Step 49-1

Methyl 2-[(2S,5R)-5-(tert-butoxycarbonylamino)tetrahydropyran-2-yl]-2,4,7-trimethyl-1,3-benzodioxole-5-carboxylate The title compound (0.154 g, 0.365 mmol, 37% yield) was obtained through the same reaction as in step 13-1 using the compound (A1d) (0.196 g, 1.00 mmol) synthesized in Reference Example 4 and tert-butyl N-[(3R,6S)-6-ethynyltetrahydropyran-3-yl]carbamate (0.338 g, 1.50 mmol) synthesized according to the method described in WO 2007105154.

$^1$H-NMR (400 MHz, CDCl$_3$) δ: 1.21-1.34 (1H, m), 1.44 (9H, s), 1.51-1.62 (1H, m), 1.66 (3H, s), 1.80-1.90 (1H, m), 2.09-2.18 (1H, m), 2.19 (3H, s), 2.39 (3H, s), 2.99-3.08 (1H, m), 3.41-3.49 (1H, m), 3.52-3.70 (1H, m), 3.84 (3H, s), 4.14-4.28 (1H, m), 7.38 (1H, s).

Step 49-2

2-[(2S,5R)-5-(tert-Butoxycarbonylamino)tetrahydropyran-2-yl]-2,4,7-trimethyl-1,3-benzodioxole-5-carboxylic Acid The title compound (0.147 g, 0.365 mmol, 100% yield) was obtained through the same reaction as in step 1-2 using methyl 2-[(2S,5R)-5-(tert-butoxycarbonylamino)tetrahydropyran-2-yl]-2,4,7-trimethyl-1,3-benzodioxole-5-carboxylate (0.154 g, 0.365 mmol) synthesized in step 49-1.

$^1$H-NMR (400 MHz, CDCl$_3$) δ: 1.24-1.35 (1H, m), 1.45 (9H, s), 1.51-1.63 (1H, m), 1.67 (3H, s), 1.80-1.90 (1H, m), 2.09-2.18 (2H, m), 2.20 (3H, s), 2.42 (3H, s), 2.99-3.09 (1H, m), 3.42-3.50 (1H, m), 3.51-3.76 (1H, m), 4.13-4.30 (1H, m), 7.52 (1H, s).

MS (APCI) m/z: 406 (M−H)$^-$.

Step 49-3 tert-Butyl N-[(3R,6S)-6-[5-[(4,6-dimethyl-2-oxo-1,2-dihydropyridin-3-yl)methylcarbamoyl]-2,4,7-trimethyl-1,3-benzodioxol-2-yl]tetrahydropyran-3-yl]carbamate The title compound (0.190 g, 0.351 mmol, 96% yield) was obtained through the same reaction as in step 1-3 using 2-[(2S,5R)-5-(tert-butoxycarbonylamino)tetrahydropyran-2-yl]-2,4,7-trimethyl-1,3-benzodioxole-5-carboxylic acid (0.147 g, 0.365 mmol) synthesized in step 49-2.

$^1$H-NMR (400 MHz, CDCl$_3$) δ: 1.20-1.32 (1H, m), 1.44 (9H, s), 1.49-1.61 (1H, m), 1.63 (3H, s), 1.77-1.87 (1H, m), 2.08-2.16 (1H, m), 2.12 (3H, s), 2.24 (6H, s), 2.38 (3H, s), 2.98-3.07 (1H, m), 3.39-3.46 (1H, m), 3.53-3.70 (1H, m), 4.13-4.21 (1H, m), 4.22-4.30 (1H, m), 4.50 (2H, d, J=5.5 Hz), 5.94 (1H, s), 6.73 (1H, s), 7.07 (1H, t, J=5.5 Hz), 11.49 (1H, br s).

MS (APCI) m/z: 542 (M+H)$^+$.

Step 49-4

2-[(2S,5R)-5-Aminotetrahydropyran-2-yl]-N-[(4,6-dimethyl-2-oxo-1,2-dihydropyridin-3-yl)methyl]-2,4,7-trimethyl-1,3-benzodioxole-5-carboxamide The title compound (0.143 g, 0.324 mmol, 92% yield) was obtained through the same reaction as in step 3-4 using tert-butyl N-[(3R,6S)-6-[5-[(4,6-dimethyl-2-oxo-1,2-dihydropyridin-3-yl)methylcarbamoyl]-2,4,7-trimethyl-1,3-benzodioxol-2-yl]tetrahydropyran-3-yl]carbamate (0.190 g, 0.351 mmol) synthesized in step 49-3.

$^1$H-NMR (400 MHz, CDCl$_3$) δ: 1.14-1.28 (1H, m), 1.43-1.58 (1H, m), 1.64 (3H, s), 1.74-1.83 (1H, m), 2.01-2.10 (1H, m), 2.12 (3H, s), 2.23 (3H, s), 2.24 (3H, s), 2.37 (3H, s), 2.78-2.90 (1H, m), 2.94-3.07 (1H, m), 3.39-3.46 (1H, m), 4.00-4.08 (1H, m), 4.50 (2H, d, J=5.5 Hz), 5.94 (1H, s), 6.73 (1H, s), 7.07 (1H, t, J=5.5 Hz), 11.80 (1H, br s).

MS (APCI) m/z: 442 (M+H)$^+$.

Step 49-5

2-[(2S,5R)-5-(Dimethylamino)tetrahydropyran-2-yl]-N-[(4,6-dimethyl-2-oxo-1,2-dihydropyridin-3-yl)methyl]-2,4,7-trimethyl-1,3-benzodioxole-5-carboxamide (49)

The title compound (0.128 g, 0.273 mmol, 84% yield) was obtained through the same reaction as in step 3-5 using 2-[(2S,5R)-5-aminotetrahydropyran-2-yl]-N-[(4,6-dimethyl-2-oxo-1,2-dihydropyridin-3-yl)methyl]-2,4,7-trimethyl-1,3-benzodioxole-5-carboxamide (0.143 g, 0.324 mmol) synthesized in step 49-4.

$^1$H-NMR (400 MHz, DMSO-d$_6$) δ: 1.26-1.46 (2H, m), 1.56 (3H, s), 1.68-1.80 (1H, m), 1.90-2.01 (1H, m), 2.07 (3H, s), 2.09 (3H, s), 2.10 (3H, s), 2.14 (6H, s), 2.17 (3H, s), 3.16 (1H, t, J=10.3 Hz), 3.44 (1H, d, J=10.3 Hz), 3.99-4.08 (1H, m), 4.22 (2H, d, J=4.9 Hz), 5.85 (1H, s), 6.67 (1H, s), 7.89 (1H, t, J=4.9 Hz), 11.7 (1H, br s).

MS (APCI) m/z: 470 (M+H)$^+$.

Example 50

2-[trans-4-(Dimethylamino)cyclohexyl]-N-[(4,6-dimethyl-2-oxo-1,2-dihydropyridin-3-yl)methyl]-7-methoxy-2,4-dimethyl-1,3-benzodioxole-5-carboxamide (50)

Step 50-1

Methyl 2-[trans-4-(tert-butoxycarbonylamino)cyclohexyl]-7-methoxy-2,4-dimethyl-1,3-benzodioxole-5-carboxylate The title compound (0.043 g, 0.098 mmol, 27% yield) was obtained through the same reaction as in step 13-1 using the compound (A1e) (0.077 g, 0.364 mmol) synthesized in Reference Example 5 and tert-butyl N-(trans-4-ethynylcyclohexyl)carbamate (0.122 g, 0.547 mmol synthesized in Reference Example 13.

$^1$H-NMR (400 MHz, CDCl$_3$) δ: 1.04-1.13 (2H, m), 1.30-1.39 (2H, m), 1.44 (9H, s), 1.60 (3H, s), 1.79-1.89 (1H, m), 1.95-1.98 (2H, m), 2.01-2.09 (2H, m), 2.37 (3H, s), 3.30-3.45 (1H, m), 3.86 (3H, s), 3.89 (3H, s), 4.37 (1H, br s), 7.21 (1H, s).

Step 50-2

2-[trans-4-(tert-Butoxycarbonylamino)cyclohexyl]-7-methoxy-2,4-dimethyl-1,3-benzodioxole-5-carboxylic Acid The title compound (0.042 g, 0.098 mmol, 100% yield) was obtained through the same reaction as in step 1-2 using methyl 2-[trans-4-(tert-butoxycarbonylamino)cyclohexyl]-7-methoxy-2,4-dimethyl-1,3-benzodioxole-5-carboxylate (0.043 g, 0.098 mmol) synthesized in step 50-1.

Step 50-3 tert-Butyl N-[trans-4-[5-[(4,6-dimethyl-2-oxo-1,2-dihydropyridin-3-yl)methylcarbamoyl]-7-methoxy-2,4-dimethyl-1,3-benzodioxol-2-yl]cyclohexyl]carbamate The title compound (0.044 g, 0.079 mmol, 80% yield) was obtained through the same reaction as in step 1-3 using 2-[trans-4-(tert-butoxycarbonylamino)cyclohexyl]-7-methoxy-2,4-dimethyl-1,3-benzodioxole-5-carboxylic acid (0.042 g, 0.098 mmol) synthesized in step 50-2.

$^1$H-NMR (400 MHz, CDCl$_3$) δ: 1.03-1.18 (2H, m), 1.28-1.37 (2H, m), 1.43 (9H, s), 1.56 (3H, s), 1.72-1.82 (1H, m), 1.90-1.97 (2H, m), 2.01-2.09 (2H, m), 2.20 (3H, s), 2.23 (3H, s), 2.38 (3H, s), 3.30-3.45 (1H, m), 3.82 (3H, s), 4.39 (1H, d, J=8.0 Hz), 4.52 (2H, d, J=6.1 Hz), 5.96 (1H, s), 6.63 (1H, s), 7.16 (1H, t, J=6.1 Hz), 12.36 (1H, br s).

MS (APCI) m/z: 556 (M+H)$^+$.

Step 50-4

2-(trans-4-Aminocyclohexyl)-N-[(4,6-dimethyl-2-oxo-1,2-dihydropyridin-3-yl)methyl]-7-methoxy-2,4-dimethyl-1,3-benzodioxole-5-carboxamide The title compound (0.033 g, 0.072 mmol, 86% yield) was obtained through the same reaction as in step 3-4 using tert-butyl N-[trans-4-[5-[(4,6-dimethyl-2-oxo-1,2-dihydropyridin-3-yl)methylcarbamoyl]-7-methoxy-2,4-dimethyl-1,3-benzodioxol-2-yl]cyclohexyl]carbamate (0.044 g, 0.079 mmol) synthesized in step 50-3.

Step 50-5

2-[trans-4-(Dimethylamino)cyclohexyl]-N-[(4,6-dimethyl-2-oxo-1,2-dihydropyridin-3-yl)methyl]-7-methoxy-2,4-dimethyl-1,3-benzodioxole-5-carboxamide (50)

The title compound (0.018 g, 0.037 mmol, 51% yield) was obtained through the same reaction as in step 3-5 using 2-(trans-4-aminocyclohexyl)-N-[(4,6-dimethyl-2-oxo-1,2-dihydropyridin-3-yl)methyl]-7-methoxy-2,4-dimethyl-1,3-benzodioxole-5-carboxamide (0.033 g, 0.072 mmol) synthesized in step 50-4.

$^1$H-NMR (400 MHz, CDCl$_3$) δ: 1.18-1.31 (4H, m), 1.57 (3H, s), 1.76-1.82 (1H, m), 1.92-2.01 (4H, m), 2.11-2.16 (1H, m), 2.21 (3H, s), 2.23 (3H, s), 2.27 (6H, s), 2.38 (3H, s), 3.83 (3H, s), 4.51 (2H, d, J=6.0 Hz), 5.94 (1H, s), 6.62 (1H, s), 7.11 (1H, t, J=6.1 Hz), 11.47 (1H, br s).

MS (APCI) m/z: 484 (M+H)$^+$.

Example 51

4,7-Dichloro-N-[(4,6-dimethyl-2-oxo-1,2-dihydropyridin-3-yl)methyl]-2-methyl-2-(1-methyl-4-piperidyl)-1,3-benzodioxole-5-carboxamide (51)

Step 51-1 tert-Butyl 4-(4,7-dichloro-5-methoxycarbonyl-2-methyl-1,3-benzodioxol-2-yl)piperidine-1-carboxylate The title compound (2.81 g, 6.30 mmol, 83% yield) was obtained through the same reaction as in step 1-1 using the compound (E2) (1.80 g, 7.59 mmol) synthesized in Reference Example 6 and tert-butyl 4-ethynylpiperidine-1-carboxylate (2.38 g, 11.4 mmol) synthesized according to the method described in WO 2008156739.

$^1$H-NMR (400 MHz, CDCl$_3$) δ: 1.36-1.44 (2H, m), 1.46 (9H, s), 1.71 (3H, s), 1.81-1.87 (2H, m), 2.00-2.10 (1H, m), 2.62-2.73 (2H, m), 3.90 (3H, s), 4.15-4.30 (2H, m), 7.52 (1H, s).

Step 51-2

2-(1-tert-Butoxycarbonyl-4-piperidyl)-4,7-dichloro-2-methyl-1,3-benzodioxole-5-carboxylic Acid The title compound (2.72 g, 6.29 mmol, 100% yield) was obtained through the same reaction as in step 1-2 using tert-butyl 4-(4,7-dichloro-5-methoxycarbonyl-2-methyl-1,3-benzodioxol-2-yl)piperidine-1-carboxylate (2.81 g, 6.30 mmol) synthesized in step 51-1.

Step 51-3 tert-Butyl 4-[4,7-dichloro-5-[(4,6-dimethyl-2-oxo-1,2-dihydropyridin-3-yl)methylcarbamoyl]-2-methyl-1,3-benzodioxol-2-yl]piperidine-1-carboxylate The title compound (2.78 g, 4.91 mmol, 78% yield) was obtained through the same reaction as in step 1-3 using 2-(1-tert-butoxycarbonyl-4-piperidyl)-4,7-dichloro-2-methyl-1,3-benzodioxole-5-carboxylic acid (2.72 g, 6.29 mmol) synthesized in step 51-2.

$^1$H-NMR (400 MHz, CDCl$_3$) δ: 1.33-1.45 (2H, m), 1.45 (9H, s), 1.67 (3H, s), 1.78-1.85 (2H, m), 1.97-2.06 (1H, m), 2.26 (3H, s), 2.37 (3H, s), 2.59-2.71 (2H, m), 4.09-4.35 (2H, m), 4.53 (2H, d, J=5.5 Hz), 5.96 (1H, s), 7.19 (1H, s), 7.53-7.61 (1H, m).

MS (APCI) m/z: 566 (M+H)$^+$.

Step 51-4

4,7-Dichloro-N-[(4,6-dimethyl-2-oxo-1,2-dihydropyridin-3-yl)methyl]-2-methyl-2-(4-piperidyl)-1,3-benzodioxole-5-carboxamide The title compound (2.13 g, 4.57 mmol, 93% yield) was obtained through the same reaction as in step 3-4 using tert-butyl 4-(4,7-dichloro-5-methoxycarbonyl-2-methyl-1,3-benzodioxol-2-yl)piperidine-1-carboxylate (2.78 g, 4.91 mmol) synthesized in step 51-3.

MS (APCI) m/z: 466 (M+H)$^+$.

Step 51-5

4,7-Dichloro-N-[(4,6-dimethyl-2-oxo-1,2-dihydropyridin-3-yl)methyl]-2-methyl-2-(1-methyl-4-piperidyl)-1,3-benzodioxole-5-carboxamide (51)

The title compound (1.04 g, 2.17 mmol, 96% yield) was obtained through the same reaction as in step 3-5 using 4,7-dichloro-N-[(4,6-dimethyl-2-oxo-1,2-dihydropyridin-3-yl)methyl]-2-methyl-2-(4-piperidyl)-1,3-benzodioxole-5-carboxamide (1.05 g, 2.25 mmol) synthesized in step 51-4.

$^1$H-NMR (400 MHz, DMSO-d$_6$) δ: 1.30-1.43 (2H, m), 1.66-1.72 (2H, m), 1.68 (3H, s), 1.75-1.83 (2H, m), 1.84-1.93 (1H, m), 2.11 (3H, s), 2.12 (3H, s), 2.17 (3H, s), 2.76-2.84 (2H, m), 4.23 (2H, d, J=4.9 Hz), 5.86 (1H, s), 6.95 (1H, s), 8.32 (1H, t, J=4.9 Hz), 11.50 (1H, s).

MS (APCI) m/z: 480 (M+H)$^+$.

Example 52

4,7-Dichloro-N-[(4,6-dimethyl-2-oxo-1,2-dihydropyridin-3-yl)methyl]-2-(1-ethyl-4-piperidyl)-2-methyl-1,3-benzodioxole-5-carboxamide (52)

The title compound (0.757 g, 1.53 mmol, 68% yield) was obtained in an ethyl form through the same reaction as in step 3-5 using 4,7-dichloro-N-[(4,6-dimethyl-2-oxo-1,2-dihydropyridin-3-yl)methyl]-2-methyl-2-(4-piperidyl)-1,3-benzodioxole-5-carboxamide (1.05 g, 2.25 mmol) synthesized in step 51-4 and acetaldehyde (1.48 g, 33.8 mmol).

$^1$H-NMR (400 MHz, DMSO-d$_6$) δ: 0.97 (3H, t, J=7.0 Hz), 1.28-1.42 (2H, m), 1.68 (3H, s), 1.68-1.74 (2H, m), 1.73-1.86 (2H, m), 1.87-1.96 (1H, m), 2.11 (3H, s), 2.17 (3H, s), 2.22-2.32 (2H, m), 2.88-2.96 (2H, m), 4.23 (2H, d, J=5.5 Hz), 5.86 (1H, s), 6.95 (1H, s), 8.32 (1H, t, J=5.5 Hz), 11.50 (1H, s).

MS (APCI) m/z: 494 (M+H)$^+$.

Example 53

4,7-Dichloro-2-[trans-4-(dimethylamino)cyclohexyl]-N-[(4,6-dimethyl-2-oxo-1,2-dihydropyridin-3-yl)methyl]-2-methyl-1,3-benzodioxole-5-carboxamide (53)

Step 53-1

Methyl 2-[trans-4-(tert-butoxycarbonylamino)cyclohexyl]-4,7-dichloro-2-methyl-1,3-benzodioxole-5-carboxylate The title compound (0.918 g, 1.92 mmol, 68% yield) was obtained through the same reaction as in step 13-1 using the compound (E2) (0.721 g, 2.83 mmol) synthesized in Reference Example 6 and tert-butyl N-(trans-4-ethynylcyclohexyl)carbamate (0.950 g, 4.25 mmol synthesized in Reference Example 13.

$^1$H-NMR (400 MHz, CDCl$_3$) δ: 1.04-1.18 (2H, m), 1.27-1.40 (2H, m), 1.43 (9H, s), 1.68 (3H, s), 1.82-2.02 (3H, m), 2.03-2.14 (2H, m), 3.32-3.48 (1H, m), 3.89 (3H, s), 4.37 (1H, br s), 7.51 (1H, s).

Step 53-2

2-[trans-4-(tert-Butoxycarbonylamino)cyclohexyl]-4,7-dichloro-2-methyl-1,3-benzodioxole-5-carboxylic Acid The title compound (0.194 g, 0.413 mmol, 92% yield) was obtained through the same reaction as in step 1-2 using methyl 2-[trans-4-(tert-butoxycarbonylamino)cyclohexyl]-4,7-dichloro-2-methyl-1,3-benzodioxole-5-carboxylate (0.215 g, 0.450 mmol) synthesized in step 53-1.

$^1$H-NMR (400 MHz, CDCl$_3$) δ: 1.06-1.20 (2H, m), 1.28-1.43 (2H, m), 1.44 (9H, s), 1.70 (3H, s), 1.84-2.02 (3H, m), 2.05-2.15 (2H, m), 3.34-3.50 (1H, m), 4.40 (1H, br s), 7.67 (1H, s).

MS (APCI) m/z: 444 (M−H)$^-$.

Step 53-3 tert-Butyl N-[trans-4-[4,7-dichloro-5-[(4,6-dimethyl-2-oxo-1,2-dihydropyridin-3-yl)methylcarbamoyl]-2-methyl-1,3-benzodioxol-2-yl]cyclohexyl]carbamate The title compound (0.225 g, 0.384 mmol, 95% yield) was obtained through the same reaction as in step 1-3 using 2-[trans-4-(tert-butoxycarbonylamino)cyclohexyl]-4,7-dichloro-2-methyl-1,3-benzodioxole-5-carboxylic acid (0.190 g, 0.405 mmol) synthesized in step 53-2.

$^1$H-NMR (400 MHz, CDCl$_3$) δ: 1.02-1.16 (2H, m), 1.24-1.38 (2H, m), 1.43 (9H, s), 1.65 (3H, s), 1.79-1.98 (3H, m), 2.03-2.12 (2H, m), 2.26 (3H, s), 2.37 (3H, s), 3.32-3.46 (1H, m), 4.38 (1H, d, J=7.9 Hz), 4.52 (2H, d, J=6.0 Hz), 5.95 (1H, s), 7.18 (1H, s), 7.55 (1H, d, J=6.0 Hz), 11.7 (1H, br s).

MS (APCI) m/z: 580 (M+H)$^+$.

Step 53-4

2-(trans-4-Aminocyclohexyl)-4,7-dichloro-N-[(4,6-dimethyl-2-oxo-1,2-dihydropyridin-3-yl)methyl]-2-methyl-1,3-benzodioxole-5-carboxamide The title compound (0.182 g, 0.378 mmol, 100% yield) was obtained through the same reaction as in step 3-4 using tert-butyl N-[trans-4-[4,7-dichloro-5-[(4,6-dimethyl-2-oxo-1,2-dihydropyridin-3-yl)methylcarbamoyl]-2-methyl-1,3-benzodioxol-2-yl]cyclohexyl]carbamate (0.221 g, 0.378 mmol) synthesized in step 53-3.

$^1$H-NMR (400 MHz, CDCl$_3$) δ: 1.03-1.18 (2H, m), 1.21-1.36 (2H, m), 1.66 (3H, s), 1.80-1.98 (5H, m), 2.26 (3H, s), 2.38 (3H, s), 2.59-2.70 (1H, m), 3.71 (2H, s), 4.52 (2H, d, J=6.1 Hz), 5.94 (1H, s), 7.18 (1H, s), 7.54 (1H, t, J=6.1 Hz).

MS (APCI) m/z: 480 (M+H)$^+$.

Step 53-5

4,7-Dichloro-2-[trans-4-(dimethylamino)cyclohexyl]-N-[(4,6-dimethyl-2-oxo-1,2-dihydropyridin-3-yl)methyl]-2-methyl-1,3-benzodioxole-5-carboxamide (53)

The title compound (0.088 g, 0.173 mmol, 46% yield) was obtained through the same reaction as in step 3-5 using 2-(trans-4-aminocyclohexyl)-4,7-dichloro-N-[(4,6-dimethyl-2-oxo-1,2-dihydropyridin-3-yl)methyl]-2-methyl-1,3-benzodioxole-5-carboxamide (0.182 g, 0.378 mmol) synthesized in step 53-4.

$^1$H-NMR (400 MHz, CDCl$_3$) δ: 1.15-1.33 (4H, m), 1.66 (3H, s), 1.79-1.89 (1H, m), 1.91-2.04 (4H, m), 2.09-2.20 (1H, m), 2.26 (3H, s), 2.27 (6H, s), 2.37 (3H, s), 4.53 (2H, d, J=5.6 Hz), 5.95 (1H, s), 7.17-7.19 (1H, s), 7.55 (1H, t, J=5.6 Hz), 11.87 (1H, br s).

MS (APCI) m/z: 508 (M+H)$^+$.

Example 54

4,7-Dichloro-2-[(2S,5R)-5-(dimethylamino)tetrahydropyran-2-yl]-N-[(4,6-dimethyl-2-oxo-1,2-dihydropyridin-3-yl)methyl]-2-methyl-1,3-benzodioxole-5-carboxamide (54)

Step 54-1

Methyl 2-[(2S,5R)-5-(tert-butoxycarbonylamino)tetrahydropyran-2-yl]-4,7-dichloro-2-methyl-1,3-benzodioxole-5-carboxylate The title compound (0.496 g, 1.07 mmol, 70% yield) was obtained through the same reaction as in step 13-1 using the compound (E2) (0.500 g, 1.54 mmol) synthesized in Reference Example 6 and tert-butyl N-[(3R,6S)-6-ethynyltetrahydropyran-3-yl]carbamate (0.520 g, 2.31 mmol) synthesized according to the method described in WO 2007105154.

$^1$H-NMR (400 MHz, CDCl$_3$) δ: 1.22-1.36 (2H, m), 1.43 (9H, s), 1.64-1.75 (1H, m), 1.75 (3H, s), 1.82-1.95 (1H, m), 2.10-2.22 (1H, m), 2.99-3.08 (1H, m), 3.48-3.55 (1H, m), 3.56-3.74 (1H, m), 3.90 (3H, s), 4.10-4.17 (1H, m), 4.25 (1H, br s), 7.52 (1H, s).

Step 54-2

2-[(2S,5R)-5-(tert-Butoxycarbonylamino)tetrahydropyran-2-yl]-4,7-dichloro-2-methyl-1,3-benzodioxole-5-carboxylic Acid The title compound (0.481 g, 1.07 mmol, 100% yield) was obtained through the same reaction as in step 1-2 using methyl 2-[(2S,5R)-5-(tert-butoxycarbonylamino)tetrahydropyran-2-yl]-4,7-dichloro-2-methyl-1,3-benzodioxole-5-carboxylate (0.496 g, 1.07 mmol) synthesized in step 54-1.

MS (ESI) m/z: 446 (M−H)$^-$.

Step 54-3 tert-Butyl N-[(3R,6S)-6-[4,7-dichloro-5-[(4,6-dimethyl-2-oxo-1,2-dihydropyridin-3-yl)methylcarbamoyl]-2-methyl-1,3-benzodioxol-2-yl]tetrahydropyran-3-yl]carbamate The title compound (0.336 g, 0.569 mmol, 53% yield) was obtained through the same reaction as in step 1-3 using 2-[(2S,5R)-5-(tert-butoxycarbonylamino)tetrahydropyran-2-yl]-4,7-dichloro-2-methyl-1,3-benzodioxole-5-carboxylic acid (0.481 g, 1.07 mmol) synthesized in step 54-2.

MS (ESI) m/z: 582 (M+H)$^+$.

Step 54-4

2-[(2S,5R)-5-Aminotetrahydropyran-2-yl]-4,7-dichloro-N-[(4,6-dimethyl-2-oxo-1,2-dihydropyridin-3-yl)methyl]-2-methyl-1,3-benzodioxole-5-carboxamide The title compound (0.176 g, 0.364 mmol, 64% yield) was obtained through the same reaction as in step 3-4 using tert-butyl N-[(3R,6S)-6-[4,7-dichloro-5-[(4,6-dimethyl-2-oxo-1,2-dihydropyridin-3-yl)methylcarbamoyl]-2-methyl-1,3-benzodioxol-2-yl]tetrahydropyran-3-yl]carbamate (0.332 g, 0.569 mmol) synthesized in (Step 54-3.

MS (ESI) m/z: 482 (M+H)$^+$.

Step 54-5

4,7-Dichloro-2-[(2S,5R)-5-(dimethylamino)tetrahydropyran-2-yl]-N-[(4,6-dimethyl-2-oxo-1,2-dihydropyridin-3-yl)methyl]-2-methyl-1,3-benzodioxole-5-carboxamide (54)

The title compound (0.036 g, 0.070 mmol, 19% yield) was obtained through the same reaction as in step 3-5 using 2-[(2S,5R)-5-aminotetrahydropyran-2-yl]-4,7-dichloro-N-[(4,6-dimethyl-2-oxo-1,2-dihydropyridin-3-yl)methyl]-2-methyl-1,3-benzodioxole-5-carboxamide (0.176 g, 0.345 mmol) synthesized in step 54-4.

$^1$H-NMR (400 MHz, CD$_3$OD) δ: 1.70 (3H, s), 2.24 (3H, s), 2.29 (3H, s), 2.35 (3H, s), 4.43 (2H, s), 6.10 (1H, s), 6.61 (1H, s), 6.98 (1H, s).

MS (ESI) m/z: 510 (M+H)$^+$.

Example 55

N-[(4,6-Dimethyl-2-oxo-1,2-dihydropyridin-3-yl)methyl]-2-ethyl-7-[6-(4-ethylpiperazin-1-yl)-3-pyridyl]-4-methyl-2-(tetrahydropyran-4-yl)-1,3-benzodioxole-5-carboxamide (55)

[Formula 41]

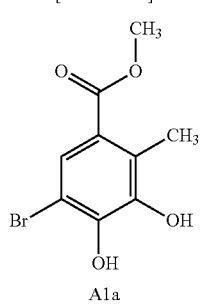
A1a

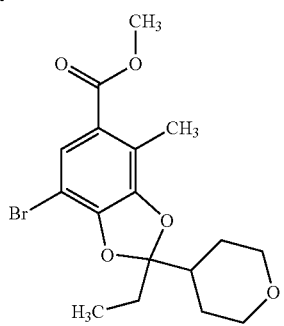
A2r

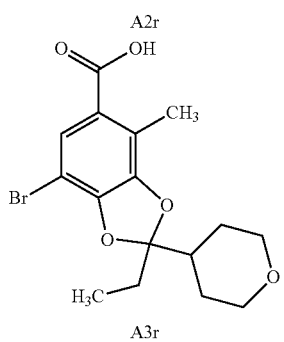
A3r

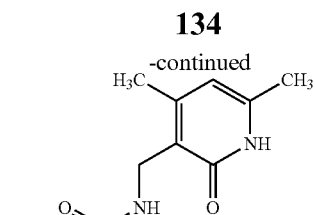

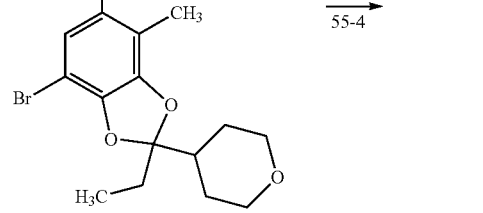

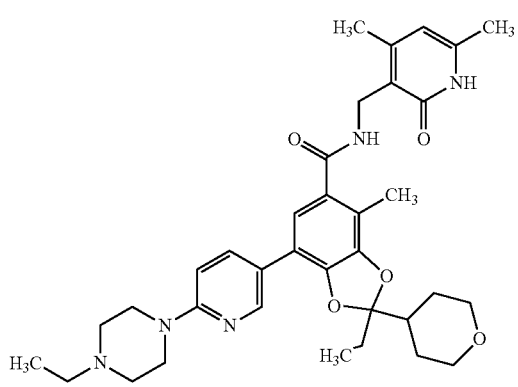 [SMILES: CCN1CCN(c2ccc(-c3cc(C(=O)NCc4c(C)cc(C)[nH]c4=O)c(C)c4c3OC(CC)(C3CCOCC3)O4)cn2)CC1]

Step 55-1

Methyl 7-bromo-2-ethyl-4-methyl-2-(tetrahydropyran-4-yl)-1,3-benzodioxole-5-carboxylate (A2r)

The compound (A1a) (2.50 g, 9.58 mmol) synthesized in Reference Example 1 was dissolved in toluene (100 mL) under a nitrogen atmosphere. To the solution, 1-tetrahydropyran-4-ylpropan-1-one (2.15 g, 14.4 mmol) and montmorillonite K10, powder (5.00 g) were added, and the mixture was refluxed for 12 hours while removing water using a Dean-Stark apparatus. Insoluble matter was removed by filtration, and the filtrate was then concentrated under reduced pressure. The obtained residue was purified by silica gel column chromatography (hexane:ethyl acetate=90:10) to obtain the title compound (0.179 mg, 0.463 mmol, 4.8% yield).

$^1$H-NMR (400 MHz, CDCl$_3$) δ: 0.98 (3H, t, J=7.3 Hz), 1.59-1.69 (4H, m), 1.98 (2H, q, J=7.3 Hz), 2.08-2.19 (1H, m), 2.39 (3H, s), 3.33-3.35 (2H, m), 3.85 (3H, s), 4.00-4.06 (2H, m), 7.66 (1H, s).

Step 55-2

7-Bromo-2-ethyl-4-methyl-2-(tetrahydropyran-4-yl)-1,3-benzodioxole-5-carboxylic Acid (A3r)

The title compound (0.122 g, 0.330 mmol, 75% yield) was obtained through the same reaction as in step 1-2 using the compound (A2r) (170 mg, 0.441 mmol) synthesized in step 55-1.

$^1$H-NMR (400 MHz, CDCl$_3$) δ: 0.99 (3H, t, J=7.3 Hz), 1.61-1.76 (4H, m), 2.00 (2H, q, J=7.3 Hz), 2.09-2.20 (1H, m), 2.43 (3H, s), 3.32-3.43 (2H, m), 4.01-4.06 (2H, m), 7.81 (1H, s).
MS (ESI) m/z: 369, 371 (M−H)⁻.

Step 55-3

7-Bromo-N-[(4,6-dimethyl-2-oxo-1,2-dihydropyridin-3-yl)methyl]-2-ethyl-4-methyl-2-(tetrahydropyran-4-yl)-1,3-benzodioxole-5-carboxamide (55p)

The title compound (0.120 g, 0.238 mmol, 72% yield) was obtained through the same reaction as in step 1-3 using the compound (A3r) (0.122 g, 0.330 mmol) synthesized in step 55-2.
$^1$H-NMR (400 MHz, CDCl$_3$) δ: 0.95 (3H, t, J=7.3 Hz), 1.57-1.65 (4H, m), 1.60 (3H, s), 1.95 (2H, q, J=7.3 Hz), 2.05-2.14 (1H, m), 2.22 (3H, s), 2.25 (3H, s), 2.37 (3H, s), 3.30-3.43 (2H, m), 3.98-4.07 (2H, m), 4.49 (2H, d, J=6.1 Hz), 5.95 (1H, s), 6.99 (1H, s), 7.18 (1H, s).
MS (ESI) m/z: 505, 507 (M+H)⁺.

Step 55-4

N-[(4,6-Dimethyl-2-oxo-1,2-dihydropyridin-3-yl)methyl]-2-ethyl-7-[6-(4-ethylpiperazin-1-yl)-3-pyridyl]-4-methyl-2-(tetrahydropyran-4-yl)-1,3-benzodioxole-5-carboxamide (55)

The compound (55p) (0.110 g, 0.218 mmol) synthesized in step 55-3 was dissolved in 1,4-dioxane (4.4 mL) and water (1.1 mL). To the solution, 6-(4-ethyl-piperazin-1-yl)pyridine-3-boronic acid pinacol ester (0.083 g, 0.261 mmol), potassium phosphate (0.139 g, 0.653 mmol), and a [1,1'-bis(diphenylphosphino)ferrocene]palladium(II) dichloride-dichloromethane complex (1:1) (0.027 g, 0.033 mmol) were added, and the mixture was stirred at 80° C. for 4 hours under a nitrogen atmosphere. After the completion of the reaction, the reaction solution was filtered through celite, and ethyl acetate was added to the filtrate. The organic layer was washed with a saturated aqueous solution of sodium bicarbonate and saturated saline and then dried over sodium sulfate. The solvent was distilled off under reduced pressure, and the obtained residue was purified by silica gel column chromatography (hexane:methanol=100:0→95:5) to obtain the title compound (0.040 g, 0.064 mmol, 30% yield).
$^1$H-NMR (400 MHz, CD$_3$OD) δ: 0.97 (3H, t, J=7.3 Hz), 1.17 (3H, t, J=7.3 Hz), 1.52-1.62 (2H, m), 1.68-1.71 (2H, m), 2.00 (2H, q, J=7.3 Hz), 2.17-2.22 (1H, m), 2.24 (6H, s), 2.37 (3H, s), 2.52-2.60 (2H, m), 2.63-2.71 (4H, m), 3.35-3.42 (2H, m), 3.60 (2H, q, J=7.3 Hz), 3.60-3.75 (2H, m), 3.92-3.98 (2H, m), 4.45 (2H, s), 6.11 (1H, s), 6.90 (1H, d, J=8.5 Hz), 7.08 (1H, s), 7.92 (1H, dd, J=8.5, 2.7 Hz), 8.51 (1H, d, J=2.7 Hz).
MS (ESI) m/z: 616 (M+H)⁺.

Example 56

N-[(4,6-Dimethyl-2-oxo-1,2-dihydropyridin-3-yl)methyl]-7-[6-(4-ethylpiperazin-1-yl)-3-pyridyl]-2,4-dimethyl-2-(tetrahydropyran-4-yl)-1,3-benzodioxole-5-carboxamide (56)

The title compound (0.154 g, 0.256 mmol, 84% yield) was obtained through the same reaction as in step 55-4 using the compound (2) (0.150 g, 0.305 mmol) synthesized in step 2-3.
$^1$H-NMR (400 MHz, DMSO-d$_6$) δ: 1.04 (3H, t, J=7.0 Hz), 1.60 (3H, s), 1.62-1.70 (2H, m), 2.11 (3H, s), 2.15-2.20 (6H, m), 2.36 (2H, q, J=7.0), 2.41-2.48 (4H, m), 3.24-3.33 (2H, m), 3.48-3.55 (4H, m), 3.85-3.93 (2H, m), 4.26 (2H, d, J=4.9 Hz), 5.86 (1H, s), 6.92 (1H, d, J=8.5 Hz), 7.04 (1H, s), 7.85 (1H, d, J=8.5 Hz), 8.11 (1H, t, J=4.9 Hz), 8.48 (1H, s), 11.48 (1H, s).
MS (ESI) m/z: 602 (M+H)⁺.

Example 57

N-[(4,6-Dimethyl-2-oxo-1,2-dihydropyridin-3-yl)methyl]-7-[6-(4-ethylpiperazin-1-yl)-3-pyridyl]-2,4-dimethyl-2-(tetrahydrofuran-3-yl)-1,3-benzodioxole-5-carboxamide (57)

The title compound (0.130 g, 0.256 mmol, 82% yield) was obtained through the same reaction as in step 55-4 using the compound (1) (0.150 g, 0.314 mmol) synthesized in step 1-3.
$^1$H-NMR (400 MHz, DMSO-d$_6$) δ: 1.04 (3H, t, J=7.3 Hz), 1.62 (3H, s), 1.76-1.87 (1H, m), 1.94-2.05 (1H, m), 2.10 (3H, s), 2.15-2.20 (6H, m), 2.31-2.40 (2H, m), 2.40-2.48 (4H, m), 2.88-2.98 (1H, m), 3.46-3.56 (4H, m), 3.59-3.68 (2H, m), 3.71-3.84 (2H, m), 4.26 (2H, d, J=4.9 Hz), 5.86 (1H, s), 6.91 (1H, d, J=8.5 Hz), 7.05 (1H, s), 7.84 (1H, dd, J=8.5, 2.4 Hz), 8.13 (1H, t, J=4.9 Hz), 8.47 (1H, d, J=2.4 Hz), 11.48 (1H, s).
MS (ESI) m/z: 588 (M+H)⁺.

Example 58

7-(Cyclopenten-1-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (58)

The title compound (0.156 g, 0.300 mmol, 64% yield) was obtained through the same reaction as in step 55-4 using the compound (14) (0.250 g, 0.470 mmol) synthesized in Example 14 and cyclopenten-1-ylboronic acid pinacol ester (0.137 g, 0.704 mmol).
$^1$H-NMR (400 MHz, CD$_3$OD) δ: 1.20-1.34 (4H, m), 1.58 (3H, s), 1.79-1.87 (1H, m), 1.92-2.03 (6H, m), 2.18 (3H, s), 2.22-2.31 (1H, m), 2.24 (3H, s), 2.29 (6H, s), 2.36 (3H, s), 2.47-2.61 (2H, m), 2.66-2.70 (2H, m), 4.43 (2H, s), 6.10 (1H, s), 6.34 (1H, m), 6.83 (1H, s).
MS (ESI) m/z: 520 (M+H)⁺.

Example 59

2-[trans-4-(Dimethylamino)cyclohexyl]-N-[(4,6-dimethyl-2-oxo-1,2-dihydropyridin-3-yl)methyl]-2,4-dimethyl-7-phenyl-1,3-benzodioxole-5-carboxamide (59)

The title compound (0.059 g, 0.112 mmol, 29.7% yield) was obtained through the same reaction as in step 55-4 using the compound (61) (0.200 g, 0.376 mmol) synthesized in Example 14 and phenylboronic acid (0.069 g, 0.563 mmol).
$^1$H-NMR (400 MHz, DMSO-d$_6$) δ: 1.22-1.36 (4H, m), 1.61 (3H, s), 1.82-1.92 (1H, m), 1.95-2.07 (4H, m), 2.22-2.31 (1H, m), 2.23 (6H, s), 2.29 (6H, s), 2.37 (3H, s), 4.45

(2H, s), 6.11 (1H, s), 7.12 (1H, s), 7.27-7.31 (1H, m), 7.36-7.43 (2H, m), 7.65-7.70 (2H, m).
MS (ESI) m/z: 530 (M+H)$^+$.

Example 60

7-(Cyclohexen-1-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (60)

The title compound (0.116 g, 0.218 mmol, 46% yield) was obtained through the same reaction as in step 55-4 using the compound (14) (0.250 g, 0.470 mmol) synthesized in Example 14 and cyclohexene-1-boronic acid pinacol ester (0.147 g, 0.704 mmol).
$^1$H-NMR (400 MHz, CD$_3$OD) δ: 1.21-1.32 (4H, m), 1.56 (3H, s), 1.61-1.68 (2H, m), 1.71-1.77 (2H, m), 1.79-1.85 (1H, m), 1.99 (4H, m), 2.17 (3H, s), 2.17-2.20 (2H, m), 2.24 (3H, s), 2.24-2.27 (1H, m), 2.29 (6H, s), 2.34-2.39 (1H, m), 2.36 (3H, s), 4.43 (2H, s), 6.10 (1H, s), 6.22-6.26 (1H, m), 6.82 (1H, s).
MS (ESI) m/z: 534 (M+H)$^+$.

Example 61

2-[trans-4-(Dimethylamino)cyclohexyl]-N-[(4,6-dimethyl-2-oxo-1,2-dihydropyridin-3-yl)methyl]-7-[6-(4-ethylpiperazin-1-yl)-3-pyridyl]-2,4-dimethyl-1,3-benzodioxole-5-carboxamide (61)

The title compound (0.195 g, 0.303 mmol, 22% yield) was obtained through the same reaction as in step 55-4 using the compound (14) (0.750 g, 1.41 mmol) synthesized in Example 14.
$^1$H-NMR (400 MHz, DMSO-d$_6$) δ: 1.04 (3H, t, J=7.3 Hz), 1.11-1.28 (5H, m), 1.58 (3H, s), 1.76-1.93 (4H, m), 2.04-2.09 (1H, m), 2.10 (3H, s), 2.13 (6H, s), 2.17 (3H, s), 2.18 (3H, s), 2.36 (2H, q, J=7.3 Hz), 2.42-2.46 (4H, m), 3.49-3.55 (4H, m), 4.25 (2H, d, J=4.9 Hz), 5.86 (1H, s), 6.92 (1H, d, J=9.1 Hz), 7.03 (1H, s), 7.84 (1H, dd, J=9.1, 2.4 Hz), 8.10 (1H, t, J=4.9 Hz), 8.47 (1H, d, J=2.4 Hz), 11.48 (1H, s).
MS (APCI) m/z: 643 (M+H)$^+$.

Example 62

7-(3,6-Dihydro-2H-pyran-4-yl)-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (62)

The title compound (0.106 g, 0.198 mmol, 42% yield) was obtained through the same reaction as in step 55-4 using the compound (14) (0.250 g, 0.470 mmol) synthesized in Example 14 and 3,6-dihydro-2H-pyran-4-boronic acid pinacol ester (0.148 g, 0.704 mmol).
$^1$H-NMR (400 MHz, CD$_3$OD) δ: 1.20-1.33 (4H, m), 1.58 (3H, s), 1.78-1.88 (1H, m), 1.94-2.05 (4H, m), 2.19 (3H, s), 2.24 (3H, s), 2.24 (1H, br s), 2.29 (6H, s), 2.36 (3H, s), 2.45-2.51 (2H, m), 3.88 (2H, t, J=5.5 Hz), 4.28-4.26 (2H, m), 4.43 (2H, s), 6.10 (1H, s), 6.34-6.38 (1H, m), 6.87 (1H, s).
MS (ESI) m/z: 536 (M+H)$^+$.

Example 63

2-[trans-4-(Dimethylamino)cyclohexyl]-N-[(4,6-dimethyl-2-oxo-1,2-dihydropyridin-3-yl)methyl]-2,4-dimethyl-7-[6-(morpholinomethyl)-3-pyridyl]-1,3-benzodioxole-5-carboxamide (63)

The title compound (0.024 g, 0.039 mmol, 2.7% yield) was obtained through the same reaction as in step 55-4 using the compound (14) (0.750 g, 1.41 mmol) synthesized in Example 14 and [6-(morpholinomethyl)-3-pyridyl]boronic acid (0.375 g, 1.69 mmol).
$^1$H-NMR (400 MHz, DMSO-d$_6$) δ: 1.11-1.24 (4H, m), 1.60 (3H, s), 1.77-1.97 (5H, m), 2.05-2.20 (1H, m), 2.11 (3H, s), 2.14 (6H, s), 2.18 (3H, s), 2.19 (3H, s), 2.40-2.46 (4H, m), 3.57-3.66 (6H, m), 4.26 (2H, d, J=4.9 Hz), 5.86 (1H, s), 7.12 (1H, s), 7.53 (1H, d, J=8.5 Hz), 8.06 (1H, dd, J=8.5, 2.4 Hz), 8.15 (1H, t, J=4.9 Hz), 8.83 (1H, d, J=2.4 Hz), 11.48 (1H, s).
MS (APCI) m/z: 630 (M+H)$^+$.

Example 64

2-[trans-4-(Dimethylamino)cyclohexyl]-N-[(4,6-dimethyl-2-oxo-1,2-dihydropyridin-3-yl)methyl]-2,4-dimethyl-7-(3-pyridyl)-1,3-benzodioxole-5-carboxamide (64)

The title compound (0.014 g, 0.026 mmol, 9.9% yield) was obtained through the same reaction as in step 55-4 using the compound (14) (0.140 g, 0.263 mmol) synthesized in Example 14 and pyridine-3-boronic acid (0.048 g, 0.394 mmol).
$^1$H-NMR (400 MHz, CD$_3$OD) δ: 1.23-1.38 (4H, m), 1.64 (3H, s), 1.86-1.95 (1H, m), 1.97-2.09 (4H, m), 2.24 (3H, s), 2.26 (3H, s), 2.33 (6H, s), 2.33-2.36 (1H, m), 2.37 (3H, s), 4.46 (2H, s), 6.11 (1H, s), 6.61 (1H, s), 7.19 (1H, s), 7.48-7.52 (1H, m), 8.14-8.18 (1H, m), 8.45-8.47 (1H, m), 8.89-8.91 (1H, m).
MS (ESI) m/z: 531 (M+H)$^+$.

Example 65

2-[trans-4-(Dimethylamino)cyclohexyl]-N-[(4,6-dimethyl-2-oxo-1,2-dihydropyridin-3-yl)methyl]-2,4-dimethyl-7-(1-methylpyrazol-4-yl)-1,3-benzodioxole-5-carboxamide Hydrochloride (65)

The title compound (0.107 g, 0.187 mmol, 50% yield) was obtained as a solid (monohydrochloride) through the same reaction as in step 55-4 using the compound (14) (0.200 g, 0.376 mmol) synthesized in Example 14 and 1-methyl-4-(4,4,5,5-tetramethyl-1,3,2-dioxaborolan-2-yl)-1H pyrazole (0.156 g, 0.751 mmol), followed by conversion to the hydrochloride with 4 M hydrochloric acid in ethyl acetate.
$^1$H-NMR (400 MHz, CD$_3$OD) δ: 1.37-1.59 (4H, m), 1.66 (3H, s), 1.97-2.04 (1H, m), 2.09-2.20 (4H, m), 2.20 (3H, s), 2.27 (3H, s), 2.40 (3H, s), 2.83 (6H, s), 3.16-3.27 (1H, m), 3.92 (3H, s), 4.46 (2H, s), 6.20 (1H, s), 7.17 (1H, s), 7.86 (1H, s), 7.98 (1H, s).
MS (ESI) m/z: 534 (M+H)$^+$.

Example 66

2-[trans-4-(Dimethylamino)cyclohexyl]-N-[(4,6-dimethyl-2-oxo-1,2-dihydropyridin-3-yl)methyl]-2,4-dimethyl-7-vinyl-1,3-benzodioxole-5-carboxamide (66)

The title compound (0.171 g, 0.357 mmol, 95% yield) was obtained through the same reaction as in step 55-4 using the compound (14) (0.200 g, 0.376 mmol) synthesized in Example 14 and 4,4,5,5-tetramethyl-2-vinyl-1,3,2-dioxaborolane (0.087 g, 0.563 mmol).

$^1$H-NMR (400 MHz, CD$_3$OD) δ: 1.21-1.35 (4H, m), 1.59 (3H, s), 1.80-1.90 (1H, m), 1.95-2.04 (4H, m), 2.18 (3H, s), 2.24 (3H, s), 2.22-2.28 (1H, m), 2.29 (6H, s), 2.36 (3H, s), 4.43 (2H, s), 5.30 (1H, d, J=12.1 Hz), 5.85 (1H, d, J=17.6 Hz), 6.11 (1H, s), 6.58 (1H, dd, J=17.6, 12.1 Hz), 6.90 (1H, s).

MS (ESI) m/z: 480 (M+H)$^+$.

Example 67

2-[trans-4-(Dimethylamino)cyclohexyl]-N-[(4,6-dimethyl-2-oxo-1,2-dihydropyridin-3-yl)methyl]-7-ethynyl-2,4-dimethyl-1,3-benzodioxole-5-carboxamide (67)

[Formula 42]

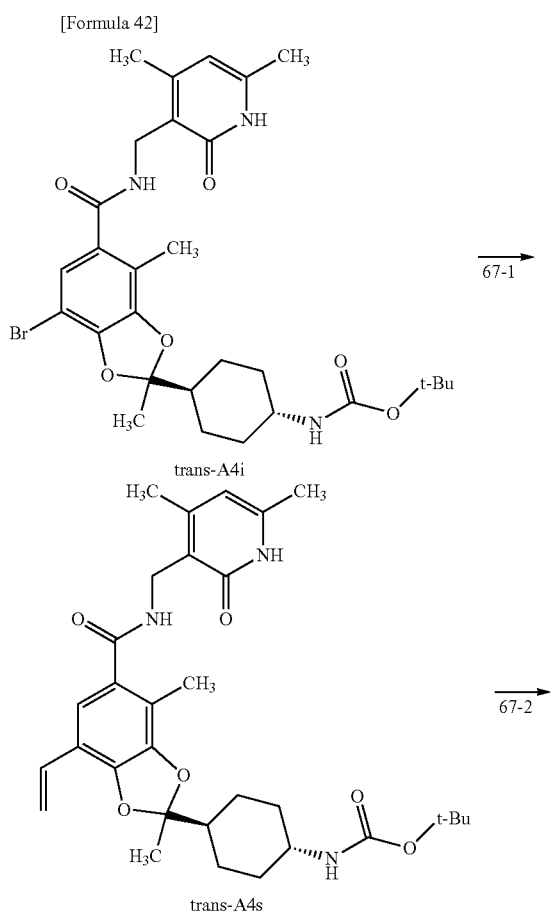
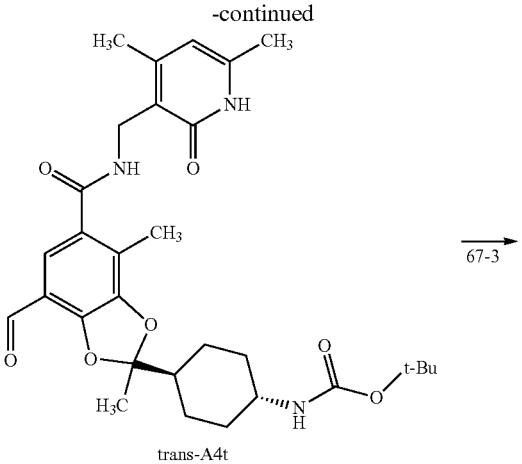
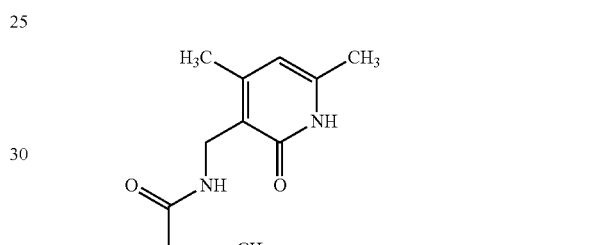
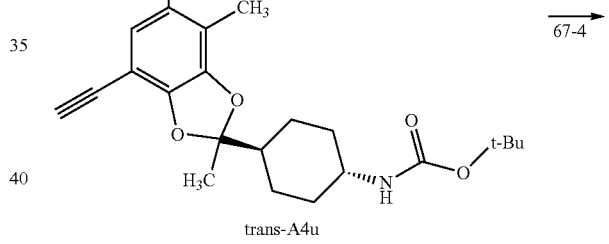

-continued

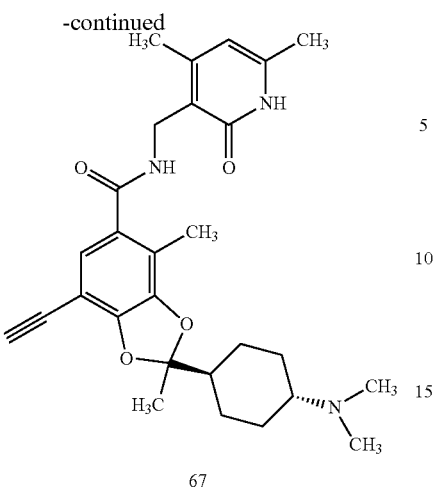

67

Step 67-1 tert-Butyl N-[trans-4-[5-[(4,6-dimethyl-2-oxo-1,2-dihydropyridin-3-yl)methylcarbamoyl]-2,4-dimethyl-7-vinyl-1,3-benzodioxol-2-yl]cyclohexyl]carbamate (trans-A4s)

The title compound (0.352 g, 0.638 mmol, 97% yield) was obtained through the same reaction as in Example 66 using the compound (trans-A4i) (0.400 g, 0.662 mmol) synthesized in step 13-3.
MS (ESI) m/z: 552 (M+H)$^+$.

Step 67-2 tert-Butyl N-[trans-4-[5-[(4,6-dimethyl-2-oxo-1,2-dihydropyridin-3-yl)methylcarbamoyl]-7-formyl-2,4-dimethyl-1,3-benzodioxol-2-yl]cyclohexyl]carbamate (trans-A4t)

The compound (trans-A4s) (0.352 g, 0.638 mmol) synthesized in step 67-1 was dissolved in tetrahydrofuran (6.0 mL) and water (3.0 mL). To the solution, microencapsulated osmium oxide (content: approximately 10%) (0.008 g, 0.032 mmol) and sodium periodate (0.273 g, 1.28 mmol) were added, and the mixture was stirred at room temperature for 17 hours. After the completion of the reaction, insoluble matter was removed by filtration, and a saturated aqueous solution of sodium nitrite was added to the filtrate, followed by extraction with ethyl acetate. The organic layer was washed with water and saturated saline and dried over anhydrous sodium sulfate. Then, the solvent was distilled off under reduced pressure, and the obtained residue was purified by silica gel column chromatography (hexane:ethyl acetate=100:0→77:23) to obtain the title compound (0.205 g, 0.369 mmol, 58% yield).
$^1$H-NMR (400 MHz, CDCl$_3$) δ: 1.04-1.15 (2H, m), 1.27-1.37 (2H, m), 1.44 (9H, s), 1.63 (3H, s), 1.79-1.89 (1H, m), 1.90-1.98 (2H, m), 2.04-2.12 (2H, m), 2.24 (3H, s), 2.31 (3H, s), 2.37 (3H, s), 3.32-3.44 (1H, m), 4.40 (1H, d, J=7.9 Hz), 4.51 (2H, d, J=6.1 Hz), 5.96 (1H, s), 7.27-7.30 (1H, t, J=6.1 Hz), 7.31 (1H, s), 10.02 (1H, s), 11.87 (1H, br s).
MS (ESI) m/z: 554 (M+H)$^+$.

Step 67-3 tert-Butyl N-[trans-4-[5-[(4,6-dimethyl-2-oxo-1,2-dihydropyridin-3-yl)methylcarbamoyl]-7-ethynyl-2,4-dimethyl-1,3-benzodioxol-2-yl]cyclohexyl]carbamate (trans-A4u)

The compound (trans-A4s) (0.200 g, 0.361 mmol) synthesized in step 67-2 was dissolved in methanol (6 mL). To the solution, potassium carbonate (0.100 g, 0.379 mmol) was added, and a solution of dimethyl (1-diazo-2-oxopropyl)phosphonate (0.073 g, 0.379 mmol) in methanol (6 mL) was gradually added dropwise under ice cooling. The reaction solution was stirred at room temperature for 17 hours and concentrated under reduced pressure. To the obtained residue, ethyl acetate was added, and the organic layer was washed with water and saturated saline and dried over anhydrous sodium sulfate. The solvent was distilled off under reduced pressure to obtain the title compound (0.154 g, 0.279 mmol, 77% yield).
$^1$H-NMR (400 MHz, CDCl$_3$) δ: 1.01-1.15 (2H, m), 1.24-1.37 (2H, m), 1.43 (9H, s), 1.59 (3H, s), 1.73-1.85 (1H, m), 1.89-1.98 (2H, m), 2.00-2.10 (2H, m), 2.26 (6H, s), 2.37 (3H, s), 3.17 (1H, s), 3.32-3.45 (1H, m), 4.38 (1H, d, J=7.9 Hz), 4.49 (2H, d, J=6.1 Hz), 5.96 (1H, s), 6.97 (1H, s), 7.25 (1H, t, J=6.1 Hz), 11.90 (1H, br s).
MS (ESI) m/z: 550 (M+H)$^+$.

Step 67-4

2-(trans-4-Aminocyclohexyl)-N-[(4,6-dimethyl-2-oxo-1,2-dihydropyridin-3-yl)methyl]-7-ethynyl-2,4-dimethyl-1,3-benzodioxole-5-carboxamide (trans-(2S)-A4u-f)

The title compound (0.123 g, 0.273 mmol, 98% yield) was obtained through the same reaction as in step 3-4 using the compound (trans-A4u) (0.154 g, 0.279 mmol) synthesized in step 67-3.
MS (ESI) m/z: 450 (M+H)$^+$.

Step 67-5

2-[trans-4-(Dimethylamino)cyclohexyl]-N-[(4,6-dimethyl-2-oxo-1,2-dihydropyridin-3-yl)methyl]-7-ethynyl-2,4-dimethyl-1,3-benzodioxole-5-carboxamide (67)

The title compound (0.053 g, 0.111 mmol, 41% yield) was obtained through the same reaction as in step 3-5 using the compound (trans-A4u-f) (0.123 g, 0.273 mmol) synthesized in step 67-4.

¹H-NMR (400 MHz, CD₃OD) δ: 1.22-1.38 (4H, m), 1.60 (3H, s), 1.80-1.90 (1H, m), 1.88-2.12 (4H, m), 2.18 (3H, s), 2.24 (3H, s), 2.24-2.29 (1H, m), 2.30 (6H, s), 2.35 (3H, s), 3.62 (1H, s), 4.41 (2H, s), 6.10 (1H, s), 6.90 (1H, s).
MS (ESI) m/z: 478 (M+H)⁺.

Example 68

7-Cyclopropyl-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (68)

The title compound (0.007 g, 0.014 mmol, 3.7% yield) was obtained through the same reaction as in step 55-4 using the compound (14) (0.200 g, 0.376 mmol) synthesized in Example 14 and cyclopropylboronic acid (0.048 g, 0.563 mmol).
¹H-NMR (400 MHz, CD₃OD) δ: 0.73-0.77 (2H, m), 0.84-0.89 (2H, m), 1.24-1.32 (4H, m), 1.55 (3H, s), 1.77-1.84 (2H, m), 1.95-2.05 (4H, m), 2.14 (3H, s), 2.24 (3H, s), 2.32-2.35 (1H, m), 2.33 (6H, s), 2.35 (3H, s), 4.41 (2H, s), 6.10 (1H, s), 6.51 (1H, s).
MS (ESI) m/z: 494 (M+H)⁺.

Example 69

2-[trans-4-(Dimethylamino)cyclohexyl]-N-[(4,6-dimethyl-2-oxo-1,2-dihydropyridin-3-yl)methyl]-2,4-dimethyl-7-[2-(4-methylpiperazin-1-yl)-4-pyridyl]-1,3-benzodioxole-5-carboxamide (69)

The title compound (0.256 g, 0.408 mmol, 29% yield) was obtained through the same reaction as in step 55-4 using the compound (14) (0.750 g, 1.41 mmol) synthesized in Example 14 and 1-methyl-4-[4-(4,4,5,5-tetramethyl-1,3,2-dioxaborolan-2-yl)-2-pyridyl]piperazine (0.513 g, 1.69 mmol).
¹H-NMR (400 MHz, DMSO-d₆) δ: 1.10-1.25 (4H, m), 1.59 (3H, s), 1.78-1.95 (5H, m), 2.01-2.09 (1H, m), 2.10 (3H, s), 2.14 (6H, s), 2.18 (3H, s), 2.19 (3H, s), 2.22 (3H, s), 2.35-2.45 (4H, m), 3.48-3.54 (4H, m), 4.26 (2H, d, J=4.9 Hz), 5.86 (1H, s), 6.97 (1H, d, J=5.5 Hz), 7.05 (1H, s), 7.15 (1H, s), 8.14 (1H, t, J=4.9 Hz), 8.16 (1H, d, J=5.5 Hz), 11.47 (1H, s).
MS (APCI) m/z: 629 (M+H)⁺.

Example 70

2-[trans-4-(Dimethylamino)cyclohexyl]-N-[(4,6-dimethyl-2-oxo-1,2-dihydropyridin-3-yl)methyl]-2,4-dimethyl-7-thiazol-5-yl-1,3-benzodioxole-5-carboxamide Hydrochloride (70)

The title compound (0.015 g, 0.027 mmol, 9.4% yield) was obtained through the same reaction as in step 55-4 using the compound (14) (0.150 g, 0.282 mmol) synthesized in Example 14 and thiazole-5-boronic acid pinacol ester (0.089 g, 0.423 mmol).
¹H-NMR (400 MHz, CD₃OD) δ: 1.35-1.52 (2H, m), 1.52-1.65 (2H, m), 1.73 (3H, s), 2.05-2.25 (5H, m), 2.30 (3H, s), 2.51 (3H, s), 2.62 (3H, s), 2.83 (6H, s), 3.18-3.30 (1H, m), 4.59 (2H, s), 6.99 (1H, s), 7.56 (1H, s), 8.67 (1H, s), 9.73 (1H, s).
MS (ESI) m/z: 537 (M+H)⁺.

Example 71

2-[trans-4-(Dimethylamino)cyclohexyl]-N-[(4,6-dimethyl-2-oxo-1,2-dihydropyridin-3-yl)methyl]-2,4-dimethyl-7-(1-methyl-3,6-dihydro-2H-pyridin-4-yl)-1,3-benzodioxole-5-carboxamide (71)

The title compound (0.144 g, 0.263 mmol, 70% yield) was obtained through the same reaction as in step 55-4 using the compound (14) (0.200 g, 0.376 mmol) synthesized in Example 14 and 1-methyl-4-(4,4,5,5-tetramethyl-1,3,2-dioxaborolan-2-yl)-3,6-dihydro-2H-pyridine (0.126 g, 0.563 mmol).
¹H-NMR (400 MHz, CD₃OD) δ: 1.19-1.33 (4H, m), 1.57 (3H, s), 1.79-1.86 (1H, m), 1.94-2.05 (4H, m), 2.18 (3H, s), 2.20-2.30 (1H, m), 2.24 (3H, s), 2.29 (6H, s), 2.35 (3H, s), 2.37 (3H, s), 2.57-2.61 (2H, m), 2.67-2.71 (2H, m), 3.11-3.14 (2H, m), 4.43 (2H, s), 6.29-6.32 (1H, m), 6.60 (1H, s), 6.87 (1H, s).
MS (ESI) m/z: 549 (M+H)⁺.

Example 72

7-Acetyl-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide Hydrochloride (72)

[Formula 43]

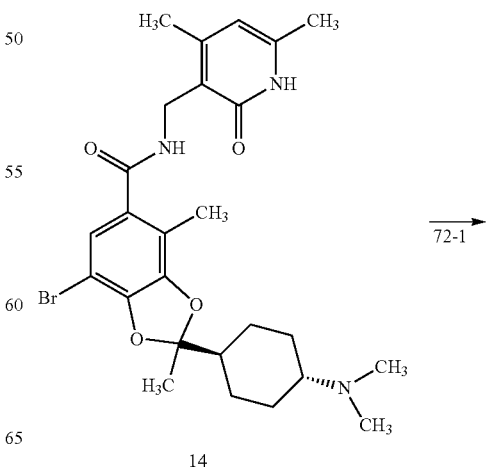

14

72-1→

-continued

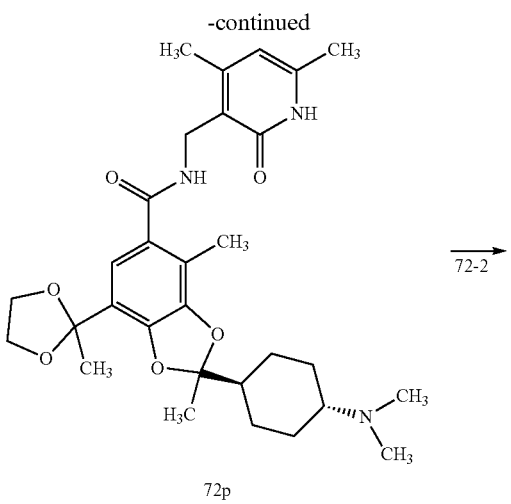

72p

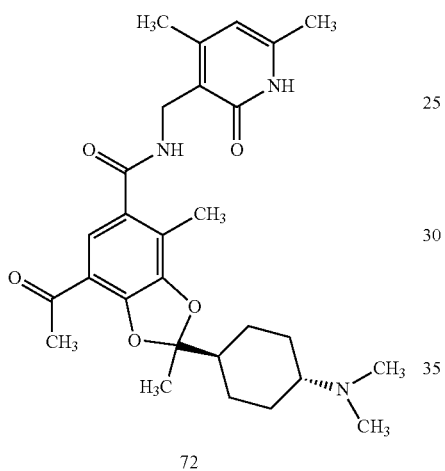

72

Step 72-1

2-[trans-4-(Dimethylamino)cyclohexyl]-N-[(4,6-dimethyl-2-oxo-1,2-dihydropyridin-3-yl)methyl]-2,4-dimethyl-7-(2-methyl-1,3-dioxolan-2-yl)-1,3-benzodioxole-5-carboxamide (72p)

To a solution of the compound (14) (500 mg, 0.939 mmol) synthesized in Example 14 in ethylene glycol (4 mL), palladium acetate (0.011 g, 0.047 mmol), 1,3-bis(diphenylphosphino)propane (0.039 g, 0.094 mmol), ethylene glycol monovinyl ether (0.165 g, 1.88 mmol), and triethylamine (0.143 g, 1.41 mmol) were added, and the mixture was reacted at 110° C. for 3 hours in a microwave reaction apparatus. After the completion of the reaction, ethyl acetate was added thereto, and the organic layer was washed with water and saturated saline and dried over anhydrous sodium sulfate. The solvent was distilled off under reduced pressure, and the obtained residue was purified by basic silica gel column chromatography (ethyl acetate:methanol=100:0→81:19) to obtain the title compound (0.104 g, 0.192 mmol, 21% yield).

MS (ESI) m/z: 540 (M+H)$^+$.

Step 72-2

7-Acetyl-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide Hydrochloride (72)

The compound (72p) (0.104 g, 0.192 mmol) synthesized in step 72-1 was dissolved in tetrahydrofuran (4 mL). To the solution, 1 M hydrochloric acid (0.404 mL, 0.404 mmol) was added, and the mixture was stirred at room temperature for 8 hours. After the completion of the reaction, the reaction solution was neutralized and rendered weakly alkaline with a 1 M aqueous sodium hydroxide solution. Ethyl acetate was added to the reaction solution, and the organic layer was washed with water and saturated saline and dried over anhydrous sodium sulfate. The solvent was distilled off under reduced pressure, and the obtained residue was then dissolved in ethyl acetate. To the solution, a 4 M solution of hydrochloric acid in 1,4-dioxane (0.050 mL) was added, and the deposited solid was filtered to obtain the title compound (0.085 g, 0.160 mmol, 83% yield) as a monohydrochloride.

$^1$H-NMR (400 MHz, CD$_3$OD) δ: 1.37-1.57 (4H, m), 1.69 (3H, s), 2.00-2.07 (1H, m), 2.10-2.19 (4H, m), 2.25 (3H, s), 2.30 (3H, s), 2.41 (3H, s), 2.55 (3H, s), 2.84 (6H, s), 3.18-3.28 (1H, m), 4.47 (2H, s), 6.32 (1H, s), 7.41 (1H, s).

MS (ESI) m/z: 496 (M+H)$^+$.

Example 73

2-[trans-4-(Dimethylamino)cyclohexyl]-N-[(4-ethyl-6-methyl-2-oxo-1,2-dihydropyridin-3-yl)methyl]-7-[6-(4-ethylpiperazin-1-yl)-3-pyridyl]-2,4-dimethyl-1,3-benzodioxole-5-carboxamide Hydrochloride (73)

The title compound (0.062 g, 0.086 mmol, 32% yield) was obtained as a dihydrochloride through the same reaction as in step 55-4 using the compound (17) (0.145 g, 0.265 mmol) synthesized in Example 17, followed by conversion to the hydrochloride by the addition of 4 M hydrochloric acid in ethyl acetate (0.060 mL).

$^1$H-NMR (400 MHz, CD$_3$OD) δ: 1.17 (3H, t, J=7.3 Hz), 1.22 (3H, t, J=7.3 Hz), 1.34-1.51 (4H, m), 1.63 (3H, s), 1.90-1.99 (1H, m), 2.05-2.15 (4H, m), 2.23 (3H, s), 2.25 (3H, s), 2.54 (2H, q, J=7.3 Hz), 2.62-2.68 (4H, m), 2.66 (6H, s), 2.73 (2H, q, J=7.3 Hz), 2.89-2.95 (1H, m), 3.56-3.63 (4H, m), 4.48 (2H, s), 6.13 (1H, s), 6.62 (1H, s), 6.86 (1H, d, J=9.1 Hz), 7.09 (1H, s), 7.89 (1H, dd, J=9.1, 2.4 Hz), 8.50 (1H, d, J=2.4 Hz).

MS (ESI) m/z: 657 (M+H)$^+$.

Example 74

2-[trans-4-(Dimethylamino)cyclohexyl]-7-[6-(4-ethylpiperazin-1-yl)-3-pyridyl]-2,4-dimethyl-N-[(6-methyl-2-oxo-4-propyl-1,2-dihydropyridin-3-yl)methyl]-1,3-benzodioxole-5-carboxamide (74)

The title compound (0.090 g, 0.134 mmol, 37% yield) was obtained through the same reaction as in step 55-4 using the compound (18) (0.205 g, 0.366 mmol) synthesized in Example 18.

$^1$H-NMR (400 MHz, CD$_3$OD) δ: 1.02 (3H, t, J=7.3 Hz), 1.15 (3H, t, J=7.0 Hz), 1.24-1.34 (4H, m), 1.60-1.68 (2H, m), 1.62 (3H, s), 1.83-1.91 (1H, m), 1.97-2.07 (4H, m), 2.20-2.28 (1H, m), 2.23 (3H, s), 2.25 (3H, s), 2.28 (6H, s), 2.50 (2H, q, J=7.3 Hz), 2.57-2.63 (4H, m), 2.67-2.72 (2H, m), 3.57-3.62 (4H, m), 4.48 (2H, s), 6.11 (1H, s), 6.52 (1H, s), 6.87 (1H, d, J=9.1 Hz), 7.07 (1H, s), 7.89 (1H, dd, J=9.1, 2.4 Hz), 8.49 (1H, d, J=2.4 Hz).
MS (ESI) m/z: 671 (M+H)$^+$.

Example 75

2-[trans-4-(Dimethylamino)cyclohexyl]-N-[(4-ethyl-6-methyl-2-oxo-1,2-dihydropyridin-3-yl)methyl]-2,4-dimethyl-7-(1-methylpyrazol-4-yl)-1,3-benzodioxole-5-carboxamide Hydrochloride (75)

The title compound (0.052 g, 0.090 mmol, 25% yield) was obtained as a monohydrochloride through the same reaction as in step 55-4 using the compound (17) (0.200 g, 0.366 mmol) synthesized in Example 17 and 1-methyl-4-(4,4,5,5-tetramethyl-1,3,2-dioxaborolan-2-yl)-1H pyrazole (0.089 g, 0.423 mmol), followed by conversion to the hydrochloride by the addition of 4 M hydrochloric acid in ethyl acetate (0.041 mL).
$^1$H-NMR (400 MHz, CD$_3$OD) δ: 1.23 (3H, t, J=7.6 Hz), 1.37-1.59 (4H, m), 1.66 (3H, s), 1.97-2.04 (1H, m), 2.10-2.18 (4H, m), 2.20 (3H, s), 2.27 (3H, s), 2.74 (2H, q, J=7.6 Hz), 2.83 (6H, s), 3.15-3.25 (1H, m), 3.92 (3H, s), 4.46 (2H, s), 6.18 (1H, s), 7.16 (1H, s), 7.85 (1H, s), 7.97 (1H, s).
MS (ESI) m/z: 548 (M+H)$^+$.

Example 76

2-[trans-4-(Dimethylamino)cyclohexyl]-N-[(4,6-dimethyl-2-oxo-1,2-dihydropyridin-3-yl)methyl]-7-ethyl-2,4-dimethyl-1,3-benzodioxole-5-carboxamide (76)

The title compound (0.054 g, 0.111 mmol, 36% yield) was obtained through the same hydrogenation reaction as in Example 23 using the compound (66) (150 mg, 0.313 mmol) synthesized in Example 66.
$^1$H-NMR (400 MHz, CD$_3$OD) δ: 1.16 (3H, t, J=7.6 Hz), 1.20-1.35 (4H, m), 1.55 (3H, s), 1.75-1.85 (1H, m), 1.94-2.06 (4H, m), 2.16 (3H, s), 2.24 (3H, s), 2.27-2.32 (1H, m), 2.31 (6H, s), 2.36 (3H, s), 2.51 (2H, m), 4.42 (2H, s), 6.10 (1H, s), 6.71 (1H, s).
MS (ESI) m/z: 482 (M+H)$^+$.

Example 77

(2R)—N-[(4,6-Dimethyl-2-oxo-1,2-dihydropyridin-3-yl)methyl]-7-[6-(4-ethylpiperazin-1-yl)-3-pyridyl]-2,4-dimethyl-2-(morpholinomethyl)-1,3-benzodioxole-5-carboxamide (77)

The title compound (11.2 g, 18.1 mmol, 70% yield) was obtained through the same reaction as in step 55-4 using the compound (45) (13.2 g, 26.0 mmol) synthesized in step 45-4.
$^1$H-NMR (400 MHz, DMSO-d$_6$) δ: 1.03 (3H, t, J=7.3 Hz), 1.68 (3H, s), 2.11 (3H, s), 2.16 (3H, s), 2.18 (3H, s), 5.67 (2H, q, J=7.3 Hz), 2.41-2.47 (4H, m), 2.49-2.55 (4H, m), 2.75 (2H, s), 3.43-3.48 (4H, m), 3.48-3.54 (4H, m), 4.26 (2H, d, J=4.9 Hz), 5.86 (1H, s), 6.90 (1H, d, J=9.2 Hz), 7.05 (1H, s), 7.82 (1H, dd, J=9.2, 2.4 Hz), 8.12 (1H, d, J=4.9 Hz), 8.46 (1H, d, J=2.4 Hz), 11.48 (1H, br s).
MS (ESI) m/z: 617 (M+H)$^+$.
Specific rotation [α]$_D^{20}$=−38.9 (C=1.0, chloroform)

Example 78

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide Hydrochloride (78)

To the compound (35) (0.205 g, 0.420 mmol) synthesized in Example 35, acetone (8.12 mL) and a 5.88 mol/L aqueous hydrochloric acid solution (0.071 mL, 0.420 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.218 g, rate of recovery: 99%).
$^1$H-NMR (400 MHz, DMSO-d$_6$) δ: 1.16-1.31 (2H, m), 1.38-1.53 (2H, m), 1.62 (3H, s), 1.87-1.99 (3H, m), 2.02-2.11 (2H, m), 2.11 (3H, s), 2.12 (3H, s), 2.17 (3H, s), 2.65 (3H, s), 2.66 (3H, s), 3.08-3.19 (1H, m), 4.22 (2H, d, J=4.8 Hz), 5.86 (1H, s), 6.86 (1H, s), 8.14 (1H, t, J=4.8 Hz), 10.31 (1H, br s), 11.48 (1H, s).
Elemental analysis Anal. Calcd for C$_{26}$H$_{34}$ClN$_3$O$_4$.HCl: C, 59.54; H, 6.73; N, 8.01; Cl, 13.52. Found: C, 55.73; H, 7.01; N, 7.52; Cl, 12.36.

Example 79

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide Methanesulfonic Acid (79)

To the compound (35) (0.205 g, 0.420 mmol) synthesized in Example 35, acetone (8.14 ml) and a 5.93 mol/L aqueous methanesulfonic acid solution (0.071 mL, 0.420 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.240 g, rate of recovery: 99%).
$^1$H-NMR (DMSO-d$_6$) δ: 1.17-1.31 (2H, m), 1.37-1.52 (2H, m), 1.62 (3H, s), 1.88-2.07 (5H, m), 2.09-2.14 (1H, m), 2.11 (3H, s), 2.12 (3H, s), 2.17 (3H, s), 2.31 (3H, s), 2.70 (3H, s), 2.72 (3H, s), 3.41 (1H, s), 4.22 (2H, d, J=5.4 Hz), 5.84-5.87 (1H, m), 6.87 (1H, br s), 8.14 (1H, t, J=5.4 Hz), 9.36 (1H, br s), 11.48 (1H, s).
Elemental analysis Anal. Calcd for C$_{26}$H$_{34}$ClN$_3$O$_4$.CH$_4$O$_3$S: C, 55.52; H, 6.56; N, 7.19; Cl, 6.07; S, 5.49. Found: C, 54.11; H, 6.65; N, 7.00; Cl, 5.86; S, 5.40.

Example 80

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate (80)

To the compound (35) (0.202 g, 0.414 mmol) synthesized in Example 35, acetone (7.97 mL) and a 4.00 mol/L aqueous p-toluenesulfonic acid solution (0.103 mL, 0.414 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.256 g, rate of recovery: 99%).

$^1$H-NMR (DMSO-d$_6$) δ: 1.15-1.32 (2H, m), 1.36-1.50 (2H, m), 1.62 (3H, s), 1.88-2.06 (5H, m), 2.11 (3H, s), 2.12 (3H, s), 2.17 (3H, s), 2.29 (3H, s), 2.70 (3H, s), 2.71 (3H, s), 3.10-3.22 (1H, m), 4.22 (2H, d, J=5.0 Hz), 5.86 (1H, s), 6.87 (1H, s), 7.11 (2H, d, J=8.2 Hz), 7.48 (2H, d, J=8.2 Hz), 8.14 (1H, t, J=5.0 Hz), 9.31 (1H, br s), 11.48 (1H, s).

Elemental analysis Anal. Calcd for C$_{26}$H$_{34}$ClN$_3$O$_4$·C$_7$H$_8$O$_3$S: C, 60.03; H, 6.41; N, 6.36; Cl, 5.37; S, 4.86. Found: C, 58.81; H, 6.48; N, 6.21; Cl, 5.32; S, 4.85.

Example 81

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide Hemifumarate (81)

To the compound (35) (0.200 g, 0.411 mmol) synthesized in Example 35, fumaric acid (0.024 g, 0.205 mmol) and ethyl acetate (8.01 mL) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.222 g, rate of recovery: 99%).

$^1$H-NMR (DMSO-d$_6$) δ: 1.10-1.34 (4H, m), 1.60 (3H, s), 1.80-1.96 (5H, m), 2.11 (3H, s), 2.12 (3H, s), 2.17 (3H, s), 2.33 (6H, s), 2.41-2.50 (2H, m), 4.22 (2H, d, J=5.1 Hz), 5.85 (1H, s), 6.45 (1H, s), 6.85 (1H, s), 8.13 (1H, t, J=5.1 Hz), 11.48 (1H, s).

Elemental analysis Anal. Calcd for C$_{26}$H$_{34}$ClN$_3$O$_4$·½C$_4$H$_4$O$_4$: C, 61.59; H, 6.64; N, 7.70; Cl, 6.49. Found: C, 59.64; H, 6.75; N, 7.46; Cl, 6.24.

Example 82

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide hemi-L-tartrate (82)

To the compound (35) (0.202 g, 0.414 mmol) synthesized in Example 35, L-tartaric acid (0.031 g, 0.208 mmol) and acetone (8.09 mL) were added at room temperature. Then, the mixture was stirred at 40° C. for approximately 20 hours and further stirred at room temperature for approximately 0.5 hours, and the deposited solid was then dried overnight at room temperature to obtain the title compound (0.233 mg, rate of recovery: 99%).

$^1$H-NMR (DMSO-d$_6$) δ: 1.10-1.37 (4H, m), 1.61 (3H, s), 1.81-1.98 (5H, m), 2.11 (3H, s), 2.12 (3H, s), 2.17 (3H, s), 2.39 (6H, s), 2.52-2.63 (1H, m), 3.86 (1H, s), 4.22 (2H, d, J=4.8 Hz), 5.85 (1H, s), 6.85 (1H, s), 8.13 (1H, t, J=4.8 Hz), 11.48 (1H, br s).

Elemental analysis Anal. Calcd for C$_{26}$H$_{34}$ClN$_3$O$_4$·½C$_4$H$_6$O$_6$: C, 59.73; H, 6.62; N, 7.46; Cl, 6.30. Found: C, 57.71; H, 6.77; N, 7.14; Cl, 6.06.

Example 83

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide phosphate (83)

To the compound (35) (0.205 g, 0.421 mmol) synthesized in Example 35, acetone (8.11 mL) and a 4.01 mol/L aqueous phosphoric acid solution (0.105 mL, 0.421 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.244 g, rate of recovery: 99%).

$^1$H-NMR (DMSO-d$_6$) δ: 1.11-1.38 (4H, m), 1.61 (3H, s), 1.81-2.00 (5H, m), 2.11 (3H, s), 2.12 (3H, s), 2.17 (3H, s), 2.39 (6H, s), 2.53-2.65 (1H, m), 4.21 (2H, d, J=4.8 Hz), 5.86 (1H, s), 6.85 (1H, s), 8.13 (1H, t, J=4.8 Hz).

Elemental analysis Anal. Calcd for C$_{26}$H$_{34}$ClN$_3$O$_4$·H$_3$PO$_4$: C, 53.29; H, 6.36; N, 7.17; Cl, 6.05; P, 5.29. Found: C, 51.10; H, 6.45; N, 7.04; Cl, 5.90; P, 5.15.

Example 84

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide Sulfate (84)

To the compound (48) (0.200 g, 0.428 mmol) synthesized in Example 48, 1-propanol (2.00 mL) and a 5.79 mol/L aqueous sulfuric acid solution (0.078 mL, 0.449 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.182 g, rate of recovery: 75%).

$^1$H-NMR (DMSO-d$_6$) δ: 1.15-1.30 (2H, m), 1.33-1.48 (2H, m), 1.55 (3H, s), 1.80-1.90 (1H, m), 1.90-2.04 (4H, m), 2.08 (3H, s), 2.11 (6H, s), 2.17 (3H, s), 2.67 (6H, s), 3.00-3.14 (1H, m), 4.22 (2H, d, J=5.0 Hz), 5.86 (1H, s), 6.68 (1H, s), 7.87 (1H, t, J=5.0 Hz), 9.51 (1H, br s).

Elemental analysis Anal. Calcd for C$_{27}$H$_{37}$N$_3$O$_4$·H$_2$SO$_4$: C, 57.32; H, 6.95; N, 7.43; S, 5.67. Found: C, 55.75; H, 7.17; N, 7.10; S, 5.05.

Example 85

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide Methanesulfonate (85)

To the compound (48) (0.202 g, 0.431 mmol) synthesized in Example 48, acetone (2.02 mL) and a 5.93 mol/L aqueous methanesulfonic acid solution (0.076 mL, 0.451 mmol) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.216 g, rate of recovery: 89%).

$^1$H-NMR (DMSO-d$_6$) δ: 1.16-1.30 (2H, m), 1.35-1.50 (2H, m), 1.56 (3H, s), 1.80-1.91 (1H, m), 1.91-2.05 (4H, m), 2.08 (3H, s), 2.11 (6H, s), 2.17 (3H, s), 2.32 (3H, s), 2.70 (3H, s), 2.71 (3H, s), 3.09-3.21 (1H, m), 4.22 (2H, d, J=5.1 Hz), 5.86 (1H, s), 6.68 (1H, s), 7.88 (1H, t, J=5.1 Hz), 9.37 (1H, br s), 11.48 (1H, s).

Elemental analysis Anal. Calcd for $C_{27}H_{37}N_3O_4 \cdot CH_4O_3S$: C, 59.65; H, 7.33; N, 7.45; S, 5.69. Found: C, 58.05; H, 7.32; N, 7.19; S, 5.54.

Example 86

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide Hemifumarate (86)

To the compound (48) (0.202 g, 0.431 mmol) synthesized in Example 48, fumaric acid (0.027 mg, 0.233 mmol) and ethyl acetate (2.02 mL) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.219 g, rate of recovery: 97%).

$^1$H-NMR (DMSO-d$_6$) δ: 1.11-1.33 (4H, m), 1.54 (3H, s), 1.73-1.84 (1H, m), 1.85-1.96 (4H, m), 2.08 (3H, s), 2.10 (3H, s), 2.11 (3H, s), 2.17 (3H, s), 2.34 (6H, s), 2.43-2.50 (1H, m), 4.22 (2H, d, J=5.2 Hz), 5.85 (1H, s), 6.46 (1H, s), 6.67 (1H, s), 7.86 (1H, t, J=5.2 Hz), 11.46 (1H, s).

Elemental analysis Anal. Calcd for $C_{27}H_{37}N_3O_4 \cdot \frac{1}{2}C_4H_4O_4$: C, 66.26; H, 7.48; N, 7.99. Found: C, 63.02; H, 7.62; N, 7.51.

Example 87

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide Maleate (87)

To the compound (48) (0.201 g, 0.430 mmol) synthesized in Example 48, maleic acid (0.053 g, 0.457 mmol) and ethyl acetate (2.01 mL) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.210 g, rate of recovery: 84%).

$^1$H-NMR (DMSO-d$_6$) δ: 1.15-1.31 (2H, m), 1.35-1.50 (2H, m), 1.56 (3H, s), 1.81-1.91 (1H, m), 1.91-2.05 (4H, m), 2.08 (3H, s), 2.11 (6H, s), 2.17 (3H, s), 2.71 (6H, s), 3.09-3.21 (1H, m), 4.22 (2H, d, J=5.0 Hz), 5.86 (1H, s), 6.03 (2H, s), 6.69 (1H, s), 7.87 (1H, t, J=5.0 Hz), 9.33 (1H, br s), 11.47 (1H, br s).

Elemental analysis Anal. Calcd for $C_{27}H_{37}N_3O_4 \cdot C_4H_4O_4$: C, 63.79; H, 7.08; N, 7.20. Found: C, 62.09; H, 7.13; N, 6.99.

Example 88

(2S)-2-[trans-4-(Dimethylamino)cyclohexyl]-N-[(4,6-dimethyl-2-oxo-1,2-dihydropyridin-3-yl)methyl]-2,4,7-trimethyl-1,3-benzodioxole-5-carboxamide Hemisuccinate (88)

To the compound (48) (0.201 g, 0.431 mmol) synthesized in Example 48, succinic acid (0.027 g, 0.229 mmol) and ethyl acetate (2.01 mL) were added at room temperature. Then, the mixture was stirred at 40° C. for approximately 20 hours and further stirred at room temperature for approximately 0.5 hours, and the deposited solid was then collected by filtration. Then, the solid was dried overnight at room temperature to obtain the title compound (0.214 g, rate of recovery: 94%).

$^1$H-NMR (DMSO-d$_6$) δ: 1.06-1.31 (4H, m), 1.54 (3H, s), 1.72-1.83 (1H, m), 1.83-1.94 (4H, m), 2.07 (3H, s), 2.10 (3H, s), 2.11 (3H, s), 2.17 (3H, s), 2.29 (6H, s), 2.32 (2H, s), 2.34-2.41 (1H, m), 4.22 (2H, d, J=4.8 Hz), 5.85 (1H, s), 6.67 (1H, s), 7.86 (1H, t, J=4.8 Hz), 11.47 (1H, br s).

Elemental analysis Anal. Calcd for $C_{27}H_{37}N_3O_4 \cdot \frac{1}{2}C_4H_6O_4$: C, 66.13; H, 7.65; N, 7.98. Found: C, 63.03; H, 7.78; N, 7.51.

Test Example 1

EZH1 Methyltransferase Inhibitory Activity Evaluation

25 μL each of reaction solutions containing varying concentrations of the compounds of Examples 1 to 77 (50 mM Tris (pH 8.8), 5 mM MgCl$_2$, 4 mM dithiothreitol, 0.005% bovine serum albumin, 0.75 μM biotin-H3 peptide, 8 ng/μL PRC2-EZH1, 1 μM S-adenosyl-L-methionine, 0.2 μM adenosyl-L-methionine, S-[methyl-$^3$H]— (PerkinElmer, Inc., #NET155H), 1% dimethyl sulfoxide, and 25-0.0061 μM compounds) was added to each well of Streptavidin FlashPlate HTS PLUS, 384-well (PerkinElmer, Inc., #SMP410A001PK) and incubated at room temperature for 2 hours. Then, each well was washed with 50 μL of a washing buffer (50 mM Tris (pH 7.6) and 150 mM NaCl)) twice. Then, the residual radioactivity was measured using TopCount NXT HTS (PerkinElmer, Inc., model C384V01). On the basis of the measured residual radioactivity, the extent of enzyme inhibition by the compounds of Examples 1 to 77 was measured at each concentration, and the obtained data was analyzed with medical statistical analysis software GraphPad Prism (GraphPad Software, Inc.) to calculate IC50 values. The PRC2-EZH1 complex was purchased from Reaction Biology Corp. (#HMT-25-115). The biotin-H3 peptide was prepared by the synthesis of a sequence from the 12- to 40-positions of human histone H3 protein (GG-KAPRKQLATKAARKSAPATGGVKKPHR), followed by N-terminal biotinylation.

Test Example 2

EZH2 Methyltransferase Inhibitory Activity Evaluation

25 μL each of reaction solutions containing varying concentrations of the compounds of Examples 1 to 77 (50 mM Tris (pH 8.8), 5 mM MgCl$_2$, 4 mM dithiothreitol, 0.005% bovine serum albumin, 0.75 μM biotin-H3 peptide, 8 ng/mL PRC2-EZH2, 1 μM S-adenosyl-L-methionine, 0.1 μM adenosyl-L-methionine, S-[methyl-$^3$H]— (PerkinElmer, Inc., #NET155H), 1% dimethyl sulfoxide, and 25-0.0061 μM compounds) was added to each well of Streptavidin FlashPlate HTS PLUS, 384-well (PerkinElmer, Inc., #SMP410A001PK) and incubated at room temperature for 2 hours. Then, each well was washed with 50 μL of a washing buffer (50 mM Tris (pH 7.6) and 150 mM NaCl) twice.

Then, the residual radioactivity was measured using TopCount NXT HTS (PerkinElmer, Inc., model C384V01). On the basis of the measured residual radioactivity, the extent of enzyme inhibition by the compounds of Examples 1 to 77 was measured at each concentration, and the obtained data was analyzed with medical statistical analysis software GraphPad Prism to calculate IC50 values. The PRC2-EZH2 complex was prepared according to the method of Cao R. et al. (Mol. Cell, 15, 57-67 (2004)).

Test Example 3

Intracellular H3K27Me3 Inhibitory Activity Evaluation

HCT116 cells were inoculated at 1500 cells/90 μL/well to a 96-well plate (IWAKI, #3860-096) and cultured overnight at 37° C. The HCT116 cells were purchased from American Type Culture Collection (ATCC). Then, 10 μL each of solutions containing the compounds of Examples 1 to 77 was added to each well, and the cells were cultured at 37° C. for 3 days. Intracellular H3K27me3 was quantified using AlphaLISA H3K27me3 Cellular Detection Kit (PerkinElmer, Inc., #AL722F). The cells thus cultured in each well were washed with 100 μL of PBS. Cell-Histone Lysis buffer diluted 6-fold with PBS was added thereto at 80 μL/well, and the plate was then incubated at room temperature for 15 minutes while shaken. Then, Cell-Histone Extraction buffer was added thereto at 40 μL/well, and the plate was incubated at room temperature for 10 minutes while shaken. 10 μL of the reaction solution was transferred from each well to each well of a 384-well plate (PerkinElmer, Inc., #6008350). An AlphaLISA anti-H3K27me3 Acceptor beads/Biotinylated Antibody anti-Histone H3 (C-ter) mixed solution was added thereto at 3.3 μL/well, and the plate was incubated at room temperature for 60 minutes. Then, Streptavidin (SA)-coated Donor beads were added thereto at 3.3 μL/well, and the plate was incubated at room temperature for 30 minutes with the plate shielded from light. Signals were measured using EnVision 2104 Multilabel Reader (PerkinElmer, Inc.). The extent of H3K27me3 inhibition by the compounds of Examples 1 to 77 was measured at each concentration, and the obtained data was analyzed with medical statistical analysis software GraphPad Prism to calculate IC50 values.

The results of Test Examples 1 to 3 are shown in Tables 1-1 and 1-2.

TABLE 1-1

| Example | Test Example 1 WT EZH1 $IC_{50}$ (μM) | Test Example 2 WT EZH2 $IC_{50}$ (μM) | Test Example 3 H3K27me3 inhibition (HCT116) $IC_{50}$ (μM) | Example | Test Example 1 WT EZH1 $IC_{50}$ (μM) | Test Example 2 WT EZH2 $IC_{50}$ (μM) | Test Example 3 H3K27me3 inhibition (HCT116) $IC_{50}$ (μM) |
|---|---|---|---|---|---|---|---|
| 1 | 0.14 | 0.024 | 0.029 | 2 | 0.052 | 0.022 | 0.009 |
| 3 | 0.66 | 0.03 | 0.026 | 4 | 0.13 | 0.025 | 0.0083 |
| 5 | 0.25 | 0.015 | 0.051 | 6 | 0.51 | 0.039 | 0.045 |
| 8 | 0.097 | 0.016 | 0.006 | 7 | 0.038 | 0.0036 | 0.0084 |
| 9 | 0.066 | 0.011 | 0.013 | 10 | 0.13 | 0.011 | 0.018 |
| 11 | 0.068 | 0.0091 | 0.0037 | 12 | 0.2 | 0.028 | 0.14 |
| 13 | 0.021 | 0.016 | 0.0059 | 14 | 0.021 | 0.024 | 0.00055 |
| 15 | 0.0074 | 0.01 | 0.00047 | 16 | 0.0094 | 0.012 | 0.0014 |
| 17 | 0.017 | 0.023 | 0.0012 | 18 | 0.019 | 0.023 | 0.0058 |
| 19 | 0.028 | 0.025 | 0.011 | 20 | 0.023 | 0.017 | 0.0028 |
| 21 | 0.06 | 0.018 | 0.01 | 22 | 0.088 | 0.014 | 0.0016 |
| 23 | 0.0041 | 0.0056 | 0.0028 | 24 | 0.14 | 0.012 | 0.019 |
| 25 | 0.11 | 0.012 | 0.045 | 26 | 0.19 | 0.023 | 0.037 |
| 27 | 0.023 | 0.022 | 0.0038 | 28 | 0.078 | 0.020 | 0.014 |
| 29 | 0.068 | 0.0094 | 0.016 | 30 | 0.18 | 0.021 | 0.016 |
| 31 | 0.11 | 0.018 | 0.009 | 32 | 0.03 | 0.017 | 0.0048 |
| 33 | 0.26 | 0.028 | 0.014 | 34 | 0.023 | 0.016 | 0.00062 |
| 35 | 0.0084 | 0.0025 | 0.00044 | 36 | 0.013 | 0.013 | 0.0016 |
| 37 | 0.028 | 0.019 | 0.0016 | 38 | 0.057 | 0.012 | 0.0028 |
| 39 | 0.04 | 0.014 | 0.0022 | 40 | 0.21 | 0.011 | 0.032 |
| 41 | 0.059 | 0.014 | 0.011 | 42 | 0.19 | 0.027 | 0.067 |
| 43 | 0.38 | 0.041 | 0.044 | 44 | 0.077 | 0.0079 | 0.014 |
| 45 | 0.11 | 0.0096 | 0.013 | 46 | 0.072 | 0.0067 | 0.0034 |

TABLE 1-2

| Example | Test Example 1 WT EZH1 $IC_{50}$ (μM) | Test Example 2 WT EZH2 $IC_{50}$ (μM) | Test Example 3 H3K27me3 inhibition (HCT116) $IC_{50}$ (μM) | Example | Test Example 1 WT EZH1 $IC_{50}$ (μM) | Test Example 2 WT EZH2 $IC_{50}$ (μM) | Test Example 3 H3K27me3 inhibition (HCT116) $IC_{50}$ (μM) |
|---|---|---|---|---|---|---|---|
| 47 | 0.022 | 0.010 | 0.0014 | 48 | 0.0089 | 0.0080 | 0.00048 |
| 49 | 0.092 | 0.018 | 0.0026 | 50 | 0.053 | 0.020 | 0.0071 |
| 51 | 0.39 | 0.035 | 0.042 | 52 | 0.37 | 0.029 | 0.037 |
| 53 | 0.026 | 0.013 | 0.00063 | 54 | 0.21 | 0.027 | 0.0038 |

TABLE 1-2-continued

| Example | Test Example 1 WT EZH1 IC$_{50}$ (μM) | Test Example 2 WT EZH2 IC$_{50}$ (μM) | Test Example 3 H3K27me3 inhibition (HCT116) IC$_{50}$ (μM) | Example | Test Example 1 WT EZH1 IC$_{50}$ (μM) | Test Example 2 WT EZH2 IC$_{50}$ (μM) | Test Example 3 H3K27me3 inhibition (HCT116) IC$_{50}$ (μM) |
|---|---|---|---|---|---|---|---|
| 55 | 0.053 | 0.028 | 0.011 | 56 | 0.068 | 0.023 | 0.0064 |
| 57 | 0.11 | 0.036 | 0.012 | 58 | 0.0044 | 0.01 | 0.0029 |
| 59 | 0.0057 | 0.0087 | 0.0018 | 60 | 0.0073 | 0.014 | 0.0037 |
| 61 | 0.008 | 0.021 | 0.01 | 62 | 0.011 | 0.0066 | 0.0055 |
| 63 | 0.017 | 0.022 | 0.013 | 64 | 0.022 | 0.014 | 0.0068 |
| 65 | 0.023 | 0.018 | 0.013 | 66 | 0.027 | 0.022 | 0.0017 |
| 67 | 0.017 | 0.019 | 0.0010 | 68 | 0.029 | 0.018 | 0.0016 |
| 69 | 0.032 | 0.024 | 0.029 | 70 | 0.038 | 0.026 | 0.0043 |
| 71 | 0.043 | 0.019 | 0.099 | 72 | 0.076 | 0.017 | 0.013 |
| 73 | 0.012 | 0.022 | 0.0061 | 74 | 0.013 | 0.029 | 0.023 |
| 75 | 0.021 | 0.026 | 0.011 | 76 | 0.02 | 0.012 | 0.00088 |
| 77 | 0.091 | 0.011 | 0.024 | | | | |

Test Example 4

Cell Growth Inhibitory Activity Evaluation

Cells were purchased from ATCC (G401 (human kidney-derived rhabdoid tumor), HepG2, LNCaP, LS180, MV4;11, NCI-H1563, NCI-H1703, NCI-H520, NCI-H522, NCI-N87, RS4;11, and THP-1), Deutsche Sammlung von Mikroorganismen und Zellkulturen GmbH (DSMZ) (KARPAS-422 (EZH2 Y641N mutant human diffuse large B-cell lymphoma) and KOPN8), and Health Science Research Resource Bank (OVMANA). The media for the culture of each cell line used were an EMEM medium supplemented with 10% FBS (LS180 and HepG2), a McCoy's 5A medium supplemented with 10% FBS (G401 (rhabdoid tumor cell line deficient in SNF5, a subunit of the SWI/SNF complex)), an RPMI1640 medium supplemented with 10% FBS (KOPN8, RS4;11, MV4;11, NCI-H1703, NCI-N87, NCI-H522, THP-1, LNCaP, OVMANA, NCI-H520, and NCI-H1563), and an RPMI1640 medium supplemented with 20% FBS (KARPAS-422). During the test period, DMSO (final concentration: 0.1%) or a solution of the compound of Example 14 in DMSO (final concentration: 1 uM (final concentration of DMSO: 0.1%) was added to the medium, and the cells of each line were cultured at 37° C. under 5% CO$_2$. The cultured cells of each line were inoculated to a 6-well culture plate for cell culture and subcultured for a total of 10 days to 11 days while passage or medium replacement was carried out at 3-day to 4-day intervals. Then, the cells were inoculated to a 96-well assay plate. On the day of inoculation to the 96-well assay plate (inoculation date) and 4 days or 5 days thereafter (effect determination date), reaction was carried out using CellTiter-Glo Luminescent Cell Viability Assay reagent (Promega Corp., #G7573) or ATPlite 1step Luminescence Assay System (PerkinElmer, Inc., #6016739) according to the attached manual. Then, the luminescence intensity of each well was measured using a plate reader (EnVision, PerkinElmer, Inc.). The extent of cell growth inhibition was calculated from the luminescence intensity of a sample-supplemented group ($T_S$) and a DMSO-supplemented group ($C_S$) measured on the inoculation date and a sample-supplemented group (T) and a DMSO-supplemented group (C) measured on the effect determination date according to the following expression:

Extent of cell growth inhibition (%)={1−(T−T$_S$)/(C−C$_S$)}×100

When the number of cells in the sample-supplemented group is decreased on the determination date compared with the inoculation date (T<T$_S$), a cytocidal effect was calculated according to the following expression:

Cytocidal rate (%)=(T−T$_S$)/T$_S$×(−100)

The results are shown in Table 2.

TABLE 2

| Cancer type | Cell line | Extent of cell growth inhibition | Cytocidal rate |
|---|---|---|---|
| Lymphoma | KARPAS-422 | >100% | 100% |
| Rhabdoid tumor | G401 | >100% | 100% |
| Leukemia | KOPN8 | >100% | 99% |
| Leukemia | RS4; 11 | >100% | 94% |
| Leukemia | MV4; 11 | >100% | 88% |
| Lung cancer | NCI-H1703 | >100% | 49% |
| Stomach cancer | NCI-N87 | >100% | 15% |
| Lung cancer | NCI-H522 | >100% | 13% |
| Leukemia | THP-1 | >100% | 7% |
| Prostate cancer | LNCaP | >100% | 6% |
| Colorectal cancer | LS180 | >100% | 6% |
| Ovarian cancer | OVMANA | 95% | — |
| Lung cancer | NCI-H520 | 80% | — |
| Liver cancer | HepG2 | 78% | — |
| Lung cancer | NCI-H1563 | 56% | — |

Test Example 5

Evaluation of Antitumor Activity Against EZH2 Y641N Mutant Human Diffuse Large B-Cell Lymphoma KARPAS-422-Subcutaneously Transplanted Model EZH2 Y641N mutant human diffuse large B-cell lymphoma KARPAS-422 cells were subcutaneously transplanted in an amount of 2×10$^7$ cells/head to the right abdomens of female SCID mice. After 30 days, the mice were grouped on the basis of their presumed tumor volumes (major axis×minor axis×minor axis/2) and body weights. The KARPAS-422 cells were purchased from DSMZ. The female SCID mice were purchased from Charles River Laboratories Japan Inc. From the day following grouping, the compound of Example 14 or the compound of Example 34 was orally administered at a dose set to 5, 25, or 200 mg/kg/day once a day for 14 consecutive days (QD×14) as the dosing schedule. The tumor volume of each individual was measured from the grouping date to 45 days thereafter (test completion date).

Test Example 6

Evaluation of Antitumor Activity Against SNF5 Deletion Mutant Human Kidney-Derived Rhabdoid Tumor G401-Subcutaneously Transplanted Model SNF5 deletion mutant human kidney-derived rhabdoid tumor G401 cells were subcutaneously transplanted in an amount of $1\times10^7$ cells/head to the right abdomens of female BALB/c-nu/nu mice. After 23 days, the mice were grouped on the basis of their presumed tumor volumes and body weights. The G401 cells were purchased from ATCC. The female BALB/c-nu/nu mice were purchased from Charles River Laboratories Japan Inc. From the day following grouping, the compound of Example 14 or the compound of Example 34 was orally administered at a dose set to 50 or 200 mg/kg/day once a day for 12 consecutive days (QD×12) as the dosing schedule. The tumor volume of each individual was measured from the grouping date to 36 days thereafter (test completion date).

The antitumor activity against the EZH2 Y641N mutant human diffuse large B-cell lymphoma KARPAS-422-subcutaneously transplanted models in Test Example 5, and the antitumor activity against the human kidney-derived rhabdoid tumor G401-subcutaneously transplanted models in Test Example 6 were calculated on their respective test completion dates according to the following expression:

Extent of tumor growth inhibition (%)=(1−$TVCt/TVCc$)×100

TVC=(Tumor volume of each individual on the test completion date)−(Tumor volume of each individual on the grouping date)
TVCt: Average TVC of the drug administration group
TVCc: Average TVC of the non-administration group As for a group whose extent of tumor growth inhibition exceeded 100% (indicated by >100%), the extent of tumor regression was calculated according to the following expression:

Extent of tumor regression (%)=Average value of (1−(Tumor volume of each individual on the test completion date/Tumor volume of each individual on the grouping date)×100

Test Example 7

Evaluation of Antitumor Activity Against Human Colorectal Cancer LS180-Subcutaneously Transplanted Model Human colorectal cancer LS180 cells were subcutaneously transplanted in an amount of $5\times10^6$ cells/head to the right abdomens of female SCID mice. After 3 days, the mice were grouped on the basis of their presumed tumor volumes and body weights. The LS180 cells were purchased from ATCC. The female SCID mice were purchased from Charles River Laboratories Japan Inc. From the day following grouping, the compound of Example 34 was orally administered at a dose set to 50 or 200 mg/kg/day twice a day for 13 consecutive days (BID×13) as the dosing schedule. The tumor volume of each individual was measured from the grouping date to 17 days thereafter (test completion date).

Test Example 8

Evaluation of Antitumor Activity Against Human Stomach Cancer NCI-N87-Subcutaneously Transplanted Model Human stomach cancer NCI-N87 cells were subcutaneously transplanted in an amount of $8\times10^6$ cells/head to the right abdomens of female BALB/c-nu/nu mice. After 12 days, the mice were grouped on the basis of their presumed tumor volumes and body weights. The NCI-N87 cells were purchased from ATCC. The female BALB/c-nu/nu mice were purchased from Charles River Laboratories Japan Inc. From the day following grouping, the compound of Example 34 was orally administered at a dose set to 50 or 200 mg/kg/day once a day for 28 consecutive days (QD×28) as the dosing schedule. The tumor volume of each individual was measured from the grouping date to 82 days thereafter (test completion date).

The antitumor activity against the human colorectal cancer LS180-subcutaneously transplanted models in Test Example 7, and the antitumor activity against the human stomach cancer NCI-N87-subcutaneously transplanted models in Test Example 8 were calculated on their respective test completion dates according to the following expression:

Extent of tumor growth inhibition (%)=(1−$TVCt/TVCc$)×100

TVC=(Tumor volume of each individual on the test completion date)−(Tumor volume of each individual on the grouping date)
TVCt: Average TVC of the drug administration group
TVCc: Average TVC of the non-administration group The results of Test Examples 5 to 8 are shown in Table 3.

TABLE 3

| Cancer type | Cell line | Dose (mg/kg) | Dosing schedule | Compound of Example 14 | | Compound of Example 34 | | Compound of Example 15 | | Compound of Example 35 | |
|---|---|---|---|---|---|---|---|---|---|---|---|
| | | | | Extent of tumor growth inhibition | Extent of tumor regression | Extent of tumor growth inhibition | Extent of tumor regression | Extent of tumor growth inhibition | Extent of tumor regression | Extent of tumor growth inhibition | Extent of tumor regression |
| Test Example 5 lymphoma | KARPAS-422 | 5 | QD × 14 | 26% | — | 44% | — | 54% | — | 52% | — |
| | | 25 | QD × 14 | 80% | — | 76% | — | >100% | 27% | >100% | 14% |
| | | 200 | QD × 14 | >100% | 50% | >100% | 52% | — | — | — | — |
| Test Example 6 rhabdoid tumor | G401 | 50 | QD × 12 | >100% | 19% | >100% | 22% | — | — | — | — |
| | | 200 | QD × 12 | >100% | 29% | >100% | 17% | — | — | — | — |
| Test Example 7 colorectal cancer | LS180 | 50 | BID × 13 | — | — | 8% | — | — | — | — | — |
| | | 200 | BID × 13 | — | — | 73% | — | — | — | — | — |
| Test Example 8 stomach cancer | NCI-N87 | 50 | QD × 28 | — | — | 80% | — | — | — | — | — |
| | | 200 | QD × 28 | — | — | 87% | — | — | — | — | — |

INDUSTRIAL APPLICABILITY

The compound represented by the general formula (I) of the present invention or the pharmacologically acceptable salt thereof has an excellent inhibitory effect on EZH1 and/or EZH2 activity and as such, is useful as a therapeutic drug for tumors.

The invention claimed is:

1. A compound represented by the formula (I) or a pharmacologically acceptable salt thereof:

[Formula 1]

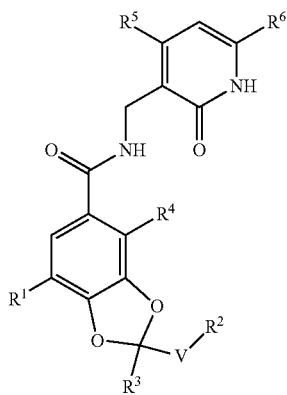

(I)

wherein
$R^1$ represents a hydrogen atom, a halogen atom, or a $C_1$-$C_6$ alkyl group optionally having 1 to 3 halogen atoms,
V represents a single bond,
$R^2$ represents a hydrogen atom, a $C_1$-$C_6$ alkyl group, or a $C_3$-$C_6$ cycloalkyl group wherein the $C_1$-$C_6$ alkyl group, or a $C_3$-$C_6$ cycloalkyl group optionally has a substituent group of —$NR^{20}R^{21}$, wherein $R^{20}$ and $R^{21}$ each independently represent a hydrogen atom, a formyl group, or a $C_1$-$C_6$ alkyl group,
$R^3$ represents a $C_1$-$C_6$ alkyl group,
$R^4$ represents a halogen atom or a $C_1$-$C_6$ alkyl group optionally having 1 to 3 halogen atoms,
$R^5$ represents a $C_1$-$C_6$ alkyl group or a $C_1$-$C_6$ alkoxy group,
$R^6$ represents a $C_1$-$C_6$ alkyl group.

2. The compound according to claim 1 or a pharmacologically acceptable salt thereof, wherein $R^1$ represents a halogen atom.

3. The compound according to claim 1 or a pharmacologically acceptable salt thereof, wherein $R^1$ represents a chloro group.

4. The compound according to claim 1 or a pharmacologically acceptable salt thereof, wherein $R^2$ represents a $C_3$-$C_6$ cycloalkyl group and the $C_3$-$C_6$ cycloalkyl group has a substituent group of —$NR^{20}R^{21}$, wherein $R^{20}$ and $R^{21}$ each independently represent a hydrogen atom, a formyl group, or a $C_1$-$C_6$ alkyl group.

5. The compound according to claim 1 or a pharmacologically acceptable salt thereof, wherein $R^3$ represents a methyl group.

6. Any one compound selected from the following group or a pharmacologically acceptable salt thereof:
   7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
   (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
   7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
   (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide,
   2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide,
   (2S)-2-[trans-4-(dimethylamino)cyclohexyl]-N-[(4,6-dimethyl-2-oxo-1,2-dihydropyridin-3-yl)methyl]-2,4,7-trimethyl-1,3-benzodioxole-5-carboxamide,
   4,7-dichloro-2-[trans-4-(dimethylamino)cyclohexyl]-N-[(4,6-dimethyl-2-oxo-1,2-dihydropyridin-3-yl)methyl]-2-methyl-1,3-benzodioxole-5-carboxamide,
   2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, and
   2-[trans-4-(dimethylamino)cyclohexyl]-N-[(4,6-dimethyl-2-oxo-1,2-dihydropyridin-3-yl)methyl]-7-ethyl-2,4-dimethyl-1,3-benzodioxole-5-carboxamide.

7. A pharmaceutical composition comprising a compound according to claim 1 or a pharmacologically acceptable salt thereof as an active ingredient.

8. The compound according to claim 1, wherein the compound is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmacologically acceptable salt thereof.

9. The compound according to claim 1, wherein the compound is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate.

* * * * *